(12) United States Patent
Silverman et al.

(10) Patent No.: US 9,816,111 B2
(45) Date of Patent: Nov. 14, 2017

(54) PROPYLENE SYNTHESIS USING ENGINEERED ENZYMES

(71) Applicant: Calysta, Inc., Menlo Park, CA (US)

(72) Inventors: Joshua A. Silverman, Los Altos Hills, CA (US); Thomas Joseph Purcell, Mountain View, CA (US)

(73) Assignee: CALYSTA, INC., Menlo Park, CA (US)

( * ) Notice: Subject to any disclaimer, the term of this patent is extended or adjusted under 35 U.S.C. 154(b) by 331 days.

(21) Appl. No.: 14/429,327

(22) PCT Filed: Sep. 18, 2013

(86) PCT No.: PCT/US2013/060460
§ 371 (c)(1),
(2) Date: Mar. 18, 2015

(87) PCT Pub. No.: WO2014/047209
PCT Pub. Date: Mar. 27, 2014

(65) Prior Publication Data
US 2015/0232886 A1    Aug. 20, 2015

Related U.S. Application Data

(60) Provisional application No. 61/702,534, filed on Sep. 18, 2012.

(51) Int. Cl.
*C12P 5/02*    (2006.01)
*C12N 1/20*    (2006.01)

(52) U.S. Cl.
CPC ............... *C12P 5/026* (2013.01); *C12N 1/20* (2013.01)

(58) Field of Classification Search
None
See application file for complete search history.

(56) References Cited

U.S. PATENT DOCUMENTS

| | | |
|---|---|---|
| 6,689,601 B2 | 2/2004 | Koffas et al. |
| 6,818,424 B2 | 11/2004 | DiCosimo et al. |
| 7,098,005 B2 | 8/2006 | Dicosimo et al. |
| 2002/0168733 A1 | 11/2002 | Clark et al. |
| 2003/0003528 A1 | 1/2003 | Brzostowicz et al. |
| 2003/0203456 A1 | 10/2003 | Clark et al. |
| 2006/0057726 A1 | 3/2006 | Sharpe |
| 2008/0026005 A1 | 1/2008 | Miguez et al. |
| 2010/0221813 A1 | 9/2010 | Miguez et al. |
| 2011/0111413 A1 | 5/2011 | Padgett et al. |
| 2011/0201089 A1 | 8/2011 | Burgard et al. |
| 2011/0236941 A1 | 9/2011 | Koepke et al. |

FOREIGN PATENT DOCUMENTS

| | | |
|---|---|---|
| EP | 0 296 484 A2 | 12/1988 |
| WO | 02/18617 A2 | 3/2002 |
| WO | 2005/087942 A1 | 9/2005 |
| WO | 2008/028055 A2 | 3/2008 |
| WO | 2011/088206 A1 | 7/2011 |
| WO | WO2011/088206 A1 * | 7/2011 |
| WO | 2012/053905 A1 | 4/2012 |

OTHER PUBLICATIONS

Akhverdyan et al., "Application of the bacteriophage Mu-driven system for the integration/amplification of target genes in the chromosomes of engineered Gram-negative bacteria-mini review," *Appl Microbiol Biotechnol* 91:857-871, 2011.
Ali et al., "Development and validation of promoter-probe vectors for the study of methane monooxygenase gene expression in *Methylococcus capsulatus* Bath," *Microbiology* 155:761-771, 2009.
Ali et al., "Duplication of the mmoX gene in Methylosinus sponum: cloning, sequencing and mutational analysis," *Microbiology* 15:2931-2942, 2006.
Gustafsson et al., "Codon Bias and Heterologous Protein Expression," *Trends Biotechnol* 22(7):346-353, 2004. (10 pages).
Hanson et al., "Methanotrophic Bacteria," *Microbiological Reviews* 60(2):439-471, 1996.
Korotkova et al., "Connection between Poly-β-Hydroxybutyrate Biosynthesis and Growth on $C_1$ and $C_2$ Compounds in the Methylotroph *Methylobacterium extorquens* AM1," *Journal of Bacteriology* 183(3):1038-1046, 2001.
Lloyd et al., "Heterologous expression of soluble methane monooxygenase genes in methanotrophs containing only particulate methane monooxygenase," *Arch Microbiol* 171:364-370, 1999.
Martin et al., "Methane monooxygenase mutants of *Methylosinus trichosporium* constructed by marker-exchange mutagenesis," *FEMS Microbiology Letters* 127:243-248, 1995.
Pieja et al., "Distribution and Selection of Poly-3-Hydroxybutyrate Production Capacity in Methanotrophic Proteobacteria," *Microbial Ecology* 62(3):564-573, 2011.
Pieja et al., "Poly-3-Hydroxybutyrate Metabolism in the Type II Methanotroph *Methylocystis parvus* OBBP," *Applied and Environmental Microbiology* 77(17):6012-6019, 2011.
Sharp et al., "Variation in the strength of selected codon usage bias among bacteria," *Nucleic Acids Research* 33(4):1141-1153, 2005.
Tanner et al., "*Clostridium ljungdahlii* sp. nov., an Acetogenic Species in Clostridial rRNA Homology Group I," *International Journal of Systematic Bacteriology* 43(2):232-236, 1993.
Topp et al., "Isolation and Characterization of an N-Methylcarbamate Insecticide-Degrading Methylotrophic Bacterium," *Applied and Environmental Microbiology* 59(10):3339-3349, 1993.
Toyoma et al., "Construction of insertion and deletion *mxa* mutants of *Methylobacterium extorquens* AMI by electroporation," *FEMS Microbiology Letters* 166:1-7, 1998.

(Continued)

*Primary Examiner* — Suzanne M Noakes
*Assistant Examiner* — Jae W Lee
(74) *Attorney, Agent, or Firm* — Seed IP Law Group LLP

(57) ABSTRACT

The present disclosure relates to biosynthetic methods for producing propylene and to genetically engineered organisms having propylene biosynthesis capability.

30 Claims, 14 Drawing Sheets

(56) References Cited

OTHER PUBLICATIONS

Van Dien et al., "Reconstruction of $C_3$ and $C_4$ metabolism in *Methylobacterium extorquens* AM1 using transposon mutagenesis," *Microbiology* 149:601-609, 2003.

Villalobos et al., "Gene Designer: a synthetic biology tool for constructing artificial DNA segments," *BMC Bioinformatics* 7:285, 2006, 8 pages.

Welch et al., "Design Parameters to Control Synthetic Gene Expression in *Escherichia coli*," *PLoS ONE* 4(9):e7002, 2009, 10 pages.

Wu et al., "Life in Hot Carbon Monoxide: The Complete Genome Sequence of *Carboxydothermus hydrogenoformans* Z-2901," *PLoS Genetics* 1(5):e65, 563-574, 2005, 12 pages.

Wu et al., "SGDB: a database of synthetic genes re-designed for optimizing protein over-expression," *Nucleic Acids Research* 35:D76-D79, 2006.

\* cited by examiner

>gi|108762234|ref|YP_629186.1| putative 4-oxalocrotonate decarboxylase [Myxococcus xanthus DK 1622]
MTATVDHEALAHFLDSARLERREVAPLTREQPALSVPDAYAIQEAGIRLRLSHGERVVGLKMGLTSE
AKRKQMNLDSPVYGVLTDRMQVPAGGVIQLSQGVHPKIEPEIAFRTARELRGTVTRDEVLDACESVF
AAMEILDSRYRDFKYFSLPDVVADNASSSLFVLGTAEHPPRAMDLTRLEMTLSVNGEPVQSARADAI
SGDPVVSVIQLCELLAQRGQVLPAGSIVLAGAATAAHMLRPGDRVQLTVEGLGIVAVSAE (SEQ ID NO:1)

>gi|148553835|ref|YP_001261417.1| 4-oxalocrotonate decarboxylase [Sphingomonas wittichii RW1]
MADLQALAERLDEAQRLARATPQLEDALSILDAYQVQRALLERRYARGERRVGIKMGFTSRAKMVQ
MGVSEMIWGRLTDGMMVEEGGTVDFDRYVHPRVEPEIAFILKRDLPGPVTLAGAAAAVEAIAPALEII
DSRYKDFRFSVTDVVADNSSSSSFVVGPWSTPSTNVSNVGMIMSVNGEPKQIGSSAAILGSPLRSLV
AAARLASEAGESLRAGDVILAGGATAAEALSPGDHIRLEVQGLGIAEFTVGRTGAASG (SEQ ID NO:2)

>gi|331698068|ref|YP_004334307.1| 4-oxalocrotonate decarboxylase [Pseudonocardia dioxanivorans CB1190]
MTDVATWAARLDDAATGTAPIAPLSGDGLTDLAVAYEVQGGVVGLRLGRGERLVGGKLGLTSRAKQ
IAMGVDRPLYGLVTSGMARNSGSRLLLEELIHPRVEPEIAFVLGEPLEGPGVTVADVLAATRYVCPAL
DVIDSRYEGFRFTHLDAIADNASSAVFALGDDLVEPRGDLALTGCVLEVDGRVVESAAGAAVMGHPA
AAVAYMANQLVATDRRLEAGWVVLSGGLTAPVPLLPGSTVTATLSGLGSVTLGAE (SEQ ID NO:3)

>gi|349796105|gb|EGZ49895.1| 4-oxalocrotonate decarboxylase [Neisseria wadsworthii 9715]
MSTLSKQQIEQLAEHLENAELQAYEVTKITDDFPDMDYEDAFDIQWEIRRR
KEARGNKIVGMKMGLTSWAKMSQMGVEHPCYGFLADYFSVPEGAAVKHDELIHPKIEAELAFVTKA
DLRGPG
CHIGDVLAATDFVMPAIEVIDSRYKDFKFDLKSVIADNSSSSRFITGGCAKPASELDLKTLGVVMEING
KVVQTGAGAAVLGHPAASVAMLANMLAERGEYLPAGSFVMIGAITAAVQVEKGDSFCVHFQDLGSIS
GRFE (SEQ ID NO:4)

>gi|255291919|dbj|BAH90408.1| 4-oxalocrotonate decarboxylase [uncultured bacterium]
MTTASPELVAELAEYLESAELEARDVTKITDAHPDLDFDDAYNIQWEIRRR
KLERGTRLAGLKAGLTSRAKMKQMGVETPIYGFLADYFERPEGGEIATADLIHPKVEAEIAVVTKAELA
GP
CHMGQALAAIDFVLPAVEIIDSRYENFRFDLVSVIADNASSSRFVLGGRMADVRDVDLRTLGVVMEK
NG
QVVELGAGAAVLNHPASVVLLANQLAERGEVIPAGTLILTGGITAAVAVEAGDAVNVRYQGLGNVT
MRFV (SEQ ID NO:5)

>gi|90416265|ref|ZP_01224197.1| 4-oxalocrotonate decarboxylase [marine gamma proteobacterium HTCC2207]
MSRTLDQETIEKLAEHLENAELQAYEVTKITDDYPNMTFTDATDVQWEIRRRKMSRGHKVVGMKMG
LTSWAKMKQMGVEMPCYGFLADYFSLPDGAQVPFDELIHPKVEAEIAFVTNKELSGRNLTVEDVLAA
TELVVPAVEIIDSRYKDFKFDLTSVQADNSSSTRFVVGSHAAKPEDFDWSTIGVVMQKNGEIIELGAG
AAVLDHPAASVAMLATMLAERDEVIPAGTFIMTGGITAAVLAKGDSIVVRYQGLGTVTMKFV (SEQ ID NO:6)

>gi|171060016|ref|YP_001792365.1| 4-oxalocrotonate decarboxylase [Leptothrix cholodnii SP-6]
MALNRTDIEALAAHLESAELEARDVTKITDDFPLMDWADAYDIQDEIRRR
KEARGHKTVGLKAGLTSFAKMKQMGVDTPCFGFVSDYMARPDGGEIKVSELIHPKVEAEICIVTKAPL
RGPG
CHVGAVLAAIDFVLPAVEIIDSRYRDFKFDLKSVIADNTSASRFVIGGRSRNVEALDLRTLGVVLEKNG
QIVSMAAGAAVLGHPAAAVAMMANHLGARGQEIPAGTFIMTGGVTEAIAVQAGDSVNVRFQDLGSV
SMRFV (SEQ ID NO:7)

*FIG. 2A*

>gi|339626941|ref|YP_004718584.1| 4-oxalocrotonate decarboxylase [Sulfobacillus acidophilus TPY]
MTGPELNRWADRVWHHQRTATPMARITEEVPHLTVEDGYAIQARLIDRRTASGEHLIGYKMGLTS
EAKQHAVGVSLPIYGRLTDAMELHTPIVDGSRLIHPRVEPELAIVLKRGLAGSVPLRDVLTAIECVLP
AWEVIDSRYEGFSFTAADVVADNASAAQFYLPPYAFSPYGRDWAEMGVTVRRNGHVRHVASAAA
VLGHPWEAVRRLAILLAQEDRELLPGQVILTGGITDAVPLSPGDRLQMTFGTLGILDVVVPVRKEDA
NAPDSY (SEQ ID NO:8)

>gi|345472866|dbj|BAK74316.1| 4-oxalocrotonate decarboxylase [Arcobacter sp. L]
MALDKSTIEKLAKHCEDAELKAYEITKITDDYPDMTYEDAYDIQWTARAAKEARGHKIVGMKMGLT
SQAKMKQMGVPNPCYGYLADYFSFGDGAEIKIDELIHPKVEAEIAFVLKNDLEGPGCHIGDVLAATD
FVMPAVEIIDSRYKDFKFDLKSVIADNSSSSRYVTGGRMRDIKDLDLKTLGVVMEINGEIVQLGAGA
AVLGHPATSIAMLANMLSQRGEKLKAGEYILSGAITAAVSVKKGDNVTVKFQDLGSLSFRFV (SEQ ID NO:9)

>gi|258651039|ref|YP_003200195.1| 4-oxalocrotonate decarboxylase [Nakamurella multipartita DSM 44233]
MSTTSITPDEIAQVLLAGERNRTEVAQFSASHPDLDVRTAYAAQRAFVQAKLDAGEQLVGYKLGLT
SRNKQRAMGVDCPLYGRVTSSMLATYGDPIPFDRFIHPRVESEIAFLLKQDVTAPATVSSVLAATD
VVFGAVDVLDSRYEGFKFTLEDVVADNASAGAFYLGPVARPATELRLDLLGCIVRVDGEVTMTAAG
AAVMGHPAAAVAWLANQLALEGESLKAGQLIFSGGVTAPVPVVPGGSVTFEFDGLGVIEVAGA
(SEQ ID NO:10)

>gi|312796808|ref|YP_004029730.1| 4-oxalocrotonate decarboxylase [Burkholderia rhizoxinica HKI 454]
MSFITEYATLLDTAARDAHEVEQFDLDARLSLEDAYAIQAASIARRLERGERRVGVKMGFTSRAKM
LQMGLSDVIWGRLTCAMQLEEGASVSFRRFVHPRVEPEIAFLLKRPLAADVTAPAALAAVEAIAPAI
EVIDSRYKNFKFTLPEVIADNASSSGFVIGAWCDPHIDFSNLGLTLNIDGQVKQVGSSAALLGHPLR
SLVAAARLSAQAGEPLQAGWIVMAGGATSAEYIAPGQYVSIDIERLGSAGFHVAD (SEQ ID NO:11)

>gi|297154945|gb|ADI04657.1| 4-oxalocrotonate decarboxylase [Streptomyces bingchenggensis BCW-1]
MTWDLDRAATALLEAEDTRTDRGPITDEWPELDLDMAYAVQDETLQRRLNRGEHIVGVKLGLTSR
AKQERMGIAAPLTAWLTDAMLLPAGAPVPQDRLIHPRAEPEIVFVMKDRLAGPGVTAATALAAVGS
VHGGIEVIDSRYRDFRFTLPDVAADNASSGRFVTGPVGVPPEKLDLAIEACLVEVDGQVADSATGA
AVQGHPAEALALAANELGRRGLAIEPGWLVLTGGMTDAVHVPPGTTVAVHFTHLGSLHLTGG
(SEQ ID NO:12)

>gi|170725767|ref|YP_001759793.1| 4-oxalocrotonate decarboxylase [Shewanella woodyi ATCC 51908]
MLIDLAKKLDQAAADAASIAQLSSTTQLSLDDAYKVQKISIEQRLIRGEKLVGYKMGFTSKAKMIQM
GVDDLIWGRLTDAMMIQDGGSIDLSKYVHPRAEPEIAFRLKKPLAGIVTKEEAYDAIDAVAGAIEVID
SRYQNFKFSLSDVIADNCSSTGFVVGPWHSPDTNIDGLSMILKVNDAEVERGSSKDILDHPLNSLIE
AARCVAQYGESLQAGQIILAGAATAAVALKPGQTISTEIEGLSPCQFSTSNNSSSQASK (SEQ ID NO:13)

>gi|339329072|ref|YP_004688764.1| 4-oxalocrotonate decarboxylase DmpH [Cupriavidus necator N-1]
MNLTQDIIQQLAEHLENAELNREPVRKITDDYPEMDWDDAYAIQDAIRAR
KEARGTRIAGLKMGLTSFAKMRQMGVTEPVYGFVTDYGACMDGGAIDTASLIHPKVEAEIAFVLKR
PLKGPG
CHIGDVLAATDFVLPAVEVIDSRYENFRFDLKSVIADNTSSARFVVGGTHRSADGIDLKNLGVVMEK
NG
EVVATAAGAAVLGHPASSVAMLANMLGARGRELPAGTFIMTGGVTEAVAVQAGDNVTVRYQHLG
TVSMRFV (SEQ ID NO:14)

*FIG. 2B*

\>gi|121592659|ref|YP_984555.1| 4-oxalocrotonate decarboxylase [Acidovorax sp. JS42]
MALAQDTIAQLAEHLENCQLQAKDTPKITDAHPDMDWDDAYAIQDAILARKLARGARVVGL
KAGLTSHAKMRQMGVTDPVFGFLVDEYVVPEGATVNTAELIHPKVEPEIAFVLKHALKGPG
CHIGAVLAATDFVLPGIEVIDSRYRDFKFDLKSVVADNTSASRFVVGGRALRPEDVDLRTVG
IVLEKNGEPVALGAGAAVLGHPAAAIAMLANHLGRRGQEIPAGSLILSGGATEAVAVAAGDS
VCLRVQGMGSVSLRFA (SEQ ID NO:15)

\>gi|119898145|ref|YP_933358.1| 4-oxalocrotonate decarboxylase [Azoarcus sp. BH72]
MSQNLTLSREDIVRLCERVEGAQTRAYAIPKLTDEYPAMTIADGYAVQSELRRRYLAQGHR
LVGWKAGLTSKAKMKQMGVDVPSIGFLTDRMARPENAAISTGDLVHPRVECEVAFVMKRE
LRGPGCTAADVLAATDYVLPAVEIIDSRFAGFKFDLPSVIADNGSSARFVGGGRARYVEELD
LRTLGVVLEKNGEIVAMGASAAVLGHPAEAIAMLVNILADLGETLPAGSFVMSGGITEAIAVQ
PGDSVVARFQELGSVSMRFVA (SEQ ID NO:16)

\>gi|326388552|ref|ZP_08210146.1| 4-oxalocrotonate decarboxylase [Novosphingobium nitrogenifigens DSM 19370]
MALAAETVAELAEFLDKAEMERREVTKITDRYPEMDWDDAYAIQRGIRERQQARGVGMAG
YKAGLTSHAKMEQMGVEEPVFGFITDVGEIPDGGTIDTATLIHPKVEAEIAFVLKDELTGPGC
DIDAVLAATACVVPALEVIDSRYKDFRFDLKSVIADNTSSARWISGGEKVPVAGLDLPNLAIV
MEKNGEVVEAATGAAVLGHPAQSVAMLANMLARRGESLPAGAFIMTGGATAAVAVAPGDT
ITVKYQALGTISVKVV (SEQ ID NO:17)

\>gi|124268508|ref|YP_001022512.1| 4-oxalocrotonate decarboxylase [Methylibium petroleiphilum PM1]
MTLTLSRSDIERLADRVEAAQDNARAIPKLTDDFPRMGLADGYAVQSELRRRRIRQGHRLV
GWKAGLTSKAKMLQMGVDVPSIGFLMSNMARTDNAQVRTDDLVHPRVECEVAFVTKKDL
HGPDCTRDEVLAATDFVLPAIEVIDSRFAGFKFDLPSVVADNGSSARFVTGARARDVADLD
LRTLGVVFEKNGVSIGMGATAAVLGHPAEAVAMLVRVLAELDEPLPAGSFVMSGGITEAVA
VTAGDHVVARYQDLGSVSVRFI (SEQ ID NO:18)

\>gi|255291893|dbj|BAH90385.1| 4-oxalocrotonate decarboxylase [uncultured bacterium]
MSLDQPNSVDDEAIIRMAERIETAQRYATPIRKLTEDYPDLTIADAYRVQTALRRNLEKKGE
RVIGWKAGLTSKPKMAQMGVSTPGVGFLTDAMERPANSKITVSDMIHPRVEAEIAFVTNKE
LSGKVTKEEVLAATDYVQPALEVIDSRFTGFKFDLESVLADNASSARFVPGGRMIRLDARDL
RTVGVVLEHNGEIAQIGAGAEVLGHPAEAIAMLVGVLDDMGEVLPAGSFVMAGAITAAVAV
KPGDSITARFYEMGSITVTFTE (SEQ ID NO:19)

\>gi|239937275|dbj|BAH79104.1| 4-oxalocrotonate decarboxylase [Paenibacillus sp. JJ-1b]
MDKTVIKDLARFLVDAEVEKKEVLKLTNEHPDLTVEDGYAIQEQLVQMKLEQGYRIVGPKM
GLTSQAKMKQMNVNEPIYGYIFDYMVVNGQELSMSELIHPKVEAEIAFILGKDIEGPGITGAQ
VLAATEYVVPALEIIDSRYQNFQFTLPDVIADNASSSRVFLGSTIKRPDNMELDLLGVTLSING
QIKDLGAGAAVVGHPANSVAMLANMLARKGLKLKAGQIILSGGITGAVMLNVGDSVTGKFD
GLGTIDFIVKE (SEQ ID NO:20)

\>gi|297530338|ref|YP_003671613.1| 4-oxalocrotonate decarboxylase [Geobacillus sp. C56-T3]
MTSLDYEKLAMELLNAEHEKREMVRLTVQYPNMTVEEAYAIQEQLVAMKQKDGYRIIGPKM
GLTSAAKMAQMGVNEPIYGYVFDYMVVPNGGTVAMNELIHPKVEAEIAFILKEDVRGPNIDA
TDILAATEYIIPALEIIDSRYANFEFALPDVIADNASSSRVVFGSRLVPPVSLELDLLGVSLSIN
GEGKAFGAGAAVLGHPANAIAMLANMLSRKGKGLKAGEIILAGAMTEAVRFVAGDVVFAQF
EQLGTVSFRSTD (SEQ ID NO:21)

*FIG. 2C*

>gi|52082278|ref|YP_081069.1| 4-oxalocrotonate decarboxylase [Bacillus licheniformis ATCC 14580]
MNTAALKDTARLLYLAETEKREVERITKDYPELTVEEAYAIQEELIQLKLWDGNSIIGPKMGLTSRAK
MKQMNVEEPIYGYIFEDMIVPNGGSIRMNELIHPKVEAEIAFVLGEDIEGPGVTKEQVLEAVAELIPV
LEVIDSRYENFSFTLPDVIADNASSSRVVLGEKVKKPDDFKLDEARVSLMINGEVKERGTGAAVVG
HPANSAAMLANMLSRKKQKLAAGSIILTGGVTGAVMLQPGDRVSAQVEGLGDVSFSVKP (SEQ ID NO:22)

>gi|226312566|ref|YP_002772460.1| 4-oxalocrotonate decarboxylase [Brevibacillus brevis NBRC 100599]
MQSELLYKRLAQKLVDAELNREVVVKLTAEYPELTVEDGYRIQDELVSLKLEQGHRIFATKMGLTS
QAKMKQMNVHEPIRGYIFDYMNIEDGILPINELIHPKVEAEIAFVLREDLEGPGITEGHVLAATDYVV
PALEIIDSRYAQFQFSLPDVIADNTSSSRVFIGSTWRKPDDLDLDLVGVTLSINGELKDLGAGAAVL
GHPAHAVAMLANMLAREGRKLYKGDLILSGGITGSHQLREGDVVVAKWGGLGSIEFVVKTR (SEQ ID NO:23)

>gi|138896787|ref|YP_001127240.1| 4-oxalocrotonate decarboxylase [Geobacillus thermodenitrificans NG80-2]
MTNELYRQLAERLAVAEREHRTVTKLTAEYPELTVEDAYRIQDELIAIKQRQGHHVAALKMGFTSR
AKMKQMNVHEPIYGYVLDYMLCEDGVLSLAELIHPKVEAEIAFILGQDLEGPGITGAQALAATEYVL
PALEIIDSRYTHFQFALPDVIADNTSASRVFFGTTLRRPEELELDLVGVTLSINGELRDLGAGAEVLC
HPANSVAMLANMLARRGCKLSAGQVILTGGITGAHPVADGDLVVARWDGLGSISFTVQG (SEQ ID NO:24)

>gi|167784121|gb|ACA01540.1| 4-oxalocrotonate decarboxylase [Geobacillus stearothermophilus]
MALTVKVSLYRKFAELLNEAEREKREVARITEEVPDLSAEEAYKIQEELIKIKTNSGHRIIGPKMGLTS
QAKMAQMKVKEPIYGYLFDYMFVPSGGAIHMSELIHPKVEVEIAFILGEDLEGPHVTSQVLSATKY
VAPALEIIDSRYQDFTFTLPDVIADNASSSRVVIGNTMTPIHSLKTDLDLIGAALYINGELKACGAGAA
VFNHPANSVAVLANMLARKGERLKAGDIILTGGITEAIQLSAGDTVIGQLDQLGDVSLSVKE (SEQ ID NO:25)

>gi|61105811|gb|AAX38571.1| NahK [Pseudomonas putida]
MNRTLNREQVLALAEHIENAELQAHDIHKVTNDYPEMTFADAYDIQWEIRRRKEARGNKIVGLKMG
LTSWAKMAQMGVETPIYGFLADYFSVPDGGVVDCSKLIHPKIEAEISVVTKAPLQGPGCHIGDVIAA
VDYVIPTVEVIDSRYENFKFDLISVVADNASSTRFITGGQMANLEDVDLRTLGVVMEKNGEVVELGA
GAAVLGHPLSSVAMLANLLAERGEHIPAGTFIMTGGITAAVSVEPGDNITVRYQGLGSVSARFI (SEQ ID NO:26)

>gi|295695615|ref|YP_003588853.1| 4-oxalocrotonate decarboxylase [Bacillus tusciae DSM 2912]
MDLESLARRVSEHQRKGLAMKKLTLEYPELTVEQAYRIQALSVERSVAEGDRFVGWKMGLTSRA
KQVSVGVDEPIYGRLLASMELRESLLSVGGLVHPRVEPELAFVLKEGLHGESVTPREVWRATECV
VPALEVIDSRYENFSFTLVDVVADNASSARFYLGEQGFSPYGARWDEVGVVMRKNGEVVQTGAG
AAVLGHPVRSVMMLTRMLAREGLGLEPGMVVLTGGITEAVPVQPGDAVEVSYEGLGSLELRVGR (SEQ ID NO:27)

>gi|228914693|ref|ZP_04078302.1| 4-oxalocrotonate decarboxylase [Bacillus thuringiensis serovar pulsiensis BGSC 4CC1]
MALVKGADLEIIDYLLQAEKERKEVVKVTDKHPDLTVEDAYKLQKRLIEQ
KMSEGSKRVGVKLGLTSKAKQQMMGIDEAIYGYLLHDMLAFEWEPLQYETLIHPKVEPEIAFLIGED
LQGTN
VTADDVLKATKYVAPALEVIDSRYLNFKFTLPDVIADNCSSSKFLLGSKWIDVKNIDLANVGMVMSK
NG
KIATTGTGAAVLGHPAEAIAWAVNKLGLQNEGLKKGDIVLSGALSEAIAFKSGDSIIAQFDDLGSVA
MFCE (SEQ ID NO:28)

*FIG. 2D*

Q04416.1
Arthrobacter sp.
MHRTSNGSHATGGNLPDVASHYPVAYEQTLDGTVGFVIDEMTPERATASVEVTD
TLRQRWGLVHGGAYCA
LAEMLATEATVAVVHEKGMMAVGQSNHTSFFRPVKEGHVRAEAVRIHAGSTTW
FWDVSLRDDAGRLCAVS
SMSIAVRPRRD (SEQ ID NO:29)

NP_060943.1
Homo sapiens
MTSMTQSLREVIKAMTKARNFERVLGKITLVSAAPGKVICEMKVEEEHTNAIGTL
HGGLTATLVDNISTM
ALLCTERGAPGVSVDMNITYMSPAKLGEDIVITAHVLKQGKTLAFTSVDLTNKATG
KLIAQGRHTKHLGN (SEQ ID NO:30)

YP_248534.1
Haemophilus influenzae
MSANFTDKNGRQSKGVLLLRTLAMPSDTNANGDIFGGWIMSQMDMGGAILAKEI
AHGRVVTVAVESMNFI
KPISVGDVVCCYGQCLKVGRSSIKIKVEVWVKKVASEPIGERYCVTDAVFTFVAV
DNNGRSRTIPRENNQ
ELEKALALISEQPL (SEQ ID NO:31)

*FIG. 3*

(R/S) 3-HB-CoA → crotonyl-CoA:
Enoyl-CoA dehydratase

Example 1
Clostridium acetobutylicum
NP_349318.1
MELNNVILEKEGKVAVVTINRPKALNALNSDTLKEMDYVIGEIENDSEVLAVILTGAGEKSF
VAGADISEMKEMNTIEGRKFGILGNKVFRRLELLEKPVIAAVNGFALGGGCEIAMSCDIRIA
SSNARFGQPEVGLGITPGFGGTQRLSRLVGMGMAKQLIFTAQNIKADEALRIGLVNKVVE
PSELMNTAKEIANKIVSNAPVAVKLSKQAINRGMQCDIDTALAFESEAFGECFSTEDQKDA
MTAFIEKRKIEGFKNR (SEQ ID NO:32)

Example 2
Clostridium pasteurianum
NP_561011.1
MENIIFNESNGIAEVIINRPKALNALNNQTITELGEVINEISKRKDIKTVIITGAGEKAF
VAGADIVEMKDLNSMEARDFSRLAQKVFSDIENMPQIVIAAVNGYALGGGCELSMACDIR
LASKKAKFGQPEVNLGILPGFAGTQRLPRLVGKGIAKELIFSTDMIDAEEAHRIGLANKV
YEPEELMDKARELANKIMSKSPVGVRLAKAAINNGLNMDTESAYNYEADLFALCFSTEDQ
LEGMNAFVDKRKADFKDK (SEQ ID NO:33)

Example 3
Streptococcus mitis
ZP_07461826.1
MSKTVLLEVKNGLGYLTINRPSALNALSSEVLKDLNLALDQIEASEDIRVVIVTGQGEKA
FVAGADIKEMDQMSPIQAHEYMTYANDTFTRLSELTQPTISVLNGYALGGGLELALSTDI
RIGYDKTMVGFPEVGLGIIPGFAGTQRMSRLIGTSKTKELIFTARMVKGQEAYDLGILNK
LVAAEELLPAAEELAAAIMKNAPLAVEKAKHIIQVGSELPLKNAIRLETEAEALLFSTED
KVEGMRAFVEKRKAVFQRK (SEQ ID NO:34)

Example 4
Bordetella pertussis
NP_882209.1
MARADDIEVRVADQVAWVTINRPQRMNALARATFAQLVEVSLELDQDPGVKVVVYTGAG
E
RAFSAGVDLKELDAAGRMTHPMGGLARNLNEVVLEMATPTIAAINGVAAGGGCELALAC
D
IRVAASTARIGLPEARVGMGANFGSVVLPQLIPRGVALELLYTGELIDMALAHRLGLVNH
VFEPAELMAQTAGLARRIADNAPLSVQRMKAMAFKSIGLPTAAALRLSVGPDPYNSEDRL
EGARAFVEKRKPRFQGR (SEQ ID NO:35)

Example 5
Rhodococcus equi
YP_004004909.1
MRTPDGPGRIQTAIDRHVAVITIDHLRRYNALTGAMLDGLTATLDRLADDPAVSVVLVTG
AGPHFCAGMDIRELRSARESGIRMEDRVTDAEEALAAFPKPTIAAISGYCIGGGAQLALA
CDIRVAAENAEFAVTPAKLGVIYPARTITRLVRTLGPATTKRLVITGDRIDADTALRVGL
VTEVVPADRLRAHAMALSKSITTRSLVSQRAAKQMIDAAAGPGIDRELEHRWAHTPNPDL
EIGLDAFLSGTPPRFEGMSS (SEQ ID NO:36)

*FIG. 4A*

Example 6
Acinetobacter haemolyticus ATCC 19194
ZP_06727774.1
MSYQFLQLEQHDQVAYVWLNRPELHNAFNTTVIEELHTCFKQLATSDDIRVVVLAGRGKS
FSAGADLNWMKQAGQASSAENEADALKLAQMLEALATLKQPTIARVHGIAFGGGMGLAS
A
CDICIASTDAKFATSEVRLGLAPSTISPYVIRAIGARQASRYFLTAERISAHEAKQIGLA
HEIADAEDLDKKVQEIIDALLLGGPHAQAASKQLIQMVSNQSMNDELLRQTAQHIAQVRQ
GSEAKEGLTAFLSKQAPAWTSNSNNNN (SEQ ID NO:37)

Example 7
Rhodococcus erythropolis SK121
YP_002765811.1
MAEFVTLEVSEGIGTIRLARPPMNALNRQVQDELAAAAHAATVDKAVKAVIVYGGEKVFA
AGADVKEMAEMDYGQIRDAIGGMQAGLGAVASIPKPTVAAITGYALGGGLEVALSADRRI
VGDNAKLGVPEILLGIIPGGGGTQRLARLIGPAKAKDLVFTGRFVGADEALAIGLVDEVV
APDDVYTAARTWASQFVGGASRALAAAKAAIDEGLNTDLESGLKIEQHLFAGLFATKDQA
IGMESFIANGPGKAEFTGE (SEQ ID NO:38)

Example 8
Corynebacterium efficiens YS-314
NP_737284.1
MTTSMTSDTTTTALNGDFNALTLTETDTYLLVEITRPEVRNAIDETMVSELHEVCSYLEL
NPKILIITGCEANGKGIFVSGADIGQMRDRRRDDALRGINNMLFHRIAQLPAPVIAAVDG
YALGGGMELALAADFRLATPGAKFGQPEAGLGIIAAAGGLWRLKALIGEAVAKEILLAGK
ILDGNEALAVHLVTEVHKPAELLDAALALAGRIAKLDPLAVRISKQVMAMPAGAHPQVDN
IAQAILFESEAKFDRMQAFLDRKKNK (SEQ ID NO:39)

Example 9
Mycobacterium parascrofulaceum ATCC BAA-614
ZP_06851895.1
MSMTFETILLEVDETDRVATITLNRPGQLNAFNRTMCEEMARAWRIVKHDASVNAVVLRA
AGDRAFSAGLDIKTPYGQPENIWNHDDPGEALSPKWQKMWKPVVCAVQGMCTAGAFYF
VN
ESDVVICSQDATFFDSHVSAGLVCALEPIGLMRRVGLGETLRIALMGNDERVCADTALRI
GLVSEVVPAQQLWNRAHEIAATIAAKPTTATQGTVKAIWESLDKPYRAAMEQGLIYTRLG
NPLGVAELAARTDPGGEAAPRTPKIR (SEQ ID NO:40)

Example 10
halophilic archaeon DL31
YP_004807167.1
MQHGPFRHIHLDREDGVVSITIDRPEKHNALNDGAMLDLSRAFAEIEFDRSVDAVVIEGA
GDEAFSAGADIEQYAGPSEDHDPMQKERQDRFYEVYREPFECHAPVIAKIDGFCVGGGLI
FAMYCDLRIASEGSQFGVPTANIGQVPTGGATRRAVELVGEATAKELVFTAGYVDAETAT
DAGLVNDVVPPEALDDRVASLIDAMGDAGREAVKNSKRAINAAVEAENPKTAREREADL
W
WEQFATAERRDLVDEFTDR (SEQ ID NO:41)

*FIG. 4B*

Example 11
Bacillus cereus 03BB108
YP_895444.1
MESNRVVTWSKENGIATIIIDNPPMNVLGSAVVEQLTVAVDTIERDDEVIVVLLTGAGEK
TFVAGGDIKSFPEWIGKGSEYAEEKSLWLQNPLNKIERLPKPVIAAINGLALGGGCELAL
SCDIRIIEEHGQIGLPEVKLGLFPGAGGTQRLPRLIGTASAKEMMFTGEPLTAEAAWRVG
LVNHIVPRGESLNKAKELAAKMARFSLPALSLMKQSIDKGLSSSLEEGLKIEAENFGHIF
QTSDVREGVEAFIEKRAPFFHHK (SEQ ID NO:42)

Example 12
ZP_02950731.1
Clostridium butyricum 5521
MELENVILEKEGHLAIVTINRPKALNALNSATLKDLDTVLEDLENDTNIYAVILTGAGEK
SFVAGADIAEMKDLNEAQGKEFGELGNKVFLRLENLNKPVIAAIQGFALGGGCEISMACD
IRIASETALFGQPEVGLGITPGFGGTQRLARIVGLGKAKEMIYTARNIKADEAYRIGLVN
KVVALEDLMNEAKKMASNIIANAPVAVKLCKDAINRGMQVGIDEAVMIEAEDFGKCFATE
DQTEGMTAFLERRKEKNFQNK (SEQ ID NO:43)

Example 13
ZP_04931253.1
Pseudomonas aeruginosa NCMG1179
MSQVLTTYETPVLPEWVDYNGHLRDAFYLLVFSYATDALMAHIGLDSQNRDASGHSLFT
L
ECHLNFLHEVKEGARVEVRTQLLGHDRKRLHIHHALYLPGSGQALALSEQMLLHVSLDG
P
RSVPFEGEVLARVEALAEAHRALPVPEGVGRVIGLPPVR (SEQ ID NO:44)

Example 14
CBK78809.1
Clostridium saccharolyticum
MGYVDYEQEGFVGIVTINRPKALNALNEEVLKDLEAAFDSIDQNTVRAVILTGAGEKSFV
AGADIAAMSTMTKEQGEAFGKYGNDIFRKIETFPIPVIAAVNGFALGGGNELAMSCDIRI
CSENAVFGQPEVGLGITPGFGGTQRLARLIGVGKAKEMLYTARNIKADEAYRLGFVNAVY
PQEELMPAAKKMAGIIAANAPIAVRNSKKAANDGLQTDMDQAIVIEEKLFGACFETEDQK
EGMAAFLEKRKEKQFKNR (SEQ ID NO:45)

Example 15
YP_004680860.1
Cupriavidus necator N-1
METIRFAVEDGVATLTLDSPARKNALSLPMRDEIGEVIRRVRADDSVRALILTAAGTDFS
SGGDISSMQVEINAEQGRKRLHKVHGWLEDLIQLDVPVIAAVDGAAYGAGFSLALTADII
LATPRARFGLPFLRMGLIPDCGVLYTLPRMIGLQRAKALMFSMRELNAQAAQDLGIVMEI
VPADSLQERARALAQAFTEASPVAVGLTKQALNASLNQDLHTMLAMEADGQGIAFSTAY
R
REAAADRFMAKQPLRYRWPD (SEQ ID NO:46)

*FIG. 4C*

R-specific enoyl-CoA dehydratase

Example 1
O32472.1; Aeromonas punctata
MSAQSLEVGQKARLSKRFGAAEVAAFAALSEDFNPLHLDPAFAATTAFERPIVHGMLLAS
LFSGLLGQQLPGKGSIYLGQSLSFKLPVFVGDEVTAEVEVTALREDKPIATLTTRIFTQG
GALAVTGEAVVKLP (SEQ ID NO:47)

Example 2
NP_032318.2; Mus musculus
MASPLRFDGRVVLVTGAGGGLGRAYALAFAERGALVIVNDLGGDFKGIGKGSSAADKVVA
EIRRKGGKAVANYDSVEAGEKLVKTALDTFGRIDVVVNNAGILRDRSFSRISDEDWDIIH
RVHLRGSFQVTRAAWDHMKKQNYGRILMTSSASGIYGNFGQANYSAAKLGILGLCNTLAI
EGRKNNIHCNTIAPNAGSRMTETVLPEDLVEALKPEYVAPLVLWLCHESCEENGGLFEVG
AGWIGKLRWERTLGAIVRKRNQPMTPEAVRDNWEKICDFSNASKPQTIQESTGGIVEVLH
KVDSEGISPNRTSHAAPAATSGFVGAVGHKLPSFSSSYTELQSIMYALGVGASVKNPKDL
KFVYEGSADFSCLPTFGVIVAQKSMMNGGLAEVPGLSFNFAKALHGEQYLELYKPLPRSG
ELKCEAVIADILDKGSGVVIVMDVYSYSGKELICYNQFSVFVVGSGGFGGKRTSEKLKAA
VAVPNRPPDAVLRDATSLNQAALYRLSGDWNPLHIDPDFASVAGFEKPILHGLCTFGFSA
RHVLQQFADNDVSRFKAIKVRFAKPVYPGQTLQTEMWKEGNRIHFQTKVHETGDVVISNA
YVDLVPASGVSTQTPSEGGELQSALVFGEIGRRLKSVGREVVKKANAVFEWHITKGGTVA
AKWTIDLKSGSGEVYQGPAKGSADVTIIISDEDFMEVVFGKLDPQKAFFSGRLKARGNIM
LSQKLQMILKDYAKL (SEQ ID NO:48)

Example 3
XP_642412.1; Dictyostelium discoideum
MTVDVKKVINHKIKPIEYNLTRKDVALYAISLGCGKKHLKFVYEGSDNFSALPTLGVIFP
GQMIVDVISEGIDGIEFDPMMLLHGEQELEILNEIPVEGVFVTESKITNLYDKGKGALLI
LQCITSEKSSGKPIFKNIFSFFIRGIGGFGGDRGPNEKPIQIPKDRAPDAISKQATSEDQ
AVIYRLAGGDLNPLHIDPEMSKIGGFEVPILHGLCTYGIASRGVLEHFCDNDPSRLKSIK
TRFTKHVYPGETIETEMWKINPTTILFQSKTNRDGSYVLSSGVAIIEPIKKGSL (SEQ ID NO:49)

Example 4
NP_000405.1; Homo sapiens
MGSPLRFDGRVVLVTGAGAGLGRAYALAFAERGALVVVNDLGGDFKGVGKGSLAADKVV
E
EIRRRGGKAVANYDSVEEGEKVVKTALDAFGRIDVVVNNAGILRDRSFARISDEDWDIIH
RVHLRGSFQVTRAAWEHMKKQKYGRIIMTSSASGIYGNFGQANYSAAKLGLLGLANSLAI
EGRKSNIHCNTIAPNAGSRMTQTVMPEDLVEALKPEYVAPLVLWLCHESCEENGGLFEVG
AGWIGKLRWERTLGAIVRQKNHPMTPEAVKANWKKICDFENASKPQSIQESTGSIIEVLS
KIDSEGGVSANHTSRATSTATSGFAGAIGQKLPPFSYAYTELEAIMYALGVGASIKDPKD
LKFIYEGSSDFSCLPTFGVIIGQKSMMGGGLAEIPGLSINFAKVLHGEQYLELYKPLPRA
GKLKCEAVVADVLDKGSGVVIIMDVYSYSEKELICHNQFSLFLVGSGGFGGKRTSDKVKV
AVAIPNRPPDAVLTDTTSLNQAALYRLSGDWNPLHIDPNFASLAGFDKPILHGLCTFGFS
ARRVLQQFADNDVSRFKAIKARFAKPVYPGQTLQTEMWKEGNRIHFQTKVQETGDIVISN
AYVDLAPTSGTSAKTPSEGGKLQSTFVFEEIGRRLKDIGPEVVKKVNAVFEWHITKGGNI
GAKWTIDLKSGSGKVYQGPAKGAADTTIILSDEDFMEVVLGKLDPQKAFFSGRLKARGNI
MLSQKLQMILKDYAKL (SEQ ID NO:50)

*FIG. 4D*

Example 5
P22414.2
Candida tropicalis
MSPVDFKDKVVIITGAGGGLGKYYSLEFAKLGAKVVVNDLGGALNGQGGNSKAADVVVDE
IVKNGGVAVADYNNVLDGDKIVETAVKNFGTVHVIINNAGILRDASMKKMTEKDYKLVID
VHLNGAFAVTKAAWPYFQKQKYGRIVNTSSPAGLYGNFGQANYASAKSALLGFAETLAKE
GAKYNIKANAIAPLARSRMTESILPPPMLEKLGPEKVAPLVLYLSSAENELTGQFFEVAA
GFYAQIRWERSGGVLFKPDQSFTAEVVAKRFSEILDYDDSRKPEYLKNQYPFMLNDYATL
TNEARKLPANDASGAPTVSLKDKVVLITGAGAGLGKEYAKWFAKYGAKVVVNDFKDATKT
VDEIKAAGGEAWPDQHDVAKDSEAIIKNVIDKYGTIDILVNNAGILRDRSFAKMSKQEWD
SVQQVHLIGTFNLSRLAWPYFVEKQFGRIINITSTSGIYGNFGQANYSSSKAGILGLSKT
MAIEGAKNNIKVNIVAPHAETAMTLTIFREQDKNLYHADQVAPLLVYLGTDDVPVTGETF
EIGGGWIGNTRWQRAKGAVSHDEHTTVEFIKEHLNEITDFTTDTENPKSTTESSMAILSA
VGGDDDDDDEDEEEDEGDEEEDEEDEEEDDPVWRFDDRDVILYNIALGATTKQLKYVYE
N
DSDFQVIPTFGHLITFNSGKSQNSFAKLLRNFNPMLLLHGEHYLKVHSWPPPTEGEIKTT
FEPIATTPKGTNVVIVHGSKSVDNKSGELIYSNEATYFIRNCQADNKVYADRPAFATNQF
LAPKRAPDYQVDVPVSEDLAALYRLSGDRNPLHIDPNFAKGAKFPKPILHGMCTYGLSAK
ALIDKFGMFNEIKARFTGIVFPGETLRVLAWKESDDTIVFQTHVVDRGTIAINNAAIKLV
GDKAKI (SEQ ID NO:51)

Example 6
NP_077368.2
Rattus norvegicus
MASPLRFDGRVVLVTGAGGGLGRAYALAFAERGALVVVNDLGGDFKGVGKGSSAADKVV
E
EIRRRGGKAVANYDSVEAGEKLVKTALDTFGRIDVVVNNAGILRDRSFSRISDEDWDIIQ
RVHLRGSFQVTRAAWDHMKKQNYGRIIMTASASGIYGNFGQANYSAAKLGLLGLANTLVI
EGRKNNIHCNTIAPNAGSRMTETVMPEDLVEALKPEYVAPLVLWLCHESCEENGGLFEVG
AGWIGKLRWERTLGAIVRKRNQPMTPEAVRDNWVKICDFSNASKPKSIQESTGGIIEVLH
KIDSEGISQNHTGQVASADASGFAGVVGHKLPSFSSSYTELQCIMYALGVGASVKNPKDL
KFVYEGSADFSCLPTFGVIVAQKSLMSGGLAEVPGLSINFAKVLHGEQYLELYKPLPRSG
ELKCEAVIADILDKGSGIVIVMDVYSYSGKELICYNQFSVFVVGSGGFGGKRTSEKLKAA
VAVPSRPPDAVLRDTTSLNQAALYRLSGDSNPLHIDPSFASIAGFEKPILHGLCTFGFSA
RHVLQQFADNDVSRFKAIKVRFAKPVYPGQTLQTEMWKEGNRIHFQTKVQETGDIVISNA
YVDLVPTSGVSAQTPSEGGALQSALVFGEIGRRLKDVGREVVKKVNAVFEWHITKNGNVA
AKWTIDLKNGSGEVYQGPAKGSADTTITISDEDFMEVVLGKLNPQNAFFSGRLKARGNIM
LSQKLQMILKDYAKL (SEQ ID NO:52)

Example 7
NP_177742.2
Arabidopsis thaliana
MATSDSEFNSDLLLAHKLPETRYTYNERDVAIYALGIGACGQDAVDSDELKFVYHRNGQD
LIQVLPTFASLFTLGSLTEGLDLPGFKYDPSLLLHGQQYIEIYRPLPSKASLINKVSLAG
LQDKGKAAILELETRSYEEGSGELLCMNRTTVFLRGAGGFSNSSQPFSYKNYPSNQGLAV
KIPQRQPLTVCEERTQPSQALLYRLSGDYNPLHSDPEFAKLAGFPRPILHGLCTLGFAIK
AIIKCVCKGDPTAVKTISGRFLTTVFPGETLITEMWLEGLRVIYQTKVKERNKTVLAGYV
DIRGLSSSL (SEQ ID NO:53)

*FIG. 4E*

| Key: | ID | geneid | Mol. Weight | Species |
|---|---|---|---|---|
| | E2 | 77843 | 27.9568 | Shewanella woodyi ATCC 51908 |
| | F2 | 77844 | 28.13915 | Cupriavidus necator N-1 |
| | G2 | 77845 | 27.51466 | Acidovorax sp. JS42 |
| | H2 | 77846 | 28.54487 | Azoarcus sp. BH72 |
| | A3 | 77847 | 27.67969 | Novosphingobium nitrogenifigens DSM 19370 |
| | B3 | 77848 | 28.41954 | Methylibium petroleiphilum PM1 |
| | C3 | 77849 | 28.91509 | uncultured bacterium |
| | D3 | 77850 | 28.12759 | Paenibacillus sp. JJ-1b |
| | E3 | 77851 | 28.20759 | Geobacillus sp. C56-T3 |
| | F3 | 77852 | 28.41669 | Bacillus licheniformis ATCC 14580 |
| | G3 | 77853 | 28.91022 | Brevibacillus brevis NBRC 100599 |
| | H3 | 77854 | 28.32947 | Geobacillus thermodenitrificans NG80-2 |

# PROPYLENE SYNTHESIS USING ENGINEERED ENZYMES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200206_403USPC_SEQUENCE_LISTING. The text file is 364 KB, was created on Mar 15, 2015 and is being submitted electronically via EFS-Web.

BACKGROUND

Propylene is primarily produced as a by-product of petroleum refining and of ethylene production using a steam cracking process. Propylene is separated from a mixture of hydrocarbons obtained from cracking or other refining processes by fractional distillation. Propylene is typically produced from non-renewable fossil fuels, petroleum, natural gas, and to a lesser extent coal. Propylene can also be produced in on-purpose reactions, such as propane dehydrogenation, metathesis or syngas-to-olefins plants.

Propylene is a major industrial chemical intermediate that is converted into a variety of chemicals and plastics. Manufacturers of polypropylene account for nearly two thirds of worldwide propylene demand. Polypropylene is a plastic that is used for the manufacture of films, packaging, caps, closures, and individual parts for the electrical and automotive industry. Propylene is also used to produce chemicals including acrylonitrile, oxo chemicals, propylene oxide, cumene, isopropanol, acrylic acid, butanol, and butanediol.

Currently, refinery by-product production of propylene can no longer satisfy market demand. There is a need for alternative processes for on-purpose propylene production, particularly a green process that exhibits increased safety, decreased harmful waste and emissions, and savings in cost and energy compared to petrochemically-derived propylene.

SUMMARY OF INVENTION

In one aspect, the present disclosure provides non-naturally occurring C1 metabolizing organisms, wherein the non-naturally occurring C1 metabolizing organisms convert a C1 substrate to propylene. In certain embodiments, the C1 metabolizing organism is: a non-naturally occurring C1 metabolizing bacterium; a non-naturally occurring obligate C1 metabolizing organism; a non-naturally occurring C1 metabolizing organism, wherein the non-naturally occurring C1 metabolizing organism does not include *Pichia pastoris*; a non-naturally occurring methanotrophic or methylotrophic bacterium; a non-naturally occurring syngas utilizing bacterium that naturally possesses the ability to utilize syngas; or a non-naturally occurring CO utilizing bacterium, wherein the non-naturally occurring CO utilizing bacterium naturally possesses the ability to utilize CO. In certain aspects, the non-naturally occurring C1 metabolizing organisms include an exogenous nucleic acid encoding an enzyme capable of decarboxylating crotonic acid (e.g., 4-oxalocrotonate decarboxylase). In further aspects, the non-naturally occurring C1 metabolizing organisms do not have a functional PHB synthase or a substantial amount of functional PHB synthase.

In another aspect, non-naturally occurring C1 metabolizing organisms include an exogenous nucleic acid encoding a crotonyl CoA thioesterase. The non-naturally occurring C1 metabolizing organism may be a non-naturally occurring C1 metabolizing bacterium; a non-naturally occurring obligate C1 metabolizing organism; a non-naturally occurring C1 metabolizing organism, wherein the C1 metabolizing organism does not include *Pichia pastoris*; a non-naturally occurring methanotrophic or methylotrophic bacterium; a non-naturally occurring syngas utilizing bacterium that naturally possesses the ability to utilize syngas; or a non-naturally occurring CO utilizing bacterium, wherein the non-naturally occurring CO utilizing bacterium naturally possesses the ability to utilize CO.

In yet another aspect, non-naturally occurring C1 metabolizing organisms include an exogenous nucleic acid encoding a crotonase. In certain embodiments, the non-naturally occurring C1 metabolizing organism is: a non-naturally occurring C1 metabolizing bacterium; a non-naturally occurring obligate C1 metabolizing organism; a non-naturally occurring C1 metabolizing organism, wherein the organism does not include *Pichia pastoris*; a non-naturally occurring methanotrophic or methylotrophic bacterium; a non-naturally occurring syngas utilizing bacterium that naturally possesses the ability to utilize syngas; or a non-naturally occurring CO utilizing bacterium, wherein the CO utilizing bacterium naturally possesses the ability to utilize CO.

In another aspect, the present disclosure provides non-naturally occurring microbial organisms, wherein the non-naturally occurring microbial organisms include an exogenous nucleic acid encoding 4-oxalocrotonate decarboxylase, and wherein the non-naturally occurring microbial organisms convert a carbon substrate to propylene. In certain embodiments, the non-naturally occurring microbial organisms further include an exogenous nucleic acid encoding crotonase, or an exogenous nucleic acid encoding crotonase and an exogenous nucleic acid encoding crotonyl thioesterase. In certain embodiments, the non-naturally occurring microbial organisms do not have a functional PHB synthase or a substantial amount of functional PHB synthase.

Also disclosed herein are methods of producing propylene in non-naturally occurring organisms described herein, wherein the methods comprise culturing the non-naturally occurring organisms under conditions sufficient to produce propylene.

BRIEF DESCRIPTION OF THE DRAWINGS

FIGS. 2A-D show exemplary 4-oxalocrotonate decarboxylase (4-OD) amino acid sequences that may be used in propylene synthesis pathways as described herein.

FIG. 3 shows exemplary crotonyl-CoA thioesterase amino acid sequences that may be used in propylene synthesis pathways as described herein.

FIGS. 4A-E show exemplary crotonase amino acid sequences that may be used in propylene synthesis pathways as described herein.

DETAILED DESCRIPTION

Figure 1:
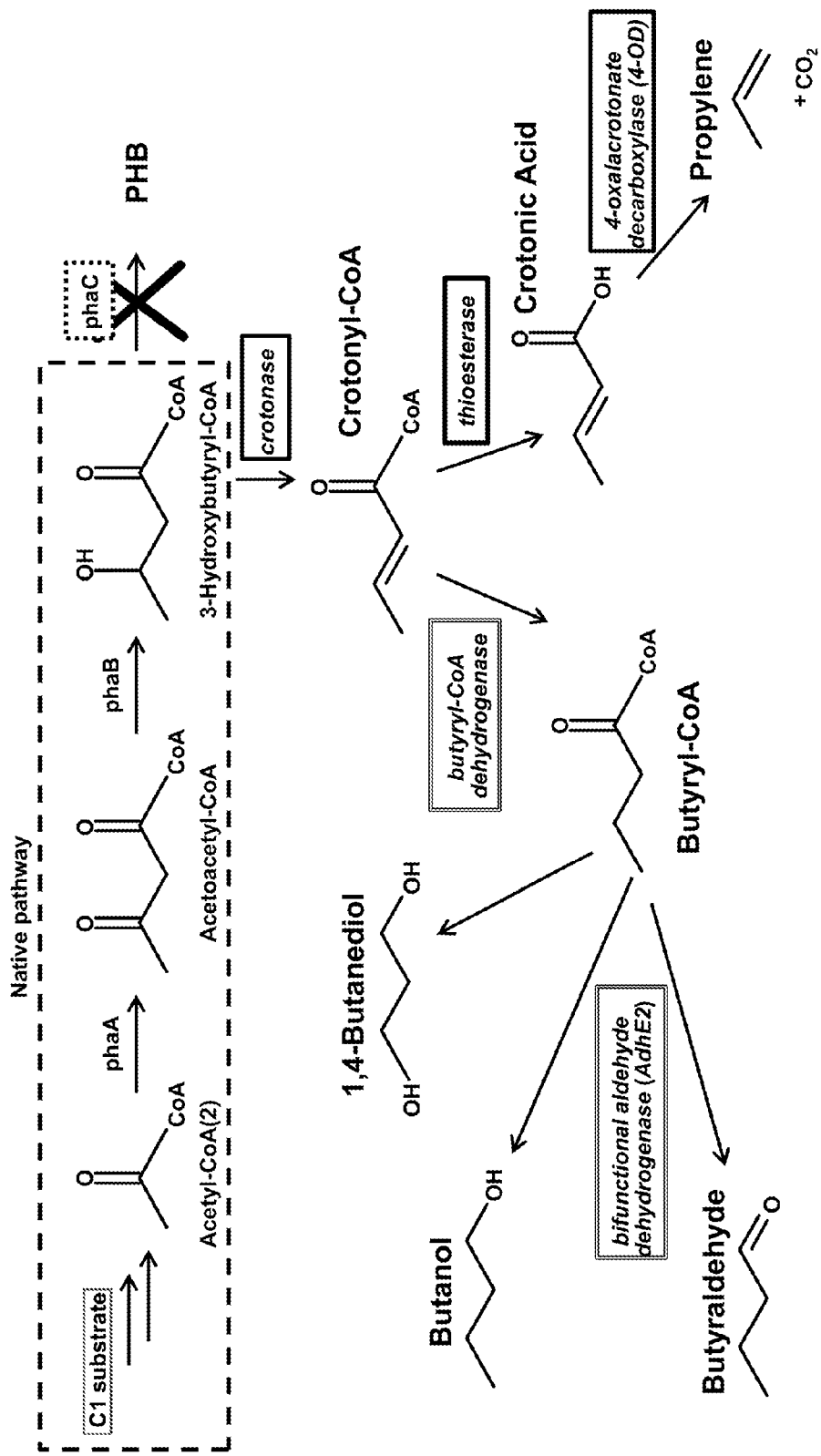
FIG. 1 shows an exemplary pathway for synthesis of propylene from acetyl CoA in a genetically modified organism. Enzymes and genes encoding enzymes for transformation of the identified substrates to products include: phaA, phaB, crotonase, crotonyl CoA thioesterase, and 4-oxalocrotonate decarboxylase.

The instant disclosure provides compositions and methods for the biocatalysis of propylene and other desirable intermediates or products from methane or other C1 substrates using genetically engineered C1 metabolizing organisms. The instant disclosure also provides compositions and methods for the biocatalysis of propylene from carbon substrates using novel metabolic enzyme(s) in genetically engineered microbial organisms.

Prior to setting forth this disclosure in more detail, it may be helpful to an understanding thereof to provide definitions of certain terms to be used herein. Additional definitions are set forth throughout this disclosure.

In the present description, the term "about" means ±20% of the indicated range, value, or structure, unless otherwise indicated. The term "consisting essentially of" limits the scope of a claim to the specified materials or steps and those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include" and "have" are used synonymously, which terms and variants thereof are intended to be construed as non-limiting. The term "comprise" means the presence of the stated features, integers, steps, or components as referred to in the claims, but that it does not preclude the presence or addition of one or more other features, integers, steps, components, or groups thereof.

As used herein, the term "non-naturally occurring" when used in reference to a bacterium or an organism means that the bacterium or organism has at least one genetic alternation that is not normally found in a naturally occurring strain of the referenced species, including wild-type strains of the referenced species. Genetic alterations include, for example, modifications introducing expressible nucleic acids encoding proteins or enzymes, other nucleic acid additions, nucleic acid deletions, nucleic acid substitutions, or other functional disruption of the bacterium or organism's genetic material. Such modifications include, for example, coding regions and functional fragments thereof for heterologous or homologous polypeptides for the referenced species. Additional modifications include, for example, non-coding regulatory regions in which the modifications alter expression of a gene or operon. Exemplary enzymes include enzymes within a crotonate synthesis pathway or propylene synthesis pathway. Genetic modifications to nucleic acid molecules encoding enzymes, or functional fragments thereof, can confer a biochemical reaction capability or a metabolic pathway capability to the non-naturally occurring organism that is altered from its naturally occurring state.

As used herein, the term "host" refers to a bacterium or organism that has not yet been genetically modified with the capability to convert a carbon substrate to crotonyl-CoA, crotonic acid, or propylene, as disclosed herein. A host C1 metabolizing bacterium or organism is selected for transformation with at least one exogenous nucleic acid encoding an enzyme to yield a non-naturally occurring C1 metabolizing bacterium or organism with the capability to convert a C1 substrate to crotonyl-CoA, crotonic acid, or propylene. A host microbial organism is selected for transformation with at least one exogenous nucleic acid encoding 4-oxalocrotonate decarboxylase to yield a non-naturally occurring microbial organism with the capability to convert a carbon substrate to propylene. A host bacterium or organism may already possess other genetic modifications conferring it with desired properties, unrelated to propylene synthesis pathways and intermediates disclosed herein. For example, a host bacterium or organism may possess genetic modifications conferring high growth, tolerance of contaminants or particular culture conditions, or ability to metabolize different carbon substrates.

As used herein, the term "microbial organism," "microorganism", "microbes", or "organism" refers to any prokaryotic or eukaryotic microbial species from the domains of Archaea, Bacteria, or Eukarya. The term is intended to include prokaryotic or eukaryotic cells or organisms having microscopic size.

As used herein, the term "C1 metabolizing bacterium" refers to any bacterium that has the ability to oxidize a C1 compound (i.e., does not contain carbon-carbon bonds). A C1 metabolizing bacterium may or may not use other carbon substrates, such as sugars and complex carbohydrates, for energy and biomass.

As used herein, the term "obligate C1 metabolizing organism" refers to those organisms which exclusively use organic compounds that do not contain carbon-carbon bonds (C1 substrate) for the generation of energy.

As used herein, the term "C1 metabolizing organism" refers to any organism that has the ability to oxidize a C1 substrate (i.e., does not contain carbon-carbon bonds) but may or may not use other carbon substrates, such as sugars and complex carbohydrates, for energy and biomass. A C1 metabolizing organism includes bacteria, yeast (not including *Pichia pastoris*), and Archaea. A C1 metabolizing organism includes C1 metabolizing bacteria.

As used herein, the term "methanotrophic bacterium" refers to any methylotrophic bacterium that has the ability to oxidize methane as its primary carbon and energy source.

As used herein, the term "methylotrophic bacterium" refers to any bacterium capable of oxidizing organic compounds that do not contain carbon-carbon bonds. An "obligate methylotrophic bacterium" is a bacterium which is limited to the use of carbon substrates that do not contain carbon-carbon bonds for the generation of energy. Facultative methylotrophs are able to utilize multi-carbon compounds in addition to single carbon substrates.

As used herein, the term "CO utilizing bacterium" refers to a bacterium that naturally possesses the ability to oxidize carbon monoxide (CO) as a source of carbon and energy. Carbon monoxide may be utilized from "synthesis gas" or "syngas", a mixture of carbon monoxide and hydrogen produced by gasification of any organic feedstock, including but not limited to coal, coal oil, natural gas, biomass, and waste organic matter. Syngas may also include $CO_2$, methane, and other gases in smaller quantities. CO utilizing bacterium does not include bacteria that must be genetically modified for growth on CO as its carbon source.

As used herein, the term "C1 substrate" or "C1 compound" refers to any carbon containing molecule or composition that lacks a carbon-carbon bond. C1 substrates include methane, methanol, formaldehyde, formic acid (formate), carbon monoxide, carbon dioxide, methylated amines (methylamine, dimethylamine, trimethylamine, etc.), methylated thiols, methyl halogens (bromomethane, chloromethane, iodomethane, dichloromethane, etc.), or cyanide.

As used herein, the term "propylene", also known as 1-propene, propene, or methylethylene, refers to an unsaturated organic compound having the chemical formula $C_3H_6$ and molecular mass of 42.08 g/mol. It has one double bond and is the second simplest member of the alkene class of hydrocarbons. Propylene is a gas at room temperature and atmospheric pressure. Propylene is a structural isomer of cyclopropane.

As used herein, "exogenous" means that the referenced molecule (e.g., nucleic acid) or referenced activity (e.g., enzyme activity) is introduced into the host bacterium or organism. The molecule can be introduced, for example, by introduction of a nucleic acid into the host genetic material such as by integration into a host chromosome or by introduction of a nucleic acid as non-chromosomal genetic material, such as on a plasmid. When the term is used in reference to expression of an encoding nucleic acid, it refers to introduction of the encoding nucleic acid in an expressible form into the bacterium or organism. When used in reference to an enzymatic activity, the term refers to an activity that is introduced into the host reference bacterium or organism. Therefore, the term "endogenous" or "native" refers to a referenced molecule or activity that is present in the host bacterium or organism. The term "heterologous" refers to a molecule or activity that is derived from a source other than the referenced species or strain whereas "homologous" refers to a molecule or activity derived from the host bacterium or organism. Accordingly, a bacterium or organism comprising an exogenous nucleic acid of the invention can utilize either or both a heterologous or homologous nucleic acid.

It is understood that when more than one exogenous nucleic acid is included in a bacterium or organism that the more than one exogenous nucleic acid refers to the referenced encoding nucleic acid or enzymatic activity, as discussed above. It is also understood, as disclosed herein, that such more than one exogenous nucleic acids can be introduced into the host bacterium or organism on separate nucleic acid molecules, on a polycistronic nucleic acid molecule, on a single nucleic acid molecule encoding a fusion protein, or a combination thereof, and still be considered as more than one exogenous nucleic acid. For example, as disclosed herein, an organism can be modified to express two or more exogenous nucleic acids encoding a desired pathway enzyme or protein (e.g., propylene pathway enzyme or protein). Where two exogenous nucleic acids encoding propylene synthesis activity are introduced into a host organism, it is understood that the two exogenous nucleic acids can be introduced as a single nucleic acid molecule, for example, on a single plasmid, on separate plasmids, can be integrated into the host chromosome at a single site or multiple sites, and still be considered two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids. Thus, the number of referenced exogenous nucleic acids or enzymatic activities refers to the number of encoding nucleic acids or the number of enzymatic activities, not the number of separate nucleic acid molecules introduced into the host organism.

As used herein, "nucleic acid" refers to a polymeric compound comprised of covalently linked subunits called nucleotides. Nucleic acids include polyribonucleic acid (RNA), polydeoxyribonucleic acid (DNA), both of which may be single or double stranded. DNA includes cDNA, genomic DNA, synthetic DNA, and semi-synthetic DNA.

As used herein, "crotonic acid" or "trans-2-butenoic acid" refers to a short-chain unsaturated carboxylic acid with the formula $CH_3CH=CHCO_2H$. As used herein, crotonic acid includes "crotonate", a salt or ester of crotonic acid.

As used herein, "4-oxalocrotonate" refers to an unsaturated carboxylic acid with the formula $HO_2C(C=O)CH_2CH=CHCO_2-$ (keto form) or $HO_2C(COH)=CHCH=CHCO_2-$ (enol form), which interconvert spontaneously. As used herein, 4-oxalocrotonate also includes salts or esters, the equivalent molecule with the alternate acid group deprotonated, the doubly unprotonated basic form of the molecule, or the doubly protonated acid form of the molecule.

As used herein, "4-oxalocrotonate decarboxylase" or "4-OD" or "4-oxalocrotonate carboxy-lase (2-oxopent-4-enoate-forming)" refers to an enzyme family that catalyzes the decarboxylation of 4-oxalocrotonate to 2-oxopent-4-enoate and $CO_2$. 4-OD is involved in the meta-cleavage pathway for the degradation of phenols, modified phenols, and catechols. As disclosed herein, 4-OD is used to catalyze the decarboxylation of crotonic acid to propylene and $CO_2$. As used herein, 4-OD also encompasses mutants or variants of a native 4-OD enzyme that has reduced or eliminated decarboxylation activity on 4-oxalocrotonate, but retains or has increased decarboxylation activity on crotonic acid as a substrate. 4-OD also refers to any enzyme capable of catalyzing the decarboxylation of crotonic acid to propylene and $CO_2$.

As used herein, "crotonyl CoA thioesterase" refers to an enzyme that catalyzes the conversion of crotonyl-CoA to crotonic acid.

As used herein, "crotonase" or "3-hydroxybutyryl-CoA dehydratase" or "enoyl-CoA hydratase" refers to an enzyme involved in the butyrate/butanol-producing pathway, which catalyzes the dehydration of 3-hydroxybutyryl-CoA to crotonyl-CoA.

As used herein, "β-ketothiolase" refers to an enzyme in the PHB synthesis pathway that catalyzes the condensation of two acetyl-CoA molecules to acetoacetyl-CoA. Biosynthesis of PHB in most bacteria is initiated by β-ketothiolase.

As used herein, "acetoacetyl coenzyme A reductase" refers to an enzyme in the PHB synthesis pathway that catalyzes the reduction of acetoacetyl-CoA to 3-hydroxybutyryl-CoA.

As used herein, "PHB synthase", also known as "PHB polymerase", refers to an enzyme in the PHB synthesis pathway that converts a hydroxybutyryl-CoA monomer into polyhydroxybutyrate.

As used herein, "polyhydroxybutyrate" or "PHB" refers to a homopolymer of hydroxybutyric acid units. PHB is a type of polyhydroxyalkanoate (PHA), which is a biological polyester. Polyhydroxybutyrate is a crystalline thermoplastic synthesized by a broad range of bacteria as a form of energy storage molecule. Poly-3-hydroxybutyrate (P3HB) form is the most common type of PHB, but other PHBs include poly-4-hydroxybutyrate (P4HB), poly(3-hydroxybutyrate-co-4-hydroxybutyrate) (P3HB-co-4HB), or other copolymers.

C1 Metabolizing Bacteria or Organisms

A variety of C1 metabolizing host organisms can be transformed or genetically engineered to produce a product of interest (e.g., propylene, crotonic acid, or crotonyl-CoA).

In certain embodiments, a C1 metabolizing organism may be a C1 metabolizing bacterium, which refers to any bacterium that has the ability to oxidize a C1 compound. A C1 metabolizing bacterium may also use other carbon substrates, such as sugars and complex carbohydrates, for energy and biomass. A C1 metabolizing bacterium includes methanotrophic bacteria (methylotrophic bacterium that has the ability to oxidize methane as an energy source) or methylotrophic bacteria (any bacterium capable of oxidizing organic compounds that do not contain carbon-carbon bonds). Methanotrophic bacteria are classified into three groups based on their carbon assimilation pathways and internal membrane structure: type I (gamma proteobacteria), type II (alpha proteobacteria, and type X (gamma proteobacteria). Type I methanotrophs use the ribulose monophosphate (RuMP) pathway for carbon assimilation whereas type II methanotrophs use the serine pathway. Type X methanotrophs use the RuMP pathway but also express low levels of enzymes of the serine pathway. Methanotrophic bacteria are grouped into several genera: *Methylomonas, Methylobacter, Methylococcus, Methylocystis, Methylosinus, Methylomicrobium, Methanomonas,* and *Methylocella*. Exemplary methantrophic bacteria include: *Methylococcus capsulatus* Bath strain, *Methylomonas* 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylobacterium organophilum* (ATCC 27,886), *Methylomonas* sp AJ-3670 (FERM P-2400), *Methylocella silvestris, Methylocella palustris* (ATCC 700799), *Methylocella tundrae, Methylacidiphilum infernorum, Methylibium petroleiphilum,* and *Methylomicrobium alcaliphilum*. Methylotrophic bacteria encompass a diverse group, including both gram-negative and gram-positive genera. Methylotrophic bacteria include facultative methylotrophs (have the ability to oxidize organic compounds which do not contain carbon-carbon bonds, but may also utilize other carbon substrates such as sugars and complex carbohydrates), obligate methylotrophs (limited to the use of organic compounds that do not contain carbon-carbon bonds), and methanotrophic bacteria. Examples of methylotrophic genera include: *Methylophilus, Methylobacillus, Methylobacterium, Hyphomicrobium, Xanthobacter, Bacillus, Paracoccus, Nocardia, Arthrobacter, Rhodopseudomonas,* and *Pseudomonas*. Exemplary methylotrophic bacteria include: *Methylobacterium extorquens, Methylobacterium radiotolerans, Methylobacterium populi, Methylobacterium chloromethanicum, Methylobacterium nodulans, Methylomonas clara, Methylibium petroleiphilum, Methylobacillus flagellates, Silicibacter pomeroyi* DSS-3, *Burkholderia phymatum* STM815, *Granulibacter bethesdensis* NIH1.1, and *Paracoccus denitrificans*.

A C1 metabolizing bacterium includes bacteria that utilize formate or cyanide or naturally possesses the ability to utilize syngas or carbon monoxide (CO) (Wu et al., 2005 PLoS Genet. 1:e65; Abrini et al., 1994, Arch. Microbiol. 161:345; WO2008/028055; Tanner et al., 1993, Int. J. Syst. Bacteriol. 43:232-236). Exemplary bacteria that naturally possesses the ability to utilize CO or syngas include: *Clostridium autoethanogenum, Clostridium ljungdahli, Clostridium ragsdalei, Clostridium carboxydivorans, Butyribacterium methylotrophicum, Clostridium woodii,* and *Clostridium neopropanologen, Pseudomonas carboxidovorans, Rhodospirillum rubrum, Thermincola carboxydiphila, Thermincola potens, Thermoanaerobacter thermohydrosulfuricus, Ralstonia eutropha, Eurobacterium limosum*. A C1 metabolizing bacterium also includes bacteria that can cleave methyl groups from organic compounds including choline (de Vries et al., 1990, FEMS Microbiol. Rev. 6:57-101) or the pesticide carbofuran (Topp et al., 1993, Appl. Environ. Microbiol. 59:3339-3349) and utilize them as sole sources of carbon.

C1 metabolizing organisms include bacteria, yeast (not including *Pichia pastoris*), and Archaea. A C1 metabolizing organism may be obligate or facultative. Examples of C1 metabolizing organisms include: *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas, Pseudomonas, Candida, Yarrowia, Hansenula, Pichia* (not including *Pichia pastoris*), *Torulopsis,* and *Rhodotorula*. Additional examples of C1 (carbon monoxide) metabolizing organisms include: *Clostridium autoethanogenum, Clostridium ljungdahli, Clostridium ragsdalei, Clostridium carboxydivorans, Butyribacterium methylotrophicum, Clostridium Woodii,* and *Clostridium neopropanologen*.

A variety of C1 substrates may be used by the C1 metabolizing organisms. It is understood to one of skill in the art that selection of a C1 substrate may be determined by which host organism is selected. For example, obligate methanotrophic bacteria are limited to the use of methane as a carbon source, whereas some methylotrophic bacteria may use a variety of C1 compounds, such as methane, methanol, methylated amines, halomethanes, and methylated compounds containing sulfur (reviewed in Hanson and Hanson, 1996, Microbiological Rev. 60:439-471). Non-limiting examples of C1 substrates include: methane, methanol, formaldehyde, formic acid (formate), carbon monoxide, carbon dioxide, methylated amines (methylamine, dimethylamine, trimethylamine, etc.), methylated thiols, or methyl halogens (bromomethane, chloromethane, iodomethane, dichloromethane, etc.). Some facultative methanotrophs and facultative methylotrophs can also grow on multi-carbon compounds. A C1 metabolizing organism may also be adapted or genetically modified to use a different C1 substrate in addition to, or instead of its usual C1 substrate. Alternatively, a C1 metabolizing organism may be adapted or genetically modified to use a multi-carbon substrate in addition to its usual C1 substrate. A selected C1 metabolizing organism may also undergo strain adaptation under selective conditions to identify variants with improved properties for production. Improved properties may include increased growth rate, yield of desired products (e.g., propylene), and tolerance of likely process contaminants. In a particular embodiment, a high growth variant C1 metabolizing organism, which is an organism capable of growth on a C1 substrate as the sole carbon and energy source and which possesses an exponential phase growth rate that is faster (i.e., shorter doubling time) than its parent, reference, or wild-type organism, is selected ((see, e.g., U.S. Pat. No. 6,689,601).

Each of the organisms of this disclosure may be grown as an isolated culture, with a heterologous organism that may aid in growth, or one or more of C1 metabolizing bacteria may be combined to generate a mixed culture.

Microbial Organisms

A variety of microbial host organisms can be transformed or genetically engineered to include a novel metabolic pathway and associated enzymes as described herein to produce propylene from a carbon substrate. Exemplary bacteria include *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi species include *Saccharomyces cerevisiae, Schizosaccharomyces pombe, Kluyveromyces lactis, Kluyveromyces marxianus, Aspergillus terreus, Aspergillus niger, Rhizopus arrhizus, Rhizopus oryzae*, and *Yarrowia lipolytica*. It is understood that any suitable microbial host organism can be used to introduce suitable genetic modifications (e.g., nucleic acid encoding 4-OD) to produce propylene.

Non-Naturally Occurring Organisms

Non-naturally occurring organisms as described herein can be produced by introducing expressible nucleic acid(s) encoding one or more enzymes involved in a desired biosynthetic pathway (e.g., propylene synthesis). Depending on the host organism selected for biosynthesis, nucleic acid(s) for one, some, or all of a particular biosynthetic pathway can be expressed. For example, if a selected host is deficient in one or more enzymes for a desired biosynthetic pathway (e.g., propylene synthesis), then expressible nucleic acid(s) for the deficient enzyme(s) are introduced into the host for subsequent exogenous expression. Alternatively, if a selected host exhibits endogenous expression of some pathway genes, but is deficient in others, then an encoding nucleic acid is needed for the deficient enzyme(s) to achieve the desired biosynthesis. Thus, non-naturally occurring organisms of the invention can be produced by introduced exogenous enzyme activities to obtain a desired biosynthetic pathway or a desired biosynthetic pathway can be obtained by introducing one or more exogenous enzyme activities that, together with one or more endogenous enzymes, produces the desired product, such as propylene. In some embodiments, non-naturally occurring organisms as described herein can also include other genetic modifications that facilitate or optimize a desired biosynthetic pathway or that confer other useful functions onto the host. For example, if a selected host exhibits endogenous expression of an enzyme that inhibits propylene biosynthetic pathway, then the host may be genetically modified so that it does not produce a functional enzyme or a substantial amount of a functional enzyme.

In certain embodiments, the present disclosure provides a non-naturally occurring C1 metabolizing bacterium; a non-naturally occurring obligate C1 metabolizing organism; a non-naturally occurring C1 metabolizing organism, wherein the non-naturally occurring C1 metabolizing organism does not include *Pichia pastoris*; a non-naturally occurring methanotrophic or methylotrophic bacterium; or a non-naturally occurring CO utilizing bacterium, wherein the non-naturally occurring CO utilizing bacterium naturally possesses the ability to utilize CO, wherein the non-naturally occurring C1 metabolizing bacterium or organism converts a C1 substrate to propylene.

In certain embodiments, the present disclosure provides a non-naturally occurring C1 metabolizing organism that is not *Pichia pastoris* and is capable of converting a C1 substrate into propylene. In certain embodiments, the non-naturally occurring C1 metabolizing organism is not *Pichia pastoris* and is a C1 metabolizing bacterium capable of converting a C1 substrate into propylene.

In certain embodiments, the non-naturally occurring C1 metabolizing organism is an obligate C1 metabolizing organism capable of converting a C1 substrate into propylene. In certain embodiments, the obligate C1 metabolizing organism is a C1 metabolizing bacterium, such as a methanotrophic or methylotrophic bacterium capable of converting a C1 substrate into propylene. In further embodiments, a C1 metabolizing bacterium may be a syngas utilizing bacterium that naturally possesses the ability to use syngas and convert a C1 substrate in the syngas into propylene. In still further embodiments, a C1 metabolizing bacterium is a CO utilizing bacterium that naturally possesses the ability to use CO and convert the CO into propylene.

In certain embodiments, any of the non-naturally occurring C1 metabolizing organisms as described herein includes an exogenous nucleic acid encoding an enzyme capable of decarboxylating crotonic acid. The exogenous nucleic acid encoding an enzyme capable of decarboxylating crotonic acid is expressed in a sufficient amount to produce propylene.

In further embodiments, the exogenous nucleic acid encoding an enzyme capable of decarboxylating crotonic acid encodes 4-oxalocrotonate decarboxylase (4-OD). 4-OD is an enzyme that catalyzes the decarboxylation of 4-oxalocrotonate to 2-oxopent-4-enoate and $CO_2$. 4-OD is involved in the meta-cleavage pathway for the degradation of phenols, modified phenols, and catechols. As disclosed herein, an exogenous nucleic acid encoding 4-OD is used to genetically engineer a novel propylene biosynthesis pathway in a non-naturally occurring organisms; 4-OD is used to catalyze decarboxylation of crotonic acid to propylene and $CO_2$ (see FIG. 1). Sources of 4-OD encoding nucleic acid molecules may include any species, prokaryotic or eukaryotic, where the encoded gene product is capable of catalyzing decarboxylation of crotonic acid to propylene and $CO_2$. Exemplary amino acid sequences of 4-OD are shown in FIGS. 2A-D.

Non-naturally occurring C1 metabolizing organisms that have an exogenous nucleic acid encoding an enzyme capable of decarboxylating crotonic acid (e.g., 4-OD) may also include one or more exogenous nucleic acids to confer a propylene biosynthetic pathway onto the C1 metabolizing organism. For example, depending on which C1 metabolizing host organism is selected, one or more exogenous nucleic acids may need to be introduced into the C1 metabolizing organism along with 4-OD in order to provide a non-naturally occurring C1 metabolizing organism with the ability to produce crotonic acid, the substrate for propylene conversion by 4-OD. In certain embodiments, a non-naturally occurring C1 metabolizing organism that has an exogenous nucleic acid encoding an enzyme capable of decarboxylating crotonic acid (e.g., 4-OD) may further include an exogenous nucleic acid encoding crotonase and/or an exogenous nucleic acid encoding a crotonyl-CoA thioesterase. An exogenous nucleic acid encoding crotonase and an exogenous nucleic acid encoding crotonyl-CoA thioesterase are expressed in a sufficient amount to produce propylene. In a specific example, a type II methanotrophic bacterium, which possesses an endogenous PHB synthesis pathway and produces 3-hydroxybutyryl-CoA, an intermediate in the PHB synthesis pathway, may comprise exogenous nucleic acids encoding a crotonase and/or a crotonyl-CoA thioesterase in addition to 4-OD (see FIG. 1). Crotonase and crotonyl-CoA thioesterase are provided to catalyze the dehydration of 3-hydroxybutyryl-CoA to crotonyl-CoA and conversion of crotonyl-CoA to crotonic acid, respectively. It is understood that any combination of one or more enzymes that can be used to engineer a propylene biosynthesis pathway can be included in a non-naturally occurring C1 metabolizing organism of the invention.

In certain embodiments, the present disclosure provides a non-naturally occurring C1 metabolizing bacterium; a non-naturally occurring obligate C1 metabolizing organism; a non-naturally occurring C1 metabolizing organism, wherein the non-naturally occurring C1 metabolizing organism does not include *Pichia pastoris*; a non-naturally occurring methanotrophic or methylotrophic bacterium; or a non-naturally occurring CO utilizing bacterium, wherein the non-naturally occurring CO utilizing bacterium naturally possesses the ability to utilize CO, wherein the non-naturally occurring C1 metabolizing bacterium or organism comprises an exogenous nucleic acid encoding a crotonyl-CoA thioesterase.

In certain embodiments, the present disclosure provides a non-naturally occurring C1 metabolizing organism that is not *Pichia pastoris* and includes an exogenous nucleic acid molecule encoding a crotonyl CoA thioesterase. In further embodiments, a non-naturally occurring C1 metabolizing organism that is not *Pichia pastoris*, may be an obligate C1 metabolizing organism containing an exogenous nucleic acid molecule encoding a crotonyl CoA thioesterase. In still further embodiments, the C1 metabolizing organism may be a C1 metabolizing bacterium or an obligate C1 metabolizing bacterium containing an exogenous nucleic acid molecule encoding a crotonyl CoA thioesterase. In some embodiments, a C1 metabolizing bacterium is a methanotrophic or methylotrophic bacterium containing an exogenous nucleic acid molecule encoding a crotonyl CoA thioesterase. In certain embodiments, a C1 metabolizing bacterium may be a syngas utilizing bacterium that naturally possesses the ability to use syngas and contains an exogenous nucleic acid molecule encoding a crotonyl CoA thioesterase. In some embodiments, a C1 metabolizing bacterium may be a CO utilizing bacterium that naturally possesses the ability to use CO and contains an exogenous nucleic acid molecule encoding a crotonyl CoA thioesterase.

Crotonyl-CoA thioesterase refers to an enzyme that catalyzes the conversion of crotonyl-CoA to crotonic acid. Sources of crotonyl-CoA thioesterase encoding nucleic acids may include any species, prokaryotic or eukaryotic, where the encoded gene product is capable of catalyzing the conversion of crotonyl-CoA to crotonic acid. Exemplary amino acid sequences for crotonyl-CoA thioesterase are shown in FIG. 3. Crotonic acid is an intermediate in the engineered propylene biosynthetic pathway disclosed herein and is a useful product in itself for the preparation of polyvinyl acetate copolymers, a synthetic butyl rubber softener, a variety of resins, fungicides, pharmaceutical intermediates, plasticizers, cosmetic polymers for hair care, and adhesives. Reduction of crotonic acid yields crotonaldehyde. Key products made from crotonaldehyde are sorbic acid, potassium sorbate (a preservative), and trimethylhydroquinone (an intermediate used in Vitamin E manufacture).

In certain embodiments, the present disclosure provides a non-naturally occurring C1 metabolizing bacterium; a non-naturally occurring obligate C1 metabolizing organism; a non-naturally occurring C1 metabolizing organism, wherein the non-naturally occurring C1 metabolizing organism does not include *Pichia pastoris*; a non-naturally occurring methanotrophic or methylotrophic bacterium; or a non-naturally occurring CO utilizing bacterium, wherein the non-naturally occurring CO utilizing bacterium naturally possesses the ability to utilize CO, wherein any of the aforementioned non-naturally occurring C1 metabolizing bacterium or organism includes an exogenous nucleic acid encoding a crotonase.

In certain embodiments, the present disclosure provides a non-naturally occurring C1 metabolizing organism that is not *Pichia pastoris* and includes an exogenous nucleic acid molecule encoding a crotonase. In certain embodiments, the non-naturally occurring C1 metabolizing organism that is not *Pichia pastoris* is a C1 metabolizing bacterium containing an exogenous nucleic acid molecule encoding a crotonase, such as a methanotrophic or methylotrophic bacterium. In some embodiments, a C1 metabolizing bacterium is a syngas utilizing bacterium that naturally possesses the ability to use syngas and contains an exogenous nucleic acid molecule encoding a crotonase. In some embodiments, a C1 metabolizing bacterium is a CO utilizing bacterium that naturally possesses the ability to use CO and contains an exogenous nucleic acid molecule encoding a crotonase. In further embodiments, a non-naturally occurring C1 metabolizing organism is an obligate C1 metabolizing organism containing an exogenous nucleic acid molecule encoding a crotonase, such as an obligate C1 metabolizing bacterium.

Crotonase, also known as 3-hydroxybutyryl-CoA dehydratase, is an enzyme involved in the butyrate/butanol-producing pathway. Crotonase catalyzes the dehydration of 3-hydyroxybutyryl-CoA to crotonyl-CoA. 3-hydroxybutyryl-CoA can be an R or S stereoisomer. Enzymes that produce and convert 3-hydroxybutyryl-CoA have defined stereospecificity preferences. Sources of crotonase encoding nucleic acids may include any species, prokaryotic or eukaryotic, where the encoded gene product is capable of catalyzing dehydration of 3-hydyroxybutyryl-CoA to crotonyl-CoA. Exemplary amino acid sequences for crotonase are shown in FIGS. 4A-E. Crotonyl-CoA is a useful intermediate that can be a substrate for an engineered propylene biosynthetic pathway (via conversion to crotonic acid by crotonyl-CoA thioesterase, which is then converted to propylene by 4-OD) or an engineered butanol/butyraldehyde biosynthetic pathway (via conversion to butyryl-CoA by butyryl-CoA dehydrogenase, which is then converted to butanol or butyraldehyde by bi-functional aldehyde dehydrogenase) (see FIG. 1).

In certain embodiments, the invention provides for a non-naturally occurring C1 metabolizing bacterium; a non-naturally occurring obligate C1 metabolizing organism; a non-naturally occurring C1 metabolizing organism, wherein the non-naturally occurring C1 metabolizing organism does not include *Pichia pastoris*; a non-naturally occurring methanotrophic or methylotrophic bacterium; or a non-naturally occurring CO utilizing bacterium, wherein the non-naturally occurring CO utilizing bacterium naturally possesses the ability to utilize CO; wherein the non-naturally occurring C1 metabolizing bacterium or organism converts a C1 substrate to propylene, and further wherein the non-naturally occurring C1 metabolizing bacterium or organism does not have a functional PHB synthase or a substantial amount of a functional PHB synthase.

In certain embodiments, a non-naturally occurring C1 metabolizing organism according to any of the embodiments disclosed herein is a C1 metabolizing bacterium that does not have a functional PHB synthase or a substantial amount of functional PHB synthase.

PHB synthase is a polyhydroxybutyrate synthesis pathway enzyme that converts hydroxybutyryl-CoA monomers into polyhydroxybutyrate (PHB) (see FIG. 1). Many prokaryotes synthesize PHB as a carbon and energy storage material. Some yeast and other eukaryotic cells may contain small amounts of low molecular mass PHBs. Two PHB synthesis pathways are known in bacteria. In one pathway, PHB is synthesized from acetyl-CoA as a result of sequential action of three enzymes: β-ketothiolase, acetoacetyl-CoA reductase, and PHB synthase (e.g., *Methylobacterium extorquens*, *Methylosinus trichosporium* OB3b, *Methylocystis* and *Methylosinus* species). PHB synthesis can also be synthesized by: β-ketothiolase, acetocetyl-CoA reductase, crotonyl-CoA hydratases (crotonases), and PHB synthase (e.g., *Methylobacterium rhodesianum*) (see, e.g., Mothes et al., 1994, Arch. Microbiol. 161:277-280; Mothes et al., 1995, Can. J. Microbiol. 41:68-72). Generally, Type II methanotrophs accumulate PHB, whereas type I methanotrophs do not. As used herein, "not having a functional PHB synthase" means that its gene expression or protein activity has been reduced to undetectable levels. Reducing gene expression or protein activity of PHB synthase may be accomplished by deletion of some or all of the gene's coding sequence, introduction of one or more nucleotides into the gene's open reading frame resulting in translation of a nonsense or non-functional protein product, expressing interfering RNA or antisense sequences that target the gene, or other methods known in the art. As used herein, "not having a substantial amount of a functional PHB synthase" means that an organism has at least 40%, 45%, 50%, 55%, 60%, 65%, 70%, 75%, 80%, 85%, 90%, 95%, or 99% less gene expression or protein activity of PHB synthase as compared to a wild type organism that has a polyhydroxybutyrate synthesis pathway.

In a specific embodiment, PHB synthase is encoded by phaC or phbC. Exemplary PHB synthase amino acid sequences are provided in Table 1. In another specific embodiment, a non-naturally occurring C1 metabolizing organism that is capable of converting a C1 substrate to propylene as disclosed herein does not produce a substantial amount of polyhydroxybutyrate. As used herein, "not producing a substantial amount of polyhydroxybutyrate" means that an organism produces at least 40%, 45%, 50%, 55%, 60%, 65%, 70%, 75%, 80%, 85%, 90%, 95%, or 99% less polyhydroxybutyrate as compared to a wildtype organism that has a polyhydroxybutyrate synthesis pathway. By knocking out PHB function in C1 metabolizing organisms with an endogenous PHB synthesis pathway through genetic modification (e.g., allelic exchange of phaC or phbC with non-functional gene), PHB production may be inhibited, allowing more 3-hydroxybutyryl-CoA to be funneled into conversion to crotonyl-CoA by crotonase (see FIG. 1). Alternatively, a C1 metabolizing organism, which is not naturally capable of PHB synthesis, may be genetically modified to possess a portion of the PHB synthesis pathway (e.g., β-ketothiolase and acetoacetyl-CoA reducatase), while excluding PHB synthase functionality. Increased amounts of crotonyl-CoA, which is converted to crotonic acid and then to propylene via crotonyl-CoA thioesterase and 4-OD, respectively, may result in increased propylene yields.

TABLE 1

Exemplary PHB synthase sequences

| Genbank Accession # | Gene Name | Amino Acid Sequence (SEQ ID NO: #) |
| --- | --- | --- |
| gi\|53719168 | poly-beta-hydroxybutyrate polymerase [*Burkholderia pseudomallei* K96243] | MQQLFESWLGAWRSFADPARAAAGDAPSPSPSPFAAFQPPQPFAFAMPAMPPMPDWS GAAAASFAGLAPVASVPPARLQKLQADYSRDCLALIQQASAATPTVPELKDRRFSADAWKASP AHGFAAAWYLLNARYLQELADALETDPKTRERIRFTVQQWTAAASPSNFLALNPEAQKNLV ETQGESLRLGMMNLLADMQRGKISQTDESQFVVGKNLAVTPGAVVYENDLIQLIQYTPTTA TVFERPLLIVPPCINKFYILDLQPENSLVAHALSCGHQVFLVSWRNADASVAHKTWDDYIDEG LLAAIDVVQQVSGREQINTLGFCVGGTMLATALAVLAARGEHPAASMTLLTSMLDFSDTGIL DVFVDEAHVQMREQTIGGKGGAPAGLMRGVEFANTFSFLRPNDLVWNYVVDNYLKGRTP APFDLLYWNGDSTSLPGPMYAWYLRNTYLENKLREPDALTVCGEPVDLSRIDVPTFIYGSRED HIVPWQTAYASTSLLTGPLKFVLGASGHIAGVINPPAKRKRSYWSYDASAKELPESANDWLD AAVEHPGSWWPVWIEWLDQYGGKKVKPRAHLGCARFPVIEPAPGRYVLQRD (SEQ ID NO: 54) |
| gi\|296445329 | poly(R)-hydroxyalkanoic acid synthase, class I [*Methylosinus trichosporium* OB3b] | MTAGRRSTAGAKRRPPHLRDAAETKLVVEEPPPAENADVSLLEAPRVNGARVAAAAPAQKK KTGKVRAKPRAPVQEPPVQEPPVREPTAEAPREAMIAIATPPAAPTAEERRLELQAAAALVA GAAAELTEAQRRSLMGQLQALEPAPPAPAPVLTPAAPPEIPAAPQRKPARDYQAGAAESTA HDFEIIAENLARLVDQGRKALAAAVGGMEPGDTRSELASNVADATKTLGAVAERWMAKPE QAVAAQADLLTGLSAIWSQTLRRFSGADVPPVVPADPSDKRFSAPEWRDNPFFDCLRQSYA LTTHWASEAVERTDGLDPQTKSKAAFYTRLIASALSPSNFVATNPELLRATLDARGENLVRG MKMLTEDLSAGRGMLKLRQSDESKFELGVDMASTPGKVVYRTPVMELIQYAPSTETVYERP LLIVPPWINKFYVLDLNREKSFVRWATGKGLTVFVVSWVNPDESQADKGFDAYMKEGVLAA LDAVQKATGAPHVAAAGYCVGGTMLAATLAYLAEKGDDRIDSVTFLATQVDFTDAGDMQ VFIDEARLAALDEAMSRTGYLEGVKMATTFNMLRPNELFWTYFVNNYMKGVEPAAFDLLT WNSDCTRIPRANHLFYLRYCYIENALSQGRMVIDGVTLNLRKVKIPIYELAAKEDHIAPARSVF TGAKYFGGEVRYVLAGAGHIAGVVNPPDKHKYQYWTGGPPMGAYEDWVKAAKESKGSW WDDWHDWITSQAPEQVAARIPGEGGLKALCDAPGDYVRVRA (SEQ ID NO: 55) |
| gi\|296445763 | Poly-beta-hydroxybutyrate polymerase domain protein [*Methylosinus trichosporium* OB3b] | MVVVDFAGRAGRLQEPAAEASPNPPAPVEEPPRRAYPIGEVPSFDTLDRAARAVAARFTQG VSPLAQMSAWLDFATHLALAPGRQIELGLAAAQSAAALAYFSAETLAGRAEAGPFVSEPHD RRFVDPGWDAPPFSLWKQGFLATEHWWRLATRETRGMTRSDAARVGFMAEQWLGAFSP SNIAWANPAVVERTREEGGANLVRGAENFAEDLLRLVLRAPNGHGEFEVGVDVAATPGEVI FRNELIELIQYGPSTETVHAEPILIVPAWIMKYYVLDLRPQNSLVRYLTAQGFTVFMISWRNPG PEDRDLTFDDYRVSGVLAALSAIDAVRPGSKVHACGYCLGGTLLSIAAAAMARDGDARLASIS LLAAQTDFSEPGELMLFVDAAQVAFLEDMMWDQGVLDTRQMAGAFAALRSNDLVWGKA VQDYLLGERRKPNDLMAWSADQTRMPYRMHSQYLRGLFLENRLTAGRYAVEGEVVALKDI SAPMFVVGTTSDHIAPWRSVYKASLFTDCELTFVLTSGGHNAGVVSEPGRSGRSYHVGLRRP GDFYVGPDKWLAAARLAEGSWWPEWAAWLAARSGDERVAPPTMGARGYPPLYPAPGRY VHQA (SEQ ID NO: 56) |

TABLE 1-continued

Exemplary PHB synthase sequences

| Genbank Accession # | Gene Name | Amino Acid Sequence (SEQ ID NO: #) |
|---|---|---|
| gi\|52841292 | phbC gene product [Legionella pneumophila subsp. pneumophila str. Philadelphia 1] | MSAMKGLEKQCCPKKRILTQSQELQEGVDFSCCAPADRGTSDNFFPFFTRLVQANLAKWTA GISPAAIGSSYSTWLWQLAQSPGVLWELAFYPVFHAKDCINNIVCVERAADGKDVRFKKDS WQPMPWRLFAEGFLQMEDWWRRATTDVPGLPNQVERTVSFWARQCLDALSPSNFVWS NPDLFHEAMRTGGLNLIQGGQIALEDWLEKLTGAPPTGSEHFIPGKQVAITPGRVVFQNHLI ELIQYEAQTKTVYKEPILILPAWIMKYYILDLSPHNSLVKWLVSQGHTVFIISWRNPDKEDQDL GMDDYYRQGAMAAIDAVSTLFPETKINLMGYCLGGTLAMITAAAMGRDKDERLNSLTLLA AQGDFTEAGELMLFVTESQVDFLKSMMREQYGLDTKQMAGSFQMLRAYDLIWSKMVQD YMHGMRRGMIDLTAWNADATRMPYKMHSEYLEKLFLRNDFAEGRYTVEGKPVAAENIKLP VFAVSTEKDHVAPWQSVYKIHLMTEGDVTFVLTGGGHNAGIISEPGHPGRSYRVHEQKQGE AYLNPESWLAMAERREGSWWREWNEWLVQQNTKKRIASSVMNPSLPEAPGTYVLQK (SEQ ID NO: 57) |
| gi\|148359804 | PHA synthase [Legionella pneumophila str. Corby] | MKKTTEKPINKTKEMPASSKKEILNPLEQTPSPEQSDPIFRFIDKLYQANLGKLTAGISPAALGT AYYSWFAQLLQSPGSMLRLAYYPLLHANDYLSNLFKYDKPRDGKDVRFHTENWSYYPWRL WAEQFLQFEDWCLQASSKVPGIPLHVKRTVTFSTRQILDALSPSNFVLTNPDLLQETIRSNGQ NLIRGTELAFQDFVEKITGSPPAGVENFIPGKQVAVTKGKVVYSNHLIELIQYTPQTEKVYKEPI LILPAWIMKYYILDLLPENSLVNWLVRQGHTVFIVSWRNPTKEDRNLGLDDDYYKLGAMDAIN AVSNAIPHTKIHLMGYCLGGTLALLTAAAMAHDHDNRLKTLSLLAAQGDFIDAGELLLFITKS EVSFLKSMMWEQGYLDTKQMSGTFQMLRSYDLIWSKMVQDYMHGTQRGMIPLLAWNA DATRMPYKMHSEYLEKLFLNNDFAEGRFILDGKPVVGENIRIPAFVVSTEKDHVAPWKSVYK THLLINSDITFVLTNGGHNAGIVSEPGHEGRYYRIRERKMDSTYLDPTNWLKKAELREGSWW IAWHDWLVNHSSQKQVSAPKLDKKLPNAPGKYVLQK (SEQ ID NO: 58) |
| gi\|326404096 | poly(3-hydroxyalkanoate) polymerase [Acidiphilium multivorum AIU301] | MPGFATFDRLSRAMFARISQGFVSPLAVADAWTDWALHLELALGKQEALAMRAATFLLRLG FWLPRAAIGEPENPPLRPPEGDRRFADEGWSAYPFNAIVQGFLVADDWWREATRQVPGLV RRHEAEVAFMARQILDIAAPTNIPWLNPEIIRRTLQEEGGFNLLRGWSNWIEDAERLLAGQGP YGAEAFPVGEVVATTAGKVVYRNELMELIQYAPATAKVTAEPVLIVPAWIMKYYILDLTPETS LVRYLVTNGHTVFIISWINPDRHDRNVGLDDYRRHGVMAALDAVSRIVPDRAIHACGYCLG GTILAIAAATMARDHDDRLASLTLLAAQTDFADAGDLMLFLDERQFLLLEDLMWDQGYLDT RQMAGAFQALRSNELVWSRLIRNYMLGERDRMTPLSAWNSDQTRMPARMHSEYLRGLFL ENRLSAGRFAVEGRVIALRDIRVPLFAVATTRDHIAPWRSVYKIALFADTDITFVLASGGHNV GVVNPPNQSIGTFQILTRRHGERYVDPDTWATLAPERQGSWWPAWRDWIGGVGTGCAA DPPPMAAPSRGLPVLGDAPGAYVHER (SEQ ID NO: 59) |
| gi\|330826932 | poly-beta-hydroxybutyrate polymerase domain-containing protein [Alicycliphilus denitrificans K601] | MPDTFSAAALADQLDTQFHAALARRFFSLSPAAGMLAASDWALHLAVSPGKCMALARLAL RQSEELAGYARERMTAGADPQLRHGVQPPAQDRRFAAPEWQQWPFNYMHQSFLLTQQ WWAAATHGVKGVEKHHENVVLAFAARQLLDVFSPGNQLATNPVVLRNRQRTLQQGGANLLRG ALNAADDLQRLAAGKPPAGTEDFVVGRDVAVTPGKVVLRNRLVELIQYTPTTEAVHPEPVLI VPAWIMKYYILDLSPHNSLIRYLVDQGHTVFCLSWKNPGYEDRDLGLDDYLKLGFHAALDAV NAIVPKRKVHATGYCLGGTLLAIAAAAMARDGDARLASLSLFAAQTDFSEPGELGLFIDESQV NLLEAQMTQGYLKASQMAGAFQMLRSYDLLWSRLVNEYLLGERFPMIVGTLTDHVAPWRSVHKLH HLTTTEITFALTSGGHNAGIVNPPGNPRRHYQLRTRPAGGNYMAPDDWLAAAPAAQGSW WPAWQEWLQARSGKPVAPPHMGARGYKAGADAPGHYVLEK (SEQ ID NO: 60) |
| gi\|222110509 | poly-beta-hydroxybutyrate polymerase domain-containing protein [Acidovorax ebreus TPSY] | MSNVATHGKADLAQPEACRPDTLDTLANAWRARSTGGLLSPAAGLLAWYDWALHLSLSPG KQRSLIEKGLHKQQRLARYALRVASAHDCPTCIEPLEQDRRFAAPAWQQWPFNVIHQGFLL QQQWWHNATTGVRGVSRHHENMVTFAGRQWLDMWSPSNFIWTNPEVLHAITQSGGA NLWRGAMNFLEDARRLALDDDAPAGVEGFEVGKDVAVTPGKVVYSNHLIELIQYSPTTPDVH AEPVLIVPSWIMKYYILDLSPHNSMVKYLVDQGHTVFILSWKNPTAADRDLGLEDYRWLGV MDALDAVTAIVPERKVQAVGYCLGGTLLAIAAAAMARDGDERLQSLTLLASETDFRESGEIAL FIDDSQLAWLEAGMWDKGYLDGKQMAGAFQMLNSRDLIWSRRVREYLLGERQTFNDLM AWNADVTRMPYRMHSEYLRRLYLDNDLAEGRYRVGGRPVALADIEVPMFIVGTVRDHVAP WPSVYKMHLLSDAELTFVLTSGGHNAGVVSEPGHPRRSFQIATRAAGDRYIDPQLWRAETP MNEGSWWPAWQQWLAQRSAGRVAPPAMGGTQAPLGDAPGTYVAMR (SEQ ID NO: 61) |
| gi\|39937303 | phaC gene product [Rhodopseudomonas palustris CGA009] | MMLQTSPPAPSAASQQIQSPARHHGPSDSDRTLHATLAPLTGGLSPTALTLAYADWLSHLF WAPTQRMDLVNDALRRGTQLAEASIGQTAPWSLIAPQPQDRRFSAPEWREPPPFNLMAQG FLLAEQWWHDATTNIRGVSEQNEKIVEFATRQMLDVWAPSNFALTNPEVLRRTVSTEGRNL ADGFRNWWEDLLELMAHEPKHDFVVGKDVAVTPGKVVYSNKLIELIQYAPATETVRPEPILI VPAWIMKYYILDLSPHNSLVKYLTEQGYTVFMISWRNPTAADRDLGLDDYRRLGVMAALDTI GAILPDRPVHAVGYCLGGTMLSIAAAMGRDGDSRLKSITLFAAQTDFTEAGELTLFINESQV AFLEDMMWNRGVLDTTQMSGAFQILRSNDLIWSRLVHEYLMGVRSEPNDLMAWNADAT RMPYRMHSEYLRKLFLDNDLAEGRYVVDGRPIALSDIHTPIFVVGTQRDHVAPWRSTFKIHLL ADADVTFCLTGGGHNAGIVSPPSPKAHGYQVMTKEADGPYVGPDDWLKQAPHEAGSWW TEWVHWLGTRSGEPVAPPRIGLPDVDPGALPNAPGSYVLQT (SEQ ID NO: 62) |
| gi\|172063316 | poly-beta-hydroxybutyrate polymerase domain-containing protein [Burkholderia | MKASVTRAPRGNESIRPSGAVEPESSMTQCPQAGTTPAEQWNRAAHANVAAMTFGLSPV SLALAMLDWGAHLAVSPGKCFDLAMQACVAAVAPAADQCEAEAGEAGDPTGLAVHAGQA DPRFAAPAWAGWPFHVYRDSFLSIQRWWRDATHGVPGVERHHEELVGFAARQWLDACS PGNFLATNPVVLDATMCSGGANLAAGALNWLEDAKALLERAGGTHAHDARTYLPGRDVAI TPGRVVWRNALCELLQYEPTTARVAREPILIVPSWIMKYYILDLQPHNSLIRFLVDAGYTVFAV SWRNPGAEARDLGLDDDYLRDGCMAALDAARSVCGGAVHTVGYCLGGTLLAIVAAALARDG RQHEALRSVTLLAAQTDFSEPGELGLFIDASELSALDALMWRQGYLDGAQMSAAFQLLNAR |

TABLE 1-continued

Exemplary PHB synthase sequences

| Genbank Accession # | Gene Name | Amino Acid Sequence (SEQ ID NO: #) |
|---|---|---|
| | ambifaria MC40-6] | DLIWSRMMSEYLLGTRTKPNDLMSWNADTTRMPYRMHSEYLTRLFLDNDLAVGRYCVDG RPVALSDIDVPTFVVGTERDHVSPWGSVYKLHLLTHHALTFVLTSGGHNAGIVSEPGHPGRH YRRATREPGAPYRSRHDFVRGTTAVDGSWWTCWRDWLHERSSGDVPARTPAAGFDAAP GTYVLET (SEQ ID NO: 63) |
| gi\|1730539 | PHAC_METEX RecName: Full = Poly(3-hydroxyalkanoate) polymerase; Short = PHA polymerase; AltName: Full = PHA synthase; AltName: Full = Poly-hydroxyalkanoic acid synthase | MGTERTNPAAPDFETIARNANQLAEVFRQSAAASLKPFEPAGQGALLPGANLQGASEIDEM TRTLTRVAETWLKDPEKALQAQTKLGQSFAALWASTLTRMQGAVTEPVVQPPPTDKRFAH ADWSANPVFDLIKQSYLLLGRWAEEMVETAEGIDEHTRHKAEFYLRQLLSAYSPSNFVMTNP ELLRQTLEEGGANLMRGMKMLQEDLEAGGGQLRVRQTDLSAFTFGKDVAVTPGEVIFRND LMELIQYAPTTETVLKRPLLIVPPWINKFYILDLNPQKSLIGWMSQGITVFVISWVNPDERH RDKDFESYMREGIETAIDMIGVATGETDVAAAGYCVGGTLLAVTLAYQAATGNRRIKSATFL TTQVDFTHAGDLKVFADEGQIKAIEERMAEHGYLEGARMANAFNMLRPNDLIWSYVVNNY VRGKAPAAFDLLYWNADATRMPAANHSFYLRNCYLNNTLAKGQMVLGNVRLDLKKVKVP VFNLATREDHIAPALSVFEGSAKFGGKVDYVLAGSGHIAGVVAPPGPKAKYGFRTGGPARGR FEDWVAAATEHPGSWWPYWYKWLEEQAPERVPARIPGTGALPSLAPAPGTYVRMKA (SEQ ID NO: 64) |
| gi\|16125629 | poly-beta-hydroxybutyrate polymerase [Caulobacter crescentus CB15] | MVETLSANLARAAVTAQGAIAEAALRQADRPAALTPDPFHVAPALNEVMTRLAAQPDRLM RAQADLFGQYMELWQTAARRAAGEDVAPVVAPAAGDKRFNDPDWASNPMFDLMKQSY LLSSNWLNGLIAEVDGVDPATKRRVEFFTKMLTDAFSPSNFLISNPAALREVVQTQGQSLVR GMENFAADLERGGGQLAISQTDLAKFKVGENVATAPGKVVYQNDILQLLQFDPTTDTVCEIP LLIFPPWINKFYIMDLRPENSMIRWLTAQGFTVFVASWVNPDQTLAAKTFEDYMVEGIYDA AQQVMTQCGVDRVNTVGYCIGGTLLSVALAHMAARGDKRINSATFFAAQQDFAEAGDLLLL FTNEEWLQSIEQQMDQAGGFLPSQSMADTFNALRGNDLIWSFFVSNYLMGKEPRPFDLLF WNADQTRMPKALHLFYLRNFYKDNALTTGKLSLGGERLDLSKVKIPIYVQSSKDDHIAPYRSV YRGARAFGGPVTFMAGSGHIAGVINHPDARKYQHWTNSELPADVSEWIAGAHEHPGSW WPHWAAWLKARSGDQVPARDPAKGKLKPLEDAPGSFVLVKSQP (SEQ ID NO: 65) |
| gi\|170744156 | unnamed protein product [Methylo-bacterium sp. 4-46] | MLATSPTQSSAAIPARPPALRLVPPVAAAGPVRDAAEPGDDLHDAGQAIDQAAHAAVARLT GGLSPAALANAWLDWSVHAAFSPGKQAELAAKAFRKGQRLQSFLWRNLLVGAQAEPCIEP LPQDHRFDDPAWRTWPFCLYQQGFLLTQQWWHNATTGVRGVARAHEEIVAFTARQMLD GVSPSNHPLTNPVVLNATLASGGANLVLGALNALEDARRGLAGLKPAGAERFAVGREVAVT EGEVVYRNDLIELIQYAPKTGAVRPEPVLIVPAWIMKYYILDLSPENSLVRHLVGQGFTVFMIS WRNPGPADRDVSFDDYRRLGVMAALDAVSAIRPGRAVHAAGYCLGGTLLSIAAATMARDG DARLASLTLFAAQVDFTEAGELTLFINESQISFLESLMRSEGVLDSKQMAGAFQLLRSNDLIW SRIVNSYLLGRREAVTDLMAWNADATRMPARMHAEYLRRLFLDNDLAEGRLRVEGRPVAL TDIRAPIFAVGTEKDHVAPWRSVFKLTMTDADVTFLLASGGHNAGIVSEPGHRGRHYRVHS RAATDRYVDPDSWLDLARLEQGSSWWPEWASWLAERSGPPEPPPPMGLPGAPTLGPAPG RYVREA (SEQ ID NO: 66) |
| gi\|146340526 | Poly-beta-hydroxybutyrate polymerase [Bradyrhizobium sp. ORS 278] | MTDVPNNTNPQKTFDAEAFATNIARAMESSGKALAAYLKPRETGEVQDRPPTELTEVVKSFT AVADYWLSDKDRASDIQTKLAKGYLDLWGSSAARRLAGEEAPPAISPSPRDKRFADPEWKSN QFYDFVMQAYLLTTQWAQDLVHNAEGLDPHTRKKAEFYVNQITNALAPSNFVMTNPEVM RQTVASSGDNLVRGMQMLAEDIEAGKGTLKIRQSDPANLEVGVNMATTPGKVIFQNEMM QLIQYAPTTETVLRTPLLIVPPWINKFYILDLRPEKSFIKWCVDQGLTVFVISWVNPDKKLGTKT WEDYMKEGPLTAMDVIEKVTGEMKVHTMGYCVGGTMLATTLAWLADKRRQRVTSATFLA AQVDFTHAGDLLVFDETQISALERDMQASGVLEGSKMAMAFNMLRSNDLIWSYVVNNYL KGGPPQAFDLLHWNSDATRMSAANHSYYLRNCYLENRLTTGTMVLDNTLLDLSKVKVPVY NLATREDHIAPADSVLYGSQFFGGPVKYVLSGSGHIAGVVNPPSSGKYQYWTNDQIHDISLK DWMKGAQEHKGSWWPDWREWLGQLDPEQVPARSVGSEAYPPIEDAPGSYVRVRA (SEQ ID NO: 67) |
| gi\|126463677 | unnamed protein product [Rhodobacter sphaeroides ATCC 17029] | MSDMKWNAEGAPAYGQALDRAARAAIAGMTRGLAPSVLATAALDWMMHLAAAPGKQA ELWEKAATASAALMQAGLQPHEAPVRDRRYASEEAWNRQPFAALRDSFLLTEDWWQTATT GLRGMDRAHEAALSFSVRQMLDVWSPSNNPFLNPEVLARTTETRGANLMQGAMNFAGD MARLATGVPMDEGGFRIGETLAATPGKVVLRTHLMELIQYSPTTREVHPEPVLIVPAWIMKY YILDLSEQNSLVRWLVAQGFTVFMISWRNPESEDRDLGLIDYLDQGPRAALKAIQTITGAPKV HAAGYCLGGTLLSIMAARMAHDHDERLASMTLFAAQVDFSEAGELALFISEAQVALLEDM MWHQGYLDSDQMSGAFTLLRSNDLIWSRMIHEYMMGERPHPNDLMTMWNADSTRMPYR MHSEYLRQLFLENRFAEGKFELEGHALSTLERLRPILAVGTETDHVAPWRSVFKIQRLTETETT FVLTSGGHNAGIVSEPGHPRRHFRIATTGRDDPYRDADEWFAETAPVEGSWWPAWGAWL AERSTPKGKLPPMGNARGGYPALCEAPGTYILQR (SEQ ID NO: 68) |
| gi\|359401847 | putative poly-beta-hydroxyalkanoate synthase [Novosphingobium pentaromativorans US6-1] | MKGLKIMVEAQIPGVGDPLDGLAETMDRAAGAMIAQATFGLSPATLAQAVSDWMLHLAA SPGKQTQLAAKALRKMTRLGDYAMRSATDAQAARAIEPLPQDRRFADPAWASAPFNLVSQ AFLLNQQWWHAATTGITGVTAHHEEMVAFAVRQWLDTVAPTNFLATNPVLQQRILETGG QCLADGLRNWMTDVEALMRGLPPAGPTEAFQVGETLATAGKGKVVYRNRLMELIQYAPTTE ARPEPILIVPAWIMKYYILDLSPENSLVQWLTAQGFTVFMISWHNPGSTDRDLEMADYLQLG PMAALDAVAAITGGASVHAAGYCLGGTLLAIAAAAMARDGDDRLASLTLLAAQTEFCEPGE LGLFIDEGQLSLLENMMWGRGYLDSAQMGGAFQMLRSNDLVWSRVLTTYLMGEREPMN DLMAWNADGTRMPYAMHSQYLRRLFLEDDLAEGRFQVNGRPIALSVLRWPMFVVGTERD HVAPWRSVFKIHRLTGAPIDFVLTSGGHNAGIVSEPGHPGRSYRLLTREADGAALDPDAWLD |

TABLE 1-continued

Exemplary PHB synthase sequences

| Genbank Accession # | Gene Name | Amino Acid Sequence (SEQ ID NO: #) |
|---|---|---|
| | | AAPRHEGSWWTAWGDWLAKLSGNAGTPPPMGATDKGYAPLADAPGHFVLER (SEQ ID NO: 69) |
| gi\|581529 | PHA synthase [Rhodococcus ruber] | MLDHVHKKLKSTLDPIGWGPAVTSVAGRAVRNPQAVTAATAEYAGRLAKIPAAATRVFNA NDPDAPMPVDPRDRRFSDTAWQENPAYFSLLQSYLATRAYVEELTEAGSGDPLQDGKARQ FANLMFDALAPSNFLWNPGVLTRAFETGGASLLRGARYAAHDILNRGGLPLKVDSDAFTVG ENLAATPGKVVFRNDLIELIQYAPQTEQVHAVPILAAPPWINKYYILDLAPGRSLAEWAVQH GRTVFMISYRNPDESMRHITMDDYYVDGIATALDVVEEITGSPKIEVLSICLGGAMAAMAAA RAFAVGDKRVSAFTMLNTLLDYSQVGELGLLTDPATLDLVEFRMQQGFLSGKEMAGSFD MIRAKDLVFNYWVSRWMKGEKPAAFDILAWNEDSTSMPAEMHSHYLRSLYGRNELAEGLY VLDGQPLNLHDIACDTYVVGAINDHIVPWTSSYQAVNLLGGDVRYVLTNGGHVAGAVNPP GKRVWFKAVGAPDAESGTPLPADPQVWDEAATRYEHSWWEDWTAWSNKRAGELVAPP AMGSTAHPPLEDAPGTYVFS (SEQ ID NO: 70) |
| gi\|227823933 | poly-beta-hydroxybutyrate polymerase domain protein [Sinorhizobium fredii NGR234] | MKTGDRPVLAADRARQAGSARAIAAQSALPCENDGADGEAFRAIDRMREALSATATGGLS PAALTLAFFDWSIHLASAPGKRMELAHMAAQNWGLLLTYMAAAATRPDAPPCIEALPGDN RFRAEGWQKQPYTVWAQAFLLGQQWWHNVTRNVPGMTPHHEDVVSFTARQWLDVFS PSNIPFANPEVIHKAMETGGANFTQGFRNWLEDVGRLATKQRPVGTEAFRVGHDTAATPG KVVYRNHLIELIQYAPATEEVLAEPILIVPAWIMKYYILDLSPHNSLIRYLVAQGHTVFCISWRN PSAKDRDLTLDDYRRLGILAALDAVSAIVPERKIHATGYCLGGTLLAIAAAAMARTEDQRLAS VTLFAAQTDFSEPGELALFIDHSQLHFLDSLMWHSGCLSADQMAGAFQLLRTNDLVWSRLV HDYLIGKRTPMTDLMAWNADPTHMPYRMHAEYLQRLYLDNELAAGRFIVDGRPAHLQNIR VPMFVVGTERDHVAPWHSVYKIHYLTDTDVTFVLTSGGHNAGIVSEPDHPRGFRIALTRES DSSVSADEWVAAATSKDGSWWPDWVEWLAGHSAPKRVTPPVIGAPERGYPPIDDAPGTY VHQR (SEQ ID NO: 71) |
| gi\|332526305 | poly-beta-hydroxybutyrate polymerase-like protein [Rubrivivax benzoatilyticus JA2] | MHNPNVAAAVLADPALDPALAAARRLDSHFHAAVAPAFSGLSPISLALAWQDWALHLATQ PATALALVARAQQSWLQAWGEMLGQAEPGNGDARFAAPAWRQWPWAPVVHGWHAT ERWWQDATDLRGVDPHHREVVRFFARQWLDMLAPSNAGLANPEVLQRTAERGGANLVD GTLHALDGWRRQHGLEPLRTPERRYEPGVDVAVTPGQVVWRNHLVELIQYLPLTASVQAEP VFIVPSWIMKYYILDLSPHNSFVKWLVEQGHTVFILSWRNPDESDALLAMQDYLELGIFDPLA QIARMIPGRRVHACGYCLGGTLLSLAAAALARPGRIARAELLPELASVSLLAAETDFTEPGEM GVLIDESQVTLLEDMMAERGFLTGAQMAGSFAYLHSRDQVWSRRLREFWLGEPDSPNDL MAWNADLTRMPAAMHSEYLRRCYLRNEIAEGRFPVEGRAVSLSDIAAPMFVVGTEKDHVS PWKSVYKIHRLADTTITFVLTSGGHNAGIVSEPGHANRRYRMATREVDGAWVDPEAWAEQ APRHEGSWWTAWHEWLLAQGSGETAKARTPAKADVVCAAPGTYVYQCWRD (SEQ ID NO: 72) |
| gi\|154253888 | unnamed protein product [Parvibaculum lavamentivorans DS-1] | MTKNKKGNTSSTIVPALDMQAHMAWAQAWSSISPESSLLAWTDWASHLANSPGKQSELL AFAGSLSEQWMSLLKKSLVSPDQEVASPEPSPTNDRRFNDPAWDQWPYNLFRSSFLIQSKW WEQATQGVWGVDPQHERLLAFGAKQWLEMVSPTNSALFNPVVLKKTIEEQGANLARGM SNFLDDLRRQLSGEPPAGTENFVVGRDVAVTEGKVVLRNQLIELIQYTPTTEKVHPEPILIIPA WIMKYYVLDLSPHNSLIRYLVAQGHTVFCISWKNPDAGRDLGMDEYLEFGLRAALDAVTSI VPEQGIHAAGYCLGGTLLAIGASAMARDGDTRLVSVSLLAAQTDFSEPGELSLFINESQVALL EASMAQTGYLTSDQMSGAFQLLRSYDLIWSRMIDEYLLGDRRPMTDLMAWNADGTRLPA KMHSQYLRRLYLNNDLSAGRYPVTGRPVSVGDIAVPVFCVGTASDHIAPWRSVYKLHLLSSA ELTFVLTTGGHNGGIVSEPGRGKRQYQIHTRAAGDGYMAPDEWQATAQTHLDSWWPAW SAWLRERSGEGVAPPLMGAESRGYPTICDAPGKYVRS (SEQ ID NO: 73) |
| gi\|53716799 | phbC gene product [Burkholderia mallei ATCC 23344] | MDTRHAPESGAPDAPLPAHPPASYAPESPYRIFDLAKEASVAKLTSGLSPASLQLALADWLIH LAAAPGKRAELATLALRHAALLGQYLLEAATGRTPAAPAQPSPGDRRFRAGAWQLEPYRFW HQSFLLAEQWWRAATRDVPGVSPHHEDVVAFSARQMLDTFAPANYVATNPEIAQRTALT GGANLAQGVWNYLDDVRRLITKQPPAGAEQFELGRNLATTPGRVVFRNHLIELLQYSPTTPD VYAQPVLIVPAWIMKYYILDLSAHNSLIRYLVGEGHTVFCISWRNVDASDRDLSLDDYRKLGV MDALDTIGAIVPGEKIHATGYCLGGTLLSIAAAAMANTGDDRLASITLLAAQTDFAEPGELQL FIDDSEIHFLESMMWERGYLGAHQMAGSFQLLMSNDLIWSRVIHDYLLGGERTPMIDLMAW NADSTRMPYRMHSEYLRHLFLDNDLATNRYVIDGQTVSVHNIRAPPFFVVGTEHDHIAPWRS VYKIHYLSGSDVTFVLTAGGHNAGIVSEPGHAKRHYRMKMTAAAAPSISPDEWLAGATDFE GSWWPAWHAWLARHSSPQRVAPPPLGKPGAHTLGDAPGTYVFQK (SEQ ID NO: 74) |
| gi\|365891729 | putative poly-beta-hydroxybutyrate polymerase (Poly(3-hydroxybutyrate) polymerase) (PHB/PHA polymerase) (PHB/PHA synthase) (Poly(3-hydroxyalkanoate) polymerase) (Polyhydroxyal | MSDAKSAAEDANSVAREFVREDHELDKAFSAVLARLTGGISPAALSMAYLDWACHLAAAPQ RQLDIARDAWQGARQLAERSLHFADSNRVPWDLIKPQANDHRFSKPQWGMQPPFNLFAQ AFLLGEDWWHKATTNIRGVDPANEAVVDFSLRQLLDMFAPSNFAATNPEVVEKIFQSGGE NLVFGWQNWLSDLMQVLQPGQASRSAEFVPGETVATAPGKVVFRNQLIELIQYAPTTAEV RPEPILIVPAWIMKYYILDLSQHNSLVRYLTDQGFTVFMISWRNPDAKDRDIAFDDYRSMGV MAALSEIGKIVPGAQIHAAGYCLGGTLLSITAAAMAREGDTRLKTITLFAAQTDFTEAGELTLFI NESQVAFLEDMMWERGYLDTTQMAGAFQLLRSNDLIWSRVSRDYLLGERAHPSDLMAW NADATRLPYRMHSEYLRKLFLNNDLAEGRYRVEGKPVSLSDIHTPMFVVGTLRDHVAPWKS TYKIHYEVDADVTFVLASGGHNAGIVAPPHEQGHSHQVRTKAADAPYLGPDEWQSTSPRIE GSWWPTWLDWLAQRSGPLDAPPRLGTEGSHELGNAPGEYVHS (SEQ ID NO: 75) |

TABLE 1-continued

Exemplary PHB synthase sequences

| Genbank Accession # | Gene Name | Amino Acid Sequence (SEQ ID NO: #) |
|---|---|---|
| | kanoic acid synthase) [*Bradyrhizobium sp.* STM 3809] | |
| gi\|338984011 | Poly(R)-hydroxyalkanoic acid synthase, class I [*Acidiphilium sp.* PM] | MAEQQNPRTEAPNLPDPAAFSRTMADIAARSQRIVAEWLQRQHEADVAIDPLNIGSAFME MMARLMANPASLIEAQIGFWQDYVTLWQHSTRRIMGIETQPVVPPDPRDKRFQHEEWKE NEIPDFIRQSYLLSARFVQDVVRRVDGLDPKTAQKVDFYARQFVDAMSPSNFALTNPQVLRK TAETGGENLLRGLSNLLRDLEAGRGQLHIRMTDAEAFSVGGNIAVTPGKVVYRNELMELIQY APATTTAHKTPLVIFPPWINKFYILDLRPKNSFIRWAVEQGHTVFVASWVNPDERLAEKDFA DYMKLGVFAALDAIEQATGERQVNAIGYCLGGTLLAATLAVMARRRDSRIKSATFLVTLTDF ADVGELGVFIDEEQLAALEDRMNRRGYLEGSAMATTFNMLRSNDLIWSFVVNNYLLGNETF PFDLLYWNSDSTRMPAAMHSFYLRNMYQKNLLSQADAITLDGTPVDLRRIKVPVYFLSCRED HIAPWASTYRATQLMAGPKRFVLAASGHIAGVINPPGSGKYNHFVNATLPANAEDWFAGA TEVAGSWWPDWQRWIAAQGRGEVPARTPGDGALPALADAPGDYVKVRSA (SEQ ID NO: 76) |

In certain embodiments, the present disclosure provides a non-naturally occurring C1 metabolizing bacterium; a non-naturally occurring obligate C1 metabolizing organism; a non-naturally occurring C1 metabolizing organism, wherein the non-naturally occurring C1 metabolizing organism does not include *Pichia pastoris*; a non-naturally occurring methanotrophic or methylotrophic bacterium; or a non-naturally occurring CO utilizing bacterium, wherein the non-naturally CO utilizing bacterium naturally possesses the ability to utilize CO; wherein the non-naturally occurring C1 metabolizing bacterium or organism converts a C1 substrate to propylene, and further wherein the non-naturally occurring C1 metabolizing bacterium or organism has a functional β-ketothiolase and/or a functional acetoacetyl coenzyme A reductase, or has a functional β-ketothiolase and/or a functional acetoacetyl coenzyme A reductase activity (i.e., has enzymes that perform the function of β-ketothiolase and acetoacetyl coenzyme A reductase).

In certain embodiments, a non-naturally occurring C1 metabolizing organism according to any of the embodiments disclosed herein is a C1 metabolizing bacterium that has a functional β-ketothiolase activity and a functional acetoacetyl coenzyme A reductase activity.

In certain embodiments a non-naturally occurring C1 metabolizing organism according to any of the embodiments disclosed herein is a C1 metabolizing bacterium that does not produce a substantial amount of polyhydroxybutyrate.

β-ketothiolase and acetoacetyl coenzyme A reductase are enzymes in a PHB synthesis pathway that catalyze the condensation of two acetyl-CoA molecules to acetoacetyl-CoA and reduction of acetoacetyl-CoA to 3-hydroxybutyryl-CoA, respectively (see FIG. 1). β-ketothiolase is an enzyme that initiates biosynthesis of PHB in most bacteria. A C1 metabolizing organism may naturally possess β-ketothiolase and acetoacetyl coenzyme A reductase as part of an endogenous PHB synthesis pathway. Alternatively, a C1 metabolizing organism may be genetically modified with exogenous nucleic acids encoding β-ketothiolase and acetoacetyl coenzyme A reductase. These enzymes allow a C1 metabolizing organism to produce 3-hydroxybutyryl-CoA, a precursor of propylene in an engineered biosynthetic pathway via crotonyl-CoA and crotonic acid as disclosed herein (i.e., 3-hydroxybutyrl-CoA is substrate of crotonase) (see FIG. 1). Exogenous nucleic acids encoding β-ketothiolase and acetoacetyl coenzyme A reductase are expressed in a sufficient amount to produce propylene. In a specific embodiment, β-ketothiolase is encoded by phaA or phbA. In another specific embodiment, acetoacetyl coenzyme A reductase is encoded by phaB, hbd, or phbB. Exemplary β-ketothiolase and acetoacetyl coenzyme A reductase amino acid sequences are provided in Tables 2 and 3, respectively.

TABLE 2

Exemplary β-ketothiolase amino acid sequences

| Genbank Accession # | Gene Name/ Organism | Amino Acid Sequence (SEQ ID NO: #) |
|---|---|---|
| gi\|52209583 | acetyl-CoA acetyltransferase [*Burkholderia pseudomallei* K96243] | MTDVVIVSAARTAVGKFGGSLAKIAAPELGASVIRAVLERAGVKPEQVSEVILGQVLTAGS GQNPARQALIAAGLPNAVPGMTINKVCGSGLKAVMLAANAVVAGDAEIVVAGGQEN MSAAPHVLPGSRDGFRMGDAKLVDSMIVDGLWDVYNKYHMGITAENVAKEYGITREA QDQFAALSQNKAEAAQKAGRFDDEIVPIEIPQRKGEPLRFATDEFVRHGVTAESLASLKP AFAKEGTVTAANASGINDGAAAVLVMSAKKAEALGLEPLARIKAYANAGVDPSVMGM GPVPASRRCLERAGWSVGDLDLMEINEAFAAQALAVHKQMGWDTSKVNVNGGAIAIG HPIGASGCRILVTLLHEMLKRDAKRGLASLCIGGGMGVALALERP (SEQ ID NO: 77) |
| gi\|296445575 | acetyl-CoA acetyltransferase [*Methylosinus trichosporium* OB3b] | MTTEIVIVSAARTAVGSFNGAFGATPAHELGAVAVKAAIERAGLAPADIDEVILGQVLGA AQGQNPARQAAIKAGVPQEKTAFGINQVCGSGLRAVALAAQQ1QAGDASVIVAGGQES MSLSQHSAHMRAGTKMGDVKFVDTMIVDGLTDAFNNYHMGITAENVAAKWQ1SRAE QDAFAVASQNKAEAAQKAGKFKDEIVPFTVSTRKGDVIVDQDEYIKHGVTLEGVAKLKP AFTKEGTVTAANASGLNDGAAALVVMSAAEAARRGLTPLARIASWATAGVDPSVMGS GPIPASRKALEKAGWKIGDLDLVEANEAFAAQALAVNKDLGWDPAIVNVNGGAIAIGHP IGASGARVLTTLLYELARRGGKRGLATLCIGGGMGVALTIER (SEQ ID NO: 78) |

TABLE 2-continued

Exemplary β-ketothiolase amino acid sequences

| Genbank Accession # | Gene Name/ Organism | Amino Acid Sequence (SEQ ID NO: #) |
|---|---|---|
| gi\|296444966 | acetyl-CoA acetyltransferase [Methylosinus trichosporium OB3b] | MSAVDPIVIVGAARTPIGALLGELKNATAPQLGAAAIRAATERAGLAPERVDDVLMGCVL SAGLGQAPARQAALGAGLGATTTGCVTINKMCGSGMKALMLAHDQLLAGSSRAIVAGG MESMSNAPYLLGRARVGRYRMGHGRLIDHMFLDGLEDAYDEGKLMGAFAEDCATTHQF TREKQDDYATASLRRAQQAAASGAFDWETTPVATHDRKTSATVTRDELPASAKIENIASL KPAFRDGGTVTAANSSAISDGAAALALMRRSEAERASLAPLAIVRAHATHAGPPHLFPIA PIGAIAKLCERAGWPLTSVDLFEINEAFAVVVLAAMRELYLPHEKVNVHGGACALGHPIG ASGARIVVTLLAALRKYDLRRGVAALCIGGGEATAMAIETIV (SEQ ID NO: 79) |
| gi\|296445504 | acetyl-CoA acetyltransferase [Methylosinus trichosporium OB3b] | MPEAYIYDAVRTPRGRGKPNGSLHEVSSLGLAVAALSALKQRNRLDGAPVDDVILGCVD PVGEAGGDIARAAAIASGFGYEVPGVQINRFCASGLDAVNFAAAQIMSGQHELTIGGGV ESMSRVGIGASGGAWPADPAIAIPSYFMPQGVSADLIATKYGFSRNDVDAYAMQSQQR AARAWEEQRFARSVTPVKDVNGLTILDHDEHMRPSTDMQSLGALKPAFAFLAEQAGFD AVAIQAHPDVEKINYVHHAGNSSGIVDGAAAVLLGSKEAGEKAGLTPRARIRAFANIGSE PALMLTGPVDVTKKLLAKAGMTFGDIDLVEVNEAFAAVVLRFLQAFSLDDSKVNVGGA IALGHPLGATGAMLVGTALDELERSGKGVALVTLCIGAGMGTATIIERV (SEQ ID NO: 80) |
| gi\|23502628 | phbA-1 gene product [Brucella suis 1330] | MSDPKSIVIASAARTAVGAFNGAFANVPAHELGAVAIKAALERAGVDAADVDEVILGQV LTAGEGQNPARQAAMGAGCPKETTAFAINQLCGSGLRAVALGMQQIVSGDAKIIVAGG QESMSMAPHCAYLRSGVKMGDFKMIDTMLKDGLTDAFHGYHMGITAENIARQWQLS RSEQDEFALASQHKAEAAQKAGRFDEEIVPFTVKARKGDVVVSADEYIRPGTTMEVLAKL KPAFDKEGTVTAGNASGINDGAAAVVLMDAGEAARRGVKPLARIVSWATAGVDPSIM GTGPIPATRKALEKAGWSVGDLDLVEANEAFAAQSCAVVRDLGLNPEIVNVNGGAIAIG HPIGASGARVLTTLLYEMERRDAKRGLATLCIGGGMGVALCVERD (SEQ ID NO: 81) |
| gi\|260682683 | acetyl-CoA acetyltransferase [Clostridium difficile CD196] | MGVMNMREVVIASAARTAVGSFGGAFKSVSAVELGVTAAKEAIKRANITPDMIDESLLG GVLTAGLGQNIARQIALGAGIPVEKPAMTINIVCGSGLRSVSMASQLIALGDADIMLVGG AENMSMSPYLVPSARYGARMGDAAFVDSMIKDGLSDIFNNYHMGITAENIAEQWNIT REEQDELALASQNKAEKAQAEGKFDEEIVPVVIKGRKGDTVVDKDEYIKPGTTMEKLAKL RPAFKKDGTVTAGNASGINDGAAMLVVMAKEKAEELGIEPLATIVSYGTAGVDPKIMGY GPVPATKKALEAANMTIEDIDLVEANEAFAAQSVAVIRDLNIDMNKVNVNGGAIAIGHPI GCSGARILTTLLYEMKRRDAKTGLATLCIGGGMGTTLIVKR (SEQ ID NO: 82) |
| gi\|147904014 | acetyl-CoA acetyltransferase 2 [Xenopus laevis] | MNSGEETVVIISAARTPIGSFNGALSTLPAHTLGSTVIKEVLKRATIKPEEVSEVIFGQVLTA GAGQNPARQASVAAGVPYSIPAWSCQMICGSGLKAVSLGAQSIKTGEADIVVAGGMEN MSQAPHLVHMRAGVKAGDVSLQDSIICDGLNDAFYKYHMGITAENVAKQWQITREEQ DQLAVQSQNRTEAAQKAGYFDKEIVPVSVPSRKGPVEVKVDEFPRHGSNVEAMSKLKPY FLKDGSGTVTPANASGINDGAAAVVLIKESEARRGLTPMARIVASAQAGLDPSIMGVG PIAAIRKAVEKAGWSLDDIDLFEINEAFAAQALAVVKDLGLNPEKVNCQGGAVALGHPLG MSGCRILVTLLYALERTGGKKGVAALCIGGGMGIAMCVERTS (SEQ ID NO: 83) |
| gi\|358447737 | acetyl-CoA acetyltransferase [Marinobacter manganoxydans Mnl7-9] | MRDVVIVAARRTAIGTFGGGLSSLSADQLGTAVIKALMEETGVAGDQINEVVLGQVLTA GVGQNPARQSAINAGIPASVPAMTINKVCGSGLKAVHMAVQAIRCGDAEMMIAGGQE SMSQAPHVLPNSRNGQRMGNWSMVDTMIKDGLWDAFNDYHMGITAENIVEKYGISR DEQDEFAAASQQKAAAAREAGYFDGQIVPVSIPQRKGDPIVVDRDEGPRDGVTAEGLG KLRAAFKKDGTVTAGNASSLNDGAAAVMVCSAEKAKELGLTPIATIKAYANAGVDPTIM GTGPIPASQRCLKLAGWSTEDLDLVEANEAFAAQAISVNRDMGWDTGKVNVNGGAIAL GHPIGASGCRILVSLLHEMVRRDVHKGLATLCIGGGMGVALAVER (SEQ ID NO: 84) |
| gi\|294011684 | acetyl-CoA C-acetyltransferase [Sphingobium japonicum UT26S] | MPLSDIVITAAKRTAVGGFMGAFGSTPAHELGRTAILAALAQAGVAPEEVDEVILGQVLT AGQGQNPARQAAVNAGIPVERTAIGVNQLCGSGLRAVALAAQAIRAGDARIMVAGGQ ESMSLAPHAQYLRGGAKMGPISLVDTMTHDGLTDAFNNYHMGITAENLAEKYQISREA QDVFSVGSQNKAEEAARASGRFKDEIAPVTVKGRKGDTIVDTDEYIRAGATLEAMQSLRP AFRKDGTVTAANASGINDGAAALVLMSAEEEAAKRDALVLARIASFATCGVDPSIMGIGP APASRQALAKAGWSLADLDLIEANEAFAAQALAVGQELGWDAEKVNVNGGAIAIGHPI GASGARVLTTLIYEMQKRDAKKGLATLCIGGGMGVAMCIER (SEQ ID NO: 85) |
| gi\|212696567 | hypothetical protein ANHYDRO_ 01105 [Anaerococcus hydrogenalis DSM7454] | MTRKVVIASAARTPVGSFGGALKSQSAADLGIVAAKAAIERAGIKPEDIDETVLGCVLQAG LGQNVARQISLGAGIPETTPAMTINKVCGSGLRTVSLAAQMILAGDVDVVLAGGAESMS NAPFLLNEARWGARMGNKKLVDEMITDGLWDVYNDYHMGVTAENVAEKYGITREMQ DDLAAVSQQRASKARAEGRFKDEIAPVEIKDRKGNVTVVEDDEYIRDGVTQEGISKLRPA FIKDGTVTAANASGINDGAACLVVMSEEKAKELGVKPLATIVSYASAGVDPKVMGTGPIP SSKKALEKAGWKVEDLDLVESNEAFAAQSYAVRNEMGFDPEKTNVNGGAIAIGHPIGGS GARILTTLLFEMQKRDSKKGLATLCIGGGMGTALVVER (SEQ ID NO: 86) |
| gi\|351728760 | acetyl-CoA acetyltransferase [Acidovorax radicis N35] | MEDIVIVSAARTAVGKFGGALAKTPATELGAIVIREAIARAGLSSDQIGEVIMGQVLAAGV GQNPARQASMKAGVAKETPALTINAVCGSGLKAVMLAAQAVAWGDSEIVVAGGQES MSLAPHVLPGSRDGQRMGDWKLIDTMIVDGLWDVYNQYHMGITAENVAKAHGITRE MQDALALGSQQKAAAAQDAGKFVDEIVGVSLAQKKGDPILFNADEYLNRKTNAEALAG LRPAFDKAGSVTAGNASGLNDGAAAVVVMSAKKAAALGLKPLARIAAFGTSGLDPATM GMGPVPASRKALQRAGWNAADVDLFELNEAFAAQACAVNKELAIDPAKVNVNGGAIA IGHPIGASGCRILVTLLHEMQRRDAKKGLAALCIGGGMGVSLAER (SEQ ID NO: 87) |

TABLE 2-continued

Exemplary β-ketothiolase amino acid sequences

| Genbank Accession # | Gene Name/ Organism | Amino Acid Sequence (SEQ ID NO: #) |
|---|---|---|
| gi\|295687835 | acetyl-CoA acetyltransferase [*Caulobacter segnis* ATCC 21756] | MSDVVIVSAARTPVGSFNGALSSLPASELGRVAIEAAISRAGLQPSDVDEVILGQVLQAG AGQGPARQASVKAGIPVESPAWSLNQLCGSGLRAVALAAQQIAAGDAAVVVAGGQES MSQAPHAQNLRGGQKMGDLSFVDTMIKDGLWDAFHGYHMGQTAENIASRWQITRA DQDAFAVASQNKEAAQKAGKFDAEIAPVTIKGRKGDTVVDKDEYIRHGVTLESISGLKP AFTKEGSVTAANASGLNDGAAALVLMSAEEAQKRGLKPLARIASWANAGVEPEIMGTG PIPASKKALEKAGWTVADLDLVESNEAFAAQSLCVVRELGLDPAKVNVNGGAIAIGHPIG ASGARVLTTLLHEMKRSGAQKGLATLCIGGGMGVAMCVEAV (SEQ ID NO: 88) |
| gi\|374996374 | unnamed protein product [*Desulfosporosinus orientis* DSM 765] | MRDVVIVSAVRTPVGSFCGALGQIPAAELGAIAVKEAINRAGITPEQVDEVILGNVLQAG LGQNPARQASIKAGIPQEVPSWTLNKVCGSGLKTVVCAAQAIMTGDADIVVAGGMEN MSLAPYVLTKARTGYRMGNDTVIDSMINDGLTDAFNNYHMGITAENIAEQFNISREEQD RYSVRSQNRAEAAIIAGKFNEEIVPVSIPQRKGDPVVVSQDEFPRFGATYEAIAKLRPAFKK DGTVTAANASGINDGAAAIVVMAKEKAEELGLTPLATIKSWASAGVDPKIMGTGPIPAS RKALEKAGLSIDDIDVVEANEAFASQTLSVAQGLNLDPEKTNVNGGAIALGHPVGASGTR ILVTLLHEMKRSNAHRGLATLCIGGGQGVALIVER (SEQ ID NO: 89) |
| gi\|330941564 | acetyl-CoA acetyltransferase [*Pseudomonas syringae* pv. pisi str. 1704B] | MHDVVIVAATRTAVGSFQGSLASVAAVDLGAAVIRQLLARTGVDGAQVDEVIMGQVLT AGAGQNPARQAAIKAGLPFSVPAMTLNKVCGSGLKALHLATQAIRCGDAEIIIAGGQEN MSLSNYVLPGARTGLRMGHASMVDTMITDGLWDAFNDYHMGITAENLAQQYDISREA QDEFAALSQQKALAAIEAGRFVDEITPILIPQRKGDPLSFATDEQPRAGTTAETLAKLKPAF KKDGTVTAGNASSLNDGAAAVMLMSAARAEQLGLPVLARIAAYANAGVDPAIMGIGPV SATRRCLNKAGWSLADLDLIEANEAFAAQSLSVGKELGLDPQKLNVNGGAIALGHPIGAS GCRVLVTLLHEMIRRDVKKGLATLCIGGGQGVALALER (SEQ ID NO: 90) |
| gi\|27375337 | atoB gene product [*Bradyrhizobium japonicum* USDA 110] | MPMSDDVVIVSAARTPVGSFNGAFATLPAHDLGAVAIKAALERGGIEPGRVSEVIMGQI LTAAQGQNPARQASIAAGIPVESPAWGVNQLCGSGLRTVALGYQALLNGDSEIVVAGG QESMSMAPHAQYLRGGVKMGALEFIDTMIKDGLWDAFNDYHMGITAENVARQWQI TRAQQDEFAVASQQKAEAAQKAGKFNDEIVPVTIKTRKGDVVVSADEYPRHGATLDAM AKLRPAFEKDGTVTAGSASGINDGAAAVVLMTAKQAAKEGKKPLARIVSWAQAGVDPK IMGSGPIPASRAALKKAGWNVGDLDLIEANEAFAAQACAVNKDLGWDTSKVNVNGGAI AIGHPVGASGARVLVTLLHEMQKRDSKKGLATLCIGGGMGIAMCLARD (SEQ ID NO: 91) |
| gi\|163738904 | Acetyl-CoA C-acetyltransferase [*Phaeobacter gallaeciensis* BS107] | MTNVVIASAARTAVGSFGGAFAKTPAHDLGAAVLQAVVERAGIDKSEVSETILGQVLTA AQGQNPARQAHINAGLPQESAAWSLNQVCGSGLRAVALAAQHIQLGDAAIVCAGGQE NMTLSPHAANLRAGHKMGDMSYIDTMIRDGLWDAFNGYHMGCTAENVAEKWQISR EMQDEFAVASQNKAEAAQKAGKFADEIAAFTVKTRKGDIIVDQDEYIRHGATIEAMQKL RPAFAKDGSVTAANASGNLDGAAATLLMSADDAEKRGIEPLARIASYATAGLDPSIMGV GPIYASRKALEKAGWSVDDLDLVEANEAFAAQACAVNKDMGWDPAIVNVNGGAIAIG HPIGASGCRVLNTLLFEMKRRDAKKGLATLCIGGGMGVAMCVERP (SEQ ID NO: 92) |
| gi\|7766963 | A Chain A, Unliganded Biosynthetic Thiolase From *Zoogloea Ramigera* | SIVIASAARTAVGSFNGAFANTPAHELGATVISAVLERAGVAAGEVNEVILGQVLPAGEG QNPARQAAMKAGVPQEATAWGMNQLCGSGLRAVALGMQQIATGDASIIVAGGMES MSMAPHCAHLRGGVKMGDFKMIDTMIKDGLTDAFYGYHMGTTAAENVAKQWQLSRD EQDAFAVASQNKAEAAAQKDGRFKDEIVPFIVKGRKGDITVDADEYIRHGATLDSMAKLR PAFDKEGTVTAGNASGLNDGAAAALLMSEAEASRRGIQPLGRIVSWATVGVDPKVMGT GPIPASRKALERAGWKIGDLDLVEANEAFAAQACAVNKDLGWDPSIVNVNGGAIAIGHP IGASGARILNTLLFEMKRRGARKGLATLCIGGGMGVAMCIESL (SEQ ID NO: 93) |
| gi\|218892041 | atoB gene product [*Pseudomonas aeruginosa* LESB58] | MQDVVIVAATRTAVGSFQGSLAGIPAPELGAAVIRRLLEQTGLDAGQVDEVILGQVLTA GSGQNPARQAAILKAGLPVGVPAMTLNKVCGSGLKALHLGAQAIRCGDAEVIVAGGQEN MSLAPYVMPGARTGLRMGHAKLVDSMIEDGLWDAFNDYHMGITAENLAEKYGLSREE QDAFAAASQQKAIAAIEGGRFRDEITPIQVPQRKGEPLSFDTDEQPRAGTTVEALAKLKPA AFRKDGSVTAGNASSLNDGAAAVLLMSAAKAKALGLPVLARIASYASAGVDPAIMGIGP VSATRRALDKAGWSLEQLDLIEANEAFAAQSLAVGRELGWDAARVNVNGGAIALGHPI GASGCRVLVTLLHEMIRRDAKKGLATLCIGGGQGVALTLARD (SEQ ID NO: 94) |
| gi\|374292777 | phbA3 gene product [*Azospirillum lipoferum* 4B] | MTEVVIAGAARTPIGSFNGALSAVPAHVLGEVAIREALARAKTDAAEVDEVILGQILTAG QGQNPARQAAVNAGIPVEATAMGINQLCGSGLRAVALGYQAIKNGDADVLVVGGQES MSMAPHVMHLRNGTKMGSAELLDTMLRDGLTDAFHGYHMGTTAENVAQKWQLTRE EQDAFAAASQQKAEAAAQKAGKFRFKDEIVPVTIKGRKGDVVVSDDEYPKHGTTPESLAKLR PAFSKDGTVTAGNASGINDGAAAVLMTAEENAAKRGVTPLARIVSWATAGVDPAIMGT GPIPASRKALEKAGWTVDDLDLIEANEAFAAQALSVNKDLGWDTSKVNVNGGAIALGH PVGASGARVLTTLLYEMQKRDAKKGLATLCIGGGMGIALCVQRD (SEQ ID NO: 95) |
| gi\|17546351 | phbA gene product [*Ralstonia solanacearum* GM11000] | MTDVVIVSAVRTAVGKFGGSLAKIPAPELGAAVIREALSRAKVAPDQVSEVIMGQVLTAG SGQNPARQALIKAGLPDMVPGMTINKVCGSGLKAVMLAANAIVAGDADIVVAGGQEN MSAAPHVLPGSRDGFRMGDTKLIDSMIVDGLWDVYNQYHMGITAENVAKQYGITREA QDAFAVASQNKAEAAQKSGRFNDEIVPILIPQRKGDPIAFAQDEFVRHGATLESMTGLKP AFDKAGTVTAANASGLNDGGAAVVVMSAARAKELGLTPLATIRAYANAGVDPKVMGM GPVPASKRCLSRAGWSVGDLDLMEINEAFAAQALAVHQQMGWDTAKVNVNGGAIAI GHPIGASGCRILVTLLHEMQKRDAKKGLASLCIGGGMGVALAVERP (SEQ ID NO: 96) |

TABLE 2-continued

Exemplary β-ketothiolase amino acid sequences

| Genbank Accession # | Gene Name/ Organism | Amino Acid Sequence (SEQ ID NO: #) |
|---|---|---|
| gi\|221198056 | Acetyl-CoA acetyltransferase [Burkholderia multivorans CGD2M] | MTDVVIVSAARTAVGKFGGSLAKVAAPELGATVIRAVLERAGVKPEQVSEVIMGQVLTA GSGQNPARQSLIKAGLPSAVPGMTINKVCGSGLKAVMLAANAIVAGDAEIVVAGGQEN MSAAPHVLPGSRDGFRMGDAKLVDTMIVDGLWDVYNQYHMGITAENVAKEYGITREE QDAFAALSQNKAEAAQKAGRFNDEIVPVSIPQRKGEPLQFATDEFVRHGVTAESLAGLK PAFAKDGTVTAANASGINDGAAAVLVMSAQKAQALGLTPLARIKAYANAGVDPSVMG MGPVPASRRCLERAGWTPGDLDLMEINEAFAAQALAVHKQMGWDTSKVNVNGGAIA IGHPIGASGCRILVTLLHEMVKRDAKRGLASLCIGGGMGVALAVERP (SEQ ID NO: 97) |
| gi\|163852882 | acetyl-CoA acetyltransferase [Methylobacterium extorquens PA1] | MAASEDIVIVGAARTPVGSFAGAFGSVPAHELGATAIKAALERAGVSPDDVDEVIFGQVL TAAAGQNPARQAAIAAGIPEKATAWGLNQVCGSGLRTVAVGMQQIANGDAKVIVAGG QESMSLSPHAQYLRGGQKMGDLKLVDTMIKDGLWDAFNGYHMGQTAENVAQAFQL TREQQDQFAVRSQNKAEAARKEGRFKEEIVPVTVKGRKGDTVVDTDEYIRDGATVEAM AKLKPAFAKDGTVTAANASGLNDGAAALVLMSASEAERRGITPLARIVSWATAGVDPKV MGTGPIPASRKALEKAGWKPADLDLIEANEAFAAQALAVNKDMGWDDEKVNVNGGAI AIGHPIGASGARVLITLLHELKRRDAKKGLATLCIGGGMGVAMCVERV (SEQ ID NO: 98) |
| gi\|169344179 | acetyl-CoA acetyltransferase [Clostridium perfringens str. JGS1495] | MREVVIASAVRTALGSFGGSLKDVPAVDLGALVIKEALNKAGVKPECVDEVLMGNVIQA GLGQNPARQAAVKAGLPVEIPSMTINKVCGSGLRCVALAAQMIKAGDADVIVAGGME NMSQGPYVLRTARFGQRMGDGKMVDAMVNDALTDAFNGYHMGITAENIAEQWGLT REMQDEFAANSQIKAEAAIKAGKFKDEIVPVVIPQRKGDPIVFDTDEFPRFGTTAEKLAKL CRPAFKKDGTVTAGNASGINDGAAALVVMSAEKAKELGVTPICKIVSYGSKGLDPSIMGYG PFYATKKALEGTGLKVEDLDLIEANEAFAAQSLAVAKDLEFDMSKVNVNGGAIALGHPVG ASGARILVTLLHEMMKRDAKRGLATLCIGGGMGTALIVER (SEQ ID NO: 99) |
| gi\|345869447 | acetyl-CoA acetyltransferase [Thiorhodococcus drewsii AZ1] | MSENIVIVDAGRTAIGTFGGSLSSLPATELGTTVLKALLARTGIAPDQIDEVILGQVLTAGV GQNPARQTTLKAGLPHAVPAMTINKVCGSGLKAVHLAMQAVACGDADIVIAGGQECM SQSSHVLPRSRDGQRMGDWKMVDTMIVDGLWDAFNQYHMGVTAENIAKQFGFTRE AQDTFAAESQQKAEAAIKAGRFKDEIVPVSIPQRKGDPLVVDTDEFPRAGTTAAGLGKLR PAFDKEGTVTAGNASGINDGAAMVVVMKESKAKELGLKPMARIVAFASAGVDPAIMGT GPIPASTKCLEKAGWTPADLDLIEANEAFAAQAMSVNKEMGWDLSKVNVNGGAISLGH PIGASGARVLVTLLHEMQHRDAKKGLATLCIGGGQGVALAVERL (SEQ ID NO: 100) |

TABLE 3

Exemplary acetoacetyl coenzyme A reductase amino acid sequences

| Genbank Accession # | Gene Name/ Organism | Amino Acid Sequence (SEQ ID NO: #) |
|---|---|---|
| gi\|52209584 | acetoacetyl- CoA reductase [Burkholderia pseudomallei K96243] | MSQRIAYVTGGMGGIGTSICQRLHKDGFRVVAGCGPNSPRRVKWLEDQKALGFDFYAS EGNVGDWDSTKQAFDKVKAEVGEIDVLVNNAGITRDVVFRKMTREDWQAVIDTNLTSL FNVTKQVIDGMVERGWGRIINISSVNGQKGQFGQTNYSTAKAGIHGFTMSLAQEVATK GVTVNTVSPGYIGTDMVKAIRPDVLEKIVATIPVRRLGSPDEIGSIVAWLASEESGFSTGAD FSLNGGLHMG (SEQ ID NO: 101) |
| gi\|296445576 | acetoacetyl- CoA reductase [Methylosinus trichosporium OB3b] | MGRTAVVTGGTRGIGEAISKALKAAGYNVAATYAGNDEAANKFKDATGIPVYKFDVSDY DACAAALAAIETDLGPVDVLVNNAGITKDRLFHKMELAQWRAVIDTNLNSLFNVTRPVI NGMRDRGFGRIIVISSINGQKGQAGQTNYSASKAGDIGFVKALAQESAAKGITVNAIAPG YIATEMVKAVPQEVLDKHIIPHIAVGRLGEPEEIARAVVFLASDEAGFITGSTLTINGGQYLT (SEQ ID NO: 102) |
| GI\|206559226 | putative Acetoacetyl- CoA reductase [Burkholderia cenocepacia J2315] | MTKRIAVVTGGMGGLGEAVSIRLNDAGHRVVVTYSPNNTGADRWLTEMHAAGREFHA YPVDVADHDSCQQCIEKIVRDVGPVDILVNNAGITRDMTLRKLDKVNWDAVIRTNLDSV FNMTKPVCDGMVERGWGRIVNISSVNGSKGSVGQTNYAAAKAGMHGFTKSLALEIAR KGVTVNTVSPGYLATKMVTAIPQDILDTKILPQIPAGRLGKPEEVAALVAYLCSEEAGFVT GSNIAINGGQHMH (SEQ ID NO: 103) |
| gi\|340047249 | acetoacetyl- CoA reductase family protein [Vibrio cholerae HE48] | MRKIALITGSKGGIGSAISTQLVSEGYRVIATYYTGNYQCALDWFNEKQFTEDQVRLLELD VTNTEECAERLAKLLEEEGTIDVVVNNAGITRDSVFKKMPHQAWKEVIDTNLNSVFNVT QPLFAAMCEKGFGRIINISSVNGLKGQFGQTNYSAAKAGMIGFSKALAAEGARYGVTVN VIAPGYTLTPMVEQMRAEVLQSIVDQVPMKRLAKPEEIANAVSYLASDAAYITGETLSVN GGLYMR (SEQ ID NO: 104) |

TABLE 3-continued

Exemplary acetoacetyl coenzyme A reductase amino acid sequences

| Genbank Accession # | Gene Name/ Organism | Amino Acid Sequence (SEQ ID NO: #) |
|---|---|---|
| gi\|356882300 | acetoacetyl-coA reductase [*Azospirillum brasilense* Sp245] | MARVAVVTGGTRGIGEAISVALKNAGYVVAANYAGNDEKAKEFSARTGIAVYKFDVSDF DAVKDGIAKISAELGPVDVVVNNAGITRDGVIHRMTPQQWNDVIATNLTSCFNLCRNVI DGMRERGFGRIVNIGSVNGQAGQYGQVNYAAAKSGIHGFTKALAQEGAAKGVTVNAI APGYIDTDMVRAVPPNVLEKIVARIPVGRLGKAEEIARGVLFLVGDDAGFITGSTLSINGG QHMY (SEQ ID NO: 105) |
| gi\|356881146 | acetoacetyl-coA reductase [*Azospirillum brasilense* Sp245] | MSQKIALVTGAMGGLGTAICQALAKDGYIVAANCLPNFEPAAAWLGQQEALGFKFYVA EGDVSDFESCKAMVAKIEADLGPVDILVNNAGITRDKFFAKMEKAQWDAVIATNLSSLF NVTQQVSAKMAERGWGRIINISSVNGVKGQAGQTNYSAAKAGVIGFTKALAAELATKG VTVNAIAPGYIGTDMVMAIREDIRQAITDSVPMKRLGRPDEIGGAVSYLASEIAGYVTGST LNINGGLNYQ (SEQ ID NO: 106) |
| gi\|119897313 | phbB1 gene product [*Azoarcus* sp. BH72] | MSRVALVTGGMGGLGEAICIKLAALGYRVVTTYSPGNSKAAEWLQAMNNMGYGFRGY PCDVSDFDSCKACIAQVTEEVGPIDVLVNNAGITRDMTFKKMTKADWDAVISTNLDSVF NMTKQVMDGMVERKWGRVINVSSVNGQKGAFGQTNYSAAKAGMHGFTKALALEVA RSGVTVNTISPGYIGTKMVMAIPQEILESKILPQIPVSRLGKPEEIAGLVAYLSSDEAAFVTG ANISINGGQHMF (SEQ ID NO: 107) |
| gi\|194289469 | acetyacetyl-CoA reductase [*Cupriavidus taiwanensis* LMG_19424] | MTQRIAYVTGGMGGIGTAICQRLARDGFRVVAGCGPNSPRREKWLEQQKALGFDFVAS EGNVADWDSTKAAFDKVKAEVGEVDVLINNAGITRDVVFRKMTRADWDAVIDTNLTSL FNVTKQVIDGMADRGWGRIVNISSVNGQKGQFGQTNYSTAKAGLHGFTMALAQEVAT KGVTVNTVSPGYIATDMVKAIRQDVLDKIVGTIPVKRLGEPEEIASICAWLASEESGFSTGA DFSLNGGLHMG (SEQ ID NO: 108) |
| gi\|307609363 | hypothetical protein LPW_06391 [*Legionella pneumophila* 130b] | MDKMIAIVTGGTGGIGSAISQRLADSYQVVACYYKDGRHEEAKKWQDEQKQLGYDIDIV YGDIAQYSDCEKITSLVMERYGRIDVLVNNAGITKHDCSLRKMTPQQWQQVLDANLTSVF NMTRNVVPVMLERGYGRIISISSINGRKGQFGQCNYASTKAALFGFTKSLALEVASKGITV NTVSPGYIETPMLAALKEDVLNSIISSIPVGRLGYPKEIADAVAFLASPDSGFITGANLDVN GGQYM (SEQ ID NO: 109) |
| gi\|352104657 | acetoacetyl-CoA reductase [*Halomonas* sp. HAL1] | MTNQAPVAWVTGGTGGIGTAICRSLADAGYLVVAGYHNPDKAKTWLETQRADGYNNI ELSGVDLSDHNACLEGAREIHDKYGPISVLVNCAGITRDGTMKKMSYEQWYEVLDTNLN SVFNTCRSVIEMMLENGYGRIINISSINGRKGQFGQVNYAAAKAGMHGLTMSLAQETAT KGITVNTVSPGYIATDMIMNIPEKVREAIRETIPVKRYGTPEEIGRLVTFLADKESGFITGAN IDINGGQFMG (SEQ ID NO: 110) |
| gi\|289671313 | acetoacetyl-CoA reductase [*Xanthomonas campestris* pv. musacearum NCPPB 4381] | MTSRVALVTGGTGGIGTAICKRLADQGHRVASNFRNEEKARDWQQRMQAQGYAFALF RGDVASSEHARALVEEVEASLGPIEVLVNNAGITDTTFHRMTAEQWHEVINTNLNSVF NVTRPVIEGMRKRGWGRVIQISSINGLKGQYGQANYAAAKAGMHGFTISLARENAAFG VTVNTVSPGYVATDMVMAVPEEVRAKIVADIPTGRLGRPEEIAYAVAFLVAEEEAAWITGS NLDINGGHHMGW (SEQ ID NO: 111) |
| gi\|330824321 | acetoacetyl-CoA reductase [*Alicycliphilus denitrificans* K601] | MNTTQRTALVTGGNRGLGAAIARALHDAGHRVIVTHTPGNTTIGQWQQAQATQGYKF AAYGVDVSNYESTQELARRIHADGHRIDILVNNAGITRDATLRKLDKAGWDAVLRTNLDS MFNVTKPFIDPMVERGWGRIVNISSINGSKGQFGQTNYSAAKAGVHGFTKALAQEVAR KGVTVNTVSPGYLATEMVMAVREDMRQKIIDAIPVGRLGQPDEIAALVAFIASEAAAFM TGSNVAMNGGQHMY (SEQ ID NO: 112) |
| gi\|146278501 | acetoacetyl-CoA reductase [*Rhodobacter sphaeroides* ATCC 17025] | MSKVALVTGGSRGIGAAISLALKNAGYTVAANYAGNDEAAQKFTAETGIKTYKWSVADY DACAEGIARVEAELGPVDVLVNNAGITRDSMFHKMTREQWKEVIDTNLSGLFNMTHPV WSGMRDRKFGRIINISSINGQKGQAGQANYSAAKAGDLGFTKALAQEGARAGITVNAIC PGYIGTEMVRAIDEKVLNERIIPQIPVGRLGEPEEIARCVVFLASDDAGFITGSTITANGGQ YFT (SEQ ID NO: 113) |
| gi\|67458545 | phbB gene product [*Rickettsia felis* URRWXCal2] | MSEIAIVTGGTRGIGKATALELKNKGLTVVANFFSNYDAAKEMEEKYGIKTKCWNVADFE ECRQAVKEIEEEFKKPVSILVNNAGITKDKMLHRMSHQDWNDVINVNLNSCFNMSSSV MEQMRNQDYGRIVNISSINAQAGQVGQTNYSAAKAGIIGFTKALARETASKNITVNCIAP GYIATEMVGAVPEDVLAKIINSIPKKRLGQPEEIARAVAFLVDENAGFITGETISINGGHN MI (SEQ ID NO: 114) |
| gi\|94497737 | Acetoacetyl-CoA reductase [*Sphingomonas* sp. SKA58] | MSRVAIVTGGTRGIGEAISLALKEMGYAVAANYAGNDEKAKAFTDKTGIAAFKWDVGD HQACLDGCAQVAEVLGPVDIVVNNAGITRDGVLAKMSFDDWNEVMRINLGGCFNMA KACFGGMRERGWGRIVNIGSINGQAGQYGQVNYAAAKSGIHGFTKALAQEGAKYGVT VNAIAPGYIDTDMVAAVPAPVLEKIVAKIPVGRLGQAHEIARGVAFFCSEDGGFVTGSTLS INGGQHMY (SEQ ID NO: 115) |

TABLE 3-continued

Exemplary acetoacetyl coenzyme A reductase amino acid sequences

| Genbank Accession # | Gene Name/ Organism | Amino Acid Sequence (SEQ ID NO: #) |
|---|---|---|
| gi\|28901060 | acetoacetyl-CoA reductase [*Vibrio parahaemolyticus* RIMD 2210633] | MKKVALITGSKGGIGSAISSQLVNDGYRVIATYFTGNYECALEWFNSKGFTKDQVRLFELD VTNTAECAEKLAQLLEEEGTIDVVVNNAGITRDGVFKKMTAQAWNDVINTNLNSLFNVT QPLFAAMCEKGGGRVINISSVNGLKGQFGQANYSAAKAGMIGFSKALAYEGARSGVTV NVIAPGYTGTPMVEQMKPEVLESITNQIPMKRLATPEEIAASVSFLVSDAGAYITGETLSV NGGLYMH (SEQ ID NO: 116) |
| gi\|161522918 | acetoacetyl-CoA reductase [*Burkholderia multivorans* ATCC 17616] | MSAKRVAFVTGGMGGLGAAISRRLHDVGMTVAVSHTEGNDHVATWLTHEREAGRTF HAFEVDVADYDSCRQCASRVLAEFGRVDVLVNNAGITHDATFVKMTKSMWDAVLRTN LDGMFNMTKPFVPGMIEGGFGRIVNIGSVNGSRGAYGQTNYAAAKAGIHGFTKALALEL ARHGVTVNTVAPGYLATAMLETVPKEVLDTKILPQIPVGRLGNPDEIAALVAFLCSDAAAF ATGAEFDVNGGMHMK (SEQ ID NO: 117) |
| gi\|161524658 | acetyacetyl-CoA reductase [*Burkholderia multivorans* ATCC 17616] | MSQRIAYVTGGMGGIGTSICQRLSKDGFKVVAGCGPNSPRRVKWLEEQKALGFDFIASE GNVGDWDSTKAAFDKVKAEVGEIDVLVNNAGITRDVVFRKMTHEDWTAVIDTNLTSLF NVTKQVIDGMVERGWGRIINISSVNGQKGQFGQTNYSTAKAGIHGFTMALAQEVATKG VTVNTVSPGYIGTDMVKAIRPDVLEKIVATIPVRRLGTPEEIGSIVAWLASNDSGFATGAD FSLNGGLHMG (SEQ ID NO: 118) |
| gi\|351728759 | 3-ketoacyl-(acyl-carrier-protein) reductase [*Acidovorax radicis* N35] | MSQKVAYVTGGMGGIGTAICQRLHKEGFKVIAGCGPTRDHAKWLAEQKALGYTFYASV GNVGDWDSTVEAFGKTKAEHGTIDVLVNNAGITRDRMFLKMSREDWDAVIETNLNSM FNVTKQVVADMVEKGWGRIVNISSVNGEKGQAGQTNYSAAKAGMHGFSMALAQELA TKGVTVNTVSPGYIGTDMVKAIRPDVLEKIVATVPVKRLGEPSEIASIIAWLASEEGGYATG ADFSVNGGLHMG (SEQ ID NO: 119) |
| gi\|240140211 | phaB gene product [*Methylobacterium extorquens* AM1] | MAQERVALVTGGTRGIGAAISKRLKDKGYKVAANYGGNDEAANAFKAETGIPVFKFDVG DLASCEAGIKAIEAELGPIDILVNNAGITRDGAFHKMTFEKWQAVIRTNLDSMFTCTRPLI EGMRSRNFGRIIIISSINGQKGQAGQTNYSAAKAGVIGFAKALAQESASKGVTVNVVAPG YIATEMVMAVPEDIRNKIISTIPTGRLGEADEIAHAVEYLASDEAGFVNGSTLTINGGQHF V (SEQ ID NO: 120) |
| gi\|148258780 | 3-oxoacyl-ACP reductase [*Bradyrhizobium sp.* BTAi1] | MARVALVTGGTRGIGAAISKALKAAGHKVAANYGGNDAAAEKFKSETEIPVYKWDVSSF DACAEGIKKVEAELGPVDILVNNAGITRDTAFHKMTLEQWSAVINTNLGSLFNMTRPVIE GMRARKFGRIINISSINGQKGQFGQVNYSAAKAGDIGFTKALALETAKAGITVNVICPGYI NTEMVQAVPKDVLEKAILPLIPVGRLGEPEEIARAVVFLAADEAGAITGSTLSINGGQYMA (SEQ ID NO: 121) |
| gi\|126728325 | Acetoacetyl-CoA reductase [*Sagittula stellata* E-37] | MARVALVTGGSRGIGEAISKALKAEGYTVAATYAGNDEKAAAFTADTGIKTYKWNVADY ESSKAGIAQVEADLGPIDVVVANAGITRDAPFHKMTPAQWNEVIDTNLTGVFNTVHPV WPGMRERKFGRIIVISSINGQKGQFAQVNYAATKAGDLGIVKSLAQEGARAGITANAICP GYIATEMVMAVPEKVRESIIGQIPAGRLGEPEEIARCVVFLASDDAGFINGSTISANGAQF FV (SEQ ID NO: 122) |
| gi\|15895965 | hbd gene product | MKKVCVIGAGTMGSGIAQAFAAKGFEVVLRDIKDEFVDRGLDFINKNLSKLVKKGKIEEA TKVEILTRISGTVDLNMAADCDLVIEAAVERMDIKKQIFADLDNICKPETILASNTSSLSITE VASATKRPDKVIGMHFFNPAPVMKLVEVIRGIATSQETFDAVKETSIAIGKDPVEVAEAPG FVVNRILIPMINEAVGILAEGIASVEDIDKAMKLGANHPMGPLELGDFIGLDICLAIMDVLY SETGDSKYRPHTLLKKYVRAGWLGRKSGKGFYDYSK (SEQ ID NO: 123) |

In certain embodiments, a non-naturally occurring C1 metabolizing organism according to any of the embodiments disclosed herein is a C1 metabolizing bacterium selected from *Methylosinus trichosporium* strain OB3b, *Methylococcus capsulatus* Bath strain, *Methylomonas methanica* 16A strain, *Methylosinus trichosporium* (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylobacterium organophilum* (ATCC 27,886), *Methylomonas* sp AJ-3670 (FERM P-2400), *Methylocella silvestris*, *Methylacidiphilum infernorum*, *Methylomicrobium alcaliphilum*, or *Methylibium petroleiphilum*.

In certain embodiments, a non-naturally occurring C1 metabolizing organism may be a syngas or CO utilizing bacterium that naturally possesses the ability to utilize syngas or CO, such as *Clostridium autoethanogenum*, *Clostridium ljungdahli*, *Clostridium ragsdalei*, *Clostridium carboxydivorans*, *Butyribacterium methylotrophicum*, *Clostridium Woodii*, *Clostridium neopropanologen Ralstonia eutropha*, or *Eurobacterium limosum*.

In certain embodiments, a non-naturally occurring C1 metabolizing organism may be a methylotrophic bacterium, such as *Methylobacterium extorquens*, *Methylobacterium radiotolerans*, *Methylobacterium populi*, *Methylobacterium chloromethanicum*, or *Methylobacterium nodulans*.

In another embodiment, the present disclosure provides non-naturally occurring microbial organisms that have been genetically modified with a novel metabolic pathway for producing propylene from a carbon substrate. More specifically, the non-naturally occurring microbial organisms include an exogenous nucleic acid encoding 4-oxalocrotonate decarboxylase and convert a carbon substrate to propylene. As described previously, 4-OD is used in a novel propylene biosynthetic pathway to catalyze decarboxylation of crotonic acid to propylene and $CO_2$ (see FIG. 1). Sources of 4-OD encoding nucleic acid molecules may include any species, prokaryotic or eukaryotic, where the encoded gene product is capable of catalyzing decarboxylation of crotonic acid to propylene and $CO_2$. Exemplary amino acid sequences of 4-OD are shown in FIG. 2.

In certain embodiments, the present disclosure provides a non-naturally occurring microbial organism containing an exogenous nucleic acid encoding a 4-oxalocrotonate decarboxylase, wherein the non-naturally occurring microbial organism is capable of converting a carbon substrate into propylene.

In certain embodiments, non-naturally occurring microbial organisms that include an exogenous nucleic acid encoding a 4-oxalocrotonate decarboxylase and convert a carbon substrate into propylene may further include an exogenous nucleic acid encoding crotonase, or further include an exogenous nucleic acid encoding a crotonase and an exogenous nucleic acid encoding a crotonyl thioesterase. Depending on the host microbial organism selected, a microbial organism may or may not have endogenous enzyme(s) that would participate with 4-OD in forming a biosynthetic propylene synthesis pathway. As described in detail previously, crotonase catalyzes the dehydration of 3-hydroxybutyryl-CoA to crotonyl-CoA. Crotonyl-CoA thioesterase catalyzes the conversion of crotonyl-CoA to crotonic acid. For example, if a host microbial organism selected is deficient in crotonase, then exogenous expression of crotonase can be included in the microbial organism. In another example, if a host microbial organism is deficient in crotonase and a thioesterase capable of converting crotonyl-CoA to crotonic acid, then exogenous expression of crotonase and crotonyl-CoA thioesterase can be included in the microbial organism. However, it is understood that exogenous expression of all of these enzymes of a propylene biosynthetic pathway (i.e., 4-OD, crotonase, and crotonyl-CoA thioesterase) may be included, even if the host microbial organism contains at least one of the propylene pathway enzymes (e.g., crotonase or crotonyl thioesterase). Expression of exogenous nucleic acids encoding enzymes of the propylene biosynthetic pathway disclosed herein is in a sufficient amount to produce propylene. Sources of crotonase and crotonyl-CoA thioesterase encoding nucleic acids may include any species, prokaryotic or eukaryotic, where the encoded gene products are capable of catalyzing dehydration of 3-hydroxybutyryl-CoA to crotonyl-CoA and conversion of crotonyl-CoA to crotonic acid, respectively. Exemplary amino acid sequences for crotonase and crotonyl-CoA thioesterase are shown in FIG. 4 and FIG. 3, respectively.

In a further embodiment, non-naturally occurring microbial organisms as described herein do not have a functional PHB synthase or a substantial amount of functional PHB synthase. As described in detail previously, by inhibiting or reducing PHB function in a microbial organism, propylene synthesis yields may be increased by funneling more 3-hydroxybutyryl-CoA into the propylene pathway via conversion to crotonyl-CoA and to crotonic acid and to propylene (see FIG. 1).

Additionally, if non-naturally occurring microbial organisms as described herein do not possess an endogenous PHB synthesis pathway, then non-naturally occurring microbial organisms may be genetically modified to include an exogenous nucleic acid encoding β-ketothiolase and an exogenous nucleic acid encoding acetoacetyl-CoA reductase to provide the capability of producing 3-hydroxybutyryl-CoA, substrate for the crotonase enzyme in the propylene synthesis pathway described herein. Non-naturally occurring microbial organisms that do possess an endogenous PHB synthesis pathway may also be genetically modified with an exogenous nucleic acid encoding β-ketothiolase and an exogenous nucleic acid encoding acetoacetyl-CoA reductase to increase expression of these enzymes. In a specific embodiment, β-ketothiolase is encoded by phaA or phbA. In another specific embodiment, acetoacetyl coenzyme A reductase is encoded by phaB or phbB. Exemplary β-ketothiolase and acetoacetyl coenzyme A reductase amino acid sequences are provided in Tables 2 and 3, respectively.

Nucleic acid sequences encoding for and amino acid sequences for proteins, protein domains and fragments thereof, for proteins described herein, such as 4-OD, crotonase, crotonyl thioesterase, acetoacetyl coenzyme A reductase, or β-ketothiolase, and domains thereof, that are described herein include natural and recombinantly engineered variants. These variants retain the function and biological activity (including enzymatic activities if applicable) associated with the parent (or wildtype) protein. These variants may have improved function and biological activity (e.g., higher enzymatic activity, improved specificity for substrate) than the parent (or wildtype protein). For example, a variant 4-OD enzyme may be engineered with reduced or eliminated decarboxylation activity on 4-oxalocrotonate, but retains or has increased decarboxylation activity on crotonic acid substrate. Conservative substitutions of amino acids are well known and may occur naturally in the polypeptide (e.g., naturally occurring genetic variants) or may be introduced when the polypeptide is recombinantly produced. Amino acid substitutions, deletions, and additions may be introduced into a polypeptide using well-known and routinely practiced mutagenesis methods (see, e.g., Sambrook et al. *Molecular Cloning: A Laboratory Manual*, 3d ed., Cold Spring Harbor Laboratory Press, NY 2001). Oligonucleotide-directed site-specific (or segment specific) mutagenesis procedures may be employed to provide an altered polynucleotide that has particular codons altered according to the substitution, deletion, or insertion desired. Deletion or truncation variants of proteins may also be constructed by using convenient restriction endonuclease sites adjacent to the desired deletion. Alternatively, random mutagenesis techniques, such as alanine scanning mutagenesis, error prone polymerase chain reaction mutagenesis, and oligonucleotide-directed mutagenesis may be used to prepare polypeptide variants (see, e.g., Sambrook et al., supra).

Differences between a wild type (or parent) nucleic acid or polypeptide and the variant thereof, may be determined by methods routinely practiced in the art to determine identity, which are designed to give the greatest match between the sequences tested. Methods to determine sequence identity can be applied from publicly available computer programs. Computer program methods to determine identity between two sequences include, for example, BLASTP, BLASTN (Altschul, S. F. et al., *J. Mol. Biol.* 215: 403-410 (1990), and FASTA (Pearson and Lipman Proc. Natl. Acad. Sci. USA 85; 2444-2448 (1988). The BLAST family of programs is publicly available from NCBI and other sources (*BLAST Manual*, Altschul, S., et al., NCBI NLM NIH Bethesda, Md.

Assays for determining whether a polypeptide variant folds into a conformation comparable to the non-variant polypeptide or fragment include, for example, the ability of the protein to react with mono- or polyclonal antibodies that are specific for native or unfolded epitopes, the retention of ligand-binding functions, the retention of enzymatic activity (if applicable), and the sensitivity or resistance of the mutant protein to digestion with proteases (see Sambrook et al., supra). Polypeptides, variants and fragments thereof, can be prepared without altering a biological activity of the resulting protein molecule (i.e., without altering one or more functional activities in a statistically significant or biologically significant manner). For example, such substitutions are generally made by interchanging an amino acid with another amino acid that is included within the same group, such as the group of polar residues, charged residues, hydrophobic residues, and/or small residues, and the like. The effect of any amino acid substitution may be determined empirically merely by testing the resulting modified protein for the ability to function in a biological assay, or to bind to a cognate ligand or target molecule.

It is understood that the non-naturally occurring microbial organisms or C1 metabolizing organisms that have been genetically modified as described herein may lead to the biosynthetic production of propylene, including other pathway intermediates (e.g., crotonate or crotonyl-CoA) and downstream products. Like other alkenes, propylene undergoes addition reactions relatively easily at room temperature due to the relative weakness of its double bond. Through polymerization, oxidation, halogenations and hydrohalogenation, alkylation, hydration, oligomerization, and hydroformylation reactions, which are well known to a person of skill in the art, propylene may be converted into other downstream products (e.g., polypropylene, propylene oxide). These addition reactions may occur spontaneously in the non-naturally occurring microbial organisms or C1 metabolizing organisms, or the organisms may be further genetically modified to add or enhance addition reaction capability (e.g., to increase conversion to polypropylene or propylene oxide). For example, in methanotrophic bacteria that are genetically modified with a biosynthetic propylene pathway, propylene that is produced may spontaneously be oxidized into propylene oxide via a methane-monooxygenase-catalyzed reaction (see, e.g., U.S. Patent Publication 2002/0168733, U.S. Patent Publication 2003/0203456). Alternatively, the non-naturally occurring microbial organisms or C1 metabolizing organisms may comprise further genetic modifications to inhibit or reduce endogenous enzyme activity that catalyze an addition reaction (e.g., to inhibit conversion to propylene oxide). In non-naturally occurring organisms that spontaneously convert or are genetically modified to convert propylene into a downstream product (e.g. propylene oxide), there may be little propylene product to recover and measure, and the downstream product (e.g., propylene oxide) may be recovered and measured as a surrogate for propylene production.

Methods of Producing Crotonic Acid or Propylene in Non-Naturally Occurring C1 Metabolizing Organisms In certain embodiments, the present disclosure provides methods of producing propylene by culturing non-naturally occurring C1 metabolizing organisms according to any of the embodiments as described herein (e.g., capable of converting a C1 substrate into propylene), under conditions sufficient to produce propylene. In a specific embodiment, the non-naturally occurring C1 metabolizing organisms as disclosed herein produce from about 0.1 grams of propylene/L/day to about 50 grams of propylene/L/day. In another embodiment, the non-naturally occurring C1 metabolizing organisms as disclosed herein produce about 0.1 g, 0.5 g, 1 g, 2 g, 3 g, 4 g, 5 g, 6 g, 7 g, 8 g, 9 g, 10 g, 11 g, 12 g, 13 g, 14 g, 15 g, 16 g, 17 g, 18 g, 19 g, 20 g, 25 g, 30 g, 35 g, 40 g, 45 g, 50 g, 55 g, or 60 g propylene/L/day.

Additionally, the present disclosure provides methods of producing propylene in non-naturally occurring microbial organisms according to any of the embodiments as described herein (e.g., having a partially heterologous propylene biosynthetic pathway), by culturing the non-naturally occurring microbial organisms under conditions sufficient to produce propylene. In a specific embodiment, the non-naturally occurring microbial organisms as disclosed herein produce from about 0.1 grams of propylene/L/day to about 50 grams of propylene/L/day. In another embodiment, the non-naturally occurring microbial organisms as disclosed herein produce about 0.1 g, 0.5 g, 1 g, 2 g, 3 g, 4 g, 5 g, 6 g, 7 g, 8 g, 9 g, 10 g, 11 g, 12 g, 13 g, 14 g, 15 g, 16 g, 17 g, 18 g, 19 g, 20 g, 25 g, 30 g, 35 g, 40 g, 45 g, 50 g, 55 g, or 60 g propylene/L/day.

Also disclosed herein are methods of producing crotonic acid by culturing non-naturally occurring C1 metabolizing organisms under conditions sufficient to produce crotonic acid, wherein the organisms include an exogenous nucleic acid encoding crotonyl-CoA thioesterase. In a specific embodiment, the non-naturally occurring C1 metabolizing organisms as disclosed herein produces from about 0.1 grams of crotonic acid/L/day to about 50 grams of crotonic acid/L/day. In another embodiment, the non-naturally occurring C1 metabolizing organism as disclosed herein produces about 0.1 g, 0.5 g, 1 g, 2 g, 3 g, 4 g, 5 g, 6 g, 7 g, 8 g, 9 g, 10 g, 11 g, 12 g, 13 g, 14 g, 15 g, 16 g, 17 g, 18 g, 19 g, 20 g, 25 g, 30 g, 35 g, 40 g, 45 g, 50 g, 55 g, or 60 g crotonic acid/L/day.

Codon Optimization

Expression of recombinant proteins is often difficult outside their original host. For example, variation in codon usage bias has been observed across different species of bacteria (Sharp et al., 2005, Nucl. Acids. Res. 33:1141-1153). Over-expression of recombinant proteins even within their native host may also be difficult. In certain embodiments of the invention, nucleic acids (e.g., a nucleic acid encoding 4-OD, crotonyl-CoA thioesterase, or crotonase) that are to be introduced into organisms of the invention may undergo codon optimization to enhance protein expression. Codon optimization refers to alteration of codons in genes or coding regions of nucleic acids for transformation of an organism to reflect the typical codon usage of the host organism without altering the polypeptide for which the DNA encodes. Codon optimization methods for optimum gene expression in heterologous organisms have been previously described (see., e.g., Welch et al., 2009, PLoS One 4:e7002; Gustafsson et al., 2004, Trends Biotechnol. 22:346-353; Wu et al., 2007, Nucl. Acids Res. 35:D76-79; Villalobos et al., 2006, BMC Bioinformatics 7:285; U.S. Patent Publication 2011/0111413; U.S. Patent Publication 2008/0292918).

Transformation Methods

Non-naturally occurring microbial organisms as described herein may be transformed to comprise at least one exogenous nucleic acid to provide the host organism with a new or enhanced activity (e.g., enzymatic activity) or may be genetically modified to remove or substantially reduce an endogenous gene function (e.g., enzymatic activity) using a variety of methods known in the art. Recombinant methods for exogenous expression of nucleic acids in microbial organisms are well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

A non-naturally occurring C1 metabolizing bacterium; non-naturally occurring obligate C1 metabolizing organism; non-naturally occurring C1 metabolizing organism, wherein the organism does not include *Pichia pastoris*; a non-naturally occurring methanotrophic or methylotrophic bacterium; or a non-naturally occurring CO utilizing bacterium as described herein may be transformed to comprise at least one exogenous nucleic acid to provide the host with a new or enhanced activity (e.g., enzymatic activity) or may be genetically modified to remove or substantially reduce an endogenous gene function (e.g., enzymatic activity) using a variety of methods known in the art. While genetic engineering tools of C1 metabolizing organisms are not as extensive as for other microbial organisms (e.g., *E. coli*), significant advances have been made allowing genetic manipulation of C1 metabolizing organisms, as summarized below.

Transformation refers to the transfer of a nucleic acid (e.g., exogenous nucleic acid) into the genome of a host organism, resulting in genetically stable inheritance. Host organisms containing the transformed nucleic acid are referred to as "non-naturally occurring" or "recombinant" or "transformed" or "transgenic" organisms.

Expression systems and expression vectors useful for the expression of heterologous nucleic acids in C1 metabolizing organisms are known. Vectors or cassettes useful for the transformation of suitable host organisms are available.

Electroporation of C1 metabolizing bacteria has been previously described in Toyama et al., 1998, FEMS Microbiol. Lett. 166:1-7 (*Methylobacterium extorquens*); Kim and Wood, 1997, Appl. Microbiol. Biotechnol. 48:105-108 (*Methylophilus methylotrophus* AS1); Yoshida et al., 2001, Biotechnol. Lett. 23:787-791 (*Methylobacillus* sp. strain 12S), and US2008/0026005 (*Methylobacterium extorquens*).

Bacterial conjugation, which refers to a particular type of transformation involving direct contact of donor and recipient cells, is more frequently used for the transfer of nucleic acids into C1 metabolizing bacteria. Bacterial conjugation involves mixing "donor" and "recipient" cells together in close contact with each other. Conjugation occurs by formation of cytoplasmic connections between donor and recipient bacteria, with unidirectional transfer of newly synthesized donor nucleic acids into the recipient cells. A recipient in a conjugation reaction is any cell that can accept nucleic acids through horizontal transfer from a donor bacterium. A donor in a conjugation reaction is a bacterium that contains a conjugative plasmid, conjugative transposon, or mobilized plasmid. The physical transfer of the donor plasmid can occur through a self-transmissible plasmid or with the assistance of a "helper" plasmid. Conjugations involving C1 metabolizing bacteria have been previously described in Stolyar et al., 1995, Mikrobiologiya 64:686-691; Motoyama et al., 1994, Appl. Micro. Biotech. 42:67-72; Lloyd et al., 1999, Archives of Microbiology 171:364-370; and Odom et al., PCT Publication WO 02/18617; Ali et al., 2006, Microbiol. 152:2931-2942.

Expression of heterologous nucleic acid molecules in C1 metabolizing bacteria is known in the art (see, e.g., U.S. Pat. No. 6,818,424, U.S. Patent Publication 2003/0003528). Mu transposon based transformation of methylotrophic bacteria has been described (see, e.g., Akhverdyan et al., 2011, Appl. Microbiol. Biotechnol. 91:857-871). A mini-Tn7 transposon system for single and multicopy expression of heterologous genes without insertional inactivation of host genes in *Methylobacterium* has been described (see, e.g. U.S. Patent Publication 2008/0026005).

Various methods for inactivating, knocking-out, or deleting endogenous gene function in C1 metabolizing organisms may be used. Allelic exchange using suicide vectors to construct deletion/insertional mutants in slow growing C1 metabolizing bacteria have also been described in Toyama and Lidstrom, 1998, Microbiol. 144:183-191; Stolyar et al., 1999, Microbiol. 145:1235-1244; Ali et al., 2006, Microbiology 152:2931-2942; Van Dien et al., 2003, Microbiol. 149:601-609.

Suitable homologous or heterologous promoters for high expression of exogenous nucleic acids may be utilized. For example, U.S. Pat. No. 7,098,005 describes the use of promoters that are highly expressed in the presence of methane or methanol for heterologous gene expression in C1 metabolizing bacteria. Additional promoters that may be used include deoxy-xylulose phosphate synthase methanol dehydrogenase operon promoter (Springer et al., 1998, FEMS Microbiol. Lett. 160:119-124); the promoter for PHA synthesis (Foellner et al. 1993, Appl. Microbiol. Biotechnol. 40:284-291); or promoters identified from native plasmid in methylotrophs (EP296484). Non-native promoters include the lac operon Plac promoter (Toyama et al., 1997, Microbiology 143:595-602) or a hybrid promoter such as Ptrc (Brosius et al., 1984, Gene 27:161-172). Regulation of expression of an exogenous nucleic acid molecule in the host C1 metabolizing organism may also be utilized. For example, an inducible/regulatable system of recombinant protein expression in methylotrophic and methanotrophic bacteria has been described in US Patent Publication 2010/0221813.

Methods of screening are disclosed in Brock, supra. Selection methods for identifying allelic exchange mutants are known in the art (see, e.g., U.S. Patent Publication No. 2006/0057726, Stolyar et al., 1999, Microbiol. 145:1235-1244; and Ali et al., 2006, Microbiology 152:2931-2942.

Culture Methods

A variety of culture methodologies may be used for the C1 metabolizing organisms described herein. For example, C1 metabolizing organisms, particularly methanotrophic or methylotrophic bacteria, may be grown by batch culture and continuous culture methodologies. In certain embodiments, the cultures are grown in a controlled culture unit, such as a fermentor, bioreactor, hollow fiber membrane bioreactor, or the like.

A classical batch culturing method is a closed system where the composition of the media is set at the beginning of the culture and not subject to external alterations during the culture process. Thus, at the beginning of the culturing process, the media is inoculated with the desired organism or organism and growth or metabolic activity is permitted to occur without adding anything to the system. Typically, however, a "batch" culture is batch with respect to the addition of carbon source and attempts are often made at controlling factors such as pH and oxygen concentration. In batch systems, the metabolite and biomass compositions of the system change constantly up to the time the culture is terminated. Within batch cultures, cells moderate through a static lag phase to a high growth logarithmic phase and finally to a stationary phase where growth rate is diminished or halted. If untreated, cells in the stationary phase will eventually die. Cells in log phase are often responsible for the bulk production of end product or intermediate in some systems. Stationary or post-exponential phase production can be obtained in other systems.

The Fed-Batch system is a variation on the standard batch system. Fed-Batch culture processes comprise a typical batch system with the modification that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors, such as pH, dissolved oxygen, and the partial pressure of waste gases such as CO2. Batch and Fed-Batch culturing methods are common and known in the art (see, e.g., Thomas D. Brock, Biotechnology: A Textbook of Industrial Microbiology, $2^{nd}$ Ed. (1989) Sinauer Associates, Inc., Sunderland, Mass.; Deshpande, 1992, Appl. Biochem. Biotechnol. 36:227, herein incorporated by reference).

Continuous cultures are "open" systems where a defined culture media is added continuously to a bioreactor and an equal amount of conditioned media is removed simultaneously for processing. Continuous cultures generally maintain the cells at a constant high liquid phase density where cells are primarily in logarithmic phase growth. Alternatively, continuous culture may be practiced with immobilized cells where carbon and nutrients are continuously added and valuable products, by-products, and waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limited nutrient, such as the carbon source or nitrogen level, at a fixed rate and allow all other parameters to modulate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art, and a variety of methods are detailed by Brock, supra.

Culture media must contain carbon substrates for the C1 metabolizing organisms. Suitable substrates include, but are not limited to C1 substrates such as methane, methanol, formaldehyde, formic acid (formate), carbon monoxide, carbon dioxide, methylated amines (methylamine, dimethylamine, trimethylamine, etc.), methylated thiols, or methyl halogens (bromomethane, chloromethane, iodomethane, dichloromethane, etc.). In certain embodiments, a non-naturally occurring C1 metabolizing organism of any of the disclosed embodiments is capable of growth on methane, methanol, formaldehyde, formic acid, carbon monoxide, carbon dioxide, methylated amines, methylated thiols, or methyl halogens as a carbon source.

A culture media may comprise a single C1 substrate as the sole carbon source for the C1 metabolizing organism, or comprise a mixture of two or more C1 substrates (mixed C1 substrates) as multiple carbon sources for the C1 metabolizing organism. Additionally, some C1 metabolizing organisms are known to utilize non-C1 substrates, such as glucosamine and a variety of amino acids for metabolic activity. For example, some *Candida* species can metabolize alanine or oleic acid (Sulter et al., 1990, Arch. Microbiol. 153:485-489). *Methylobacterium extorquens* AM1 is capable of growth on a limited number of C2, C3, and C4 substrates (Van Dien et al., 2003, Microbiol. 149:601-609). Alternatively, a C1 metabolizing organism may be engineered with the ability to utilize alternative carbon substrates. Hence, it is contemplated that a culture media may comprise a mixture of carbon substrates, with single and multi-carbon compounds (mixed carbon sources), depending on the C1 metabolizing organism selected. In certain embodiments, a C1 substrate provided in a mixed carbon source may be a primary carbon source for a C1 metabolizing organism. A carbon source may be added to culture media initially, provided to culture media intermittently, or supplied continuously.

Propylene Separation and Recovery

Propylene or propylene oxide produced by the non-naturally occurring organisms described herein may be dissolved in the liquid phase or present as gas in the headspace of the culture container. Propylene may be mixed with other gases in the headspace, such as $O_2$, $CO_2$, $H_2O$ vapor, or methane. Methods for recovering propylene from a gas mixture have been previously described, and include for example, continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration (see., e.g., Bai et al., 2000, J. Memb. Sci. 174:67-79; Shi et al., 2006, J. Membr. Sci. 282:115-123; Membranes: Separation of Organic Vapors from Gas Streams, by Ohlrogge and Sturken, Ullmann's Encyclopedia of Industrial Chemistry, 2002, Wiley-VCH Verlag GmbH & Co., KGaA; U.S. Pat. No. 4,348,476; Hou et al., 1984, Applied Microbio. and Biotechnol. 19:1-4; each of the preceding references are incorporated herein by reference, in their entirety). A person skilled in the art can adapt propylene recovery methods used in fluidic cracking process (see, e.g., U.S. Pat. Nos. 3,893,905; 6,308,532; 6,730,142; 7,875,758) to recover propylene from a fermentation off-gas mixture.

Measuring Propylene Production

Methods for measuring propylene and propylene oxide production are well known in the art and include HPLC (high performance liquid chromatography), GC-MS (gas chromatography-mass spectrometry), GC-FID (gas chromatography-flame ionization detector) and LC-MS (liquid chromatography-mass spectrometry). Methods of measuring propylene and propylene oxide concentration have also been described in, for example, Brown et al., 1963, Anal. Chem. 35:2172-2176; Lin et al., 2000, J. Am. Chem. Soc. 122: 11275-11285; Lee and Hwang, J. Membrane Sci. 73:37-45; U.S. Patent Publication 2010/0197986; U.S. Patent Publication 2003/0203456; U.S. Patent Publication 2002/0168733; Stanley and Dalton, 1992, Biocatalysis & Biotransformation 6:163-175; each of which is incorporated herein by reference in its entirety).

Measuring PHB Production

In certain embodiments, the non-naturally occurring organisms as described herein do not produce a substantial amount of polyhydroxybutyrate (PHB). As used herein, "not producing a substantial amount of polyhydroxybutyrate" means that an organism produces at least 40%, 45%, 50%, 55%, 60%, 65%, 70%, 75%, 80%, 85%, 90%, 95%, 99% less polyhydroxybutyrate as compared to a wildtype organism that has a polyhydroxybutyrate synthesis pathway. Methods for determining PHB concentration are well known in the art. Braunegg et al., (1978, European J. Appl. Microbiol. Biotechnol. 6:29-37) describe a gas chromatographic method for determining PHB concentration comprising a mild acid or alkaline methanolysis of PHB directly without previous extraction from the cells, which is followed by gas chromatography of the 3-hydroxybutyric acid methylester. A quantitative staining method for detecting PHB in viable cells has also been described (see., e.g., Tyo et al., 2006, Appl. Environ. Microbiol. 72:3412-3417). Stopped-flow attenuated total reflection FT-IR spectrometry has been used to determine intracellular PHB content in bacteria (see., e.g., Jarute et al., 2004, Anal. Chem. 76:6353-6358). Additional methods for measuring PHB have been described in Huang and Reusch, 1996, J. Biol. Chem. 271:22196-22202; Henneke et al., 2005, Bioprocess & Biosystems Engineering 27:359-364; Pieja et al., 2011, Appl. Environ. Microbiol. 77:6012-6019; Taguchi et al., 2001, FEMS Microbiol. Letters 198:65-71.

Additional methods for measuring PHB synthesis may include measuring PHB synthase expression (see., e.g., Langenbach et al., 1997, FEMS Microbiol. Lett. 150:303-309; Solaiman et al., 2008, J. Ind. Microbiol. & Biotechnol. 35:111-120) or enzyme activity (see., e.g., Schubert et al., 1988, J. Bacteriol. 170:5837-5847; Liebergesell et al., 1994, Eur. J. Biochem. 226:71-80; Valentin and Steinbuchel, 1994, Appl. Microbiol. Biotechnol. 40:699-709).

EXAMPLES

Example 1

*Methylosinus Trichosporium* Methanotroph

Preparation of NMS Media.

| | |
|---|---|
| $MgSO_4 \cdot 7H_2O$ | 1.0 g |
| $CaCl_2 \cdot 6H_2O$ | 0.20 g |
| Chelated Iron Solution (see below) | 2.0 ml |
| $KNO_3$ | 1.0 g |
| Trace Element Solution (see below) | 0.5 ml |
| $KH_2PO_4$ | 0.272 g |
| $Na_2HPO_4 \cdot 12H_2O$ | 0.717 g |
| Purified Agar (e.g., Oxoid L28) | 12.5 g |
| Distilled deionized water | 1.0 L |
| Adjust pH to 6.8. Autoclave at 121° C. for 15 minutes. | |

Chelated Iron Solution:

| | |
|---|---|
| Ferric (III) ammonium citrate* | 0.1 g |
| EDTA, sodium salt | 0.2 g |
| HCl (concentrated) | 0.3 ml |
| Distilled deionized water | 100.0 ml |

*0.5 g of Ferric (III) chloride may be substituted.
Use 2.0 ml of this chelated iron solution per liter of final medium.

Trace Element Solution:

| | |
|---|---|
| EDTA | 500.0 mg |
| $FeSO_4 \cdot 7H_2O$ | 200.0 mg |
| $ZnSO_4 \cdot 7H_2O$ | 10.0 mg |
| $MnCl_2 \cdot 4H_2O$ | 3.0 mg |
| $H_3BO_3$ | 30.0 mg |
| $CoCl_2 \cdot 6H_2O$ | 20.0 mg |
| $CaCl_2 \cdot 2H_2O$ | 1.0 mg |
| $NiCl_2 \cdot 6H_2O$ | 2.0 mg |
| $Na_2MoO_4 \cdot 2H_2O$ | 3.0 mg |
| Distilled water | 1.0 L |
| Autoclave at 121° C. for 15 minutes. | |

Growth and Conjugations. The procedure for conjugating plasmids from *E. coli* into methanotrophs was based on the method developed by Martin, H. & Murrell, J. C. (1995), FEMS Microbiol. Lett. 127: 243-248.

Briefly, a mobilizing plasmid to be conjugated was first transformed into *E. coli* S17-1 using standard electroporation methods. Transformation was confirmed by selection of kanamycin-resistant colonies on LB-agar containing 20 μg/mL kanamycin. Transformed colonies were inoculated into LB media containing 20 μg/mL kanamycin and shaken overnight at 37° C. A 10 mL aliquot of the overnight culture was then collected on a sterile 47 mm nitrocellulose filter (0.2 mm pore size). The *E. coli* donor strain was washed on the filter with 50 mL sterile NMS media to remove residual media and antibiotic.

In parallel, a sample of the *M. trichosporium* OB3b recipient strain was inoculated into 100 mL serum bottles containing 20-50 mL NMS media. The headspace of the bottles was then flushed with a 1:1 mixture of oxygen and methane, and the bottles were sealed with butyl butyl rubber septa and crimped. The bottles were shaken continuously in a 30° C. incubator until reaching an OD600 of approximately 0.3. The cells were then collected on the same filter as the *E. coli* donor strain. The filter was again washed with 50 mL of sterile NMS media. The filter was placed (cells up) on an NMS agar plate containing 0.02% (w/v) protease peptone and incubated for 24 h at 30° C. in the presence of methane and oxygen. After 24 h, cells were re-suspended in 10 mL sterile (NMS) medium before being concentrated by centrifugation. The pellet was re-suspended in 1 mL sterile NMS media. Aliquots (100 μl) were spread onto NMS agar plates containing 10 μg/mL kanamycin.

The plates were incubated in sealed chambers containing a 1:1 mixture of methane and oxygen maintained at 30° C. The gas mixture was replenished every 2 days until colonies formed, typically after 7-14 days. Colonies were streaked onto NMS plates containing kanamycin to confirm kanamycin resistance as well as to further isolate transformed methanotroph cells from residual *E. coli* donor cells.

Deletion of phaC. A synthetic cDNA construct of the *M. trichosporium* OB3b phaC gene was synthesized, incorporating several stop mutations and frame shifts in the 5' region of the gene. This cDNA construct was cloned into an appropriate vector for conjugation, but lacking an origin of replication that functions in methanotrophs, and introduced into *M. trichosporium* OB3b using the methods described above. This technique ensures that any kanamycin resistant *M. trichosporium* OB3b colonies must have been incorporated into the genome by recombination.

Identification of homologous recombination events is well-established in the art, and typically performed by PCR and sequencing using unique primers in the genome and the vector construct to confirm proper insertion. Homologous recombinants are then grown in the absence of selective pressure (e.g., kanamycin) for several generations, and sensitive clones which have lost the resistance marker are identified by replica plating (or equivalent technique). Approximately 50% of sensitive revertants possess the mutated form of the target gene in place of the wild-type version.

Loss of phaC function is confirmed by growing the cells under nitrogen limited conditions and measuring PHB content as described in Pieja A J, Rostkowski K H, Criddle C S, Distribution and selection of poly-3-hydroxybutyrate production capacity in methanotrophic proteobacteria. Microb. Ecol. 2011 October; 62(3):564-73. Briefly, the putative knockout clones inoculated into 100 mL serum bottles containing 20-50 mL NMS media. The headspace of the bottles was then flushed with a 1:1 mixture of oxygen and methane, and the bottles were sealed with butyl rubber septa and crimped. The bottles were shaken continuously in a 30° C. incubator until reaching an OD600 of approximately 0.3-0.6 to ensure the cells are in logarithmic phase growth. Cells are collected by centrifugation at 4,816×g (4,700 rpm) for 8 min, washed once with nitrogen-free NMS media medium, and re-suspended in nitrogen-free NMS medium to induce PHB production. 20-50 mL aliquots of washed cells are then transferred to serum bottles, sealed, and methane and oxygen added as described above. Cultures are then incubated at 30° C. on orbital shakers at 150 rpm. Assays for optical density and PHB production are performed every 1 to 2 h for the first 20 h.

(5% phenyl)-methylpolysiloxane; Agilent Technologies] and a flame ionization detector (FID). dl-β-Hydroxybutyric acid sodium salt is used as a standard.

Introduction of Propylene pathway. Selected crotonase (SEQ ID NO:32), crotonyl-CoA thioesterase (SEQ ID NO:29), and 4-oxalocrotonate decarboxylase (SEQ ID NO:10) sequences were codon optimized (see Table 4) and synthesized with appropriate promoters. The genes are then cloned and transformed into the phaC knockout strain as described above. Transformation is confirmed by resistance of the cells to antibiotic selection, and gene expression is confirmed by northern blot (to confirm RNA transcription), western blot, or ELISA methods (to confirm protein expression).

TABLE 4

Codon optimized sequences for M. trichosporium OB3b

| Reference Sequence | Codon optimized sequence (SEQ ID NO: #) |
|---|---|
| crotonase (SEQ ID NO: 32) | ATGGAGCTGAATAACGTCATCCTGGAAAAAGAAGGCAAGGTCGCGGTCGTCACGATCAACC GCCCCAAGGCTCTGAACGCGCTCAATAGCGACACCCTCAAAGAGATGGACTACGTCATCGGC GAGATCGAGAACGACTCCGAGGTGCTGGCCGTCATCCTCACCGGAGCGGGCGAGAAGTCGT TCGTGGCTGGGGCGGATATCAGCGAGATGAAAGAGATGAATACCATTGAAGGCCGCAAGTT CGGCATCCTGGGCAACAAGGTGTTCCGTCGCCTGGAGCTGCTGGAGAAGCCGGTCATTGCG GCGGTGAATGGCTTCGCGCTCGGCGGTGGCTGCGAGATCGCGATGTCGTGCGACATCCGCA TCGCCTCGTCGAACGCCCGCTTCGGACAGCCGGAAGTCGGCCTCGGCATCACGCCCGGATTC GGCGGCACTCAGCGCCTCAGCCGCCTGGTGGGCATGGGCATGGCTAAGCAGCTGATCTTCA CGGCGCAGAACATCAAGGCTGACGAGGCGCTCCGCATCGGCCTGGTCAACAAGGTGGTGG AGCGTCGGAACTCATGAACACGGCGAAAGAGATTGCGAACAAAATCGTGTCGAATGCGCC GGTGGCGGTCAAGCTGAGCAAGCAGGCGATCAACCGTGGCATGCAGTGCGATATCGACACT GCGCTCGCCTTCGAGTCCGAGGCGTTCGGCGAGTGCTTCTCCACCGAAGATCAGAAAGATGC TATGACCGCCTTCATCGAAAAGCGGAAGATCGAGGGCTTCAAGAACCGC (SEQ ID NO: 124) |
| crotonyl-CoA thioesterase (SEQ ID NO: 29) | ATGCATCGCACCTCGAACGGCTCCCATGCCACGGGTGGCAATCTCCCCGACGTCGCCTCGCA TTACCCCGTGGCGTACGAGCAGACCCTGGACGGCACCGTGGGCTTCGTCATCGATGAGATG ACGCCCGAGCGTGCCACCGCCTCGGTGGAAGTTACCGACACGCTCCGCCAGCGCTGGGGCC TCGTCCACGGCGGTGCTTACTGTGCGTTGGCGGAGATGCTGGCCACGGAAGCCACGGTCGC CGTGGTGCATGAGAAGGGCATGATGGCGGTCGGCCAGTCGAATCACACCAGCTTCTTCCGC CCTGTGAAAGAGGGCCACGTGCGTGCCGAGGCCGTGCGTATTCACGCGGGCTCGACCACGT GGTTCTGGGACGTCAGCCTGCGGGACGACGCGGGTCGCCTCTGCGCCGTGTCGTCGATGTC CATCGCGGTCCGCCCTCGCCGTGAC (SEQ ID NO: 125) |
| 4-oxalocrotonate decarboxylase (SEQ ID NO: 10) | ATGTCCACGACCAGCATCACCCCCGGATGAGATCGCCCAGGTGCTGCTGGCTGGCGAGCGCA ACCGCACCGAGGTGGCGCAGTTCTCGGCGAGCCACCCCGACCTCGACGTCCGGACGGCCTA TGCGGCCCAGCGCGCTTTCGTCCAGGCCAAGCTGGATGCGGGCGAGCAGCTCGTCGGCTAT AAGCTGGGCCTGACCAGCCGCAACAAGCAGCGCGCCATGGGCGTCGACTGCCCGCTGTATG GCCGCGTCACGTCCTCGATGCTCGCGACGTATGGCGATCCCATCCCGTTCGACCGCTTCATCC ATCCGCGCGTCGAATCGGAGATCGCGTTCCTGCTCAAGCAGGATGTGACCGCTCCGGCGACC GTGTCGTCGGTCCTCGCGGCCACCGACGTCGTGTTCGGAGCGGTCGACGTGCTCGACTCGC GCTACGAGGGGTTCAAGTTCACGCTCGAGGATGTCGTGGCCGATAACGCGAGCGCGGGAG CGTTCTACCTCGGACCGGTCGCCCGTCCGGCCACCGAGCTCCGCCTCGACCTGCTGGGATGC ATCGTTCGCGTGGACGGCGAGGTCACCATGACCGCCGCTGGTGCGGCCGTCATGGGCCATC CCGCCGCGGCGGTCGCGTGGCTCGCCAACCAGCTCGCGCTCGAGGGCGAATCGCTGAAGGC CGGACAGCTGATCTTCTCGGGTGGCGTCACTGCGCCCGTCCCGGTCGTTCCTGGCGGCAGCG TCACGTTCGAGTTCGATGGCCTGGGCGTCATCGAGGTGGCTGGCGCC (SEQ ID NO: 126) |

PHB concentration determination. PHB concentration is measured directly via gas chromatography. For each sample, 5 to 10 mg of freeze-dried biomass is weighed out on an analytical balance, transferred to a 12-ml glass vial, and sealed with a polytetrafluoroethylene (PTFE)-lined plastic cap. 2 mL of methanol acidified with sulfuric acid (3%, vol/vol) and containing 1.0 g/L benzoic acid and 2 ml of chloroform are added to each vial. The vials are shaken gently and then heated at 100° C. for 3.5 h. Once the vials cool to room temperature, 1 ml deionized water is added to each. The vials are subjected to vortex mixing for 30 s and allowed to stand until phase separation is complete. The organic phase is analyzed using an Agilent 6890N gas chromatograph equipped with an HP-5 column [containing Production of Propylene from methane. phaC-deleted M. trichosporium transformed with a vector containing genes encoding crotonase and 4-oxalocrotonate decarboxylase are inoculated into 100 mL serum bottles containing 20-50 mL NMS media and 10 ug/mL kanamycin. The bottle headspace is flushed with a 1:1 mixture of methane and oxygen, and the bottles are sealed with butyl rubber septa and crimped. The bottles are then shaken continuously while being incubated at 30° C. The headspace gas is refreshed every 2 days as above; however, immediately prior to refreshing the headspace, samples are drawn from both the liquid phase and headspace using a 10 μL Hamilton syringe and injected into a HP5890 GC equipped with a CP-PoraBOND U 25 m×0.32 mm column and an FID maintained at 200° C. The injector is connected in splitless mode and maintained at 250° C. Samples are run with He Gas at 7.3 ml/min as a carrier gas; the oven program is set as follows: hold at 50° C. 1.5 min; ramp to 300° C. at 10° C./min; hold at 300° C. 10 min. Propylene is identified by retention time compared to pure propylene diluted in air or dissolved in pure H$_2$O. Samples are also taken to measure optical density of the culture, allowing quantitation of specific propylene production rates per cell. Note that because methane is the only carbon source provided to the cells, all propylene produced must have been derived from methane.

Example 2

Methylococcus Capsulatus Bath Strain Methanotroph

Growth and Conjugations. The procedure for conjugating plasmids from E. coli into M. capsulatus was based on the method reported in Ali, H. & Murrell, J. C. (2009). Development and validation of promoter-probe vectors for the study of methane monooxygenase gene expression in Methylococcus capsulatus Bath. Microbiology (2009), 155:761-771.

Briefly, a mobilizing plasmid to be conjugated was first transformed into E. coli S17-1 using standard electroporation methods. Transformation was confirmed by selection of kanamycin-resistant colonies on LB-agar containing 20 µg/mL kanamycin. Transformed colonies were inoculated into LB media containing 20 µg/mL kanamycin and shaken overnight at 37° C. A 10 mL aliquot of the overnight culture was then collected on a sterile 47 mm nitrocellulose filter (0.2 mm pore size). The E. coli donor strain was washed on the filter with 50 mL sterile NMS to remove residual media and antibiotic.

In parallel, a sample of the M. capsulatus recipient strain was inoculated into 100 mL serum bottles containing 20-50 mL NMS media. The headspace of the bottles was then flushed with a 1:1 mixture of oxygen and methane, and the bottles were sealed with butyl rubber septa and crimped. The bottles were shaken continuously in a 45° C. incubator until reaching an OD600 of approximately 0.3. The cells were then collected on the same filter as the E. coli donor strain. The filter was again washed with 50 mL of sterile NMS media. The filter was placed (cells up) on an NMS agar plate containing 0.02% (w/v) proteose peptone and incubated for 24 h at 37° C. in the presence of methane and oxygen. After 24 h, cells were re-suspended in 10 mL sterile (NMS) medium before being concentrated by centrifugation. The pellet was re-suspended in 1 mL sterile NMS media. Aliquots (100 µl) were spread onto NMS agar plates containing 10 µg/mL kanamycin.

The plates were incubated in sealed chambers containing a 1:1 mixture of methane and oxygen maintained at 45° C. The gas mixture was replenished every 2 days until colonies formed, typically after 7-14 days. Colonies were streaked onto NMS plates containing kanamycin to confirm kanamycin resistance as well as to further isolate transformed methanotroph cells from residual E. coli donor cells.

Introduction of Propylene synthesis pathway. Note that M. capsulatus does not have a native PHA pathway, hence no pathway genes (i.e., phaC) need to be deleted. However, phaA and phaB function must be introduced to the cells to provide the substrate for the crotonase enzyme (i.e., 3-hydroxybutryl-CoA).

Selected phaA (SEQ ID NO:77), phaB (SEQ ID NO:123), crotonase (SEQ ID NO:32), crotonyl-CoA thioesterase (SEQ ID NO:29), and 4-oxalocrotonate decarboxylase (SEQ ID NO:10) sequences were codon optimized (see Table 5) and synthesized with appropriate promoters. The genes are then cloned and transformed into M. capsulatus as described above. Transformation is confirmed by resistance of the cells to antibiotic selection, and gene expression is confirmed by northern blot (to confirm RNA transcription), western blot, or ELISA methods (to confirm protein expression).

TABLE 5

| Codon Optimized Sequences for M. capsulatus | |
| --- | --- |
| Reference Sequence | Codon Optimized Sequence (SEQ ID NO: #) |
| phaA (SEQ ID NO: 77) | ATGACCGACGTGGTCATCGTGTCGGCAGCCCGCACAGCAGTGGGTAAATTCGGCGGCT CGCTGGCCAAGATCGCAGCCCCGGAGCTGGGCGCCTCGGTCATCCGAGCGGTATTGGA ACGAGCCGGAGTGAAGCCCGAGCAGGTGTCGGAAGTCATCTTGGGCCAAGTGCTTACT GCCGGCAGCGGCCAAAACCCAGCCCGGCAGGCGTTGATCGCCGCAGGGCTCCCGAAC GCCGTCCCGGGCATGACGATCAACAAGGTGTGTGGCAGCGGCCTCAAGGCGGTCATGC TCGCGGCCAATGCGGTCGTAGCAGGGGACGCGGAAATCGTCGTGGCAGGCGGCCAGG AAAACATGAGCGCTGCGCCGCACGTGCTGCCCGGCTCCCGCGACGGCTTCCGGATGGG AGACGCCAAGTTGGTGGATTCAATGATCGTTGACGGGTTGTGGGACGTTTACAACAAG TACCATATGGGCATCACCGCAGAAAATGTGGCGAAAGAATATGGTATCACCCGCGAGG CCCAGGACCAGTTCGCCGCCTTGAGCCAGAACAAGGCCGAAGCTGCCCAGAAAGCGG GTCGCTTCGACGATGAAATCGTACCGATCGAAATCCCGCAACGGAAGGGCGAGCCCCT GCGCTTCGCGACCGATGAATTCGTCCGGCACGGGGTCACGGCCGAGTCCCTCGCGAGC CTCAAGCCGGCCTTCGCCAAAGAAGGCACCGTGACCGCCGCTAACGCGAGCGGCATCA ACGACGGCGCAGCCGCAGTCCTGGTTATGTCGGCGAAGAAGGCCGAAGCCCTGGGGC TGGAGCCCCTGGCCCGGATCAAGGCGTACGCCAATGCGGGAGTGGATCCGTCCGTAAT GGGAATGGGCCCTGTCCCCGCCTCGCGACGGTGCCTGGAGCGCGCAGGGTGGTCGGT AGGCGACCTCGATCTCATGGAGATCAATGAAGCGTTCGCGGCTCAGGCGCTCGCGGTG CACAAGCAGATGGGCTGGGATACCTCGAAGGTTAACGTGAACGGCGGTGCCATCGCG ATCGGCCACCCCATCGGGGCCTCAGGCTGCCGCATCCTGGTCACCCTGCTGCATGAAAT GCTGAAGCGCGATGCCAAGCGGGGACTGGCGTCGCTCTGCATCGGCGGTGGCATGGG TGTCGCCTTGGCCCTCGAGCGGCCG (SEQ ID NO: 127) |
| phaB (SEQ ID NO: 123) | ATGAAGAAGGTGTGCGTCATCGGAGCCGGCACCATGGGTTCCGGGATCGCGCAGGCCT TTGCCGCCAAGGGCTTCGAAGTGGTGCTGCGTGACATCAAAGACGAGTTCGTCGACCG TGGTTTGGATTTCATCAACAAGAACCTGTCGAAACTCGTCAAGAAAGGCAAGATCGAA GAGGCAACGAAGGTTGAGATTCTCACCCGTATAAGCGGGACGGTGGACCTGAACATG GCGGCTGATTGTGACCTGGTGATCGAAGCCGCGGTGGAACGCATGGACATCAAGAAG |

TABLE 5-continued

Codon Optimized Sequences for *M. capsulatus*

| Reference Sequence | Codon Optimized Sequence (SEQ ID NO: #) |
|---|---|
| | CAGATCTTCGCAGATCTGGACAATATCTGCAAGCCAGAGACGATTCTTGCGAGCAATAC<br>CAGCAGTCTGTCCATCACCGAGGTCGCATCCGCGACGAAACGGCCGGACAAAGTGATC<br>GGCATGCACTTCTTCAACCCTGCGCCCGTCATGAAGTTGGTGGAAGTGATCCGGGGCAT<br>CGCCACAAGCCAGGAAACCTTCGACGCTGTGAAAGAGACGTCGATCGCGATCGGGAAA<br>GACCCGGTCGAGGTGGCGGAAGCACCCGGCTTCGTCGTCAATGGATCCTGATCCCGA<br>TGATCAATGAAGCAGTCGGCATCTTGGCCGAGGGCATTGCCAGCGTCGAAGATATCGA<br>CAAGGCCATGAAGCTGGGCGCCAACCATCCGATGGGACCCCTGGAACTGGGAGACTTC<br>ATCGGGCTGGACATCTGCCTGGCCATCATGGACGTTCTCTACAGCGAAACGGGCGACTC<br>GAAGTATCGCCCGCATACCCTGCTGAAGAAATACGTCCGTGCAGGCTGGCTGGGACGC<br>AAGTCCGGCAAGGGCTTCTACGACTATTCCAAG (SEQ ID NO: 128) |
| crotonase<br>(SEQ ID NO: 32) | ATGGAACTTAACAATGTGATCCTGGAGAAAGAAGGTAAAGTCGCCGTGGTGACCATTA<br>ATCGCCCCAAGGCCCTGAACGCCCTGAATTCTGACACGCTGAAAGAAATGGACTACGT<br>GATCGGCGAAATCGAGAACGACTCCGAGGTGCTGGCCGTGATCCTGACCGGCGCAGG<br>CGAAAAGTCGTTCGTTGCCGGAGCGGATATCTCCGAGATGAAAGAGATGAACACCATT<br>GAGGGCAGGAAGTTCGGCATCCTGGGCAATAAAGTCTTTCGCCGGCTCGAGCTCCTGG<br>AGAAGCCGGTAATTGCCGCCGTTAATGGCTTCGCGCTCGGTGGCGGATGTGAAATCGC<br>GATGAGCTGCGACATCCGCATAGCGAGTAGTAACGCGCGGTTCGGCCAGCCCGAGGTC<br>GGCCTGGGCATCACGCCCGGATTCGGTGGCACTCAGCGGCTGTCGCGCCTGGTGGCA<br>TGGGGATGGCCAAGCAGCTGATCTTCACCGCGCAGAACATCAAAGCCGACGAAGCCCT<br>GCGCATAGGGTTGGTGAACAAAGTCGTGGAGCCGAGCGAGTTGATGAACACCGCCAA<br>AGAGATCGCCAACAAGATCGTCTCGAACGCACCGGTCGCGGTGAAATTGTCGAAGCAG<br>GCCATCAACCGCGGCATGCAGTGCGATATCGATACCGCCCTCGCCTTCGAGTCGGAAGC<br>CTTTGGTGAATGCTTCTCCACCGAAGATCAAAAAGACGCCATGACCGCCTTCATAGAGA<br>AGCGCAAGATCGAGGGTTTTAAGAACCGG (SEQ ID NO: 129) |
| crotonyl-CoA<br>thioesterase<br>(SEQ ID NO: 29) | ATGCATCGGACCAGCAACGGCAGCCACGCCACAGGTGGCAATCTGCCGGACGTCGCTA<br>GCCACTATCCGGTCGCCTACGAGCAGACCCTTGATGGGACGGTGGGCTTCGTGATCGA<br>CGAGATGACGCCAGAGCGAGCGACCGCTAGCGTCGAAGTCACCGATACGTTGCGGCA<br>GCGGTGGGGCCTGGTCCATGGCGGTGCGTATTGCGCGCTTGCCGAAATGCTGGCCACC<br>GAGGCTACCGTCGCCGTCGTCCACGAAAAGGGGATGATGGCGGTTGGTCAGTCGAACC<br>ATACGTCGTTCTTTCGTCCCGTGAAAGAGGGCCACGTGCGGGCAGAAGCCGTCCGTATT<br>CACGCCGGCAGCACCACCTGGTTCTGGGATGTTTCGCTGCGCGATGACGCCGGCAGGC<br>TGTGCGCCGTCAGTTCCATGTCAATCGCCGTCCGTCCACGCCGGGAT (SEQ ID NO: 130) |
| 4-oxalocrotonate<br>decarboxylase<br>(SEQ ID NO: 10) | ATGTCGACGACGTCCATTACCCCGGACGAGATTGCCCAGGTGCTGCTCGCTGGGGAAC<br>GGAACCGCACCGAAGTGGCCCAGTTCTCCGCGTCCCATCCGGACCTGGATGTTCGCACC<br>GCCTATGCCGCCCAGCGTGCTTTTGTCCAGGCCAAGCTGGACGCGGGAGAGCAGCTCG<br>TCGGCTACAAGCTGGGCCTTACGAGTCGGAACAAGCAGCGTGCCATGGGTGTGGACTG<br>CCCGCTGTACGGGCGAGTGACGAGCTCTATGCTGGCGACCTACGGGGACCCGATCCCG<br>TTTGACCGCTTCATCCATCCGCGGGTCGAAAGCGAGATTGCGTTCCTGTTGAAACAGGA<br>CGTGACCGCTCCGGCCACCGTGTCGTCCGTTCTGGCCGCCACGGACGTCGTCTTTGGCG<br>CGGTCGACGTACTGGACTCCCGGTACGAAGGCTTCAAGTTCACCCTCGAAGATGTGGT<br>GGCCGACAACGCCAGCGCTGGCGCGTTCTATCTCGGACCCGTGGCACGTCCCGCTACC<br>GAGTTGCGCCTGGACTTGTTGGGGTGCATCGTACGTGTGGACGGCGAAGTCACGATGA<br>CCGCGGCTGGCGCAGCCGTGATGGGCCACCCGGCAGCGGCAGTGGCCTGGCTCGCGA<br>ACCAGCTGGCGCTGGAAGGGGAATCCCTGAAAGCCGGTCAACTGATCTTCTCGGGTGG<br>GGTCACGGCACCCGTCCCTGTGGTGCCTGGCGGATCGGTGACCTTCGAGTTCGATGGC<br>CTTGGCGTGATCGAGGTGGCCGGAGCA (SEQ ID NO: 131) |

Production of Propylene from methane. *M. capsulatus* transformed with the vector described above are inoculated into 100 mL serum bottles containing 2050 mL NMS media and 10 µg/mL kanamycin. The bottle headspace is flushed with a 1:1 mixture of methane and oxygen, and the bottles are sealed with butyl rubber septa and crimped. The bottles are then shaken continuously while being incubated at 42-45° C. The headspace gas is refreshed every 2 days as above; however, immediately prior to refreshing the headspace, samples are drawn from both the liquid phase and headspace using a 10 µL Hamilton syringe and injected into a HP5890 GC equipped with a CP-PoraBOND U 25 m×0.32 mm column and an FID maintained at 200° C. The injector is connected in splitless mode and maintained at 250° C. Samples are run with He Gas at 7.3 ml/min as a carrier gas; the oven program is set as follows: hold at 50° C. 1.5 min; ramp to 300° C. at 10° C./min; hold at 300° C. 10 min. Propylene is identified by retention time compared to pure propylene diluted in air or dissolved in pure $H_2O$. Samples are also taken to measure optical density of the culture, allowing quantitation of specific propylene production rates per cell. Note that because methane is the only carbon source provided to the cells, all propylene produced must have been derived from methane.

Example 3

*Methylobacterium Extorquens* Methylotroph

Growth and Transformation. The procedure for introducing plasmids into *M. extorquens* has been demonstrated in Ueda S., Matsumoto S., Shimizu S., and Yamane T., Transformation of a Methylotrophic Bacterium, *Methylobacterium extorquens*, with a Broad-Host-Range Plasmid by Electroporation, Appl. Environ. Microbiol., 1991, April; 57(4): 924-926.

Briefly, wild-type (wt) *M. extorquens* is cultured at 30° C. in NMS media supplemented with 1% methanol. Cells of *M.*

*extorquens* NR-2 grown to the middle logarithmic phase (1.4×10$^9$/ml) are harvested by centrifugation at 6,000×g for 10 min and washed with electroporation buffer (10 mM Tris-HCl, 2 mM MgCl$_2$. 6H$_2$O, 10% [wt/vol] sucrose [pH 7.5]). Cells are re-suspended in the same buffer at a cell concentration of 7.0×10$^{10}$/ml. The cell suspension and the solution of vector (70 µg/mL) are mixed at a ratio of 9:1 (vol/vol) in an Eppendorf tube. The mixture (10 µL) is then transferred into a space between the electrodes of a chamber, where it is equilibrated for 3 min. After being subjected to 10 pulses of a 10 kV/cm electric field for 300 µsec/pulse, a 5 µL aliquot of the mixture is transferred to an Eppendorf tube. 0.2 mL of NMS medium is then added to the tube. The cell suspension is then incubated for 2 h at 30° C. to allow expression of the antibiotic resistance genes prior to plating on NMS plates containing 1% methanol and 20 µg/mL kanamycin.

The plates were incubated at 30° C. until colonies formed. Colonies were streaked onto duplicate plates to confirm kanamycin resistance as well as to further isolate transformed methylotroph cells from residual *E. coli* donor cells.

Deletion of phaC. The deletion of the phaC gene has been described in Korotkova N., Lidstrom M. E., Connection between poly-beta-hydroxybutyrate biosynthesis and growth on C(1) and C(2) compounds in the methylotroph *Methylobacterium extorquens* AM1, J. Bacteriol. 2001 February; 183(3):1038-46.

Briefly, insertion cassettes containing a kanamycin resistance marker were constructed with flanking sequences homologous to the areas flanking the phaC gene in the *M. extorquens* genome. A tetracycline resistance gene was incorporated elsewhere in the plasmid. Transformants were initially selected for resistance to kanamycin, and then screened for sensitivity to tetracycline to identify potential double cross-over recombination events. Correct insertion into and deletion of the phaC gene was confirmed by PCR.

Loss of phaC function is confirmed by growing the cells under nitrogen limited conditions and measuring PHA content as described in Pieja A J, Rostkowski K H, Criddle C S, Distribution and selection of poly-3-hydroxybutyrate production capacity in methanotrophic proteobacteria, Microb. Ecol. 2011 October; 62(3):564-73.

Introduction of Propylene synthesis pathway. Selected crotonase (SEQ ID NO:32), crotonyl-coA thioesterase (SEQ ID NO:29), and 4-oxalocrotonate decarboxylase (SEQ ID NO:10) sequences were codon optimized (see Table 6) and synthesized with appropriate promoters. The genes are then cloned and transformed into the phaC knockout strain as described above. Transformation is confirmed by resistance of the cells to antibiotic selection, and gene expression is confirmed by northern blot (to confirm RNA transcription), western blot, or ELISA methods (to confirm protein expression).

TABLE 6

Codon Optimized Sequences for *M. extorquens*

| Reference Sequence | Codon Optimized Sequence (SEQ ID NO: #) |
|---|---|
| crotonase (SEQ ID NO: 32) | ATGGAGCTGAACAACGTCATCCTCGAAAAAGAGGGCAAGGTGGCGGTCGTCACCATC AACCGCCCCAAGGCCCTCAACGCGCTCAACAGCGACACGCTCAAAGAAATGGATTAC GTCATCGGCGAGATCGAGAACGATTCCGAGGTGCTCGCCGTGATCCTCACCGGTGCG GGCGAAAAGTCGTTCGTGGCGGGTGCGGATATCTCCGAAATGAAAGAAATGAACACG ATCGAGGGCCGGAAGTTCGGCATCCTCGGCAACAAGGTTTTCCGCCGTCTCGAGTTGT TGGAGAAGCCGGTCATTGCCGCCGTGAATGGCTTCGCCCTCGGTGGTGGCTGCGAGA TCGCCATGAGCTGCGACATCCGGATCGCGTCGAGCAACGCCCGTTTCGGCCAGCCGG AAGTCGGCTTGGGCATCACCCCGGGCTTCGGCGGCACGCAGCGCCTCTCGCGGCTCG TCGGCATGGGCATGGCCAAGCAGCTCATCTTCACCGCCCAGAATATCAAGGCGGACG AGGCGCTGCGCATTGGCCTCGTTAACAAGGTCGTGGAGCCCTCGGAGCTCATGAACA CCGCGAAAGAGATCGCGAACAAGATCGTGTCCAACGCACCGGTGGCCGTCAAGCTCT CGAAGCAGGCCATCAACCGCGGCATGCAGTGCGATATCGACACCGCGCTCGCGTTCG AGAGCGAGGCGTTCGGGGAGTGCTTCTCGACCGAAGATCAGAAGGACGCCATGACC GCCTTCATCGAGAAGCGCAAGATCGAAGGCTTCAAGAACCGC (SEQ ID NO: 132) |
| crotonyl-coA thioesterase (SEQ ID NO: 29) | ATGCACCGCACCTCGAACGGCTCGCACGCCACCGGTGGCAACCTGCCGGACGTCGCCT CGCATTACCCGGTCGCGTACGAACAGACCCTGGACGGGACGGTGGGCTTCGTCATCG ATGAGATGACGCCCGAGCGCGCGACGGCCTCGGTCGAGGTGACCGACACGCTCCGCC AGCGCTGGGGCCTCGTCCACGGCGGTGCGTACTGCGCCCTCGCCGAGATGCTCGCCA CCGAGGCGACGGTGGCCGTGGTCCATGAGAAGGGCATGATGGCGGTGGGGCAGAGC AACCACACGAGCTTCTTTCGCCCGGTGAAAGAGGGCCACGTCCGCGCAGAGGCCGTG CGCATCCACGCGGGCTCCACCACCTGGTTTTGGGATGTGTCGCTGCGCGATGACGCAG GCCGCCTTTGCGCCGTGTCCAGCATGTCGATCGCGGTGCGGCCCCGCCGCGAC (SEQ ID NO: 133) |
| 4-oxalocrotonate decarboxylase (SEQ ID NO: 10) | ATGAGCACCACGTCGATCACCCCGGACGAGATCGCGCAGGTGCTGCTGGCAGGCGAG CGCAACCGGACCGAGGTCGCCCAGTTCAGCGCCTCGCACCCGGACCTCGACGTGCGC ACGGCGTATGCTGCGCAGCGGGCGTTCGTGCAGGCCAAGCTCGATGCGGGCGAGCA GTTGGTCGGCTACAAGCTCGGCCTGACCTCGCGGAATAAGCAGCGGGCCATGGGCGT CGACTGCCCGTTGTATGGTCGCGTCACCAGCAGCATGCTGGCGACCTACGGCGACCCC ATCCCCTTCGACCGCTTCATCCATCCGCGCGTCGAATCGGAAATCGCCTTCCTGCTGAA GCAGGATGTCACCGCCCCGGCCACCGTCTCGTCGGTCCTCGCCGCGACCGACGTCGTT TTCGGCGCTGTCGACGTGCTGGATAGCCGCTACGAGGGCTTCAAGTTCACGCTGGAA GATGTGGTCGCGGACAACGCCAGCGCCGGAGCCTTCTACCTCGGTCCCGTCGCCCGTC CGGCCACGGAGCTCCGGCTCGACTTGCTCGGCTGCATCGTCCGGGTCGACGGCGAGG TTACCATGACCGCAGCGGGAGCCGCCGTGATGGGCCACCCCGCAGCCGCGGTGGCCT GGCTCGCCAACCAGCTCGCCCTCGAGGGCGAGTCGCTGAAAGCCGGCCAGCTGATCT TCAGCGGCGTGTGACGGCGCCGGTCCCCGTCGTGCCCGGTGGCTCGGTCACCTTCG AGTTCGACGGACTGGGCGTCATCGAGGTGGCCGGCGCC (SEQ ID NO: 134) |

Production of Propylene from methanol. phaC-deleted *M. extorquens* transformed with a vector containing genes encoding crotonase and 4-oxalocrotonate decarboxylase are inoculated into 100 mL sealed flasks containing 20-50 mL NMS media, 125 mM methanol, 50 µg/mL rifamycin, and 10 µg/mL kanamycin. The flask headspace is flushed with oxygen and sealed to prevent loss of the propylene product. The flasks are then shaken continuously while being incubated at 30° C. The headspace gas is refreshed every day; however, immediately prior to refreshing the headspace, samples are drawn from both the liquid phase and headspace using a 10 µL Hamilton syringe and injected into a HP5890 GC equipped with a CP-PoraBOND U 25 m×0.32 mm column and an FID maintained at 200° C. The injector is connected in splitless mode and maintained at 250° C. Samples are run with He Gas at 7.3 ml/min as a carrier gas; the oven program is set as follows: hold at 50° C. 1.5 min; ramp to 300° C. at 10° C./min; hold at 300° C. 10 min. Propylene is identified by retention time compared to pure propylene diluted in air or dissolved in pure $H_2O$. Samples are also taken to measure optical density of the culture, allowing quantitation of specific propylene production rates per cell. Note that because methanol is the only carbon source provided to the cells, all propylene produced must have been derived from methanol.

Example 4

*Clostridium Autoethanogenum*

Growth and transformation. *C. autoethanogenum* is cultivated anaerobically in modified PETC medium (ATCC medium 1754) at 37° C. in modified PETC media.

The modified PETC medium contains (per L) 1 g $NH_4Cl$, 0.4 g KCl, 0.2 g $MgSO_4 \times 7\ H_2O$, 0.8 g NaCl, 0.1 g $KH_2PO_4$, 20 mg $CaCl_2 \times 2\ H_2O$, 10 ml trace elements solution (see below), 10 ml Wolfe's vitamin solution (see below), 2 g $NaHCO_3$, and 1 mg resazurin. After the pH is adjusted to 5.6, the medium is boiled, dispensed anaerobically, and autoclaved at 121° C. for 15 min. Steel mill waste gas (composition: 44% CO, 32% $N_2$, 22% $CO_2$, 2% $H_2$) or equivalent synthetic mixtures are used as carbon source. The media has a final pH of 5.9 and is reduced with Cystein-HCl and $Na_2S$ in a concentration of 0.008% (w/v).

The trace elements solution consists of 2 g nitrilotriacetic acid (adjusted to pH 6 with KOH before addition of the remaining ingredients), 1 g $MnSO_4$, 0.8 g $Fe(SO_4)_2$ $(NH_4)_2 \times 6\ H_2O$, 0.2 g $CoCl_2 \times 6\ H_2O$, 0.2 mg $ZnSO_4 \times 7\ H_2O$, 20 mg $CuCl_2 \times 2\ H_2O$, 20 mg $NiCl_2 \times 6\ H_2O$, 20 mg $Na_2MoO_4 \times 2\ H_2O$, 20 mg $Na_2SeO_4$, and 20 mg $Na_2WO_4$ per liter.

Wolfe's vitamin solution (Wolin et al., 1963, J. Biol. Chem. 238:2882-2886) contains (per L) 2 mg biotin, 2 mg folic acid, 10 mg pyridoxine hydrochloride, 5 mg thiamine-HCl, 5 mg riboflavin, 5 mg nicotinic acid, 5 mg calcium D-(+)-pantothenate, 0.1 mg vitamin B12, 5 mg p-aminobenzoic acid, and 5 mg thioctic acid.

Growth experiments are carried out in a volume of 100 ml PETC media in plastic-coated 500-ml-Schott Duran® GL45 bottles with butyl rubber stoppers and 200 kPa steel mill waste gas as sole energy and carbon source. Growth is monitored by measuring the optical density at 600 nm (OD600 nm).

Transformation methods for *C. autoethanogenum* are performed as described in U.S. Patent Publication 2011/0236941.

Briefly, to make competent cells, a 50 ml culture of *C. autoethanogenum* is subcultured to fresh media for 3 consecutive days. These cells are used to inoculate 50 ml PETC media containing 40 mM DL-threonine at an OD600 nm of 0.05. When the culture reaches an OD600 nm of 0.4, the cells are transferred into an anaerobic chamber and harvested at 4,700×g and 4° C. The culture is twice washed with ice-cold electroporation buffer (270 mM sucrose, 1 mM $MgCl_2$, 7 mM sodium phosphate, pH 7.4) and finally suspended in a volume of 600 µl fresh electroporation buffer. This mixture is transferred into a pre-cooled electroporation cuvette with a 0.4 cm electrode gap containing 1 µg of the methylated plasmid mix and immediately pulsed using the Gene pulser Xcell electroporation system (Bio-Rad) with the following settings: 2.5 kV, 600 µl, and 25 µF. Time constants of 3.7-4.0 ms are achieved. The culture is transferred into 5 ml fresh media. Regeneration of the cells is monitored at a wavelength of 600 nm using a Spectronic Helios Epsilon Spectrophotometer (Thermo) equipped with a tube holder. After an initial drop in biomass, the cells start growing again. Once the biomass has doubled from that point, the cells are harvested, suspended in 200 µl fresh media and plated on selective PETC plates (containing 1.2% Bacto™ Agar (BD)) with 4 µg/µl Clarithromycin. After 4-5 days of incubation with 30 psi steel mill gas at 37° C., 15-80 colonies per plate are clearly visible.

The colonies are used to inoculate 2 ml PETC media containing 4 µg/µl Clarithromycin. When growth occurs, the culture is upscaled into 5 ml and later 50 ml PETC media containing 4 µg/µl Clarithromycin and 30 psi steel mill gas as sole carbon source.

Confirmation of Successful Transformation:

To verify the DNA transfer, a plasmid mini prep is performed from 10 ml culture volume using the QIAprep Spin Miniprep Kit (Qiagen). The quality of the isolated plasmid DNA is sufficient to run a control PCR. The PCR is performed with Illustra PuReTaq Ready-To-Go™ PCR Beads (GE Healthcare) using standard conditions (95° C. for 5 min; 32 cycles of 95° C. for 30 s, 50° C. for 30 s, and 72° C. for 1 min; 72° C. for 10 min). As a further control, 1 µl of each of the partly degraded isolated plasmids are re-transformed in *E. coli* XL1-Blue MRF' Kan (Stratagene), from where the plasmids can be isolated cleanly and verified by restriction digests.

Introduction of Propylene synthesis pathway. Note that *C. autoethanogenum* does not have a native PHA pathway, hence no pathway genes need to be deleted. However, phaA and phaB function must be introduced to the cells to provide the substrate for the crotonase enzyme.

Selected phaA (SEQ ID NO:77), phaB (SEQ ID NO:123), crotonase (SEQ ID NO:32), crotonyl-coA thioesterase (SEQ ID NO:29), and 4-oxalocrotonate decarboxylase (SEQ ID NO:10) sequences were codon optimized (see Table 7) and synthesized with appropriate promoters. The genes are then cloned and transformed into *C. autoethanogenum* as described above. Transformation is confirmed by resistance of the cells to antibiotic selection, and gene expression is confirmed by northern blot (to confirm RNA transcription), western blot, or ELISA methods (to confirm protein expression).

TABLE 7

Codon Optimized Sequences for *C. autoethanogenum*

| Reference Sequence | Codon Optimized Sequence (SEQ ID NO: #) |
| --- | --- |
| phaA (SEQ ID NO: 77) | ATGACAGATGTAGTGATAGTTTCAGCAGCTAGAACAGCTGTTGGTAAATTCGGTGGTTC GTTAGCGAAAATAGCTGCTCCTGAATTAGGAGCTTCAGTAATTAGAGCTGTATTAGAAA GAGCAGGTGTAAAACCTGAGCAAGTGTCTGAAGTCATATTAGGGCAAGTCTTGACTGCA GGGTCAGGTCAGAATCCTGCAAGACAAGCCTTAATAGCTGCGGGACTTCCTAATGCAGT ACCTGGGATGACAATCAATAAAGTTTGTGGATCAGGTCTAAAAGCAGTTATGTTGGCTG CAAATGCGGTTGTAGCTGGAGAGCGCTGAAATAGTTGTGGCGGGTGGACAAGAAAACAT GAGTGCAGCACCACATGTTCTACCTGGCAGTAGAGATGGATTTCGAATGGGAGATGCAA AGCTAGTAGATAGCATGATAGTAGATGGATTATGGGATGTTTACAATAAGTATCATATG GGAATAACTGCAGAAAATGTAGCAAAAGAATATGGAATTACACGTGAAGCTCAAGACCA ATTTGCAGCACTTTCACAGAATAAGGCTGAAGCAGCACAAAAAGCTGGAAGATTTGATG ATGAAATAGTTCCTATTGAAATTCCACAAAGAAAGGGAGAACCACTTAGATTTGCCACTG ATGAATTTGTAAGGCATGGAGTAACAGCTGAATCTCTTGCAAGTTTGAAACCAGCGTTTG CCAAAGAGGGAACTGTGACTGCTGCTAATGCTTCAGGCATAAATGATGGAGCTGCAGCA GTCCTTGTTATGTCTGCGAAGAAAGCAGAAGCTCTTGGCCTTGAACCTTTGGCACGTATT AAGGCTTATGCCAATGCTGGAGTTGATCCTTCTGTTATGGGAATGGGACCTGTACCGGCA AGTAGAAGATGCCTAGAAAGAGCAGGATGGAGTGTAGGTGATTAGATCTTATGGAGA TTAATGAGGCTTTTGCTGCACAAGCGTTGGCTGTTCATAAGCAAATGGGTTGGGATACAT CAAAAGTTAATGTAAATGGCGGTGCAATAGCAATTGGACATCCAATAGGAGCATCTGGT TGCAGAATACTTGTTACTCTTCTTCATGAAATGTTGAAAAGAGATGCTAAAAGAGGTTTA GCATCATTATGTATAGGTGGTGGCATGGGAGTAGCTTTAGCATTAGAAAGACCG (SEQ ID NO: 135) |
| phaB (SEQ ID NO: 123) | ATGAAAAAGGTTTGTGTTATAGGTGCAGGTACTATGGGTTCAGGTATTGCTCAGGCATTT GCAGCCAAAGGGTTTGAAGTTGTTTTAAGGGACATAAAAGATGAATTCGTGGATAGGG GATTAGATTTTATAAATAAGAACTTAAGTAAGCTTGTAAAGAAGGGCAAAATTGAAGAG GCTACTAAAGTAGAAATCTTGACGAGAATAAGTGGTACCGTAGATCTTAACATGGCTGC AGATTGTGATTTAGTTATTGAAGCTGCGGTCGAAAGAATGGACATTAAGAAACAGATTTT TGCAGACTTAGATAACATATGTAAGCCAGAAACTATCTTAGCCAGTAATACAAGCTCATT ATCAATTACTGAAGTAGCAAGTGCGACAAAAAGGCCTGATAAAGTAATTGGAATGCATT TCTTTAATCCAGCACCTGTTATGAAATTAGTGGAAGTTATAAGGGGAATAGCAACTTCAC AAGAAACTTTTGATGCAGTGAAAGAAACCTCAATTGCAATAGGTAAAGACCCCGTTGAA GTTGCTGAAGCACCAGGTTTTGTTGTTAATAGAATACTAATACCAATGATAAATGAAGCA GTTGGAATCCTTGCAGAAGGTATAGCAAGTGTAGAAGATATTGACAAAGCAATGAAATT AGGTGCAAACCATCCAATGGGTCCTTTGGAATTAGGAGATTTCATTGGATTAGATATATG TTTAGCAATAATGGATGTACTATATTCTGAGACTGGAGATTCTAAGTACAGGCCTCATAC TTTACTTAAGAAATATGTAAGGGCGGGATGGTTAGGAAGAAAGTCTGGAAAGGGCTTTT ATGATTATAGTAAG (SEQ ID NO: 136) |
| crotonase (SEQ ID NO: 32) | ATGGAACTTAACAATGTAATACTTGAAAAAGAAGGCAAAGTAGCTGTTGTAACAATAAA CAGGCCAAAAGCTCTAAATGCACTTAATTCCGACACTCTTAAAGAAATGGATTACGTTAT AGGTGAGATAGAAAATGATTCTGAAGTACTAGCTGTAATACTTACAGGTGCTGGTGAGA AATCATTTGTGGCAGGAGCAGATATTTCTGAAATGAAAGAATGAATACTATTGAGGGG AGAAAATTCGGGATACTTGGAAACAAGGTTTTTAGAAGGTTAGAATTACTTGAGAAACC AGTAATAGCTGCCGTAAATGGATTTGCATTAGGTGGCGGATGTGAAATAGCAATGTCAT GCGATATCCGAATCGCATCTTCTAATGCAAGATTTGGGCAACCTGAAGTTGGATTAGGAA TCACTCCCGGATTTGGCGGTACACAAAGACTTAGCAGATTAGTAGGTATGGGAATGGCT AAGCAACTAATTTTTACGGCTCAGAACATAAAAGCAGATGAAGCTCTTAGGATTGGACTT GTGAATAAAGTAGTAGAACCGTCGGAGCTTATGAATACAGCAAAAGAAATTGCAAACAA AATAGTAAGTAATGCACCAGTGGCAGTTAAACTTTCGAAACAAGCAATCAATAGGGGCA TGCAATGCGATATAGATACGGCTTTGGCATTTGAAAGTGAAGCATTTGGGGAATGTTTTT CAACGGAAGATCAAAAGATGCTATGACAGCCTTTATTGAGAAAGAAAGATAGAGGG ATTTAAGAATAGA (SEQ ID NO: 137) |
| crotonyl-coA thioesterase (SEQ ID NO: 29) | ATGCACAGAACATCTAATGGATCACATGCAACAGGTGGCAATCTACCAGATGTTGCAAG TCATTATCCGGTAGCTTATGAACAGACATTAGATGGAACCGTTGGTTTTGTGATAGATGA AATGACTCCAGAAAGAGCTACAGCTTCCGTCGAGGTAACTGATACATTACGTCAGAGGT GGGGTTTGGTTCATGGTGGAGCATATTGTGCTCTTGCGGAAATGTTGGCTACTGAAGCA ACAGTTGCAGTTGTACATGAAAAAGGTATGATGGCAGTTGGTCAATCTAATCACACCAG CTTTTTCAGGCCAGTTAAAGAAGGTCATGTTAGAGCCGAGGCGGTTAGGATACATGCAG GAAGTACAACCTGGTTTTGGGATGTTTCTTTAAGAGATGATGCTGGTAGATTATGTGCTG TTAGCAGTATGTCCATTGCAGTAAGACCAAGAAGAGAT (SEQ ID NO: 138) |
| 4-oxalocrotonate decarboxylase (SEQ ID NO: 10) | ATGAGCACTACTAGTATAACACCAGATGAAATTGCTCAAGTACTATTAGCTGGAGAAAG AAATAGAACAGAAGTAGCACAGTTTTCAGCTTCACACCCGGATTTAGATGTAAGAACGG CTTATGCTGCTCAAAGAGCATTTGTTCAAGCAAAACTTGATGCAGGAGAGCAGTTAGTA GGCTATAAGCTTGGACTTACATCTAGGAATAAACAAAGAGCTATGGGTGTAGATTGCCC ACTTTATGGAAGAGTTACGTCCTCTATGTTGGCCACATATGGAGATCCAATACCATTCGA |

TABLE 7-continued

Codon Optimized Sequences for *C. autoethanogenum*

| Reference Sequence | Codon Optimized Sequence (SEQ ID NO: #) |
|---|---|
| | CAGATTCATACATCCTAGAGTTGAGTCTGAAATTGCATTCTTATTGAAACAAGATGTTACT |
| | GCTCCTGCTACAGTATCATCCGTACTTGCTGCAACTGATGTAGTTTTTGGTGCAGTGGAT |
| | GTTTTGGATTCAAGATATGAAGGATTTAAGTTTACTCTAGAAGATGTAGTTGCAGATAAT |
| | GCCAGTGCAGGAGCTTTTTACCTTGGACCTGTTGCTAGACCTGCTACAGAGTTAAGACTT |
| | GATTTACTAGGATGTATAGTTAGAGTTGACGGAGAAGTTACAATGACAGCGGCTGGTGC |
| | CGCTGTTATGGGACACCCTGCTGCTGCTGTAGCATGGTTAGCTAATCAACTTGCACTTGA |
| | GGGTGAAAGCTTGAAGGCAGGTCAGCTTATCTTTAGCGGTGGGGTCACTGCTCCTGTTC |
| | CAGTAGTTCCTGGTGGAAGCGTGACCTTTGAATTTGATGGCCTAGGTGTAATAGAAGTA |
| | GCAGGAGCC (SEQ ID NO: 139) |

Production of Propylene from carbon monoxide. *C. ethanogenum* transformed with the vector described above are used to inoculate 2 ml PETC media containing 4 µg/µl Clarithromycin. When growth occurs, the culture is upscaled into 5 ml and later 50 ml PETC media containing 4 µg/µl Clarithromycin and 30 psi steel mill gas as sole carbon source. The bottles are then shaken continuously while being incubated at 37° C. The headspace gas is refreshed every 2 days; however, immediately prior to refreshing the headspace, samples are drawn from both the liquid phase and headspace using a 10 µL Hamilton syringe and injected into a HP5890 GC equipped with a CP-PoraBOND U 25 m×0.32 mm column and an FID maintained at 200° C. The injector is connected in splitless mode and maintained at 250° C. Samples are run with He Gas at 7.3 ml/min as a carrier gas; the oven program is set as follows: hold at 50° C. 1.5 min; ramp to 300° C. at 10° C./min; hold at 300° C. 10 min. Propylene is identified by retention time compared to pure propylene diluted in air or dissolved in pure $H_2O$. Samples are also taken to measure optical density of the culture, allowing quantitation of specific propylene production rates per cell. Note that because carbon monoxide is the only carbon source provided to the cells, all propylene produced must have been derived from carbon monoxide.

Example 5

*Escherichia Coli* Heterotroph

Growth and Transformation. Growth and transformation methods for *E. coli* are well-known in the art. *E. coli* strains were transformed by electroporation using the appropriate plasmids. A single colony from a fresh transformation was then used to seed an overnight culture grown in Luria Broth (LB) supplemented with 1.5% (w/v) glucose and appropriate antibiotics at 37° C. in a rotary shaker (200 r.p.m.). Antibiotics were used at a concentration of 50 µg/ml for strains with a single resistance marker. For strains with multiple resistance markers, kanamycin and chloramphenicol were used at 25 µg/ml and carbenicillin was used at 50 µg/ml.

Figure 5:
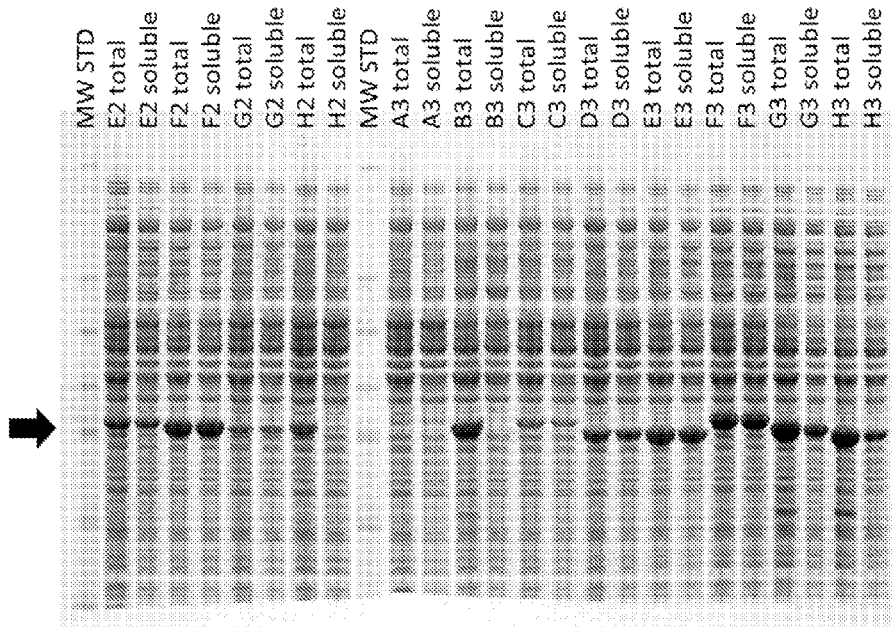
FIG. 5 shows SDS-PAGE analysis of heterogeneously expressed 4-OD genes in *E. coli*. The first lane for each sample shows total cell protein and the second lane for each sample shows soluble protein following lysis and clarification. The arrow on the left shows the approximate migration of 4-OD proteins (note sequence variation causes slight changes in migration for each individual 4-OD sequence).
Figure 6:
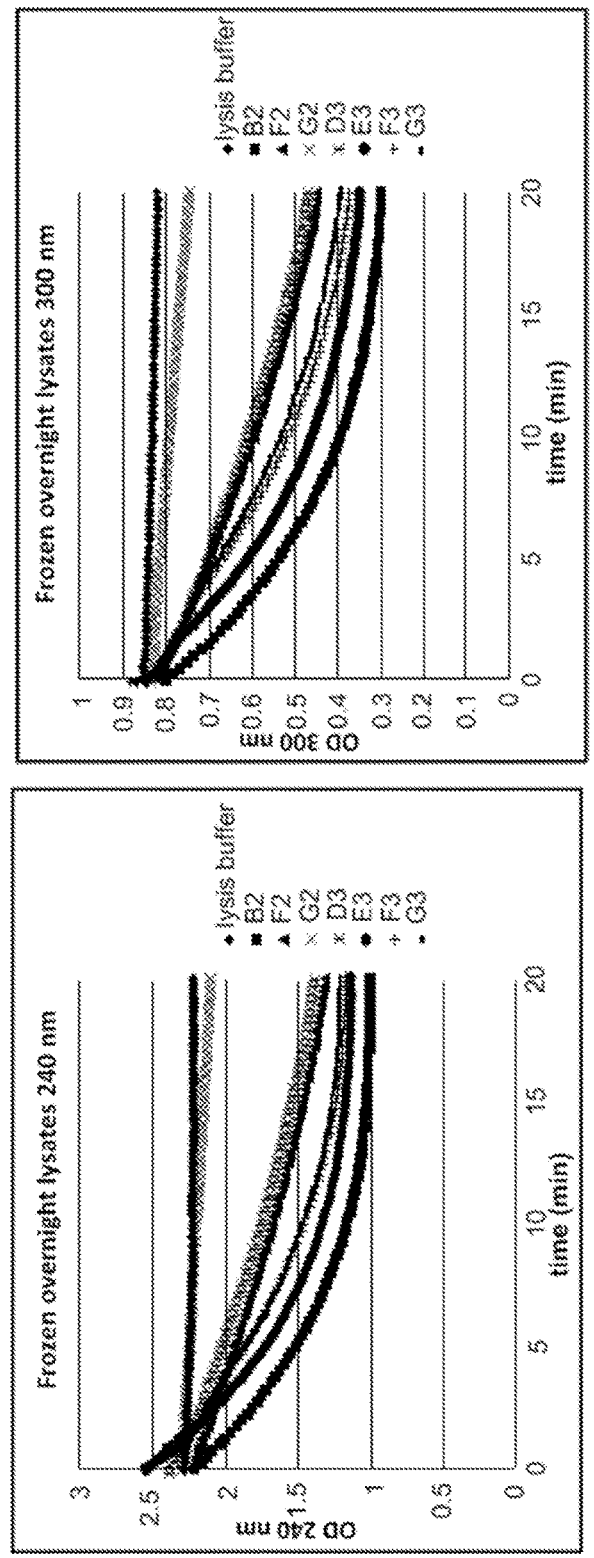
FIG. 6 shows sample 4-OD activity assays run under conditions as described showing decarboxylation of 4-oxalocrotonate.

Cloning and expression of 4-OD genes. 4-OD genes were identified from BLAST searching of the NCBI database using the *Pseudomonas putida* 4-OD sequence as a starting sequence. 24 individual 4-OD proteins were chosen for expression studies. The proteins were reverse-translated and codon-optimized for *E. coli* using commercial methods (DNA2.0, Inc. Menlo Park, Calif.). The genes were then cloned under control of a T7 promoter and expressed in *E. coli* BL21 (DE3). Briefly, single colonies were inoculated into 2 mL cultures of LB containing 50 µg/mL kanamycin and shaken overnight at 37° C. 1 mL of the saturated overnight culture was then inoculated into 200 mL LB containing 50 µg/mL kanamycin in a 2 L flask. The flasks were then shaken at 37° C. for 3-4 hours until an OD600 of 0.5-1.0 was reached. The cultures were induced by addition of 1 mM IPTG and shaken for additional 3 h at 37° C. Cells were harvested by centrifugation and analyzed by SDS-PAGE to confirm protein expression (see FIG. 5). Activity in cell lysates was confirmed by measuring decarboxylation activity on 4-oxalocrotonate (see FIG. 6).

4-OD Lysate Preparation:

Lysates were generated by resuspending induced *E. coli* cell pellet (equivalent to 1 mL culture) in 0.5 mL lysis buffer (20 mM $KHPO_4$ pH 8.0; 0.3 M KCl; 10% (w/v) glycerol; 0.1% NP-40; 0.5 mg/ml lysozyme; 1 mM PMSF). Cells were sonicated 5 seconds and then centrifuged for 15 min at 15,000×g, 4° C. The cleared supernatant was assayed immediately or stored at −80° C. for later assay.

4-Oxalocrotonate Decarboxylation Activity Assay:

The assay buffer comprised 100 mM Tris-HCl pH 7.4; 3.3 mM $MgSO_4$; 1 mM 4-oxalocrotonate (the stock solution of 4-oxalocrotonate was pre-equilibrated with a 1:100 dilution of *E. coli* lysate expressing 4-oxalocrotonate tautomerase from *Pseudomonas putida* (UniProtKB/Swiss-Prot Accession No. Q01468, geneid 87856) to achieve a distribution of keto and enol forms of 4-oxalocrotonate). Total reaction volume was 200 µl in a 96 well UV transparent plate and read on a SpectraMax Plate Reader (Molecular Devices). The reaction was initiated by addition of 4-OD containing lysates at 1:10 to 1:1000 final dilutions. Reactions were run at 25° C. Consumption of substrate was monitored by measuring drop in absorbance at 240 nm for the keto tautomer and at 300 nm for the enol tautomer (see FIG. 6).

Figure 7:
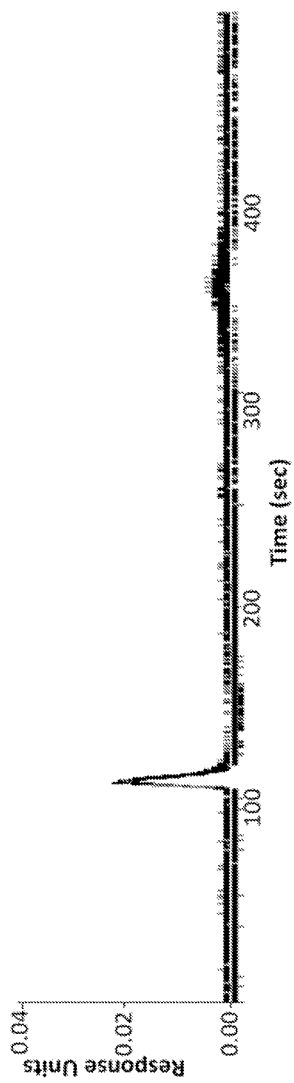
FIG. 7 shows a sample chromatogram of propylene detected on a HP5890 GC-FID under the assay conditions as described.

Crotonate Decarboxylation Assay:

The assay buffer comprised 100 mM Tris-HCl pH 7.4; 3.3 mM $MgSO_4$; 87.2 mM crotonic acid. Reactions were initiated by adding lysates to a final concentration of 1:10 to 1:100 in 1 ml volume in a TargetDP vial (2 ml total volume). Reactions were incubated from 12 to 72 hours at room temperature. Generated propylene was detected by injection of 0.5 µl aqueous phase plus 2 µl headspace gas onto a HP5890 GC equipped with a CP-PoraBOND U 25 m×0.32 mm column and an FID maintained at 200° C. The injector was connected in splitless mode and maintained at 250° C. Samples were run with He Gas at 7.3 ml/min as a carrier gas; the oven program was set as follows: hold at 50° C. 1.5 min; ramp to 300° C. at 10° C./min; hold at 300° C. 10 min. Propylene was identified by retention time compared to pure propylene diluted in air or dissolved in pure $H_2O$ (see FIG. 7).

Introduction of Propylene Synthesis Pathway.

Introduction of the pathway is performed essentially as described in Bond-Watts et al., Enzyme mechanism as a kinetic control element for designing synthetic biofuel pathways. Nat. Chem. Biol. 2011 7: 222-227.

Selected phaA (SEQ ID NO:77), phaB (SEQ ID NO:123), crotonase (SEQ ID NO:32), crotonyl-coA thioesterase (SEQ ID NO:29), and 4-oxalocrotonate decarboxylase (SEQ ID NO:10) sequences were codon optimized (see Table 8) and synthesized with appropriate promoters. The genes are then cloned and transformed into *E. coli* strain BL21 (DE3). Transformation is confirmed by resistance of the cells to antibiotic selection, and gene expression is confirmed by northern blot (to confirm RNA transcription), western blot, or ELISA methods (to confirm protein expression).

TABLE 8

Codon Optimized Sequences for *E. coli*

| Reference Sequence | Codon Optimized Sequence (SEQ ID NO: #) |
|---|---|
| phaA (SEQ ID NO: 77) | ATGACCGACGTGGTGATCGTGAGCGCTGCGCGCACGGCGGTTGGCAAGTTTGGTGGTA GCCTGGCGAAGATCGCGGCACCGGAGTTGGGCGCCAGCGTTATTCGTGCCGTCCTGGAA CGCGCAGGTGTGAAACCGGAGCAGGTGAGCGAAGTGATCCTGGGTCAAGTGCTGACCG CAGGCAGCGGTCAAAACCCGGCACGTCAAGCCTTGATTGCCGCAGGTCTGCCAAACGCT GTTCCGGGCATGACCATTAACAAAGTGTGTGGTTCTGGTCTGAAAGCGGTGATGCTGGC TGCGAACGCGGTTGTCGCCGGTGATGCGGAAATTGTGGTCGCGGGTGGCCAGGAGAAT ATGTCCGCAGCTCCGCACGTGCTGCCGGGCAGCCGTGACGGTTTCCGTATGGGCGATGC TAAATTGGTAGATAGCATGATTGTTGACGGCTTGTGGGACGTGTATAACAAATATCACAT GGGTATCACCGCGGAAAACGTTGCGAAAGAGTACGGTATCACCCGTGAGGCGCAGGAC CAGTTTGCCGCACTGAGCCAGAACAAGGCCGAAGCGGCGCAAAAAGCAGGCCGTTTTG ATGATGAGATCGTTCCGATTGAGATTCCGCAGCGTAAAGGTGAACCGCTGCGCTTCGCT ACCGACGAGTTTGTCCGTCACGGCGTTACCGCCGAATCCCTGGCCTCTTTGAAACCGGCG TTTGCTAAAGAGGGTACCGTCACCGCGGCAAACGCAAGCGGTATTAACGATGGCGCAGC AGCTGTCCTGGTTATGTCCGCGAAGAAGGCAGAAGCGTTGGGCCTGGAGCCGCTGGCTC GCATTAAAGCATATGCCAATGCCGGCGTTGATCCGAGCGTTATGGGCATGGGTCCGGTC CCGGCAAGCCGTCGTTGCCTGGAGCGTGCAGGCTGGTCCGTTGGCGACCTGGATCTGAT GGAGATCAATGAAGCCTTCGCAGCGCAGGCGCTGGCAGTGCACAAGCAGATGGGTTGG GACACCAGCAAGGTTAATGTCAATGGTGGCGCAATCGCCATTGGCCATCCTATCGGTGC GAGCGGTTGTCGTATTTTGGTTACCCTGCTGCATGAAATGCTGAAACGCGACGCCAAGC GTGGCCTGGCTAGCCTGTGCATCGGTGGTGGTATGGGTGTGGCGCTGGCGCTGGAACG TCCA (SEQ ID NO: 140) |
| phaB (SEQ ID NO: 123) | ATGAAGAAAGTATGCGTCATCGGTGCGGGCACCATGGGCAGCGGTATTGCGCAGGCGT TTGCAGCCAAGGGCTTCGAGGTGGTCCTGCGCGATATCAAAGATGAGTTCGTTGATCGC GGTTTGGACTTCATCAACAAAAACCTGAGCAAGCTGGTTAAGAAGGGTAAGATCGAAGA GGCGACGAAGGTTGAAATTCTGACCCGCATCAGCGGTACTGTTGACCTGAATATGGCGG CAGACTGCGATTGGTTATTGAAGCTGCGGTCGAGCGTATGGACATTAAGAAGCAGATT TTCGCCGATCTGGACAACATTTGTAAGCCGGAGACGATTCTGGCGAGCAACACCAGCAG CTTGAGCATTACCGAGGTGGCCTCTGCCACGAAGCGTCCGGATAAGGTCATCGGTATGC ACTTCTTTAACCCGGCTCCGGTGATGAAACTGGTCGAGGTGATCCGCGGTATTGCTACCA GCCAAGAAACGTTTGACGCGTGTGAAAGAGACGTCGATCGCTATCGGCAAGGATCCGGTT GAGGTGGCAGAAGCTCCGGGTTTTGTGGTGAATCGCATCCTGATCCCGATGATCAACGA GGCCGTAGGTATCCTGGCCGAGGGTATTGCCTCTGTGGAAGATATCGACAAGGCGATGA AACTGGGTGCTAATCACCCGATGGGTCCGTTGGAGCTGGGTGACTTCATCGGTCTGGAC ATTTGTCTGGCGATCATGGACGTTCTGTACTCTGAGACGGGCGACAGCAAATATCGCCCG CACACCCTGCTGAAAAAGTACGTTCGTGCTGGTTGGCTGGGTCGTAAGTCTGGCAAAGG CTTCTACGATTACAGCAAG (SEQ ID NO: 141) |
| crotonase (SEQ ID NO: 32) | ATGGAGCTGAATAATGTGATTCTGGAGAAAGAGGGCAAAGTCGCTGTTGTTACGATTAA CCGCCCGAAGGCATTGAACGCCCTGAACAGCGATACCCTGAAAGAGATGGATTACGTGA TTGGCGAGATCGAAAACGACAGCGAAGTTCTGGCCGTCATTCTGACTGGTGCCGGTGAA AAGAGCTTTGTCGCGGGTGCAGATATTAGCGAGATGAAAGAGATGAATACGATCGAAG GTCGTAAATTCGGTATCCTGGGCAATAAAGTCTTTCGTCGTTTGGAACTGCTGGAGAAAC CTGTCATCGCTGCCGTGAATGGCTTCGCGCTGGGCGGTGGCTGCGAGATTGCAATGAGC TGCGATATCCGTATCGCGAGCAGCAATGCGCGTTTCGGTCAACCGGAAGTGGGTCTGGG TATCACGCCGGGTTTTGGTGGCACCCAACGCCTGAGCCGTTTGGTTGGCATGGGTATGG CAAAACAACTGATCTTTACCGCGCAGAACATCAAAGCAGATGAAGCTCTGCGCATTGGCT TGGTCAATAAGGTGGTTGAGCCGAGCGAACTGATGAACACGGCGAAAGAGATCGCGAA CAAGATCGTGAGCAATGCACCGGTGGCCGTCAAACTGAGCAAACAGGCCATCAATCGTG GTATGCAATGTGATATCGACACCGCGCTGGCATTCGAAAGCGAGGCATTTGGTGAGTGC TTCAGCACGGAAGATCAAAAGGATGCAATGACGGCGTTCATTGAAAAACGTAAGATTGA AGGCTTCAAGAACCGC (SEQ ID NO: 142) |
| crotonyl-coA thioesterase (SEQ ID NO: 29) | ATGCATCGTACGAGCAACGGCAGCCACGCCACCGGTGGCAATCTGCCTGATGTCGCGAG CCATTATCCGGTTGCATACGAACAGACCCTGGACGGCACCGTCGGTTTCGTGATTGACGA AATGACTCCGGAGCGTGCCACCGCGAGCGTTGAGGTCACCGATACCCTGCGCCAGCGTT GGGGTCTGGTTCATGGTGGTCATATTGTGCGTTGGCAGAGATGTTGGCGACTGAAGCG ACCGTCGCAGTAGTCCATGAAAAGGGCATGATGGCGGTGGGCCAAAGCAATCACACCA GCTTTTTCCGTCCGGTTAAAGAGGGCCATGTTCGCGCAGAGGCGGTGCGTATTCACGCG GGTAGCACGACCTGGTTCTGGGACGTTAGCCTGCGCGATGACGCAGGTCGTCTGTGTGC AGTTAGCAGCATGTCTATTGCTGTCCGTCCGCGTCGCGAC (SEQ ID NO: 143) |

TABLE 8-continued

Codon Optimized Sequences for *E. coli*

| Reference Sequence | Codon Optimized Sequence (SEQ ID NO: #) |
|---|---|
| 4-oxalocrotonate decarboxylase (SEQ ID NO: 10) | ATGAGCACCACGAGCATTACCCCGGACGAAATCGCGCAGGTTCTGCTGGCAGGCGAGC GTAATCGCACCGAGGTGGCGCAATTTTCTGCGTCGCACCCGGATTTGGATGTCCGTACCG CGTACGCGGCACAACGTGCGTTCGTTCAGGCTAAACTGGACGCAGGTGAACAACTGGTC GGTTACAAATTGGGTCTGACGTCTCGTAATAAGCAGCGCGCAATGGGTGTCGACTGCCC GCTGTACGGCCGTGTTACCAGCAGCATGCTGGCCACCTATGGTGATCCGATTCCGTTTGA CCGCTTTATTCACCCACGTGTGGAGTCCGAAATTGCGTTCCTGCTGAAGCAAGATGTGAC CGCACCGGCGACGGTCAGCAGCGTTCTGGCAGCGACTGACGTCGTGTTTGGCGCGGTTG ACGTCCTGGATAGCCGTTACGAGGGCTTCAAGTTCACCCTGGAAGATGTTGTTGCAGAC AATGCATCTGCGGGTGCTTTCTATCTGGGTCCAGTTGCACGTCCAGCGACGGAGCTGCGT CTGGATCTGCTGGGTTGCATTGTGCGCGTCGACGGCGAAGTGACCATGACCGCAGCGGG TGCCGCGGTTATGGGCCACCCGGCAGCGGCCGTTGCGTGGCTGGCCAATCAGCTGGCCC TGGAAGGTGAAAGCCTGAAGGCGGGTCAGCTGATCTTCAGCGGTGGTGTCACTGCGCC GGTCCCGGTTGTGCCGGGTGGCAGCGTGACCTTCGAGTTTGACGGCCTGGGTGTCATCG AAGTGGCAGGTGCA (SEQ ID NO: 144) |

Production of Propylene from glycerol. Overnight cultures of freshly transformed *E. coli* strains are grown for 12-16 h in Terrific Broth (TB) at 37° C. and used to inoculate TB (50 ml) with 1.5% (w/v) glycerol and appropriate antibiotics to an optical density at 600 nm (OD600) of 0.05 in a 250 ml-baffled flask. The cultures are grown at 37° C. in a rotary shaker (200 r.p.m.) and induced with IPTG (1.0 mM) and L-arabinose (0.2% (w/v) (these inducers are dependent on the promoters used for plasmid construction; choice of inducer are apparent to those of skill in the art) at OD600=0.35-0.45. At this time, the growth temperature is reduced to 30° C., and the culture flasks are sealed with butyl rubber stoppers to prevent propylene evaporation. Additional glucose (1% (w/v)) is added concurrent with culture sampling after 1 d. Flasks are unsealed for 10 to 30 min every 24 h then resealed after sampling. Samples are drawn from both the liquid phase and headspace using a 10 µL Hamilton syringe and injected into a HP5890 GC equipped with a CP-PoraBOND U 25 m×0.32 mm column and an FID maintained at 200° C. The injector is connected in splitless mode and maintained at 250° C. Samples are run with He Gas at 7.3 ml/min as a carrier gas; the oven program is set as follows: hold at 50° C. 1.5 min; ramp to 300° C. at 10° C./min; hold at 300° C. 10 min. Propylene is identified by retention time compared to pure propylene diluted in air or dissolved in pure $H_2O$. Samples are also taken to measure optical density of the culture, allowing quantitation of specific propylene production rates per cell.

Production of Propylene from glucose. Overnight cultures of freshly transformed *E. coli* strains are grown for 12-16 h in Terrific Broth (TB) at 37° C. and used to inoculate TB (50 ml) with 1.5% (w/v) glucose replacing the standard glycerol supplement and appropriate antibiotics to an optical density at 600 nm (OD600) of 0.05 in a 250 ml-baffled flask. The cultures are grown at 37° C. in a rotary shaker (200 r.p.m.) and induced with IPTG (1.0 mM) and L-arabinose (0.2% (w/v)) at OD600=0.35-0.45. At this time, the growth temperature is reduced to 30° C., and the culture flasks are sealed with butyl rubber stoppers to prevent propylene evaporation. Additional glucose (1% (w/v)) is added concurrent with culture sampling after 1 d. Flasks are unsealed for 10 to 30 min every 24 h then resealed after sampling. Samples are drawn from both the liquid phase and headspace using a 10 µL Hamilton syringe and injected into a HP5890 GC equipped with a CP-PoraBOND U 25 m×0.32 mm column and an FID maintained at 200° C. The injector is connected in splitless mode and maintained at 250° C. Samples are run with He Gas at 7.3 ml/min as a carrier gas; the oven program is set as follows: hold at 50° C. 1.5 min; ramp to 300° C. at 10° C./min; hold at 300° C. 10 min. Propylene is identified by retention time compared to pure propylene diluted in air or dissolved in pure $H_2O$. Samples are also taken to measure optical density of the culture, allowing quantitation of specific propylene production rates per cell.

The disclosure of U.S. Provisional Application No. 61/702,534, filed on Sep. 18, 2012, is incorporated by reference herein in its entirety.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Application No. 61/702,534 filed on Sep. 18, 2012, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A non-naturally occurring C1 metabolizing bacterium, wherein the non-naturally occurring C1 metabolizing bacterium the bacterium comprises a heterologous nucleic acid molecule encoding 4-oxalocrotonate decarboxylase, a heterologous nucleic acid molecule encoding a crotonyl CoA thioesterase, and a heterologous nucleic acid molecule encoding a crotonase, and wherein the non-naturally occurring C1 metabolizing bacterium converts a C1 substrate to propylene.

2. The non-naturally occurring C1 metabolizing bacterium of claim 1, wherein the non-naturally occurring C1 metabolizing bacterium is an obligate C1 metabolizing bacterium.

3. The non-naturally occurring C1 metabolizing bacterium of claim 2, wherein the C1 metabolizing bacterium is a methanotrophic bacterium or a methylotrophic bacterium.

4. The non-naturally occurring C1 metabolizing bacterium of claim 1, wherein the C1 metabolizing bacterium is a CO utilizing bacterium that naturally possesses the ability to utilize CO.

5. The non-naturally occurring C1 metabolizing bacterium of claim 1, wherein the non-naturally occurring C1 metabolizing bacterium does not have a functional PHB synthase or a substantial amount of functional PHB synthase.

6. The non-naturally occurring C1 metabolizing bacterium of claim 5, wherein the PHB synthase is encoded by phaC or phbC.

7. The non-naturally occurring C1 metabolizing bacterium of claim 1, wherein the non-naturally occurring C1 metabolizing bacterium has a functional β-ketothiolase activity and a functional acetoacetyl coenzyme A reductase activity.

8. The non-naturally occurring C1 metabolizing bacterium of claim 7, wherein the β-ketothiolase is encoded by phaA or phbA.

9. The non-naturally occurring C1 metabolizing bacterium of claim 7, wherein the acetoacetyl coenzyme A reductase is encoded by phaB or phbB.

10. The non-naturally occurring C1 metabolizing bacterium of claim 1, wherein the non-naturally occurring C1 metabolizing bacterium does not produce a substantial amount of polyhydroxybutyrate.

11. The non-naturally occurring C1 metabolizing bacterium of claim 1, wherein the non-naturally occurring C1 metabolizing bacterium is selected from *Methylosinus trichosporium*OB3b, *Methylococcus capsulatus* Bath, *Methylomonas methanica* 16a,*Methylosinus trichosporium, Methylosinus sporium, Methylocystis parvus, Methylomonas methanica, Methylomonas albus, Methylobacter capsulatus, Methylobacterium organophilum, Methylomonas* sp AJ-3670, *Methylocella silvestris, Methylaciollphilum infernorum, Methylomicrobium alcahphilum*, or *Methylibium petrolelphilum*.

12. The non-naturally occurring C1 metabolizing bacterium of claim 4, wherein the CO utilizing bacterium is selected from *Clostridium autoethanogenum, Clostridium ljungdahli, Clostridium ragsdalei, Clostridium carboxydivorans, Butyribacterium methylotrophicum, Clostridium woodii*, or *Clostridium neopropanologen*.

13. The non-naturally occurring C1 metabolizing bacterium of claim 3, wherein the methylotrophic bacterium is *Methylobacterium extorquens, Methylobacterium radiotolerans, Methylobacterium populi, Methylobacterium chloromethanicum*, or *Methylobacterium nodulans*.

14. The non-naturally occurring C1 metabolizing bacterium of claim 1, wherein the non-naturally occurring C1 metabolizing bacterium is capable of growth on methane, methanol, formaldehyde, formic acid, carbon monoxide, carbon dioxide, methylated amines, methylated thiols, or methyl halogens as a carbon source.

15. The non-naturally occurring C1 metabolizing bacterium of claim 1, wherein the encoded crotonase, crotonyl CoA thioesterase, and 4-oxalocrotonate decarboxylase are encoded on a single nucleic acid molecule.

16. A method for producing propylene comprising culturing the non-naturally occurring C1 metabolizing bacterium of claim 1 on a C1 substrate under conditions sufficient to produce propylene.

17. The method of claim 16, wherein the heterologous nucleic acid molecule encodes a 4-oxalocrotonate decarboxylase.

18. The method of claim 17, wherein the encoded crotonase, crotonyl CoA thioesterase, and 4-oxalocrotonate decarboxylase are encoded on a single nucleic acid molecule.

19. The method of claim 16, wherein the non-naturally occurring C1 metabolizing bacterium:
 (a) does not have a functional PHB synthase or a substantial amount of functional PHB synthase; and/or
 (b) has a functional β-ketothiolase activity and a functional acetoacetyl coenzyme A reductase activity; and/or
 (c) does not produce a substantial amount of polyhydroxybutyrate.

20. The method of claim 19, wherein the PHB synthase is encoded by phaC or phbC.

21. The method of claim 19, wherein the β-ketothiolase is encoded by phaA or phbA.

22. The method of claim 19, wherein the acetoacetyl coenzyme A reductase is encoded by phaB or phbB.

23. The method of claim 16, wherein the non-naturally occurring C1 metabolizing bacterium is an obligate C1 metabolizing bacterium.

24. The method of claim 16, wherein non-naturally occurring C1 metabolizing bacterium is a methanotrophic bacterium or a methylotrophic bacterium.

25. The method of claim 24, wherein the methanotrophic bacterium is selected from *Methylosinus trichosporium* OB3b, *Methylococcus capsulatus* Bath, *Methylomonas methanica* 16a, *Methylosinus trichosporium, Methylosinus sporium, Methylocystis parvus, Methylomonas methanica, Methylomonas albus, Methylobacter capsulatus, Methylobacterium organophilum , Methylomonas* sp AJ-3670,

*Methylocella silvestris, Methylacidiphilum infernorum, Methylomicrobium alcaliphilum,* or *Methylibium petroleiphilum.*

26. The method of claim 24, wherein the methylotrophic bacterium is selected from *Methylobacterium extorquens, Methylobacterium radiotolerans, Methylobacterium populi, Methylobacterium chloromethanicum,* or *Methylobacterium nodulans.*

27. The method of claim 16, wherein the C1 metabolizing bacterium is a CO utilizing bacterium that naturally possesses the ability to utilize CO.

28. The method of claim 27, wherein the CO utilizing bacterium is *Clostridium autoethanogenum, Clostridium ljungdahli, Clostridium ragsdalei, Clostridium carboxydivorans, Butyribacterium methylotrophicum, Clostridium woodii,* or *Clostridium neopropanologen.*

29. The method of claim 16, wherein the C1 substrate comprises methane, methanol, formaldehyde, formic acid, carbon monoxide, carbon dioxide, methylated amines, methylated thiols, or methyl halogens.

30. The method of claim 16, wherein the non-naturally occurring C1 metabolizing bacterium produces from about 0.1 g propylene/L/day to about 50 g propylene/L/day.

* * * * *

SEQUENCE LISTING

<160> NUMBER OF SEQ ID NOS: 144

<210> SEQ ID NO 1
<211> LENGTH: 261
<212> TYPE: PRT
<213> ORGANISM: Myxococcus xanthus

<400> SEQUENCE: 1

```
Met Thr Ala Thr Val Asp His Glu Ala Leu Ala His Phe Leu Asp Ser
 1               5                  10                  15

Ala Arg Leu Glu Arg Arg Glu Val Ala Pro Leu Thr Arg Glu Gln Pro
            20                  25                  30

Ala Leu Ser Val Pro Asp Ala Tyr Ala Ile Gln Glu Ala Gly Ile Arg
        35                  40                  45

Leu Arg Leu Ser His Gly Glu Arg Val Val Gly Leu Lys Met Gly Leu
50                  55                  60

Thr Ser Glu Ala Lys Arg Lys Gln Met Asn Leu Asp Ser Pro Val Tyr
65                  70                  75                  80

Gly Val Leu Thr Asp Arg Met Gln Val Pro Ala Gly Gly Val Ile Gln
                85                  90                  95

Leu Ser Gln Gly Val His Pro Lys Ile Glu Pro Glu Ile Ala Phe Arg
            100                 105                 110

Thr Ala Arg Glu Leu Arg Gly Thr Val Thr Arg Asp Gly Val Leu Asp
        115                 120                 125

Ala Cys Glu Ser Val Phe Ala Ala Met Glu Ile Leu Asp Ser Arg Tyr
130                 135                 140

Arg Asp Phe Lys Tyr Phe Ser Leu Pro Asp Val Val Ala Asp Asn Ala
145                 150                 155                 160

Ser Ser Ser Leu Phe Val Leu Gly Thr Ala Glu His Pro Pro Arg Ala
                165                 170                 175

Met Asp Leu Thr Arg Leu Glu Met Thr Leu Ser Val Asn Gly Glu Pro
            180                 185                 190

Val Gln Ser Ala Arg Ala Asp Ala Ile Ser Gly Asp Pro Val Val Ser
        195                 200                 205

Val Ile Gln Leu Cys Glu Leu Leu Ala Gln Arg Gly Gln Val Leu Pro
210                 215                 220

Ala Gly Ser Ile Val Leu Ala Gly Ala Ala Thr Ala Ala His Met Leu
225                 230                 235                 240

Arg Pro Gly Asp Arg Val Gln Leu Thr Val Glu Gly Leu Gly Ile Val
                245                 250                 255

Ala Val Ser Ala Glu
            260
```

<210> SEQ ID NO 2
<211> LENGTH: 259
<212> TYPE: PRT
<213> ORGANISM: Sphingomonas wittichii

<400> SEQUENCE: 2

```
Met Ala Asp Leu Gln Ala Leu Ala Glu Arg Leu Asp Glu Ala Gln Arg
 1               5                  10                  15

Leu Ala Arg Ala Thr Pro Gln Leu Glu Asp Ala Leu Ser Ile Leu Asp
            20                  25                  30

Ala Tyr Gln Val Gln Arg Ala Leu Leu Glu Arg Arg Tyr Ala Arg Gly
        35                  40                  45

Glu Arg Arg Val Gly Ile Lys Met Gly Phe Thr Ser Arg Ala Lys Met
50                  55                  60

Val Gln Met Gly Val Ser Glu Met Ile Trp Gly Arg Leu Thr Asp Gly
65                  70                  75                  80

Met Met Val Glu Glu Gly Gly Thr Val Asp Phe Asp Arg Tyr Val His
                85                  90                  95
```

```
Pro Arg Val Glu Pro Glu Ile Ala Phe Ile Leu Lys Arg Asp Leu Pro
            100                 105                 110

Gly Pro Val Thr Leu Ala Gly Ala Ala Ala Val Glu Ala Ile Ala
            115                 120                 125

Pro Ala Leu Glu Ile Ile Asp Ser Arg Tyr Lys Asp Phe Arg Phe Ser
130                 135                 140

Val Thr Asp Val Val Ala Asp Asn Ser Ser Ser Ser Phe Val Val
145                 150                 155                 160

Gly Pro Trp Ser Thr Pro Ser Thr Asn Val Ser Asn Val Gly Met Ile
            165                 170                 175

Met Ser Val Asn Gly Glu Pro Lys Gln Ile Gly Ser Ser Ala Ala Ile
            180                 185                 190

Leu Gly Ser Pro Leu Arg Ser Leu Val Ala Ala Arg Leu Ala Ser
            195                 200                 205

Glu Ala Gly Glu Ser Leu Arg Ala Gly Asp Val Ile Leu Ala Gly Gly
            210                 215                 220

Ala Thr Ala Ala Glu Ala Leu Ser Pro Gly Asp His Ile Arg Leu Glu
225                 230                 235                 240

Val Gln Gly Leu Gly Ile Ala Glu Phe Thr Val Gly Arg Thr Gly Ala
            245                 250                 255

Ala Ser Gly

<210> SEQ ID NO 3
<211> LENGTH: 256
<212> TYPE: PRT
<213> ORGANISM: Pseudonocardia dioxanivorans

<400> SEQUENCE: 3

Met Thr Asp Val Ala Thr Trp Ala Ala Arg Leu Asp Asp Ala Ala Thr
1               5                   10                  15

Gly Thr Ala Pro Ile Ala Pro Leu Ser Gly Asp Gly Leu Thr Asp Leu
            20                  25                  30

Ala Val Ala Tyr Glu Val Gln Gly Gly Val Val Gly Leu Arg Leu Gly
            35                  40                  45

Arg Gly Glu Arg Leu Val Gly Gly Lys Leu Gly Leu Thr Ser Arg Ala
50                  55                  60

Lys Gln Ile Ala Met Gly Val Asp Arg Pro Leu Tyr Gly Leu Val Thr
65                  70                  75                  80

Ser Gly Met Ala Arg Asn Ser Gly Ser Arg Leu Leu Leu Glu Glu Leu
            85                  90                  95

Ile His Pro Arg Val Glu Pro Glu Ile Ala Phe Val Leu Gly Glu Pro
            100                 105                 110

Leu Glu Gly Pro Gly Val Thr Val Ala Asp Val Leu Ala Ala Thr Arg
            115                 120                 125

Tyr Val Cys Pro Ala Leu Asp Val Ile Asp Ser Arg Tyr Glu Gly Phe
130                 135                 140

Arg Phe Thr His Leu Asp Ala Ile Ala Asp Asn Ala Ser Ser Ala Val
145                 150                 155                 160

Phe Ala Leu Gly Asp Asp Leu Val Glu Pro Arg Gly Asp Leu Ala Leu
            165                 170                 175

Thr Gly Cys Val Leu Glu Val Asp Gly Arg Val Val Glu Ser Ala Ala
            180                 185                 190

Gly Ala Ala Val Met Gly His Pro Ala Ala Ala Val Ala Tyr Met Ala
            195                 200                 205
```

Asn Gln Leu Val Ala Thr Asp Arg Arg Leu Glu Ala Gly Trp Val Val
            210                 215                 220

Leu Ser Gly Gly Leu Thr Ala Pro Val Pro Leu Pro Gly Ser Thr
225                 230                 235                 240

Val Thr Ala Thr Leu Ser Gly Leu Gly Ser Val Thr Leu Gly Ala Glu
                245                 250                 255

<210> SEQ ID NO 4
<211> LENGTH: 263
<212> TYPE: PRT
<213> ORGANISM: Neisseria wadsworthii

<400> SEQUENCE: 4

Met Ser Thr Leu Ser Lys Gln Gln Ile Glu Gln Leu Ala Glu His Leu
1               5                   10                  15

Glu Asn Ala Glu Leu Gln Ala Tyr Glu Val Thr Lys Ile Thr Asp Asp
            20                  25                  30

Phe Pro Asp Met Asp Tyr Glu Asp Ala Phe Asp Ile Gln Trp Glu Ile
        35                  40                  45

Arg Arg Arg Lys Glu Ala Arg Gly Asn Lys Ile Val Gly Met Lys Met
50                  55                  60

Gly Leu Thr Ser Trp Ala Lys Met Ser Gln Met Gly Val Glu His Pro
65                  70                  75                  80

Cys Tyr Gly Phe Leu Ala Asp Tyr Phe Ser Val Pro Glu Gly Ala Ala
                85                  90                  95

Val Lys His Asp Glu Leu Ile His Pro Lys Ile Glu Ala Glu Leu Ala
            100                 105                 110

Phe Val Thr Lys Ala Asp Leu Arg Gly Pro Gly Cys His Ile Gly Asp
        115                 120                 125

Val Leu Ala Ala Thr Asp Phe Val Met Pro Ala Ile Glu Val Ile Asp
130                 135                 140

Ser Arg Tyr Lys Asp Phe Lys Phe Asp Leu Lys Ser Val Ile Ala Asp
145                 150                 155                 160

Asn Ser Ser Ser Ser Arg Phe Ile Thr Gly Gly Cys Ala Lys Pro Ala
                165                 170                 175

Ser Glu Leu Asp Leu Lys Thr Leu Gly Val Val Met Glu Ile Asn Gly
            180                 185                 190

Lys Val Val Gln Thr Gly Ala Gly Ala Ala Val Leu Gly His Pro Ala
        195                 200                 205

Ala Ser Val Ala Met Leu Ala Asn Met Leu Ala Glu Arg Gly Glu Tyr
210                 215                 220

Leu Pro Ala Gly Ser Phe Val Met Ile Gly Ala Ile Thr Ala Ala Val
225                 230                 235                 240

Gln Val Glu Lys Gly Asp Ser Phe Cys Val His Phe Gln Asp Leu Gly
                245                 250                 255

Ser Ile Ser Gly Arg Phe Glu
            260

<210> SEQ ID NO 5
<211> LENGTH: 262
<212> TYPE: PRT
<213> ORGANISM: Artificial Sequence
<220> FEATURE:
<223> OTHER INFORMATION: Uncultured bacterium

<400> SEQUENCE: 5

```
Met Thr Thr Ala Ser Pro Glu Leu Val Ala Glu Leu Ala Glu Tyr Leu
 1               5                  10                  15
Glu Ser Ala Glu Leu Glu Ala Arg Asp Val Thr Lys Ile Thr Asp Ala
             20                  25                  30
His Pro Asp Leu Asp Phe Asp Asp Ala Tyr Asn Ile Gln Trp Glu Ile
         35                  40                  45
Arg Arg Arg Lys Leu Glu Arg Gly Thr Arg Leu Ala Gly Leu Lys Ala
 50                  55                  60
Gly Leu Thr Ser Arg Ala Lys Met Lys Gln Met Gly Val Glu Thr Pro
 65                  70                  75                  80
Ile Tyr Gly Phe Leu Ala Asp Tyr Phe Glu Arg Pro Glu Gly Gly Glu
                 85                  90                  95
Ile Ala Thr Ala Asp Leu Ile His Pro Lys Val Glu Ala Glu Ile Ala
             100                 105                 110
Val Val Thr Lys Ala Glu Leu Ala Gly Pro Cys His Met Gly Gln Ala
             115                 120                 125
Leu Ala Ala Ile Asp Phe Val Leu Pro Ala Val Glu Ile Ile Asp Ser
         130                 135                 140
Arg Tyr Glu Asn Phe Arg Phe Asp Leu Val Ser Val Ile Ala Asp Asn
145                 150                 155                 160
Ala Ser Ser Arg Phe Val Leu Gly Gly Arg Met Ala Asp Val Arg
                165                 170                 175
Asp Val Asp Leu Arg Thr Leu Gly Val Val Met Glu Lys Asn Gly Gln
             180                 185                 190
Val Val Glu Leu Gly Ala Gly Ala Ala Val Leu Asn His Pro Val Ala
             195                 200                 205
Ser Val Val Leu Leu Ala Asn Gln Leu Ala Glu Arg Gly Glu Val Ile
         210                 215                 220
Pro Ala Gly Thr Leu Ile Leu Thr Gly Gly Ile Thr Ala Ala Val Ala
225                 230                 235                 240
Val Glu Ala Gly Asp Ala Val Asn Val Arg Tyr Gln Gly Leu Gly Asn
                245                 250                 255
Val Thr Met Arg Phe Val
            260

<210> SEQ ID NO 6
<211> LENGTH: 264
<212> TYPE: PRT
<213> ORGANISM: marine gamma proteobacterium

<400> SEQUENCE: 6

Met Ser Arg Thr Leu Asp Gln Glu Thr Ile Glu Lys Leu Ala Glu His
 1               5                  10                  15
Leu Glu Asn Ala Glu Leu Gln Ala Tyr Glu Val Thr Lys Ile Thr Asp
             20                  25                  30
Asp Tyr Pro Asn Met Thr Phe Thr Asp Ala Thr Asp Val Gln Trp Glu
         35                  40                  45
Ile Arg Arg Arg Lys Met Ser Arg Gly His Lys Val Val Gly Met Lys
 50                  55                  60
Met Gly Leu Thr Ser Trp Ala Lys Met Lys Gln Met Gly Val Glu Met
 65                  70                  75                  80
Pro Cys Tyr Gly Phe Leu Ala Asp Tyr Phe Ser Leu Pro Asp Gly Ala
                 85                  90                  95
Gln Val Pro Phe Asp Glu Leu Ile His Pro Lys Val Glu Ala Glu Ile
             100                 105                 110
```

```
Ala Phe Val Thr Asn Lys Glu Leu Ser Gly Arg Asn Leu Thr Val Glu
            115                 120                 125

Asp Val Leu Ala Ala Thr Glu Leu Val Val Pro Ala Val Glu Ile Ile
        130                 135                 140

Asp Ser Arg Tyr Lys Asp Phe Lys Phe Asp Leu Thr Ser Val Gln Ala
145                 150                 155                 160

Asp Asn Ser Ser Thr Arg Phe Val Val Gly Ser His Ala Ala Lys
                165                 170                 175

Pro Glu Asp Phe Asp Trp Ser Thr Ile Gly Val Val Met Gln Lys Asn
                180                 185                 190

Gly Glu Ile Ile Glu Leu Gly Ala Gly Ala Ala Val Leu Asp His Pro
            195                 200                 205

Ala Ala Ser Val Ala Met Leu Ala Thr Met Leu Ala Glu Arg Asp Glu
        210                 215                 220

Val Ile Pro Ala Gly Thr Phe Ile Met Thr Gly Gly Ile Thr Ala Ala
225                 230                 235                 240

Val Leu Val Ala Lys Gly Asp Ser Ile Val Val Arg Tyr Gln Gly Leu
                245                 250                 255

Gly Thr Val Thr Met Lys Phe Val
                260

<210> SEQ ID NO 7
<211> LENGTH: 262
<212> TYPE: PRT
<213> ORGANISM: Leptothrix cholodnii

<400> SEQUENCE: 7

Met Ala Leu Asn Arg Thr Asp Ile Glu Ala Leu Ala Ala His Leu Glu
 1               5                  10                  15

Ser Ala Glu Leu Glu Ala Arg Asp Val Thr Lys Ile Thr Asp Asp Phe
            20                  25                  30

Pro Leu Met Asp Trp Ala Asp Ala Tyr Asp Ile Gln Asp Glu Ile Arg
        35                  40                  45

Arg Arg Lys Glu Ala Arg Gly His Lys Thr Val Gly Leu Lys Ala Gly
 50                  55                  60

Leu Thr Ser Phe Ala Lys Met Lys Gln Met Gly Val Asp Thr Pro Cys
 65                  70                  75                  80

Phe Gly Phe Val Ser Asp Tyr Met Ala Arg Pro Asp Gly Gly Glu Ile
                85                  90                  95

Lys Val Ser Glu Leu Ile His Pro Lys Val Glu Ala Glu Ile Cys Ile
            100                 105                 110

Val Thr Lys Ala Pro Leu Arg Gly Pro Gly Cys His Val Gly Ala Val
        115                 120                 125

Leu Ala Ala Ile Asp Phe Val Leu Pro Ala Val Glu Ile Ile Asp Ser
130                 135                 140

Arg Tyr Arg Asp Phe Lys Phe Asp Leu Lys Ser Val Ile Ala Asp Asn
145                 150                 155                 160

Thr Ser Ala Ser Arg Phe Val Ile Gly Gly Arg Ser Arg Asn Val Glu
                165                 170                 175

Ala Leu Asp Leu Arg Thr Leu Gly Val Val Leu Glu Lys Asn Gly Gln
            180                 185                 190

Ile Val Ser Met Ala Gly Ala Ala Val Leu Gly His Pro Ala Ala
        195                 200                 205

Ala Val Ala Met Met Ala Asn His Leu Gly Ala Arg Gly Gln Glu Ile
```

```
            210                 215                 220
Pro Ala Gly Thr Phe Ile Met Thr Gly Gly Val Thr Glu Ala Ile Ala
225                 230                 235                 240

Val Gln Ala Gly Asp Ser Val Asn Val Arg Phe Gln Asp Leu Gly Ser
                245                 250                 255

Val Ser Met Arg Phe Val
            260
```

<210> SEQ ID NO 8
<211> LENGTH: 270
<212> TYPE: PRT
<213> ORGANISM: Sulfobacillus acidophilus

<400> SEQUENCE: 8

```
Met Thr Gly Pro Glu Leu Asn Arg Trp Ala Asp Arg Val Trp His His
1               5                   10                  15

Gln Arg Thr Ala Thr Pro Met Ala Arg Ile Thr Glu Glu Val Pro His
                20                  25                  30

Leu Thr Val Glu Asp Gly Tyr Ala Ile Gln Ala Arg Leu Ile Asp Arg
            35                  40                  45

Arg Thr Ala Ser Gly Glu His Leu Ile Gly Tyr Lys Met Gly Leu Thr
        50                  55                  60

Ser Glu Ala Lys Gln His Ala Val Gly Val Ser Leu Pro Ile Tyr Gly
65                  70                  75                  80

Arg Leu Thr Asp Ala Met Glu Leu His Thr Pro Ile Val Asp Gly Ser
                85                  90                  95

Arg Leu Ile His Pro Arg Val Glu Pro Glu Leu Ala Ile Val Leu Lys
            100                 105                 110

Arg Gly Leu Ala Gly Ser Val Pro Leu Arg Asp Val Leu Thr Ala Ile
        115                 120                 125

Glu Cys Val Leu Pro Ala Trp Glu Val Ile Asp Ser Arg Tyr Glu Gly
130                 135                 140

Phe Ser Phe Thr Ala Ala Asp Val Val Ala Asp Asn Ala Ser Ala Ala
145                 150                 155                 160

Gln Phe Tyr Leu Pro Pro Tyr Ala Phe Ser Pro Tyr Gly Arg Asp Trp
                165                 170                 175

Ala Glu Met Gly Val Thr Val Arg Arg Asn Gly His Val Arg His Val
            180                 185                 190

Ala Ser Ala Ala Ala Val Leu Gly His Pro Trp Glu Ala Val Arg Arg
        195                 200                 205

Leu Ala Ile Leu Leu Ala Gln Glu Asp Arg Glu Leu Leu Pro Gly Gln
210                 215                 220

Val Ile Leu Thr Gly Gly Ile Thr Asp Ala Val Pro Leu Ser Pro Gly
225                 230                 235                 240

Asp Arg Leu Gln Met Thr Phe Gly Thr Leu Gly Ile Leu Asp Val Val
                245                 250                 255

Val Pro Val Arg Lys Glu Asp Ala Asn Ala Pro Asp Ser Tyr
            260                 265                 270
```

<210> SEQ ID NO 9
<211> LENGTH: 262
<212> TYPE: PRT
<213> ORGANISM: Arcobacter sp. L

<400> SEQUENCE: 9

```
Met Ala Leu Asp Lys Ser Thr Ile Glu Lys Leu Ala Lys His Cys Glu
```

```
            1               5                  10                 15
Asp Ala Glu Leu Lys Ala Tyr Glu Ile Thr Lys Ile Thr Asp Asp Tyr
                    20                 25                 30

Pro Asp Met Thr Tyr Glu Asp Ala Tyr Asp Ile Gln Trp Thr Ala Arg
            35                 40                 45

Ala Ala Lys Glu Ala Arg Gly His Lys Ile Val Gly Met Lys Met Gly
            50                 55                 60

Leu Thr Ser Gln Ala Lys Met Lys Gln Met Gly Val Pro Asn Pro Cys
 65                 70                 75                 80

Tyr Gly Tyr Leu Ala Asp Tyr Phe Ser Phe Gly Asp Gly Ala Glu Ile
                    85                 90                 95

Lys Ile Asp Glu Leu Ile His Pro Lys Val Glu Ala Glu Ile Ala Phe
            100                105                110

Val Leu Lys Asn Asp Leu Glu Gly Pro Gly Cys His Ile Gly Asp Val
            115                120                125

Leu Ala Ala Thr Asp Phe Val Met Pro Ala Val Glu Ile Ile Asp Ser
            130                135                140

Arg Tyr Lys Asp Phe Lys Phe Asp Leu Lys Ser Val Ile Ala Asp Asn
145                 150                155                160

Ser Ser Ser Ser Arg Tyr Val Thr Gly Gly Arg Met Arg Asp Ile Lys
                    165                170                175

Asp Leu Asp Leu Lys Thr Leu Gly Val Val Met Glu Ile Asn Gly Glu
            180                185                190

Ile Val Gln Leu Gly Ala Gly Ala Ala Val Leu Gly His Pro Ala Thr
            195                200                205

Ser Ile Ala Met Leu Ala Asn Met Leu Ser Gln Arg Gly Glu Lys Leu
            210                215                220

Lys Ala Gly Glu Tyr Ile Leu Ser Gly Ala Ile Thr Ala Ala Val Ser
225                 230                235                240

Val Lys Lys Gly Asp Asn Val Thr Val Lys Phe Gln Asp Leu Gly Ser
                    245                250                255

Leu Ser Phe Arg Phe Val
            260

<210> SEQ ID NO 10
<211> LENGTH: 261
<212> TYPE: PRT
<213> ORGANISM: Nakamurella multipartita

<400> SEQUENCE: 10

Met Ser Thr Thr Ser Ile Thr Pro Asp Glu Ile Ala Gln Val Leu Leu
 1               5                  10                 15

Ala Gly Glu Arg Asn Arg Thr Glu Val Ala Gln Phe Ser Ala Ser His
                    20                 25                 30

Pro Asp Leu Asp Val Arg Thr Ala Tyr Ala Ala Gln Arg Ala Phe Val
            35                 40                 45

Gln Ala Lys Leu Asp Ala Gly Glu Gln Leu Val Gly Tyr Lys Leu Gly
            50                 55                 60

Leu Thr Ser Arg Asn Lys Gln Arg Ala Met Gly Val Asp Cys Pro Leu
 65                 70                 75                 80

Tyr Gly Arg Val Thr Ser Ser Met Leu Ala Thr Tyr Gly Asp Pro Ile
                    85                 90                 95

Pro Phe Asp Arg Phe Ile His Pro Arg Val Glu Ser Glu Ile Ala Phe
            100                105                110
```

```
Leu Leu Lys Gln Asp Val Thr Ala Pro Ala Thr Val Ser Ser Val Leu
            115                 120                 125

Ala Ala Thr Asp Val Val Phe Gly Ala Val Asp Val Leu Asp Ser Arg
        130                 135                 140

Tyr Glu Gly Phe Lys Phe Thr Leu Glu Asp Val Val Ala Asp Asn Ala
145                 150                 155                 160

Ser Ala Gly Ala Phe Tyr Leu Gly Pro Val Ala Arg Pro Ala Thr Glu
                165                 170                 175

Leu Arg Leu Asp Leu Leu Gly Cys Ile Val Arg Val Asp Gly Glu Val
                180                 185                 190

Thr Met Thr Ala Ala Gly Ala Ala Val Met Gly His Pro Ala Ala Ala
            195                 200                 205

Val Ala Trp Leu Ala Asn Gln Leu Ala Leu Glu Gly Glu Ser Leu Lys
        210                 215                 220

Ala Gly Gln Leu Ile Phe Ser Gly Gly Val Thr Ala Pro Val Pro Val
225                 230                 235                 240

Val Pro Gly Gly Ser Val Thr Phe Glu Phe Asp Gly Leu Gly Val Ile
                245                 250                 255

Glu Val Ala Gly Ala
            260

<210> SEQ ID NO 11
<211> LENGTH: 255
<212> TYPE: PRT
<213> ORGANISM: Burkholderia rhizoxinica

<400> SEQUENCE: 11

Met Ser Phe Ile Thr Glu Tyr Ala Thr Leu Leu Asp Thr Ala Ala Arg
1               5                   10                  15

Asp Ala His Glu Val Gln Phe Asp Leu Asp Ala Arg Leu Ser Leu
            20                  25                  30

Glu Asp Ala Tyr Ala Ile Gln Ala Ala Ser Ile Ala Arg Arg Leu Glu
        35                  40                  45

Arg Gly Glu Arg Arg Val Gly Val Lys Met Gly Phe Thr Ser Arg Ala
    50                  55                  60

Lys Met Leu Gln Met Gly Leu Ser Asp Val Ile Trp Gly Arg Leu Thr
65                  70                  75                  80

Cys Ala Met Gln Leu Glu Glu Gly Ala Ser Val Ser Phe Arg Arg Phe
                85                  90                  95

Val His Pro Arg Val Glu Pro Glu Ile Ala Phe Leu Leu Lys Arg Pro
            100                 105                 110

Leu Ala Ala Asp Val Thr Ala Pro Ala Leu Ala Ala Val Glu Ala
        115                 120                 125

Ile Ala Pro Ala Ile Glu Val Ile Asp Ser Arg Tyr Lys Asn Phe Lys
    130                 135                 140

Phe Thr Leu Pro Glu Val Ile Ala Asp Asn Ala Ser Ser Gly Phe
145                 150                 155                 160

Val Ile Gly Ala Trp Cys Asp Pro His Ile Asp Phe Ser Asn Leu Gly
                165                 170                 175

Leu Thr Leu Asn Ile Asp Gly Gln Val Lys Gln Val Gly Ser Ser Ala
            180                 185                 190

Ala Leu Leu Gly His Pro Leu Arg Ser Leu Val Ala Ala Arg Leu
        195                 200                 205

Ser Ala Gln Ala Gly Glu Pro Leu Gln Ala Gly Trp Ile Val Met Ala
    210                 215                 220
```

Gly Gly Ala Thr Ser Ala Glu Tyr Ile Ala Pro Gly Gln Tyr Val Ser
225                 230                 235                 240

Ile Asp Ile Glu Arg Leu Gly Ser Ala Gly Phe His Val Ala Asp
                245                 250                 255

<210> SEQ ID NO 12
<211> LENGTH: 259
<212> TYPE: PRT
<213> ORGANISM: Streptomyces bingchenggensis

<400> SEQUENCE: 12

Met Thr Trp Asp Leu Asp Arg Ala Ala Thr Ala Leu Leu Glu Ala Glu
1               5                   10                  15

Asp Thr Arg Thr Asp Arg Gly Pro Ile Thr Asp Glu Trp Pro Glu Leu
                20                  25                  30

Asp Leu Asp Met Ala Tyr Ala Val Gln Asp Glu Thr Leu Gln Arg Arg
            35                  40                  45

Leu Asn Arg Gly Glu His Ile Val Gly Val Lys Leu Gly Leu Thr Ser
    50                  55                  60

Arg Ala Lys Gln Glu Arg Met Gly Ile Ala Ala Pro Leu Thr Ala Trp
65                  70                  75                  80

Leu Thr Asp Ala Met Leu Leu Pro Ala Gly Ala Pro Val Pro Gln Asp
                85                  90                  95

Arg Leu Ile His Pro Arg Ala Glu Pro Glu Ile Val Phe Val Met Lys
                100                 105                 110

Asp Arg Leu Ala Gly Pro Gly Val Thr Ala Ala Thr Ala Leu Ala Ala
            115                 120                 125

Val Gly Ser Val His Gly Gly Ile Glu Val Ile Asp Ser Arg Tyr Arg
    130                 135                 140

Asp Phe Arg Phe Thr Leu Pro Asp Val Ala Ala Asp Asn Ala Ser Ser
145                 150                 155                 160

Gly Arg Phe Val Thr Gly Pro Val Gly Val Pro Pro Glu Lys Leu Asp
                165                 170                 175

Leu Ala Ile Glu Ala Cys Leu Val Glu Val Asp Gly Gln Val Ala Asp
                180                 185                 190

Ser Ala Thr Gly Ala Ala Val Gln Gly His Pro Ala Glu Ala Leu Ala
            195                 200                 205

Leu Ala Ala Asn Glu Leu Gly Arg Arg Gly Leu Ala Ile Glu Pro Gly
    210                 215                 220

Trp Leu Val Leu Thr Gly Gly Met Thr Asp Ala Val His Val Pro Pro
225                 230                 235                 240

Gly Thr Thr Val Ala Val His Phe Thr His Leu Gly Ser Leu His Leu
                245                 250                 255

Thr Gly Gly

<210> SEQ ID NO 13
<211> LENGTH: 261
<212> TYPE: PRT
<213> ORGANISM: Shewanella woodyi

<400> SEQUENCE: 13

Met Leu Ile Asp Leu Ala Lys Lys Leu Asp Gln Ala Ala Ala Asp Ala
1               5                   10                  15

Ala Ser Ile Ala Gln Leu Ser Ser Thr Thr Gln Leu Ser Leu Asp Asp
                20                  25                  30

```
Ala Tyr Lys Val Gln Lys Ile Ser Ile Glu Gln Arg Leu Ile Arg Gly
         35                  40                  45

Glu Lys Leu Val Gly Tyr Lys Met Gly Phe Thr Ser Lys Ala Lys Met
 50                  55                  60

Ile Gln Met Gly Val Asp Asp Leu Ile Trp Gly Arg Leu Thr Asp Ala
 65                  70                  75                  80

Met Met Ile Gln Asp Gly Gly Ser Ile Asp Leu Ser Lys Tyr Val His
                 85                  90                  95

Pro Arg Ala Glu Pro Glu Ile Ala Phe Arg Leu Lys Lys Pro Leu Ala
            100                 105                 110

Gly Ile Val Thr Lys Glu Ala Tyr Asp Ala Ile Asp Ala Val Ala
            115                 120                 125

Gly Ala Ile Glu Val Ile Asp Ser Arg Tyr Gln Asn Phe Lys Phe Ser
    130                 135                 140

Leu Ser Asp Val Ile Ala Asp Asn Cys Ser Ser Thr Gly Phe Val Val
145                 150                 155                 160

Gly Pro Trp His Ser Pro Asp Thr Asn Ile Asp Gly Leu Ser Met Ile
                165                 170                 175

Leu Lys Val Asn Asp Ala Glu Val Glu Arg Gly Ser Ser Lys Asp Ile
            180                 185                 190

Leu Asp His Pro Leu Asn Ser Leu Ile Glu Ala Ala Arg Cys Val Ala
    195                 200                 205

Gln Tyr Gly Glu Ser Leu Gln Ala Gly Gln Ile Ile Leu Ala Gly Ala
210                 215                 220

Ala Thr Ala Ala Val Ala Leu Lys Pro Gly Gln Thr Ile Ser Thr Glu
225                 230                 235                 240

Ile Glu Gly Leu Ser Pro Cys Gln Phe Ser Thr Ser Asn Asn Ser Ser
                245                 250                 255

Ser Gln Ala Ser Lys
            260

<210> SEQ ID NO 14
<211> LENGTH: 262
<212> TYPE: PRT
<213> ORGANISM: Cupriavidus necator

<400> SEQUENCE: 14

Met Asn Leu Thr Gln Asp Ile Ile Gln Gln Leu Ala Glu His Leu Glu
 1               5                  10                  15

Asn Ala Glu Leu Asn Arg Glu Pro Val Arg Lys Ile Thr Asp Asp Tyr
             20                  25                  30

Pro Glu Met Asp Trp Asp Asp Ala Tyr Ala Ile Gln Asp Ala Ile Arg
         35                  40                  45

Ala Arg Lys Glu Ala Arg Gly Thr Arg Ile Ala Gly Leu Lys Met Gly
 50                  55                  60

Leu Thr Ser Phe Ala Lys Met Arg Gln Met Gly Val Thr Glu Pro Val
 65                  70                  75                  80

Tyr Gly Phe Val Thr Asp Tyr Gly Ala Cys Met Asp Gly Gly Ala Ile
                 85                  90                  95

Asp Thr Ala Ser Leu Ile His Pro Lys Val Glu Ala Glu Ile Ala Phe
            100                 105                 110

Val Leu Lys Arg Pro Leu Lys Gly Pro Gly Cys His Ile Gly Asp Val
            115                 120                 125

Leu Ala Ala Thr Asp Phe Val Leu Pro Ala Val Glu Val Ile Asp Ser
    130                 135                 140
```

```
Arg Tyr Glu Asn Phe Arg Phe Asp Leu Lys Ser Val Ile Ala Asp Asn
145                 150                 155                 160

Thr Ser Ser Ala Arg Phe Val Val Gly Gly Thr His Arg Ser Ala Asp
                165                 170                 175

Gly Ile Asp Leu Lys Asn Leu Gly Val Val Met Glu Lys Asn Gly Glu
            180                 185                 190

Val Val Ala Thr Ala Ala Gly Ala Ala Val Leu Gly His Pro Ala Ser
        195                 200                 205

Ser Val Ala Met Leu Ala Asn Met Leu Gly Ala Arg Gly Arg Glu Leu
    210                 215                 220

Pro Ala Gly Thr Phe Ile Met Thr Gly Val Thr Glu Ala Val Ala
225                 230                 235                 240

Val Gln Ala Gly Asp Asn Val Thr Val Arg Tyr Gln His Leu Gly Thr
                245                 250                 255

Val Ser Met Arg Phe Val
            260

<210> SEQ ID NO 15
<211> LENGTH: 262
<212> TYPE: PRT
<213> ORGANISM: Acidovorax sp.

<400> SEQUENCE: 15

Met Ala Leu Ala Gln Asp Thr Ile Ala Gln Leu Ala Glu His Leu Glu
1               5                   10                  15

Asn Cys Gln Leu Gln Ala Lys Asp Thr Pro Lys Ile Thr Asp Ala His
            20                  25                  30

Pro Asp Met Asp Trp Asp Asp Ala Tyr Ala Ile Gln Asp Ala Ile Leu
        35                  40                  45

Ala Arg Lys Leu Ala Arg Gly Ala Arg Val Val Gly Leu Lys Ala Gly
    50                  55                  60

Leu Thr Ser His Ala Lys Met Arg Gln Met Gly Val Thr Asp Pro Val
65                  70                  75                  80

Phe Gly Phe Leu Val Asp Glu Tyr Val Val Pro Glu Gly Ala Thr Val
                85                  90                  95

Asn Thr Ala Glu Leu Ile His Pro Lys Val Glu Pro Glu Ile Ala Phe
            100                 105                 110

Val Leu Lys His Ala Leu Lys Gly Pro Gly Cys His Ile Gly Ala Val
        115                 120                 125

Leu Ala Ala Thr Asp Phe Val Leu Pro Gly Ile Glu Val Ile Asp Ser
    130                 135                 140

Arg Tyr Arg Asp Phe Lys Phe Asp Leu Lys Ser Val Val Ala Asp Asn
145                 150                 155                 160

Thr Ser Ala Ser Arg Phe Val Val Gly Gly Arg Ala Leu Arg Pro Glu
                165                 170                 175

Asp Val Asp Leu Arg Thr Val Gly Ile Val Leu Glu Lys Asn Gly Glu
            180                 185                 190

Pro Val Ala Leu Gly Ala Gly Ala Ala Val Leu Gly His Pro Ala Ala
        195                 200                 205

Ala Ile Ala Met Leu Ala Asn His Leu Gly Arg Arg Gly Gln Glu Ile
    210                 215                 220

Pro Ala Gly Ser Leu Ile Leu Ser Gly Gly Ala Thr Glu Ala Val Ala
225                 230                 235                 240

Val Ala Ala Gly Asp Ser Val Cys Leu Arg Val Gln Gly Met Gly Ser
```

Val Ser Leu Arg Phe Ala
        260

<210> SEQ ID NO 16
<211> LENGTH: 267
<212> TYPE: PRT
<213> ORGANISM: Azoarcus sp.

<400> SEQUENCE: 16

Met Ser Gln Asn Leu Thr Leu Ser Arg Glu Asp Ile Val Arg Leu Cys
1               5                   10                  15

Glu Arg Val Glu Gly Ala Gln Thr Arg Ala Tyr Ala Ile Pro Lys Leu
            20                  25                  30

Thr Asp Glu Tyr Pro Ala Met Thr Ile Ala Asp Gly Tyr Ala Val Gln
        35                  40                  45

Ser Glu Leu Arg Arg Arg Tyr Leu Ala Gln Gly His Arg Leu Val Gly
    50                  55                  60

Trp Lys Ala Gly Leu Thr Ser Lys Ala Lys Met Lys Gln Met Gly Val
65                  70                  75                  80

Asp Val Pro Ser Ile Gly Phe Leu Thr Asp Arg Met Ala Arg Pro Glu
                85                  90                  95

Asn Ala Ala Ile Ser Thr Gly Asp Leu Val His Pro Arg Val Glu Cys
            100                 105                 110

Glu Val Ala Phe Val Met Lys Arg Glu Leu Arg Gly Pro Gly Cys Thr
        115                 120                 125

Ala Ala Asp Val Leu Ala Ala Thr Asp Tyr Val Leu Pro Ala Val Glu
    130                 135                 140

Ile Ile Asp Ser Arg Phe Ala Gly Phe Lys Phe Asp Leu Pro Ser Val
145                 150                 155                 160

Ile Ala Asp Asn Gly Ser Ser Ala Arg Phe Val Gly Gly Gly Arg Ala
                165                 170                 175

Arg Tyr Val Glu Glu Leu Asp Leu Arg Thr Leu Gly Val Val Leu Glu
            180                 185                 190

Lys Asn Gly Glu Ile Val Ala Met Gly Ala Ser Ala Ala Val Leu Gly
        195                 200                 205

His Pro Ala Glu Ala Ile Ala Met Leu Val Asn Ile Leu Ala Asp Leu
    210                 215                 220

Gly Glu Thr Leu Pro Ala Gly Ser Phe Val Met Ser Gly Gly Ile Thr
225                 230                 235                 240

Glu Ala Ile Ala Val Gln Pro Gly Asp Ser Val Val Ala Arg Phe Gln
                245                 250                 255

Glu Leu Gly Ser Val Ser Met Arg Phe Val Ala
            260                 265

<210> SEQ ID NO 17
<211> LENGTH: 262
<212> TYPE: PRT
<213> ORGANISM: Novosphingobium nitrogenifigens

<400> SEQUENCE: 17

Met Ala Leu Ala Ala Glu Thr Val Ala Glu Leu Ala Glu Phe Leu Asp
1               5                   10                  15

Lys Ala Glu Met Glu Arg Arg Glu Val Thr Lys Ile Thr Asp Arg Tyr
            20                  25                  30

Pro Glu Met Asp Trp Asp Asp Ala Tyr Ala Ile Gln Arg Gly Ile Arg

```
                35                  40                  45
Glu Arg Gln Gln Ala Arg Gly Val Gly Met Ala Gly Tyr Lys Ala Gly
 50                  55                  60

Leu Thr Ser His Ala Lys Met Glu Gln Met Gly Val Glu Glu Pro Val
 65                  70                  75                  80

Phe Gly Phe Ile Thr Asp Val Gly Glu Ile Pro Asp Gly Gly Thr Ile
                 85                  90                  95

Asp Thr Ala Thr Leu Ile His Pro Lys Val Glu Ala Glu Ile Ala Phe
                100                 105                 110

Val Leu Lys Asp Glu Leu Thr Gly Pro Gly Cys Asp Ile Asp Ala Val
            115                 120                 125

Leu Ala Ala Thr Ala Cys Val Val Pro Ala Leu Glu Val Ile Asp Ser
        130                 135                 140

Arg Tyr Lys Asp Phe Arg Phe Asp Leu Lys Ser Val Ile Ala Asp Asn
145                 150                 155                 160

Thr Ser Ser Ala Arg Trp Ile Ser Gly Gly Glu Lys Val Pro Val Ala
                165                 170                 175

Gly Leu Asp Leu Pro Asn Leu Ala Ile Val Met Glu Lys Asn Gly Glu
            180                 185                 190

Val Val Glu Ala Ala Thr Gly Ala Ala Val Leu Gly His Pro Ala Gln
        195                 200                 205

Ser Val Ala Met Leu Ala Asn Met Leu Ala Arg Arg Gly Glu Ser Leu
    210                 215                 220

Pro Ala Gly Ala Phe Ile Met Thr Gly Gly Ala Thr Ala Ala Val Ala
225                 230                 235                 240

Val Ala Pro Gly Asp Thr Ile Thr Val Lys Tyr Gln Ala Leu Gly Thr
                245                 250                 255

Ile Ser Val Lys Val Val
            260

<210> SEQ ID NO 18
<211> LENGTH: 264
<212> TYPE: PRT
<213> ORGANISM: Methylibium petroleiphilum

<400> SEQUENCE: 18

Met Thr Leu Thr Leu Ser Arg Ser Asp Ile Glu Arg Leu Ala Asp Arg
 1               5                  10                  15

Val Glu Ala Ala Gln Asp Asn Ala Arg Ala Ile Pro Lys Leu Thr Asp
                20                  25                  30

Asp Phe Pro Arg Met Gly Leu Ala Asp Gly Tyr Ala Val Gln Ser Glu
            35                  40                  45

Leu Arg Arg Arg Arg Ile Arg Gln Gly His Arg Leu Val Gly Trp Lys
 50                  55                  60

Ala Gly Leu Thr Ser Lys Ala Lys Met Leu Gln Met Gly Val Asp Val
 65                  70                  75                  80

Pro Ser Ile Gly Phe Leu Met Ser Asn Met Ala Arg Thr Asp Asn Ala
                 85                  90                  95

Gln Val Arg Thr Asp Asp Leu Val His Pro Arg Val Glu Cys Glu Val
            100                 105                 110

Ala Phe Val Thr Lys Lys Asp Leu His Gly Pro Asp Cys Thr Arg Asp
        115                 120                 125

Glu Val Leu Ala Ala Thr Asp Phe Val Leu Pro Ala Ile Glu Val Ile
    130                 135                 140
```

```
Asp Ser Arg Phe Ala Gly Phe Lys Phe Asp Leu Pro Ser Val Val Ala
145                 150                 155                 160

Asp Asn Gly Ser Ser Ala Arg Phe Val Thr Gly Ala Arg Ala Arg Asp
            165                 170                 175

Val Ala Asp Leu Asp Leu Arg Thr Leu Gly Val Val Phe Glu Lys Asn
                180                 185                 190

Gly Val Ser Ile Gly Met Gly Ala Thr Ala Ala Val Leu Gly His Pro
            195                 200                 205

Ala Glu Ala Val Ala Met Leu Val Arg Val Leu Ala Glu Leu Asp Glu
    210                 215                 220

Pro Leu Pro Ala Gly Ser Phe Val Met Ser Gly Gly Ile Thr Glu Ala
225                 230                 235                 240

Val Ala Val Thr Ala Gly Asp His Val Ala Arg Tyr Gln Asp Leu
                245                 250                 255

Gly Ser Val Ser Val Arg Phe Ile
            260
```

<210> SEQ ID NO 19
<211> LENGTH: 268
<212> TYPE: PRT
<213> ORGANISM: Artificial Sequence
<220> FEATURE:
<223> OTHER INFORMATION: Uncultured bacterium

<400> SEQUENCE: 19

```
Met Ser Leu Asp Gln Pro Asn Ser Val Asp Asp Glu Ala Ile Ile Arg
  1               5                  10                  15

Met Ala Glu Arg Ile Glu Thr Ala Gln Arg Tyr Ala Thr Pro Ile Arg
            20                  25                  30

Lys Leu Thr Glu Asp Tyr Pro Asp Leu Thr Ile Ala Asp Ala Tyr Arg
        35                  40                  45

Val Gln Thr Ala Leu Arg Arg Asn Leu Glu Lys Lys Gly Glu Arg Val
    50                  55                  60

Ile Gly Trp Lys Ala Gly Leu Thr Ser Lys Pro Lys Met Ala Gln Met
65                  70                  75                  80

Gly Val Ser Thr Pro Gly Val Gly Phe Leu Thr Asp Ala Met Glu Arg
                85                  90                  95

Pro Ala Asn Ser Lys Ile Thr Val Ser Asp Met Ile His Pro Arg Val
            100                 105                 110

Glu Ala Glu Ile Ala Phe Val Thr Asn Lys Glu Leu Ser Gly Lys Val
        115                 120                 125

Thr Lys Glu Glu Val Leu Ala Ala Thr Asp Tyr Val Gln Pro Ala Leu
    130                 135                 140

Glu Val Ile Asp Ser Arg Phe Thr Gly Phe Lys Phe Asp Leu Glu Ser
145                 150                 155                 160

Val Leu Ala Asp Asn Ala Ser Ser Ala Arg Phe Val Pro Gly Gly Arg
                165                 170                 175

Met Ile Arg Leu Asp Ala Arg Asp Leu Arg Thr Val Gly Val Val Leu
            180                 185                 190

Glu His Asn Gly Glu Ile Ala Gln Ile Gly Ala Gly Ala Glu Val Leu
        195                 200                 205

Gly His Pro Ala Glu Ala Ile Ala Met Leu Val Gly Val Leu Asp Asp
    210                 215                 220

Met Gly Glu Val Leu Pro Ala Gly Ser Phe Val Met Ala Gly Ala Ile
225                 230                 235                 240
```

```
Thr Ala Ala Val Ala Val Lys Pro Gly Asp Ser Ile Thr Ala Arg Phe
            245                 250                 255

Tyr Glu Met Gly Ser Ile Thr Val Thr Phe Thr Glu
            260                 265

<210> SEQ ID NO 20
<211> LENGTH: 260
<212> TYPE: PRT
<213> ORGANISM: Paenibacillus sp.

<400> SEQUENCE: 20

Met Asp Lys Thr Val Ile Lys Asp Leu Ala Arg Phe Leu Val Asp Ala
  1               5                  10                  15

Glu Val Glu Lys Lys Glu Val Leu Lys Leu Thr Asn Glu His Pro Asp
             20                  25                  30

Leu Thr Val Glu Asp Gly Tyr Ala Ile Gln Glu Gln Leu Val Gln Met
         35                  40                  45

Lys Leu Glu Gln Gly Tyr Arg Ile Val Gly Pro Lys Met Gly Leu Thr
 50                  55                  60

Ser Gln Ala Lys Met Lys Gln Met Asn Val Asn Glu Pro Ile Tyr Gly
 65                  70                  75                  80

Tyr Ile Phe Asp Tyr Met Val Val Asn Gly Gln Glu Leu Ser Met Ser
                 85                  90                  95

Glu Leu Ile His Pro Lys Val Glu Ala Glu Ile Ala Phe Ile Leu Gly
            100                 105                 110

Lys Asp Ile Glu Gly Pro Gly Ile Thr Gly Ala Gln Val Leu Ala Ala
            115                 120                 125

Thr Glu Tyr Val Val Pro Ala Leu Glu Ile Ile Asp Ser Arg Tyr Gln
        130                 135                 140

Asn Phe Gln Phe Thr Leu Pro Asp Val Ile Ala Asp Asn Ala Ser Ser
145                 150                 155                 160

Ser Arg Val Phe Leu Gly Ser Thr Ile Lys Arg Pro Asp Asn Met Glu
                165                 170                 175

Leu Asp Leu Leu Gly Val Thr Leu Ser Ile Asn Gly Gln Ile Lys Asp
            180                 185                 190

Leu Gly Ala Gly Ala Ala Val Val Gly His Pro Ala Asn Ser Val Ala
        195                 200                 205

Met Leu Ala Asn Met Leu Ala Arg Lys Gly Leu Lys Leu Lys Ala Gly
    210                 215                 220

Gln Ile Ile Leu Ser Gly Gly Ile Thr Gly Ala Val Met Leu Asn Val
225                 230                 235                 240

Gly Asp Ser Val Thr Gly Lys Phe Asp Gly Leu Gly Thr Ile Asp Phe
                245                 250                 255

Ile Val Lys Glu
            260

<210> SEQ ID NO 21
<211> LENGTH: 261
<212> TYPE: PRT
<213> ORGANISM: Geobacillus sp.

<400> SEQUENCE: 21

Met Thr Ser Leu Asp Tyr Glu Lys Leu Ala Met Glu Leu Leu Asn Ala
  1               5                  10                  15

Glu His Glu Lys Arg Glu Met Val Arg Leu Thr Val Gln Tyr Pro Asn
             20                  25                  30
```

```
Met Thr Val Glu Glu Ala Tyr Ala Ile Gln Glu Gln Leu Val Ala Met
            35                  40                  45
Lys Gln Lys Asp Gly Tyr Arg Ile Ile Gly Pro Lys Met Gly Leu Thr
 50                      55                  60
Ser Ala Ala Lys Met Ala Gln Met Gly Val Asn Glu Pro Ile Tyr Gly
 65                  70                  75                  80
Tyr Val Phe Asp Tyr Met Val Pro Asn Gly Thr Val Ala Met
                 85                  90                  95
Asn Glu Leu Ile His Pro Lys Val Glu Ala Ile Ala Phe Ile Leu
                100                 105                 110
Lys Glu Asp Val Arg Gly Pro Asn Ile Asp Ala Thr Asp Ile Leu Ala
                115                 120                 125
Ala Thr Glu Tyr Ile Ile Pro Ala Leu Glu Ile Ile Asp Ser Arg Tyr
130                 135                 140
Ala Asn Phe Glu Phe Ala Leu Pro Asp Val Ile Ala Asp Asn Ala Ser
145                 150                 155                 160
Ser Ser Arg Val Val Phe Gly Ser Arg Leu Val Pro Pro Val Ser Leu
                165                 170                 175
Glu Leu Asp Leu Leu Gly Val Ser Leu Ser Ile Asn Gly Glu Gly Lys
                180                 185                 190
Ala Phe Gly Ala Gly Ala Ala Val Leu Gly His Pro Ala Asn Ala Ile
                195                 200                 205
Ala Met Leu Ala Asn Met Leu Ser Arg Lys Gly Lys Gly Leu Lys Ala
                210                 215                 220
Gly Glu Ile Ile Leu Ala Gly Ala Met Thr Glu Ala Val Arg Phe Val
225                 230                 235                 240
Ala Gly Asp Val Val Phe Ala Gln Phe Glu Gln Leu Gly Thr Val Ser
                245                 250                 255
Phe Arg Ser Thr Asp
                260

<210> SEQ ID NO 22
<211> LENGTH: 261
<212> TYPE: PRT
<213> ORGANISM: Bacillus licheniformis

<400> SEQUENCE: 22

Met Asn Thr Ala Ala Leu Lys Asp Thr Ala Arg Leu Leu Tyr Leu Ala
 1               5                  10                  15
Glu Thr Glu Lys Arg Glu Val Glu Arg Ile Thr Lys Asp Tyr Pro Glu
                20                  25                  30
Leu Thr Val Glu Glu Ala Tyr Ala Ile Gln Glu Glu Leu Ile Gln Leu
            35                  40                  45
Lys Leu Trp Asp Gly Asn Ser Ile Ile Gly Pro Lys Met Gly Leu Thr
 50                  55                  60
Ser Arg Ala Lys Met Lys Gln Met Asn Val Glu Glu Pro Ile Tyr Gly
 65                  70                  75                  80
Tyr Ile Phe Glu Asp Met Ile Val Pro Asn Gly Gly Ser Ile Arg Met
                 85                  90                  95
Asn Glu Leu Ile His Pro Lys Val Glu Ala Ile Ala Phe Val Leu
                100                 105                 110
Gly Glu Asp Ile Glu Gly Pro Gly Val Thr Lys Glu Gln Val Leu Glu
                115                 120                 125
Ala Val Ala Glu Leu Ile Pro Val Leu Glu Val Ile Asp Ser Arg Tyr
130                 135                 140
```

Glu Asn Phe Ser Phe Thr Leu Pro Asp Val Ile Ala Asp Asn Ala Ser
145                 150                 155                 160

Ser Ser Arg Val Val Leu Gly Glu Lys Val Lys Pro Asp Asp Phe
            165                 170                 175

Lys Leu Asp Glu Ala Arg Val Ser Leu Met Ile Asn Gly Glu Val Lys
            180                 185                 190

Glu Arg Gly Thr Gly Ala Ala Val Val Gly His Pro Ala Asn Ser Ala
            195                 200                 205

Ala Met Leu Ala Asn Met Leu Ser Arg Lys Lys Gln Lys Leu Ala Ala
210                 215                 220

Gly Ser Ile Ile Leu Thr Gly Gly Val Thr Gly Ala Val Met Leu Gln
225                 230                 235                 240

Pro Gly Asp Arg Val Ser Ala Gln Val Glu Gly Leu Gly Asp Val Ser
            245                 250                 255

Phe Ser Val Lys Pro
            260

<210> SEQ ID NO 23
<211> LENGTH: 262
<212> TYPE: PRT
<213> ORGANISM: Brevibacillus brevis

<400> SEQUENCE: 23

Met Gln Ser Glu Leu Leu Tyr Lys Arg Leu Ala Gln Lys Leu Val Asp
1               5                   10                  15

Ala Glu Leu Asn Arg Glu Val Val Lys Leu Thr Ala Glu Tyr Pro
            20                  25                  30

Glu Leu Thr Val Glu Asp Gly Tyr Arg Ile Gln Asp Glu Leu Val Ser
            35                  40                  45

Leu Lys Leu Glu Gln Gly His Arg Ile Phe Ala Thr Lys Met Gly Leu
50                  55                  60

Thr Ser Gln Ala Lys Met Lys Gln Met Asn Val His Glu Pro Ile Arg
65                  70                  75                  80

Gly Tyr Ile Phe Asp Tyr Met Asn Ile Glu Asp Gly Ile Leu Pro Ile
                85                  90                  95

Asn Glu Leu Ile His Pro Lys Val Glu Ala Glu Ile Ala Phe Val Leu
            100                 105                 110

Arg Glu Asp Leu Glu Gly Pro Gly Ile Thr Glu Gly His Val Leu Ala
            115                 120                 125

Ala Thr Asp Tyr Val Val Pro Ala Leu Glu Ile Ile Asp Ser Arg Tyr
            130                 135                 140

Ala Gln Phe Gln Phe Ser Leu Pro Asp Val Ile Ala Asp Asn Thr Ser
145                 150                 155                 160

Ser Ser Arg Val Phe Ile Gly Ser Thr Trp Arg Lys Pro Asp Asp Leu
            165                 170                 175

Asp Leu Asp Leu Val Gly Val Thr Leu Ser Ile Asn Gly Glu Leu Lys
            180                 185                 190

Asp Leu Gly Ala Gly Ala Ala Val Leu Gly His Pro Ala His Ala Val
            195                 200                 205

Ala Met Leu Ala Asn Met Leu Ala Arg Glu Gly Arg Lys Leu Tyr Lys
210                 215                 220

Gly Asp Leu Ile Leu Ser Gly Gly Ile Thr Gly Ser His Gln Leu Arg
225                 230                 235                 240

Glu Gly Asp Val Val Val Ala Lys Trp Gly Gly Leu Gly Ser Ile Glu

```
                        245                 250                 255
Phe Val Val Lys Thr Arg
                260

<210> SEQ ID NO 24
<211> LENGTH: 260
<212> TYPE: PRT
<213> ORGANISM: Geobacillus thermodenitrificans

<400> SEQUENCE: 24

Met Thr Asn Glu Leu Tyr Arg Gln Leu Ala Glu Arg Leu Ala Val Ala
 1               5                  10                  15

Glu Arg Glu His Arg Thr Val Thr Lys Leu Thr Ala Glu Tyr Pro Glu
            20                  25                  30

Leu Thr Val Glu Asp Ala Tyr Arg Ile Gln Asp Glu Leu Ile Ala Ile
        35                  40                  45

Lys Gln Arg Gln Gly His His Val Ala Ala Leu Lys Met Gly Phe Thr
    50                  55                  60

Ser Arg Ala Lys Met Lys Gln Met Asn Val His Glu Pro Ile Tyr Gly
65                  70                  75                  80

Tyr Val Leu Asp Tyr Met Leu Cys Glu Asp Gly Val Leu Ser Leu Ala
                85                  90                  95

Glu Leu Ile His Pro Lys Val Glu Ala Glu Ile Ala Phe Ile Leu Gly
            100                 105                 110

Gln Asp Leu Glu Gly Pro Gly Ile Thr Gly Ala Gln Ala Leu Ala Ala
        115                 120                 125

Thr Glu Tyr Val Leu Pro Ala Leu Glu Ile Ile Asp Ser Arg Tyr Thr
    130                 135                 140

His Phe Gln Phe Ala Leu Pro Asp Val Ile Ala Asp Asn Thr Ser Ala
145                 150                 155                 160

Ser Arg Val Phe Phe Gly Thr Thr Leu Arg Arg Pro Glu Glu Leu Glu
                165                 170                 175

Leu Asp Leu Val Gly Val Thr Leu Ser Ile Asn Gly Glu Leu Arg Asp
            180                 185                 190

Leu Gly Ala Gly Ala Glu Val Leu Cys His Pro Ala Asn Ser Val Ala
        195                 200                 205

Met Leu Ala Asn Met Leu Ala Arg Arg Gly Cys Lys Leu Ser Ala Gly
    210                 215                 220

Gln Val Ile Leu Thr Gly Gly Ile Thr Gly Ala His Pro Val Ala Asp
225                 230                 235                 240

Gly Asp Leu Val Val Ala Arg Trp Asp Gly Leu Gly Ser Ile Ser Phe
                245                 250                 255

Thr Val Gln Gly
            260

<210> SEQ ID NO 25
<211> LENGTH: 267
<212> TYPE: PRT
<213> ORGANISM: Geobacillus stearothermophilus

<400> SEQUENCE: 25

Met Ala Leu Thr Val Lys Val Ser Leu Tyr Arg Lys Phe Ala Glu Leu
 1               5                  10                  15

Leu Asn Glu Ala Glu Arg Glu Lys Arg Glu Val Ala Arg Ile Thr Glu
            20                  25                  30

Glu Val Pro Asp Leu Ser Ala Glu Glu Ala Tyr Lys Ile Gln Glu Glu
```

```
            35                  40                  45
Leu Ile Lys Ile Lys Thr Asn Ser Gly His Arg Ile Ile Gly Pro Lys
 50                  55                  60

Met Gly Leu Thr Ser Gln Ala Lys Met Ala Gln Met Lys Val Lys Glu
 65                  70                  75                  80

Pro Ile Tyr Gly Tyr Leu Phe Asp Tyr Met Phe Val Pro Ser Gly Gly
                 85                  90                  95

Ala Ile His Met Ser Glu Leu Ile His Pro Lys Val Glu Val Glu Ile
                100                 105                 110

Ala Phe Ile Leu Gly Glu Asp Leu Glu Gly Pro His Val Thr Ser Thr
                115                 120                 125

Gln Val Leu Ser Ala Thr Lys Tyr Val Ala Pro Ala Leu Glu Ile Ile
            130                 135                 140

Asp Ser Arg Tyr Gln Asp Phe Thr Phe Thr Leu Pro Asp Val Ile Ala
145                 150                 155                 160

Asp Asn Ala Ser Ser Arg Val Val Ile Gly Asn Thr Met Thr Pro
                165                 170                 175

Ile His Ser Leu Lys Thr Asp Leu Asp Leu Ile Gly Ala Ala Leu Tyr
                180                 185                 190

Ile Asn Gly Glu Leu Lys Ala Cys Gly Ala Gly Ala Ala Val Phe Asn
                195                 200                 205

His Pro Ala Asn Ser Val Ala Val Leu Ala Asn Met Leu Ala Arg Lys
                210                 215                 220

Gly Glu Arg Leu Lys Ala Gly Asp Ile Ile Leu Thr Gly Gly Ile Thr
225                 230                 235                 240

Glu Ala Ile Gln Leu Ser Ala Gly Asp Thr Val Ile Gly Gln Leu Asp
                245                 250                 255

Gln Leu Gly Asp Val Ser Leu Ser Val Lys Glu
                260                 265
```

<210> SEQ ID NO 26
<211> LENGTH: 264
<212> TYPE: PRT
<213> ORGANISM: Pseudomonas putida

<400> SEQUENCE: 26

```
Met Asn Arg Thr Leu Asn Arg Glu Gln Val Leu Ala Leu Ala Glu His
  1               5                  10                  15

Ile Glu Asn Ala Glu Leu Gln Ala His Asp Ile His Lys Val Thr Asn
                 20                  25                  30

Asp Tyr Pro Glu Met Thr Phe Ala Asp Ala Tyr Asp Ile Gln Trp Glu
                 35                  40                  45

Ile Arg Arg Arg Lys Glu Ala Arg Gly Asn Lys Ile Val Gly Leu Lys
 50                  55                  60

Met Gly Leu Thr Ser Trp Ala Lys Met Ala Gln Met Gly Val Glu Thr
 65                  70                  75                  80

Pro Ile Tyr Gly Phe Leu Ala Asp Tyr Phe Ser Val Pro Asp Gly Gly
                 85                  90                  95

Val Val Asp Cys Ser Lys Leu Ile His Pro Lys Ile Glu Ala Glu Ile
                100                 105                 110

Ser Val Val Thr Lys Ala Pro Leu Gln Gly Pro Gly Cys His Ile Gly
                115                 120                 125

Asp Val Ile Ala Ala Val Asp Tyr Val Ile Pro Thr Val Glu Val Ile
            130                 135                 140
```

```
Asp Ser Arg Tyr Glu Asn Phe Lys Phe Asp Leu Ile Ser Val Val Ala
145                 150                 155                 160

Asp Asn Ala Ser Ser Thr Arg Phe Ile Thr Gly Gly Gln Met Ala Asn
                165                 170                 175

Leu Glu Asp Val Asp Leu Arg Thr Leu Gly Val Val Met Glu Lys Asn
            180                 185                 190

Gly Glu Val Val Glu Leu Gly Ala Gly Ala Ala Val Leu Gly His Pro
        195                 200                 205

Leu Ser Ser Val Ala Met Leu Ala Asn Leu Leu Ala Glu Arg Gly Glu
    210                 215                 220

His Ile Pro Ala Gly Thr Phe Ile Met Thr Gly Gly Ile Thr Ala Ala
225                 230                 235                 240

Val Ser Val Glu Pro Gly Asp Asn Ile Thr Val Arg Tyr Gln Gly Leu
                245                 250                 255

Gly Ser Val Ser Ala Arg Phe Ile
            260

<210> SEQ ID NO 27
<211> LENGTH: 257
<212> TYPE: PRT
<213> ORGANISM: Bacillus tusciae

<400> SEQUENCE: 27

Met Asp Leu Glu Ser Leu Ala Arg Arg Val Ser Glu His Gln Arg Lys
 1               5                  10                  15

Gly Leu Ala Met Lys Lys Leu Thr Leu Glu Tyr Pro Glu Leu Thr Val
            20                  25                  30

Glu Gln Ala Tyr Arg Ile Gln Ala Leu Ser Val Glu Arg Ser Val Ala
        35                  40                  45

Glu Gly Asp Arg Phe Val Gly Trp Lys Met Gly Leu Thr Ser Arg Ala
    50                  55                  60

Lys Gln Val Ser Val Gly Val Asp Glu Pro Ile Tyr Gly Arg Leu Leu
65                  70                  75                  80

Ala Ser Met Glu Leu Arg Glu Ser Leu Leu Ser Val Gly Gly Leu Val
                85                  90                  95

His Pro Arg Val Glu Pro Glu Leu Ala Phe Val Leu Lys Glu Gly Leu
            100                 105                 110

His Gly Glu Ser Val Thr Pro Arg Glu Val Trp Arg Ala Thr Glu Cys
        115                 120                 125

Val Val Pro Ala Leu Glu Val Ile Asp Ser Arg Tyr Glu Asn Phe Ser
    130                 135                 140

Phe Thr Leu Val Asp Val Val Ala Asp Asn Ala Ser Ser Ala Arg Phe
145                 150                 155                 160

Tyr Leu Gly Glu Gln Gly Phe Ser Pro Tyr Gly Ala Arg Trp Asp Glu
                165                 170                 175

Val Gly Val Val Met Arg Lys Asn Gly Glu Val Val Gln Thr Gly Ala
            180                 185                 190

Gly Ala Ala Val Leu Gly His Pro Val Arg Ser Val Met Met Leu Thr
        195                 200                 205

Arg Met Leu Ala Arg Glu Gly Leu Gly Leu Glu Pro Gly Met Val Val
    210                 215                 220

Leu Thr Gly Gly Ile Thr Glu Ala Val Pro Val Gln Pro Gly Asp Ala
225                 230                 235                 240

Val Glu Val Ser Tyr Glu Gly Leu Gly Ser Leu Glu Leu Arg Val Gly
                245                 250                 255
```

Arg

```
<210> SEQ ID NO 28
<211> LENGTH: 262
<212> TYPE: PRT
<213> ORGANISM: Bacillus thuringiensis serovar pulsiensis

<400> SEQUENCE: 28
```

| | | | | | | | | | | | | | | |
|---|---|---|---|---|---|---|---|---|---|---|---|---|---|---|
| Met | Ala | Leu | Val | Lys | Gly | Ala | Asp | Leu | Glu | Ile | Ile | Asp | Tyr | Leu | Leu |
| 1 | | | | 5 | | | | | 10 | | | | | 15 | |
| Gln | Ala | Glu | Lys | Glu | Arg | Lys | Glu | Val | Val | Lys | Val | Thr | Asp | Lys | His |
| | | | 20 | | | | | 25 | | | | | 30 | | |
| Pro | Asp | Leu | Thr | Val | Glu | Asp | Ala | Tyr | Lys | Leu | Gln | Lys | Arg | Leu | Ile |
| | | | 35 | | | | | 40 | | | | | 45 | | |
| Glu | Gln | Lys | Met | Ser | Glu | Gly | Ser | Lys | Arg | Val | Gly | Val | Lys | Leu | Gly |
| | 50 | | | | | 55 | | | | | 60 | | | | |
| Leu | Thr | Ser | Lys | Ala | Lys | Gln | Gln | Met | Met | Gly | Ile | Asp | Glu | Ala | Ile |
| 65 | | | | | 70 | | | | | 75 | | | | | 80 |
| Tyr | Gly | Tyr | Leu | Leu | His | Asp | Met | Leu | Ala | Phe | Glu | Trp | Glu | Pro | Leu |
| | | | | 85 | | | | | 90 | | | | | 95 | |
| Gln | Tyr | Glu | Thr | Leu | Ile | His | Pro | Lys | Val | Glu | Pro | Glu | Ile | Ala | Phe |
| | | | | 100 | | | | | 105 | | | | | 110 | |
| Leu | Ile | Gly | Glu | Asp | Leu | Gln | Gly | Thr | Asn | Val | Thr | Ala | Asp | Asp | Val |
| | | | 115 | | | | | 120 | | | | | 125 | | |
| Leu | Lys | Ala | Thr | Lys | Tyr | Val | Ala | Pro | Ala | Leu | Glu | Val | Ile | Asp | Ser |
| | 130 | | | | | 135 | | | | | 140 | | | | |
| Arg | Tyr | Leu | Asn | Phe | Lys | Phe | Thr | Leu | Pro | Asp | Val | Ile | Ala | Asp | Asn |
| 145 | | | | | 150 | | | | | 155 | | | | | 160 |
| Cys | Ser | Ser | Ser | Lys | Phe | Leu | Leu | Gly | Ser | Lys | Trp | Ile | Asp | Val | Lys |
| | | | | 165 | | | | | 170 | | | | | 175 | |
| Asn | Ile | Asp | Leu | Ala | Asn | Val | Gly | Met | Val | Met | Ser | Lys | Asn | Gly | Lys |
| | | | | 180 | | | | | 185 | | | | | 190 | |
| Ile | Ala | Thr | Thr | Gly | Thr | Gly | Ala | Ala | Val | Leu | Gly | His | Pro | Ala | Glu |
| | | | 195 | | | | | 200 | | | | | 205 | | |
| Ala | Ile | Ala | Trp | Ala | Val | Asn | Lys | Leu | Gly | Leu | Gln | Asn | Glu | Gly | Leu |
| | 210 | | | | | 215 | | | | | 220 | | | | |
| Lys | Lys | Gly | Asp | Ile | Val | Leu | Ser | Gly | Ala | Leu | Ser | Glu | Ala | Ile | Ala |
| 225 | | | | | 230 | | | | | 235 | | | | | 240 |
| Phe | Lys | Ser | Gly | Asp | Ser | Ile | Ile | Ala | Gln | Phe | Asp | Asp | Leu | Gly | Ser |
| | | | | 245 | | | | | 250 | | | | | 255 | |
| Val | Ala | Met | Phe | Cys | Glu | | | | | | | | | | |
| | | | 260 | | | | | | | | | | | | |

```
<210> SEQ ID NO 29
<211> LENGTH: 151
<212> TYPE: PRT
<213> ORGANISM: Arthrobacter sp.

<400> SEQUENCE: 29
```

| | | | | | | | | | | | | | | | |
|---|---|---|---|---|---|---|---|---|---|---|---|---|---|---|---|
| Met | His | Arg | Thr | Ser | Asn | Gly | Ser | His | Ala | Thr | Gly | Gly | Asn | Leu | Pro |
| 1 | | | | 5 | | | | | 10 | | | | | 15 | |
| Asp | Val | Ala | Ser | His | Tyr | Pro | Val | Ala | Tyr | Glu | Gln | Thr | Leu | Asp | Gly |
| | | | 20 | | | | | 25 | | | | | 30 | | |
| Thr | Val | Gly | Phe | Val | Ile | Asp | Glu | Met | Thr | Pro | Glu | Arg | Ala | Thr | Ala |
| | | | 35 | | | | | 40 | | | | | 45 | | |

```
Ser Val Glu Val Thr Asp Thr Leu Arg Gln Arg Trp Gly Leu Val His
 50                  55                  60

Gly Gly Ala Tyr Cys Ala Leu Ala Glu Met Leu Ala Thr Glu Ala Thr
 65                  70                  75                  80

Val Ala Val Val His Glu Lys Gly Met Met Ala Val Gly Gln Ser Asn
                 85                  90                  95

His Thr Ser Phe Phe Arg Pro Val Lys Glu Gly His Val Arg Ala Glu
                100                 105                 110

Ala Val Arg Ile His Ala Gly Ser Thr Thr Trp Phe Trp Asp Val Ser
            115                 120                 125

Leu Arg Asp Asp Ala Gly Arg Leu Cys Ala Val Ser Ser Met Ser Ile
130                 135                 140

Ala Val Arg Pro Arg Arg Asp
145                 150

<210> SEQ ID NO 30
<211> LENGTH: 140
<212> TYPE: PRT
<213> ORGANISM: Homo sapiens

<400> SEQUENCE: 30

Met Thr Ser Met Thr Gln Ser Leu Arg Glu Val Ile Lys Ala Met Thr
  1               5                  10                  15

Lys Ala Arg Asn Phe Glu Arg Val Leu Gly Lys Ile Thr Leu Val Ser
                 20                  25                  30

Ala Ala Pro Gly Lys Val Ile Cys Glu Met Lys Val Glu Glu Glu His
             35                  40                  45

Thr Asn Ala Ile Gly Thr Leu His Gly Gly Leu Thr Ala Thr Leu Val
 50                  55                  60

Asp Asn Ile Ser Thr Met Ala Leu Leu Cys Thr Glu Arg Gly Ala Pro
 65                  70                  75                  80

Gly Val Ser Val Asp Met Asn Ile Thr Tyr Met Ser Pro Ala Lys Leu
                 85                  90                  95

Gly Glu Asp Ile Val Ile Thr Ala His Val Leu Lys Gln Gly Lys Thr
            100                 105                 110

Leu Ala Phe Thr Ser Val Asp Leu Thr Asn Lys Ala Thr Gly Lys Leu
            115                 120                 125

Ile Ala Gln Gly Arg His Thr Lys His Leu Gly Asn
130                 135                 140

<210> SEQ ID NO 31
<211> LENGTH: 154
<212> TYPE: PRT
<213> ORGANISM: Haemophilus influenzae

<400> SEQUENCE: 31

Met Ser Ala Asn Phe Thr Asp Lys Asn Gly Arg Gln Ser Lys Gly Val
  1               5                  10                  15

Leu Leu Leu Arg Thr Leu Ala Met Pro Ser Asp Thr Asn Ala Asn Gly
                 20                  25                  30

Asp Ile Phe Gly Gly Trp Ile Met Ser Gln Met Asp Met Gly Gly Ala
             35                  40                  45

Ile Leu Ala Lys Glu Ile Ala His Gly Arg Val Val Thr Val Ala Val
 50                  55                  60

Glu Ser Met Asn Phe Ile Lys Pro Ile Ser Val Gly Asp Val Val Cys
 65                  70                  75                  80
```

```
Cys Tyr Gly Gln Cys Leu Lys Val Gly Arg Ser Ser Ile Lys Ile Lys
            85                  90                  95

Val Glu Val Trp Val Lys Lys Val Ala Ser Glu Pro Ile Gly Glu Arg
            100                 105                 110

Tyr Cys Val Thr Asp Ala Val Phe Thr Phe Val Ala Val Asp Asn Asn
            115                 120                 125

Gly Arg Ser Arg Thr Ile Pro Arg Glu Asn Asn Gln Glu Leu Glu Lys
            130                 135                 140

Ala Leu Ala Leu Ile Ser Glu Gln Pro Leu
145                 150

<210> SEQ ID NO 32
<211> LENGTH: 261
<212> TYPE: PRT
<213> ORGANISM: Clostridium acetobutylicum

<400> SEQUENCE: 32

Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
            35                  40                  45

Val Leu Ala Val Ile Leu Thr Gly Ala Gly Glu Lys Ser Phe Val Ala
        50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
            115                 120                 125

Arg Phe Gly Gln Pro Glu Val Gly Leu Gly Ile Thr Pro Gly Phe Gly
        130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
            195                 200                 205

Leu Ser Lys Gln Ala Ile Asn Arg Gly Met Gln Cys Asp Ile Asp Thr
        210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260

<210> SEQ ID NO 33
<211> LENGTH: 258
<212> TYPE: PRT
<213> ORGANISM: Clostridium pasteurianum
```

-continued

```
<400> SEQUENCE: 33

Met Glu Asn Ile Ile Phe Asn Glu Ser Asn Gly Ile Ala Glu Val Ile
1               5                   10                  15

Ile Asn Arg Pro Lys Ala Leu Asn Ala Leu Asn Asn Gln Thr Ile Thr
            20                  25                  30

Glu Leu Gly Glu Val Ile Asn Glu Ile Ser Lys Arg Lys Asp Ile Lys
        35                  40                  45

Thr Val Ile Ile Thr Gly Ala Gly Glu Lys Ala Phe Val Ala Gly Ala
    50                  55                  60

Asp Ile Val Glu Met Lys Asp Leu Asn Ser Met Glu Ala Arg Asp Phe
65                  70                  75                  80

Ser Arg Leu Ala Gln Lys Val Phe Ser Asp Ile Glu Asn Met Pro Gln
                85                  90                  95

Ile Val Ile Ala Ala Val Asn Gly Tyr Ala Leu Gly Gly Gly Cys Glu
            100                 105                 110

Leu Ser Met Ala Cys Asp Ile Arg Leu Ala Ser Lys Lys Ala Lys Phe
        115                 120                 125

Gly Gln Pro Glu Val Asn Leu Gly Ile Leu Pro Gly Phe Ala Gly Thr
    130                 135                 140

Gln Arg Leu Pro Arg Leu Val Gly Lys Gly Ile Ala Lys Glu Leu Ile
145                 150                 155                 160

Phe Ser Thr Asp Met Ile Asp Ala Glu Glu Ala His Arg Ile Gly Leu
                165                 170                 175

Ala Asn Lys Val Tyr Glu Pro Glu Glu Leu Met Asp Lys Ala Arg Glu
            180                 185                 190

Leu Ala Asn Lys Ile Met Ser Lys Ser Pro Val Gly Val Arg Leu Ala
        195                 200                 205

Lys Ala Ala Ile Asn Asn Gly Leu Asn Met Asp Thr Glu Ser Ala Tyr
    210                 215                 220

Asn Tyr Glu Ala Asp Leu Phe Ala Leu Cys Phe Ser Thr Glu Asp Gln
225                 230                 235                 240

Leu Glu Gly Met Asn Ala Phe Val Asp Lys Arg Lys Ala Asp Phe Lys
                245                 250                 255

Asp Lys

<210> SEQ ID NO 34
<211> LENGTH: 259
<212> TYPE: PRT
<213> ORGANISM: Streptococcus mitis

<400> SEQUENCE: 34

Met Ser Lys Thr Val Leu Leu Glu Val Lys Asn Gly Leu Gly Tyr Leu
1               5                   10                  15

Thr Ile Asn Arg Pro Ser Ala Leu Asn Ala Leu Ser Ser Glu Val Leu
            20                  25                  30

Lys Asp Leu Asn Leu Ala Leu Asp Gln Ile Glu Ala Ser Glu Asp Ile
        35                  40                  45

Arg Val Val Ile Val Thr Gly Gln Gly Glu Lys Ala Phe Val Ala Gly
    50                  55                  60

Ala Asp Ile Lys Glu Met Asp Gln Met Ser Pro Ile Ala His Glu
65                  70                  75                  80

Tyr Met Thr Tyr Ala Asn Asp Thr Phe Thr Arg Leu Ser Glu Leu Thr
                85                  90                  95
```

Gln Pro Thr Ile Ser Val Leu Asn Gly Tyr Ala Leu Gly Gly Leu
              100                 105                 110

Glu Leu Ala Leu Ser Thr Asp Ile Arg Ile Gly Tyr Asp Lys Thr Met
              115                 120                 125

Val Gly Phe Pro Glu Val Gly Leu Gly Ile Ile Pro Gly Phe Ala Gly
      130                 135                 140

Thr Gln Arg Met Ser Arg Leu Ile Gly Thr Ser Lys Thr Lys Glu Leu
145                 150                 155                 160

Ile Phe Thr Ala Arg Met Val Lys Gly Gln Glu Ala Tyr Asp Leu Gly
                  165                 170                 175

Ile Leu Asn Lys Leu Val Ala Ala Glu Glu Leu Leu Pro Ala Ala Glu
              180                 185                 190

Glu Leu Ala Ala Ala Ile Met Lys Asn Ala Pro Leu Ala Val Glu Lys
              195                 200                 205

Ala Lys His Ile Ile Gln Val Gly Ser Glu Leu Pro Leu Lys Asn Ala
          210                 215                 220

Ile Arg Leu Glu Thr Glu Ala Glu Ala Leu Leu Phe Ser Thr Glu Asp
225                 230                 235                 240

Lys Val Glu Gly Met Arg Ala Phe Val Glu Lys Arg Lys Ala Val Phe
                  245                 250                 255

Gln Arg Lys

<210> SEQ ID NO 35
<211> LENGTH: 257
<212> TYPE: PRT
<213> ORGANISM: Bordetella pertussis

<400> SEQUENCE: 35

Met Ala Arg Ala Asp Asp Ile Glu Val Arg Val Ala Asp Gln Val Ala
1 5 10 15

Trp Val Thr Ile Asn Arg Pro Gln Arg Met Asn Ala Leu Ala Arg Ala
20 25 30

Thr Phe Ala Gln Leu Val Glu Val Ser Leu Glu Leu Asp Gln Asp Pro
35 40 45

Gly Val Lys Val Val Val Tyr Thr Gly Ala Gly Glu Arg Ala Phe Ser
50 55 60

Ala Gly Val Asp Leu Lys Glu Leu Asp Ala Ala Gly Arg Met Thr His
65 70 75 80

Pro Met Gly Gly Leu Ala Arg Asn Leu Asn Glu Val Val Leu Glu Met
85 90 95

Ala Thr Pro Thr Ile Ala Ala Ile Asn Gly Val Ala Ala Gly Gly Gly
100 105 110

Cys Glu Leu Ala Leu Ala Cys Asp Ile Arg Val Ala Ala Ser Thr Ala
115 120 125

Arg Ile Gly Leu Pro Glu Ala Arg Val Gly Met Gly Ala Asn Phe Gly
130 135 140

Ser Val Val Leu Pro Gln Leu Ile Pro Arg Gly Val Ala Leu Glu Leu
145 150 155 160

Leu Tyr Thr Gly Glu Leu Ile Asp Met Ala Leu Ala His Arg Leu Gly
165 170 175

Leu Val Asn His Val Phe Glu Pro Ala Glu Leu Met Ala Gln Thr Ala
180 185 190

Gly Leu Ala Arg Arg Ile Ala Asp Asn Ala Pro Leu Ser Val Gln Arg
195 200 205

```
Met Lys Ala Met Ala Phe Lys Ser Ile Gly Leu Pro Thr Ala Ala Ala
        210                 215                 220

Leu Arg Leu Ser Val Gly Pro Asp Pro Tyr Asn Ser Glu Asp Arg Leu
225                 230                 235                 240

Glu Gly Ala Arg Ala Phe Val Glu Lys Arg Lys Pro Arg Phe Gln Gly
                    245                 250                 255

Arg
```

<210> SEQ ID NO 36
<211> LENGTH: 260
<212> TYPE: PRT
<213> ORGANISM: Rhodococcus equi

<400> SEQUENCE: 36

```
Met Arg Thr Pro Asp Gly Pro Gly Arg Ile Gln Thr Ala Ile Asp Arg
  1               5                  10                  15

His Val Ala Val Ile Thr Ile Asp His Leu Arg Arg Tyr Asn Ala Leu
                 20                  25                  30

Thr Gly Ala Met Leu Asp Gly Leu Thr Ala Thr Leu Asp Arg Leu Ala
             35                  40                  45

Asp Asp Pro Ala Val Ser Val Val Leu Val Thr Gly Ala Gly Pro His
 50                  55                  60

Phe Cys Ala Gly Met Asp Ile Arg Glu Leu Arg Ser Ala Arg Glu Ser
 65                  70                  75                  80

Gly Ile Arg Met Glu Asp Arg Val Thr Asp Ala Glu Ala Leu Ala
                 85                  90                  95

Ala Phe Pro Lys Pro Thr Ile Ala Ala Ile Ser Gly Tyr Cys Ile Gly
                100                 105                 110

Gly Gly Ala Gln Leu Ala Leu Ala Cys Asp Ile Arg Val Ala Ala Glu
            115                 120                 125

Asn Ala Glu Phe Ala Val Thr Pro Ala Lys Leu Gly Val Ile Tyr Pro
130                 135                 140

Ala Arg Thr Ile Thr Arg Leu Val Arg Thr Leu Gly Pro Ala Thr Thr
145                 150                 155                 160

Lys Arg Leu Val Ile Thr Gly Asp Arg Ile Asp Ala Asp Thr Ala Leu
                165                 170                 175

Arg Val Gly Leu Val Thr Glu Val Val Pro Ala Asp Arg Leu Arg Ala
            180                 185                 190

His Ala Met Ala Leu Ser Lys Ser Ile Thr Thr Arg Ser Leu Val Ser
        195                 200                 205

Gln Arg Ala Ala Lys Gln Met Ile Asp Ala Ala Gly Pro Gly Ile
    210                 215                 220

Asp Arg Glu Leu Glu His Arg Trp Ala His Thr Pro Asn Pro Asp Leu
225                 230                 235                 240

Glu Ile Gly Leu Asp Ala Phe Leu Ser Gly Thr Pro Pro Arg Phe Glu
                245                 250                 255

Gly Met Ser Ser
            260
```

<210> SEQ ID NO 37
<211> LENGTH: 267
<212> TYPE: PRT
<213> ORGANISM: Acinetobacter haemolyticus

<400> SEQUENCE: 37

```
Met Ser Tyr Gln Phe Leu Gln Leu Glu Gln His Asp Gln Val Ala Tyr
```

```
            1               5                  10                 15
Val Trp Leu Asn Arg Pro Glu Leu His Asn Ala Phe Asn Thr Thr Val
               20                  25                 30
Ile Glu Glu Leu His Thr Cys Phe Lys Gln Leu Ala Thr Ser Asp Asp
               35                  40                 45
Ile Arg Val Val Val Leu Ala Gly Arg Gly Lys Ser Phe Ser Ala Gly
 50                 55                 60
Ala Asp Leu Asn Trp Met Lys Gln Ala Gly Gln Ala Ser Ser Ala Glu
 65                 70                 75                  80
Asn Glu Ala Asp Ala Leu Lys Leu Ala Gln Met Leu Glu Ala Leu Ala
                85                  90                 95
Thr Leu Lys Gln Pro Thr Ile Ala Arg Val His Gly Ile Ala Phe Gly
               100                 105                110
Gly Gly Met Gly Leu Ala Ser Ala Cys Asp Ile Cys Ile Ala Ser Thr
               115                 120                125
Asp Ala Lys Phe Ala Thr Ser Glu Val Arg Leu Gly Leu Ala Pro Ser
130                 135                140
Thr Ile Ser Pro Tyr Val Ile Arg Ala Ile Gly Ala Arg Gln Ala Ser
145                 150                 155                160
Arg Tyr Phe Leu Thr Ala Glu Arg Ile Ser Ala His Glu Ala Lys Gln
               165                 170                175
Ile Gly Leu Ala His Glu Ile Ala Asp Ala Glu Asp Leu Asp Lys Lys
               180                 185                190
Val Gln Glu Ile Ile Asp Ala Leu Leu Leu Gly Gly Pro His Ala Gln
               195                 200                205
Ala Ala Ser Lys Gln Leu Ile Gln Met Val Ser Asn Gln Ser Met Asn
210                 215                 220
Asp Glu Leu Leu Arg Gln Thr Ala Gln His Ile Ala Gln Val Arg Gln
225                 230                 235                240
Gly Ser Glu Ala Lys Glu Gly Leu Thr Ala Phe Leu Ser Lys Gln Ala
                245                 250                255
Pro Ala Trp Thr Ser Asn Ser Asn Asn Asn
               260                 265

<210> SEQ ID NO 38
<211> LENGTH: 259
<212> TYPE: PRT
<213> ORGANISM: Rhodococcus erythropolis

<400> SEQUENCE: 38

Met Ala Glu Phe Val Thr Leu Glu Val Ser Glu Gly Ile Gly Thr Ile
 1               5                  10                 15
Arg Leu Ala Arg Pro Pro Met Asn Ala Leu Asn Arg Gln Val Gln Asp
               20                  25                 30
Glu Leu Ala Ala Ala His Ala Ala Thr Val Asp Lys Ala Val Lys
               35                  40                 45
Ala Val Ile Val Tyr Gly Gly Glu Lys Val Phe Ala Ala Gly Ala Asp
 50                 55                 60
Val Lys Glu Met Ala Glu Met Asp Tyr Gly Gln Ile Arg Asp Ala Ile
 65                 70                 75                 80
Gly Gly Met Gln Ala Gly Leu Gly Ala Val Ala Ser Ile Pro Lys Pro
                85                  90                 95
Thr Val Ala Ile Thr Gly Tyr Ala Leu Gly Gly Gly Leu Glu Val
               100                 105                110
```

```
Ala Leu Ser Ala Asp Arg Arg Ile Val Gly Asp Asn Ala Lys Leu Gly
            115                 120                 125

Val Pro Glu Ile Leu Leu Gly Ile Ile Pro Gly Gly Gly Thr Gln
130                 135                 140

Arg Leu Ala Arg Leu Ile Gly Pro Ala Lys Ala Lys Asp Leu Val Phe
145                 150                 155                 160

Thr Gly Arg Phe Val Gly Ala Asp Glu Ala Leu Ala Ile Gly Leu Val
                165                 170                 175

Asp Glu Val Val Ala Pro Asp Val Tyr Thr Ala Ala Arg Thr Trp
            180                 185                 190

Ala Ser Gln Phe Val Gly Gly Ala Ser Arg Ala Leu Ala Ala Lys
        195                 200                 205

Ala Ala Ile Asp Glu Gly Leu Asn Thr Asp Leu Glu Ser Gly Leu Lys
210                 215                 220

Ile Glu Gln His Leu Phe Ala Gly Leu Phe Ala Thr Lys Asp Gln Ala
225                 230                 235                 240

Ile Gly Met Glu Ser Phe Ile Ala Asn Gly Pro Gly Lys Ala Glu Phe
                245                 250                 255

Thr Gly Glu

<210> SEQ ID NO 39
<211> LENGTH: 266
<212> TYPE: PRT
<213> ORGANISM: Corynebacterium efficiens

<400> SEQUENCE: 39

Met Thr Thr Ser Met Thr Ser Asp Thr Thr Thr Ala Leu Asn Gly
 1               5                  10                  15

Asp Phe Asn Ala Leu Thr Leu Thr Glu Thr Asp Thr Tyr Leu Leu Val
             20                  25                  30

Glu Ile Thr Arg Pro Glu Val Arg Asn Ala Ile Asp Glu Thr Met Val
            35                  40                  45

Ser Glu Leu His Glu Val Cys Ser Tyr Leu Glu Leu Asn Pro Lys Ile
 50                  55                  60

Leu Ile Ile Thr Gly Cys Glu Ala Asn Gly Lys Gly Ile Phe Val Ser
65                  70                  75                  80

Gly Ala Asp Ile Gly Gln Met Arg Asp Arg Arg Asp Ala Leu
                85                  90                  95

Arg Gly Ile Asn Asn Met Leu Phe His Arg Ile Ala Gln Leu Pro Ala
                100                 105                 110

Pro Val Ile Ala Ala Val Asp Gly Tyr Ala Leu Gly Gly Met Glu
            115                 120                 125

Leu Ala Leu Ala Ala Asp Phe Arg Leu Ala Thr Pro Gly Ala Lys Phe
130                 135                 140

Gly Gln Pro Glu Ala Gly Leu Gly Ile Ile Ala Ala Gly Gly Leu
145                 150                 155                 160

Trp Arg Leu Lys Ala Leu Ile Gly Glu Ala Val Ala Lys Glu Ile Leu
                165                 170                 175

Leu Ala Gly Lys Ile Leu Asp Gly Asn Glu Ala Leu Ala Val His Leu
            180                 185                 190

Val Thr Glu Val His Lys Pro Ala Glu Leu Leu Asp Ala Ala Leu Ala
        195                 200                 205

Leu Ala Gly Arg Ile Ala Lys Leu Asp Pro Leu Ala Val Arg Ile Ser
210                 215                 220
```

```
Lys Gln Val Met Ala Met Pro Ala Gly Ala His Pro Gln Val Asp Asn
225                 230                 235                 240

Ile Ala Gln Ala Ile Leu Phe Glu Ser Glu Ala Lys Phe Asp Arg Met
                245                 250                 255

Gln Ala Phe Leu Asp Arg Lys Lys Asn Lys
            260                 265
```

<210> SEQ ID NO 40
<211> LENGTH: 266
<212> TYPE: PRT
<213> ORGANISM: Mycobacterium parascrofulaceum

<400> SEQUENCE: 40

```
Met Ser Met Thr Phe Glu Thr Ile Leu Leu Glu Val Asp Glu Thr Asp
1               5                   10                  15

Arg Val Ala Thr Ile Thr Leu Asn Arg Pro Gly Gln Leu Asn Ala Phe
            20                  25                  30

Asn Arg Thr Met Cys Glu Glu Met Ala Arg Ala Trp Arg Ile Val Lys
        35                  40                  45

His Asp Ala Ser Val Asn Ala Val Leu Arg Ala Ala Gly Asp Arg
    50                  55                  60

Ala Phe Ser Ala Gly Leu Asp Ile Lys Thr Pro Tyr Gly Gln Pro Glu
65                  70                  75                  80

Asn Ile Trp Asn His Asp Asp Pro Gly Glu Ala Leu Ser Pro Lys Trp
                85                  90                  95

Gln Lys Met Trp Lys Pro Val Val Cys Ala Val Gln Gly Met Cys Thr
            100                 105                 110

Ala Gly Ala Phe Tyr Phe Val Asn Glu Ser Asp Val Val Ile Cys Ser
        115                 120                 125

Gln Asp Ala Thr Phe Phe Asp Ser His Val Ser Ala Gly Leu Val Cys
    130                 135                 140

Ala Leu Glu Pro Ile Gly Leu Met Arg Arg Val Gly Leu Gly Glu Thr
145                 150                 155                 160

Leu Arg Ile Ala Leu Met Gly Asn Asp Glu Arg Val Cys Ala Asp Thr
                165                 170                 175

Ala Leu Arg Ile Gly Leu Val Ser Glu Val Val Pro Ala Gln Gln Leu
            180                 185                 190

Trp Asn Arg Ala His Glu Ile Ala Ala Thr Ile Ala Ala Lys Pro Thr
        195                 200                 205

Thr Ala Thr Gln Gly Thr Val Lys Ala Ile Trp Glu Ser Leu Asp Lys
    210                 215                 220

Pro Tyr Arg Ala Ala Met Glu Gln Gly Leu Ile Tyr Thr Arg Leu Gly
225                 230                 235                 240

Asn Pro Leu Gly Val Ala Glu Leu Ala Ala Arg Thr Asp Pro Gly Gly
                245                 250                 255

Glu Ala Ala Pro Arg Thr Pro Lys Ile Arg
            260                 265
```

<210> SEQ ID NO 41
<211> LENGTH: 259
<212> TYPE: PRT
<213> ORGANISM: halophilic archaeon

<400> SEQUENCE: 41

```
Met Gln His Gly Pro Phe Arg His Ile His Leu Asp Arg Glu Asp Gly
1               5                   10                  15
```

-continued

Val Val Ser Ile Thr Ile Asp Arg Pro Glu Lys His Asn Ala Leu Asn
            20                  25                  30

Asp Gly Ala Met Leu Asp Leu Ser Arg Ala Phe Ala Glu Ile Glu Phe
        35                  40                  45

Asp Arg Ser Val Asp Ala Val Ile Glu Gly Ala Gly Asp Glu Ala
50                  55                  60

Phe Ser Ala Gly Ala Asp Ile Glu Gln Tyr Ala Gly Pro Ser Glu Asp
65                  70                  75                  80

His Asp Pro Met Gln Lys Glu Arg Gln Asp Arg Phe Tyr Glu Val Tyr
                85                  90                  95

Arg Glu Pro Phe Glu Cys His Ala Pro Val Ile Ala Lys Ile Asp Gly
            100                 105                 110

Phe Cys Val Gly Gly Gly Leu Ile Phe Ala Met Tyr Cys Asp Leu Arg
        115                 120                 125

Ile Ala Ser Glu Gly Ser Gln Phe Gly Val Pro Thr Ala Asn Ile Gly
    130                 135                 140

Gln Val Pro Thr Gly Gly Ala Thr Arg Arg Ala Val Glu Leu Val Gly
145                 150                 155                 160

Glu Ala Thr Ala Lys Glu Leu Val Phe Thr Ala Gly Tyr Val Asp Ala
                165                 170                 175

Glu Thr Ala Thr Asp Ala Gly Leu Val Asn Asp Val Val Pro Pro Glu
            180                 185                 190

Ala Leu Asp Asp Arg Val Ala Ser Leu Ile Asp Ala Met Gly Asp Ala
        195                 200                 205

Gly Arg Glu Ala Val Lys Asn Ser Lys Arg Ala Ile Asn Ala Ala Val
    210                 215                 220

Glu Ala Glu Asn Pro Lys Thr Ala Arg Glu Arg Glu Ala Asp Leu Trp
225                 230                 235                 240

Trp Glu Gln Phe Ala Thr Ala Glu Arg Arg Asp Leu Val Asp Glu Phe
                245                 250                 255

Thr Asp Arg

<210> SEQ ID NO 42
<211> LENGTH: 263
<212> TYPE: PRT
<213> ORGANISM: Bacillus cereus

<400> SEQUENCE: 42

Met Glu Ser Asn Arg Val Val Thr Trp Ser Lys Glu Asn Gly Ile Ala
1               5                   10                  15

Thr Ile Ile Ile Asp Asn Pro Pro Met Asn Val Leu Gly Ser Ala Val
            20                  25                  30

Val Glu Gln Leu Thr Val Ala Val Asp Thr Ile Glu Arg Asp Asp Glu
        35                  40                  45

Val Ile Val Val Leu Leu Thr Gly Ala Gly Glu Lys Thr Phe Val Ala
50 55 60

Gly Gly Asp Ile Lys Ser Phe Pro Glu Trp Ile Gly Lys Gly Ser Glu
65 70 75 80

Tyr Ala Glu Glu Lys Ser Leu Trp Leu Gln Asn Pro Leu Asn Lys Ile
85 90 95

Glu Arg Leu Pro Lys Pro Val Ile Ala Ala Ile Asn Gly Leu Ala Leu
100 105 110

Gly Gly Gly Cys Glu Leu Ala Leu Ser Cys Asp Ile Arg Ile Ile Glu
115 120 125

```
Glu His Gly Gln Ile Gly Leu Pro Glu Val Lys Leu Gly Leu Phe Pro
            130                 135                 140

Gly Ala Gly Gly Thr Gln Arg Leu Pro Arg Leu Ile Gly Thr Ala Ser
145                 150                 155                 160

Ala Lys Glu Met Met Phe Thr Gly Pro Leu Thr Ala Glu Ala Ala
                165                 170                 175

Trp Arg Val Gly Leu Val Asn His Ile Val Pro Arg Gly Glu Ser Leu
            180                 185                 190

Asn Lys Ala Lys Glu Leu Ala Ala Lys Met Ala Arg Phe Ser Leu Pro
            195                 200                 205

Ala Leu Ser Leu Met Lys Gln Ser Ile Asp Lys Gly Leu Ser Ser Ser
210                 215                 220

Leu Glu Glu Gly Leu Lys Ile Glu Ala Glu Asn Phe Gly His Ile Phe
225                 230                 235                 240

Gln Thr Ser Asp Val Arg Glu Gly Val Glu Ala Phe Ile Glu Lys Arg
                245                 250                 255

Ala Pro Phe Phe His His Lys
            260

<210> SEQ ID NO 43
<211> LENGTH: 261
<212> TYPE: PRT
<213> ORGANISM: Clostridium butyricum

<400> SEQUENCE: 43

Met Glu Leu Glu Asn Val Ile Leu Glu Lys Glu Gly His Leu Ala Ile
1               5                   10                  15

Val Thr Ile Asn Arg Pro Lys Ala Leu Asn Ala Leu Asn Ser Ala Thr
            20                  25                  30

Leu Lys Asp Leu Asp Thr Val Leu Glu Asp Leu Glu Asn Asp Thr Asn
        35                  40                  45

Ile Tyr Ala Val Ile Leu Thr Gly Ala Gly Glu Lys Ser Phe Val Ala
    50                  55                  60

Gly Ala Asp Ile Ala Glu Met Lys Asp Leu Asn Glu Ala Gln Gly Lys
65                  70                  75                  80

Glu Phe Gly Glu Leu Gly Asn Lys Val Phe Leu Arg Leu Glu Asn Leu
                85                  90                  95

Asn Lys Pro Val Ile Ala Ile Gln Gly Phe Ala Leu Gly Gly Gly
            100                 105                 110

Cys Glu Ile Ser Met Ala Cys Asp Ile Arg Ile Ala Ser Glu Thr Ala
        115                 120                 125

Leu Phe Gly Gln Pro Glu Val Gly Leu Gly Ile Thr Pro Gly Phe Gly
130                 135                 140

Gly Thr Gln Arg Leu Ala Arg Ile Val Gly Leu Gly Lys Ala Lys Glu
145                 150                 155                 160

Met Ile Tyr Thr Ala Arg Asn Ile Lys Ala Asp Glu Ala Tyr Arg Ile
                165                 170                 175

Gly Leu Val Asn Lys Val Val Ala Leu Glu Asp Leu Met Asn Glu Ala
            180                 185                 190

Lys Lys Met Ala Ser Asn Ile Ile Ala Asn Ala Pro Val Ala Val Lys
            195                 200                 205

Leu Cys Lys Asp Ala Ile Asn Arg Gly Met Gln Val Gly Ile Asp Glu
        210                 215                 220

Ala Val Met Ile Glu Ala Glu Asp Phe Gly Lys Cys Phe Ala Thr Glu
225                 230                 235                 240
```

```
Asp Gln Thr Glu Gly Met Thr Ala Phe Leu Glu Arg Arg Lys Glu Lys
                245                 250                 255
Asn Phe Gln Asn Lys
            260

<210> SEQ ID NO 44
<211> LENGTH: 159
<212> TYPE: PRT
<213> ORGANISM: Pseudomonas aeruginosa

<400> SEQUENCE: 44

Met Ser Gln Val Leu Thr Thr Tyr Glu Thr Pro Val Leu Pro Glu Trp
 1               5                  10                  15
Val Asp Tyr Asn Gly His Leu Arg Asp Ala Phe Tyr Leu Leu Val Phe
                20                  25                  30
Ser Tyr Ala Thr Asp Ala Leu Met Ala His Ile Gly Leu Asp Ser Gln
            35                  40                  45
Asn Arg Asp Ala Ser Gly His Ser Leu Phe Thr Leu Glu Cys His Leu
        50                  55                  60
Asn Phe Leu His Glu Val Lys Glu Gly Ala Arg Val Glu Val Arg Thr
 65                 70                  75                  80
Gln Leu Leu Gly His Asp Arg Lys Arg Leu His Ile His His Ala Leu
                85                  90                  95
Tyr Leu Pro Gly Ser Gly Gln Ala Leu Ala Leu Ser Glu Gln Met Leu
            100                 105                 110
Leu His Val Ser Leu Asp Gly Pro Arg Ser Val Pro Phe Glu Gly Glu
        115                 120                 125
Val Leu Ala Arg Val Glu Ala Leu Ala Glu Ala His Arg Ala Leu Pro
130                 135                 140
Val Pro Glu Gly Val Gly Arg Val Ile Gly Leu Pro Pro Val Arg
145                 150                 155

<210> SEQ ID NO 45
<211> LENGTH: 258
<212> TYPE: PRT
<213> ORGANISM: Clostridium saccharolyticum

<400> SEQUENCE: 45

Met Gly Tyr Val Asp Tyr Glu Gln Glu Gly Phe Val Gly Ile Val Thr
 1               5                  10                  15
Ile Asn Arg Pro Lys Ala Leu Asn Ala Leu Asn Glu Glu Val Leu Lys
                20                  25                  30
Asp Leu Glu Ala Ala Phe Asp Ser Ile Asp Gln Asn Thr Val Arg Ala
            35                  40                  45
Val Ile Leu Thr Gly Ala Gly Glu Lys Ser Phe Val Ala Gly Ala Asp
        50                  55                  60
Ile Ala Ala Met Ser Thr Met Thr Lys Glu Gln Gly Glu Ala Phe Gly
 65                 70                  75                  80
Lys Tyr Gly Asn Asp Ile Phe Arg Lys Ile Glu Thr Phe Pro Ile Pro
                85                  90                  95
Val Ile Ala Ala Val Asn Gly Phe Ala Leu Gly Gly Gly Asn Glu Leu
            100                 105                 110
Ala Met Ser Cys Asp Ile Arg Ile Cys Ser Glu Asn Ala Val Phe Gly
        115                 120                 125
Gln Pro Glu Val Gly Leu Gly Ile Thr Pro Gly Phe Gly Gly Thr Gln
        130                 135                 140
```

```
Arg Leu Ala Arg Leu Ile Gly Val Gly Lys Ala Lys Glu Met Leu Tyr
145                 150                 155                 160

Thr Ala Arg Asn Ile Lys Ala Asp Glu Ala Tyr Arg Leu Gly Phe Val
            165                 170                 175

Asn Ala Val Tyr Pro Gln Glu Glu Leu Met Pro Ala Ala Lys Lys Met
        180                 185                 190

Ala Gly Ile Ile Ala Ala Asn Ala Pro Ile Ala Val Arg Asn Ser Lys
    195                 200                 205

Lys Ala Ala Asn Asp Gly Leu Gln Thr Asp Met Asp Gln Ala Ile Val
210                 215                 220

Ile Glu Glu Lys Leu Phe Gly Ala Cys Phe Glu Thr Glu Asp Gln Lys
225                 230                 235                 240

Glu Gly Met Ala Ala Phe Leu Glu Lys Arg Lys Glu Lys Gln Phe Lys
            245                 250                 255

Asn Arg

<210> SEQ ID NO 46
<211> LENGTH: 259
<212> TYPE: PRT
<213> ORGANISM: Cupriavidus necator N-1

<400> SEQUENCE: 46

Met Glu Thr Ile Arg Phe Ala Val Glu Asp Gly Val Ala Thr Leu Thr
1               5                   10                  15

Leu Asp Ser Pro Ala Arg Lys Asn Ala Leu Ser Leu Pro Met Arg Asp
            20                  25                  30

Glu Ile Gly Glu Val Ile Arg Arg Val Arg Ala Asp Asp Ser Val Arg
        35                  40                  45

Ala Leu Ile Leu Thr Ala Ala Gly Thr Asp Phe Ser Ser Gly Gly Asp
    50                  55                  60

Ile Ser Ser Met Gln Val Glu Ile Asn Ala Glu Gln Gly Arg Lys Arg
65                  70                  75                  80

Leu His Lys Val His Gly Trp Leu Glu Asp Leu Ile Gln Leu Asp Val
                85                  90                  95

Pro Val Ile Ala Ala Val Asp Gly Ala Ala Tyr Gly Ala Gly Phe Ser
            100                 105                 110

Leu Ala Leu Thr Ala Asp Ile Ile Leu Ala Thr Pro Arg Ala Arg Phe
        115                 120                 125

Gly Leu Pro Phe Leu Arg Met Gly Leu Ile Pro Asp Cys Gly Val Leu
    130                 135                 140

Tyr Thr Leu Pro Arg Met Ile Gly Leu Gln Arg Ala Lys Ala Leu Met
145                 150                 155                 160

Phe Ser Met Arg Glu Leu Asn Ala Gln Ala Gln Asp Leu Gly Ile
                165                 170                 175

Val Met Glu Ile Val Pro Ala Asp Ser Leu Gln Glu Arg Ala Arg Ala
            180                 185                 190

Leu Ala Gln Ala Phe Thr Glu Ala Ser Pro Val Ala Val Gly Leu Thr
        195                 200                 205

Lys Gln Ala Leu Asn Ala Ser Leu Asn Gln Asp Leu His Thr Met Leu
    210                 215                 220

Ala Met Glu Ala Asp Gly Gln Gly Ile Ala Phe Ser Thr Ala Tyr Arg
225                 230                 235                 240

Arg Glu Ala Ala Asp Arg Phe Met Ala Lys Gln Pro Leu Arg Tyr Arg
                245                 250                 255
```

Trp Pro Asp

<210> SEQ ID NO 47
<211> LENGTH: 134
<212> TYPE: PRT
<213> ORGANISM: Aeromonas punctata

<400> SEQUENCE: 47

```
Met Ser Ala Gln Ser Leu Glu Val Gly Gln Lys Ala Arg Leu Ser Lys
 1               5                  10                  15

Arg Phe Gly Ala Ala Glu Val Ala Ala Phe Ala Ala Leu Ser Glu Asp
                20                  25                  30

Phe Asn Pro Leu His Leu Asp Pro Ala Phe Ala Ala Thr Thr Ala Phe
            35                  40                  45

Glu Arg Pro Ile Val His Gly Met Leu Leu Ala Ser Leu Phe Ser Gly
        50                  55                  60

Leu Leu Gly Gln Gln Leu Pro Gly Lys Gly Ser Ile Tyr Leu Gly Gln
65                  70                  75                  80

Ser Leu Ser Phe Lys Leu Pro Val Phe Val Gly Asp Glu Val Thr Ala
                85                  90                  95

Glu Val Glu Val Thr Ala Leu Arg Glu Asp Lys Pro Ile Ala Thr Leu
                100                 105                 110

Thr Thr Arg Ile Phe Thr Gln Gly Gly Ala Leu Ala Val Thr Gly Glu
            115                 120                 125

Ala Val Val Lys Leu Pro
        130
```

<210> SEQ ID NO 48
<211> LENGTH: 735
<212> TYPE: PRT
<213> ORGANISM: Mus musculus

<400> SEQUENCE: 48

```
Met Ala Ser Pro Leu Arg Phe Asp Gly Arg Val Val Leu Val Thr Gly
 1               5                  10                  15

Ala Gly Gly Gly Leu Gly Arg Ala Tyr Ala Leu Ala Phe Ala Glu Arg
                20                  25                  30

Gly Ala Leu Val Ile Val Asn Asp Leu Gly Gly Asp Phe Lys Gly Ile
            35                  40                  45

Gly Lys Gly Ser Ser Ala Ala Asp Lys Val Val Ala Glu Ile Arg Arg
        50                  55                  60

Lys Gly Gly Lys Ala Val Ala Asn Tyr Asp Ser Val Glu Ala Gly Glu
65                  70                  75                  80

Lys Leu Val Lys Thr Ala Leu Asp Thr Phe Gly Arg Ile Asp Val Val
                85                  90                  95

Val Asn Asn Ala Gly Ile Leu Arg Asp Arg Ser Phe Ser Arg Ile Ser
                100                 105                 110

Asp Glu Asp Trp Asp Ile Ile His Arg Val His Leu Arg Gly Ser Phe
            115                 120                 125

Gln Val Thr Arg Ala Ala Trp Asp His Met Lys Lys Gln Asn Tyr Gly
        130                 135                 140

Arg Ile Leu Met Thr Ser Ser Ala Ser Gly Ile Tyr Gly Asn Phe Gly
145                 150                 155                 160

Gln Ala Asn Tyr Ser Ala Ala Lys Leu Gly Ile Leu Gly Leu Cys Asn
                165                 170                 175
```

```
Thr Leu Ala Ile Glu Gly Arg Lys Asn Asn Ile His Cys Asn Thr Ile
            180                 185                 190

Ala Pro Asn Ala Gly Ser Arg Met Thr Glu Thr Val Leu Pro Glu Asp
        195                 200                 205

Leu Val Glu Ala Leu Lys Pro Glu Tyr Val Ala Pro Leu Val Leu Trp
210                 215                 220

Leu Cys His Glu Ser Cys Glu Glu Asn Gly Gly Leu Phe Glu Val Gly
225                 230                 235                 240

Ala Gly Trp Ile Gly Lys Leu Arg Trp Glu Arg Thr Leu Gly Ala Ile
                245                 250                 255

Val Arg Lys Arg Asn Gln Pro Met Thr Pro Glu Ala Val Arg Asp Asn
            260                 265                 270

Trp Glu Lys Ile Cys Asp Phe Ser Asn Ala Ser Lys Pro Gln Thr Ile
        275                 280                 285

Gln Glu Ser Thr Gly Gly Ile Val Glu Val Leu His Lys Val Asp Ser
    290                 295                 300

Glu Gly Ile Ser Pro Asn Arg Thr Ser His Ala Ala Pro Ala Ala Thr
305                 310                 315                 320

Ser Gly Phe Val Gly Ala Val Gly His Lys Leu Pro Ser Phe Ser Ser
                325                 330                 335

Ser Tyr Thr Glu Leu Gln Ser Ile Met Tyr Ala Leu Gly Val Gly Ala
            340                 345                 350

Ser Val Lys Asn Pro Lys Asp Leu Lys Phe Val Tyr Glu Gly Ser Ala
        355                 360                 365

Asp Phe Ser Cys Leu Pro Thr Phe Gly Val Ile Val Ala Gln Lys Ser
    370                 375                 380

Met Met Asn Gly Gly Leu Ala Glu Val Pro Gly Leu Ser Phe Asn Phe
385                 390                 395                 400

Ala Lys Ala Leu His Gly Glu Gln Tyr Leu Glu Leu Tyr Lys Pro Leu
                405                 410                 415

Pro Arg Ser Gly Glu Leu Lys Cys Glu Ala Val Ile Ala Asp Ile Leu
            420                 425                 430

Asp Lys Gly Ser Gly Val Val Ile Val Met Asp Val Tyr Ser Tyr Ser
        435                 440                 445

Gly Lys Glu Leu Ile Cys Tyr Asn Gln Phe Ser Val Phe Val Val Gly
    450                 455                 460

Ser Gly Gly Phe Gly Gly Lys Arg Thr Ser Glu Lys Leu Lys Ala Ala
465                 470                 475                 480

Val Ala Val Pro Asn Arg Pro Asp Ala Val Leu Arg Asp Ala Thr
                485                 490                 495

Ser Leu Asn Gln Ala Ala Leu Tyr Arg Leu Ser Gly Asp Trp Asn Pro
            500                 505                 510

Leu His Ile Asp Pro Asp Phe Ala Ser Val Ala Gly Phe Glu Lys Pro
        515                 520                 525

Ile Leu His Gly Leu Cys Thr Phe Gly Phe Ser Ala Arg His Val Leu
    530                 535                 540

Gln Gln Phe Ala Asp Asn Asp Val Ser Arg Phe Lys Ala Ile Lys Val
545                 550                 555                 560

Arg Phe Ala Lys Pro Val Tyr Pro Gly Gln Thr Leu Gln Thr Glu Met
                565                 570                 575

Trp Lys Glu Gly Asn Arg Ile His Phe Gln Thr Lys Val His Glu Thr
            580                 585                 590

Gly Asp Val Val Ile Ser Asn Ala Tyr Val Asp Leu Val Pro Ala Ser
```

```
                595                 600                 605
Gly Val Ser Thr Gln Thr Pro Ser Glu Gly Glu Leu Gln Ser Ala
            610                 615                 620

Leu Val Phe Gly Glu Ile Gly Arg Arg Leu Lys Ser Val Gly Arg Glu
625                 630                 635                 640

Val Val Lys Lys Ala Asn Ala Val Phe Glu Trp His Ile Thr Lys Gly
                645                 650                 655

Gly Thr Val Ala Ala Lys Trp Thr Ile Asp Leu Lys Ser Gly Ser Gly
            660                 665                 670

Glu Val Tyr Gln Gly Pro Ala Lys Gly Ser Ala Asp Val Thr Ile Ile
        675                 680                 685

Ile Ser Asp Glu Asp Phe Met Glu Val Val Phe Gly Lys Leu Asp Pro
    690                 695                 700

Gln Lys Ala Phe Phe Ser Gly Arg Leu Lys Ala Arg Gly Asn Ile Met
705                 710                 715                 720

Leu Ser Gln Lys Leu Gln Met Ile Leu Lys Asp Tyr Ala Lys Leu
                725                 730                 735

<210> SEQ ID NO 49
<211> LENGTH: 294
<212> TYPE: PRT
<213> ORGANISM: Dictyostelium discoideum

<400> SEQUENCE: 49

Met Thr Val Asp Val Lys Lys Val Ile Asn His Lys Ile Lys Pro Ile
1               5                   10                  15

Glu Tyr Asn Leu Thr Arg Lys Asp Val Ala Leu Tyr Ala Ile Ser Leu
            20                  25                  30

Gly Cys Gly Lys Lys His Leu Lys Phe Val Tyr Glu Gly Ser Asp Asn
        35                  40                  45

Phe Ser Ala Leu Pro Thr Leu Gly Val Ile Phe Pro Gly Gln Met Ile
    50                  55                  60

Val Asp Val Ile Ser Glu Gly Ile Asp Gly Ile Glu Phe Asp Pro Met
65                  70                  75                  80

Met Leu Leu His Gly Glu Gln Glu Leu Glu Ile Leu Asn Glu Ile Pro
                85                  90                  95

Val Glu Gly Val Phe Val Thr Glu Ser Lys Ile Thr Asn Leu Tyr Asp
            100                 105                 110

Lys Gly Lys Gly Ala Leu Leu Ile Leu Gln Cys Ile Thr Ser Glu Lys
        115                 120                 125

Ser Ser Gly Lys Pro Ile Phe Lys Asn Ile Phe Ser Phe Phe Ile Arg
    130                 135                 140

Gly Ile Gly Gly Phe Gly Gly Asp Arg Gly Pro Asn Glu Lys Pro Ile
145                 150                 155                 160

Gln Ile Pro Lys Asp Arg Ala Pro Asp Ala Ile Ser Lys Gln Ala Thr
                165                 170                 175

Ser Glu Asp Gln Ala Val Ile Tyr Arg Leu Ala Gly Gly Asp Leu Asn
            180                 185                 190

Pro Leu His Ile Asp Pro Glu Met Ser Lys Ile Gly Gly Phe Glu Val
        195                 200                 205

Pro Ile Leu His Gly Leu Cys Thr Tyr Gly Ile Ala Ser Arg Gly Val
    210                 215                 220

Leu Glu His Phe Cys Asp Asn Asp Pro Ser Arg Leu Lys Ser Ile Lys
225                 230                 235                 240
```

```
Thr Arg Phe Thr Lys His Val Tyr Pro Gly Glu Thr Ile Glu Thr Glu
                245                 250                 255

Met Trp Lys Ile Asn Pro Thr Thr Ile Leu Phe Gln Ser Lys Thr Asn
            260                 265                 270

Arg Asp Gly Ser Tyr Val Leu Ser Ser Gly Val Ala Ile Ile Glu Pro
        275                 280                 285

Ile Lys Lys Gly Ser Leu
    290

<210> SEQ ID NO 50
<211> LENGTH: 736
<212> TYPE: PRT
<213> ORGANISM: Homo sapiens

<400> SEQUENCE: 50

Met Gly Ser Pro Leu Arg Phe Asp Gly Arg Val Val Leu Val Thr Gly
  1               5                  10                  15

Ala Gly Ala Gly Leu Gly Arg Ala Tyr Ala Leu Ala Phe Ala Glu Arg
                20                  25                  30

Gly Ala Leu Val Val Val Asn Asp Leu Gly Gly Asp Phe Lys Gly Val
            35                  40                  45

Gly Lys Gly Ser Leu Ala Ala Asp Lys Val Val Glu Glu Ile Arg Arg
    50                  55                  60

Arg Gly Gly Lys Ala Val Ala Asn Tyr Asp Ser Val Glu Glu Gly Glu
65                  70                  75                  80

Lys Val Val Lys Thr Ala Leu Asp Ala Phe Gly Arg Ile Asp Val Val
                85                  90                  95

Val Asn Asn Ala Gly Ile Leu Arg Asp Arg Ser Phe Ala Arg Ile Ser
            100                 105                 110

Asp Glu Asp Trp Asp Ile Ile His Arg Val His Leu Arg Gly Ser Phe
        115                 120                 125

Gln Val Thr Arg Ala Ala Trp Glu His Met Lys Lys Gln Lys Tyr Gly
    130                 135                 140

Arg Ile Ile Met Thr Ser Ser Ala Ser Gly Ile Tyr Gly Asn Phe Gly
145                 150                 155                 160

Gln Ala Asn Tyr Ser Ala Ala Lys Leu Gly Leu Leu Gly Leu Ala Asn
                165                 170                 175

Ser Leu Ala Ile Glu Gly Arg Lys Ser Asn Ile His Cys Asn Thr Ile
            180                 185                 190

Ala Pro Asn Ala Gly Ser Arg Met Thr Gln Thr Val Met Pro Glu Asp
        195                 200                 205

Leu Val Glu Ala Leu Lys Pro Glu Tyr Val Ala Pro Leu Val Leu Trp
    210                 215                 220

Leu Cys His Glu Ser Cys Glu Glu Asn Gly Gly Leu Phe Glu Val Gly
225                 230                 235                 240

Ala Gly Trp Ile Gly Lys Leu Arg Trp Glu Arg Thr Leu Gly Ala Ile
                245                 250                 255

Val Arg Gln Lys Asn His Pro Met Thr Pro Glu Ala Val Lys Ala Asn
            260                 265                 270

Trp Lys Lys Ile Cys Asp Phe Glu Asn Ala Ser Lys Pro Gln Ser Ile
        275                 280                 285

Gln Glu Ser Thr Gly Ser Ile Ile Glu Val Leu Ser Lys Ile Asp Ser
    290                 295                 300

Glu Gly Gly Val Ser Ala Asn His Thr Ser Arg Ala Thr Ser Thr Ala
305                 310                 315                 320
```

```
Thr Ser Gly Phe Ala Gly Ala Ile Gly Gln Lys Leu Pro Phe Ser
                325                 330                 335

Tyr Ala Tyr Thr Glu Leu Glu Ala Ile Met Tyr Ala Leu Gly Val Gly
                340                 345                 350

Ala Ser Ile Lys Asp Pro Lys Asp Leu Lys Phe Ile Tyr Glu Gly Ser
                355                 360                 365

Ser Asp Phe Ser Cys Leu Pro Thr Phe Gly Val Ile Gly Gln Lys
                370                 375                 380

Ser Met Met Gly Gly Leu Ala Glu Ile Pro Gly Leu Ser Ile Asn
385                 390                 395                 400

Phe Ala Lys Val Leu His Gly Glu Gln Tyr Leu Glu Leu Tyr Lys Pro
                405                 410                 415

Leu Pro Arg Ala Gly Lys Leu Lys Cys Glu Ala Val Val Ala Asp Val
                420                 425                 430

Leu Asp Lys Gly Ser Gly Val Val Ile Ile Met Asp Val Tyr Ser Tyr
                435                 440                 445

Ser Glu Lys Glu Leu Ile Cys His Asn Gln Phe Ser Leu Phe Leu Val
                450                 455                 460

Gly Ser Gly Gly Phe Gly Gly Lys Arg Thr Ser Asp Lys Val Lys Val
465                 470                 475                 480

Ala Val Ala Ile Pro Asn Arg Pro Pro Asp Ala Val Leu Thr Asp Thr
                485                 490                 495

Thr Ser Leu Asn Gln Ala Ala Leu Tyr Arg Leu Ser Gly Asp Trp Asn
                500                 505                 510

Pro Leu His Ile Asp Pro Asn Phe Ala Ser Leu Ala Gly Phe Asp Lys
                515                 520                 525

Pro Ile Leu His Gly Leu Cys Thr Phe Gly Phe Ser Ala Arg Arg Val
                530                 535                 540

Leu Gln Gln Phe Ala Asp Asn Asp Val Ser Arg Phe Lys Ala Ile Lys
545                 550                 555                 560

Ala Arg Phe Ala Lys Pro Val Tyr Pro Gly Gln Thr Leu Gln Thr Glu
                565                 570                 575

Met Trp Lys Glu Gly Asn Arg Ile His Phe Gln Thr Lys Val Gln Glu
                580                 585                 590

Thr Gly Asp Ile Val Ile Ser Asn Ala Tyr Val Asp Leu Ala Pro Thr
                595                 600                 605

Ser Gly Thr Ser Ala Lys Thr Pro Ser Glu Gly Gly Lys Leu Gln Ser
                610                 615                 620

Thr Phe Val Phe Glu Glu Ile Gly Arg Arg Leu Lys Asp Ile Gly Pro
625                 630                 635                 640

Glu Val Val Lys Lys Val Asn Ala Val Phe Glu Trp His Ile Thr Lys
                645                 650                 655

Gly Gly Asn Ile Gly Ala Lys Trp Thr Ile Asp Leu Lys Ser Gly Ser
                660                 665                 670

Gly Lys Val Tyr Gln Gly Pro Ala Lys Gly Ala Ala Asp Thr Thr Ile
                675                 680                 685

Ile Leu Ser Asp Glu Asp Phe Met Glu Val Val Leu Gly Lys Leu Asp
                690                 695                 700

Pro Gln Lys Ala Phe Phe Ser Gly Arg Leu Lys Ala Arg Gly Asn Ile
705                 710                 715                 720

Met Leu Ser Gln Lys Leu Gln Met Ile Leu Lys Asp Tyr Ala Lys Leu
                725                 730                 735
```

<210> SEQ ID NO 51
<211> LENGTH: 906
<212> TYPE: PRT
<213> ORGANISM: Candida tropicalis

<400> SEQUENCE: 51

Met Ser Pro Val Asp Phe Lys Asp Lys Val Ile Ile Thr Gly Ala
1               5                   10                  15

Gly Gly Gly Leu Gly Lys Tyr Tyr Ser Leu Glu Phe Ala Lys Leu Gly
            20                  25                  30

Ala Lys Val Val Asn Asp Leu Gly Gly Ala Leu Asn Gly Gln Gly
        35                  40                  45

Gly Asn Ser Lys Ala Ala Asp Val Val Asp Glu Ile Val Lys Asn
    50                  55                  60

Gly Gly Val Ala Val Ala Asp Tyr Asn Asn Val Leu Asp Gly Asp Lys
65                  70                  75                  80

Ile Val Glu Thr Ala Val Lys Asn Phe Gly Thr Val His Val Ile Ile
                85                  90                  95

Asn Asn Ala Gly Ile Leu Arg Asp Ala Ser Met Lys Lys Met Thr Glu
            100                 105                 110

Lys Asp Tyr Lys Leu Val Ile Asp Val His Leu Asn Gly Ala Phe Ala
        115                 120                 125

Val Thr Lys Ala Ala Trp Pro Tyr Phe Gln Lys Gln Lys Tyr Gly Arg
    130                 135                 140

Ile Val Asn Thr Ser Ser Pro Ala Gly Leu Tyr Gly Asn Phe Gly Gln
145                 150                 155                 160

Ala Asn Tyr Ala Ser Ala Lys Ser Ala Leu Leu Gly Phe Ala Glu Thr
                165                 170                 175

Leu Ala Lys Glu Gly Ala Lys Tyr Asn Ile Lys Ala Asn Ala Ile Ala
            180                 185                 190

Pro Leu Ala Arg Ser Arg Met Thr Glu Ser Ile Leu Pro Pro Pro Met
        195                 200                 205

Leu Glu Lys Leu Gly Pro Glu Lys Val Ala Pro Leu Val Leu Tyr Leu
    210                 215                 220

Ser Ser Ala Glu Asn Glu Leu Thr Gly Gln Phe Phe Glu Val Ala Ala
225                 230                 235                 240

Gly Phe Tyr Ala Gln Ile Arg Trp Glu Arg Ser Gly Gly Val Leu Phe
                245                 250                 255

Lys Pro Asp Gln Ser Phe Thr Ala Glu Val Val Ala Lys Arg Phe Ser
            260                 265                 270

Glu Ile Leu Asp Tyr Asp Asp Ser Arg Lys Pro Glu Tyr Leu Lys Asn
        275                 280                 285

Gln Tyr Pro Phe Met Leu Asn Asp Tyr Ala Thr Thr Asn Glu Ala
    290                 295                 300

Arg Lys Leu Pro Ala Asn Asp Ala Ser Gly Ala Pro Thr Val Ser Leu
305                 310                 315                 320

Lys Asp Lys Val Val Leu Ile Thr Gly Ala Gly Ala Gly Leu Gly Lys
                325                 330                 335

Glu Tyr Ala Lys Trp Phe Ala Lys Tyr Gly Ala Lys Val Val Val Asn
            340                 345                 350

Asp Phe Lys Asp Ala Thr Lys Thr Val Asp Glu Ile Lys Ala Ala Gly
        355                 360                 365

Gly Glu Ala Trp Pro Asp Gln His Asp Val Ala Lys Asp Ser Glu Ala
    370                 375                 380

```
Ile Ile Lys Asn Val Ile Asp Lys Tyr Gly Thr Ile Asp Ile Leu Val
385                 390                 395                 400

Asn Asn Ala Gly Ile Leu Arg Asp Arg Ser Phe Ala Lys Met Ser Lys
                405                 410                 415

Gln Glu Trp Asp Ser Val Gln Gln Val His Leu Ile Gly Thr Phe Asn
            420                 425                 430

Leu Ser Arg Leu Ala Trp Pro Tyr Phe Val Glu Lys Gln Phe Gly Arg
        435                 440                 445

Ile Ile Asn Ile Thr Ser Thr Ser Gly Ile Tyr Gly Asn Phe Gly Gln
    450                 455                 460

Ala Asn Tyr Ser Ser Ser Lys Ala Gly Ile Leu Gly Leu Ser Lys Thr
465                 470                 475                 480

Met Ala Ile Glu Gly Ala Lys Asn Asn Ile Lys Val Asn Ile Val Ala
                485                 490                 495

Pro His Ala Glu Thr Ala Met Thr Leu Thr Ile Phe Arg Glu Gln Asp
            500                 505                 510

Lys Asn Leu Tyr His Ala Asp Gln Val Ala Pro Leu Leu Val Tyr Leu
        515                 520                 525

Gly Thr Asp Asp Val Pro Val Thr Gly Glu Thr Phe Glu Ile Gly Gly
    530                 535                 540

Gly Trp Ile Gly Asn Thr Arg Trp Gln Arg Ala Lys Gly Ala Val Ser
545                 550                 555                 560

His Asp Glu His Thr Thr Val Glu Phe Ile Lys Glu His Leu Asn Glu
                565                 570                 575

Ile Thr Asp Phe Thr Thr Asp Thr Glu Asn Pro Lys Ser Thr Thr Glu
            580                 585                 590

Ser Ser Met Ala Ile Leu Ser Ala Val Gly Gly Asp Asp Asp Asp Asp
        595                 600                 605

Asp Glu Asp Glu Glu Glu Asp Glu Gly Asp Glu Glu Glu Asp Glu Glu
    610                 615                 620

Asp Glu Glu Glu Asp Asp Pro Val Trp Arg Phe Asp Asp Arg Asp Val
625                 630                 635                 640

Ile Leu Tyr Asn Ile Ala Leu Gly Ala Thr Thr Lys Gln Leu Lys Tyr
                645                 650                 655

Val Tyr Glu Asn Asp Ser Asp Phe Gln Val Ile Pro Thr Phe Gly His
            660                 665                 670

Leu Ile Thr Phe Asn Ser Gly Lys Ser Gln Asn Ser Phe Ala Lys Leu
        675                 680                 685

Leu Arg Asn Phe Asn Pro Met Leu Leu Leu His Gly Glu His Tyr Leu
    690                 695                 700

Lys Val His Ser Trp Pro Pro Thr Glu Gly Glu Ile Lys Thr Thr
705                 710                 715                 720

Phe Glu Pro Ile Ala Thr Thr Pro Lys Gly Thr Asn Val Val Ile Val
                725                 730                 735

His Gly Ser Lys Ser Val Asp Asn Lys Ser Gly Glu Leu Ile Tyr Ser
            740                 745                 750

Asn Glu Ala Thr Tyr Phe Ile Arg Asn Cys Gln Ala Asp Asn Lys Val
        755                 760                 765

Tyr Ala Asp Arg Pro Ala Phe Ala Thr Asn Gln Phe Leu Ala Pro Lys
    770                 775                 780

Arg Ala Pro Asp Tyr Gln Val Asp Val Pro Val Ser Glu Asp Leu Ala
785                 790                 795                 800
```

-continued

```
Ala Leu Tyr Arg Leu Ser Gly Asp Arg Asn Pro Leu His Ile Asp Pro
                805                 810                 815

Asn Phe Ala Lys Gly Ala Lys Phe Pro Lys Pro Ile Leu His Gly Met
            820                 825                 830

Cys Thr Tyr Gly Leu Ser Ala Lys Ala Leu Ile Asp Lys Phe Gly Met
            835                 840                 845

Phe Asn Glu Ile Lys Ala Arg Phe Thr Gly Ile Val Phe Pro Gly Glu
850                 855                 860

Thr Leu Arg Val Leu Ala Trp Lys Glu Ser Asp Thr Ile Val Phe
865                 870                 875                 880

Gln Thr His Val Val Asp Arg Gly Thr Ile Ala Ile Asn Asn Ala Ala
                885                 890                 895

Ile Lys Leu Val Gly Asp Lys Ala Lys Ile
            900                 905

<210> SEQ ID NO 52
<211> LENGTH: 735
<212> TYPE: PRT
<213> ORGANISM: Rattus norvegicus

<400> SEQUENCE: 52

Met Ala Ser Pro Leu Arg Phe Asp Gly Arg Val Val Leu Val Thr Gly
1               5                   10                  15

Ala Gly Gly Gly Leu Gly Arg Ala Tyr Ala Leu Ala Phe Ala Glu Arg
            20                  25                  30

Gly Ala Leu Val Val Val Asn Asp Leu Gly Gly Asp Phe Lys Gly Val
        35                  40                  45

Gly Lys Gly Ser Ser Ala Ala Asp Lys Val Val Glu Glu Ile Arg Arg
    50                  55                  60

Arg Gly Gly Lys Ala Val Ala Asn Tyr Asp Ser Val Glu Ala Gly Glu
65                  70                  75                  80

Lys Leu Val Lys Thr Ala Leu Asp Thr Phe Gly Arg Ile Asp Val Val
                85                  90                  95

Val Asn Asn Ala Gly Ile Leu Arg Asp Arg Ser Phe Ser Arg Ile Ser
            100                 105                 110

Asp Glu Asp Trp Asp Ile Ile Gln Arg Val His Leu Arg Gly Ser Phe
        115                 120                 125

Gln Val Thr Arg Ala Ala Trp Asp His Met Lys Lys Gln Asn Tyr Gly
    130                 135                 140

Arg Ile Ile Met Thr Ala Ser Ala Ser Gly Ile Tyr Gly Asn Phe Gly
145                 150                 155                 160

Gln Ala Asn Tyr Ser Ala Ala Lys Leu Gly Leu Leu Gly Leu Ala Asn
                165                 170                 175

Thr Leu Val Ile Glu Gly Arg Lys Asn Asn Ile His Cys Asn Thr Ile
            180                 185                 190

Ala Pro Asn Ala Gly Ser Arg Met Thr Glu Thr Val Met Pro Glu Asp
        195                 200                 205

Leu Val Glu Ala Leu Lys Pro Glu Tyr Val Ala Pro Leu Val Leu Trp
    210                 215                 220

Leu Cys His Glu Ser Cys Glu Glu Asn Gly Gly Leu Phe Glu Val Gly
225                 230                 235                 240

Ala Gly Trp Ile Gly Lys Leu Arg Trp Glu Arg Thr Leu Gly Ala Ile
                245                 250                 255

Val Arg Lys Arg Asn Gln Pro Met Thr Pro Glu Ala Val Arg Asp Asn
            260                 265                 270
```

```
Trp Val Lys Ile Cys Asp Phe Ser Asn Ala Ser Lys Pro Lys Ser Ile
            275                 280                 285

Gln Glu Ser Thr Gly Gly Ile Ile Glu Val Leu His Lys Ile Asp Ser
        290                 295                 300

Glu Gly Ile Ser Gln Asn His Thr Gly Gln Val Ala Ser Ala Asp Ala
305                 310                 315                 320

Ser Gly Phe Ala Gly Val Val Gly His Lys Leu Pro Ser Phe Ser Ser
                325                 330                 335

Ser Tyr Thr Glu Leu Gln Cys Ile Met Tyr Ala Leu Gly Val Gly Ala
            340                 345                 350

Ser Val Lys Asn Pro Lys Asp Leu Lys Phe Val Tyr Glu Gly Ser Ala
        355                 360                 365

Asp Phe Ser Cys Leu Pro Thr Phe Gly Val Ile Val Ala Gln Lys Ser
370                 375                 380

Leu Met Ser Gly Gly Leu Ala Glu Val Pro Gly Leu Ser Ile Asn Phe
385                 390                 395                 400

Ala Lys Val Leu His Gly Glu Gln Tyr Leu Glu Leu Tyr Lys Pro Leu
                405                 410                 415

Pro Arg Ser Gly Glu Leu Lys Cys Glu Ala Val Ile Ala Asp Ile Leu
            420                 425                 430

Asp Lys Gly Ser Gly Ile Val Ile Val Met Asp Val Tyr Ser Tyr Ser
        435                 440                 445

Gly Lys Glu Leu Ile Cys Tyr Asn Gln Phe Ser Val Phe Val Val Gly
        450                 455                 460

Ser Gly Gly Phe Gly Lys Arg Thr Ser Glu Lys Leu Lys Ala Ala
465                 470                 475                 480

Val Ala Val Pro Ser Arg Pro Pro Asp Ala Val Leu Arg Asp Thr Thr
                485                 490                 495

Ser Leu Asn Gln Ala Ala Leu Tyr Arg Leu Ser Gly Asp Ser Asn Pro
            500                 505                 510

Leu His Ile Asp Pro Ser Phe Ala Ser Ile Ala Gly Phe Glu Lys Pro
        515                 520                 525

Ile Leu His Gly Leu Cys Thr Phe Gly Phe Ser Ala Arg His Val Leu
        530                 535                 540

Gln Gln Phe Ala Asp Asn Asp Val Ser Arg Phe Lys Ala Ile Lys Val
545                 550                 555                 560

Arg Phe Ala Lys Pro Val Tyr Pro Gly Gln Thr Leu Gln Thr Glu Met
                565                 570                 575

Trp Lys Glu Gly Asn Arg Ile His Phe Gln Thr Lys Val Gln Glu Thr
            580                 585                 590

Gly Asp Ile Val Ile Ser Asn Ala Tyr Val Asp Leu Val Pro Thr Ser
        595                 600                 605

Gly Val Ser Ala Gln Thr Pro Ser Glu Gly Gly Ala Leu Gln Ser Ala
    610                 615                 620

Leu Val Phe Gly Glu Ile Gly Arg Arg Leu Lys Asp Val Gly Arg Glu
625                 630                 635                 640

Val Val Lys Lys Val Asn Ala Val Phe Glu Trp His Ile Thr Lys Asn
                645                 650                 655

Gly Asn Val Ala Ala Lys Trp Thr Ile Asp Leu Lys Asn Gly Ser Gly
            660                 665                 670

Glu Val Tyr Gln Gly Pro Ala Lys Gly Ser Ala Asp Thr Thr Ile Thr
        675                 680                 685
```

```
Ile Ser Asp Glu Asp Phe Met Glu Val Val Leu Gly Lys Leu Asn Pro
    690                 695                 700

Gln Asn Ala Phe Phe Ser Gly Arg Leu Lys Ala Arg Gly Asn Ile Met
705                 710                 715                 720

Leu Ser Gln Lys Leu Gln Met Ile Leu Lys Asp Tyr Ala Lys Leu
            725                 730                 735

<210> SEQ ID NO 53
<211> LENGTH: 309
<212> TYPE: PRT
<213> ORGANISM: Arabidopsis thaliana

<400> SEQUENCE: 53

Met Ala Thr Ser Asp Ser Glu Phe Asn Ser Asp Leu Leu Leu Ala His
1               5                   10                  15

Lys Leu Pro Glu Thr Arg Tyr Thr Tyr Asn Glu Arg Asp Val Ala Ile
            20                  25                  30

Tyr Ala Leu Gly Ile Gly Ala Cys Gly Gln Asp Ala Val Asp Ser Asp
        35                  40                  45

Glu Leu Lys Phe Val Tyr His Arg Asn Gly Gln Asp Leu Ile Gln Val
    50                  55                  60

Leu Pro Thr Phe Ala Ser Leu Phe Thr Leu Gly Ser Leu Thr Glu Gly
65                  70                  75                  80

Leu Asp Leu Pro Gly Phe Lys Tyr Asp Pro Ser Leu Leu His Gly
                85                  90                  95

Gln Gln Tyr Ile Glu Ile Tyr Arg Pro Leu Pro Ser Lys Ala Ser Leu
            100                 105                 110

Ile Asn Lys Val Ser Leu Ala Gly Leu Gln Asp Lys Gly Lys Ala Ala
        115                 120                 125

Ile Leu Glu Leu Glu Thr Arg Ser Tyr Glu Glu Gly Ser Gly Glu Leu
    130                 135                 140

Leu Cys Met Asn Arg Thr Thr Val Phe Leu Arg Gly Ala Gly Gly Phe
145                 150                 155                 160

Ser Asn Ser Ser Gln Pro Phe Ser Tyr Lys Asn Tyr Pro Ser Asn Gln
                165                 170                 175

Gly Leu Ala Val Lys Ile Pro Gln Arg Gln Pro Leu Thr Val Cys Glu
            180                 185                 190

Glu Arg Thr Gln Pro Ser Gln Ala Leu Leu Tyr Arg Leu Ser Gly Asp
        195                 200                 205

Tyr Asn Pro Leu His Ser Asp Pro Glu Phe Ala Lys Leu Ala Gly Phe
    210                 215                 220

Pro Arg Pro Ile Leu His Gly Leu Cys Thr Leu Gly Phe Ala Ile Lys
225                 230                 235                 240

Ala Ile Ile Lys Cys Val Cys Lys Gly Asp Pro Thr Ala Val Lys Thr
                245                 250                 255

Ile Ser Gly Arg Phe Leu Thr Thr Val Phe Pro Gly Glu Thr Leu Ile
            260                 265                 270

Thr Glu Met Trp Leu Glu Gly Leu Arg Val Ile Tyr Gln Thr Lys Val
        275                 280                 285

Lys Glu Arg Asn Lys Thr Val Leu Ala Gly Tyr Val Asp Ile Arg Gly
    290                 295                 300

Leu Ser Ser Ser Leu
305

<210> SEQ ID NO 54
```

<211> LENGTH: 601
<212> TYPE: PRT
<213> ORGANISM: Burkholderia pseudomallei

<400> SEQUENCE: 54

```
Met Gln Gln Leu Phe Glu Ser Trp Leu Gly Ala Trp Arg Ser Phe Ala
 1               5                  10                  15

Asp Pro Ala Arg Ala Ala Ala Gly Asp Ala Pro Ser Pro Ser Pro Ser
            20                  25                  30

Pro Phe Ala Ala Phe Gln Pro Gln Pro Phe Ala Phe Ala Met Pro
        35                  40                  45

Ala Met Pro Pro Met Pro Asp Trp Ser Gly Ala Ala Ser Phe Ala
50                  55                  60

Gly Leu Ala Pro Val Ala Ser Val Pro Pro Ala Arg Leu Gln Lys Leu
65                  70                  75                  80

Gln Ala Asp Tyr Ser Arg Asp Cys Leu Ala Leu Ile Gln Gln Ala Ser
                85                  90                  95

Ala Ala Thr Pro Thr Val Pro Glu Leu Lys Asp Arg Arg Phe Ser Ala
            100                 105                 110

Asp Ala Trp Lys Ala Ser Pro Ala His Gly Phe Ala Ala Ala Trp Tyr
        115                 120                 125

Leu Leu Asn Ala Arg Tyr Leu Gln Glu Leu Ala Asp Ala Leu Glu Thr
    130                 135                 140

Asp Pro Lys Thr Arg Glu Arg Ile Arg Phe Thr Val Gln Gln Trp Thr
145                 150                 155                 160

Ala Ala Ala Ser Pro Ser Asn Phe Leu Ala Leu Asn Pro Glu Ala Gln
                165                 170                 175

Lys Asn Leu Val Glu Thr Gln Gly Glu Ser Leu Arg Leu Gly Met Met
            180                 185                 190

Asn Leu Leu Ala Asp Met Gln Arg Gly Lys Ile Ser Gln Thr Asp Glu
        195                 200                 205

Ser Gln Phe Val Val Gly Lys Asn Leu Ala Val Thr Pro Gly Ala Val
    210                 215                 220

Val Tyr Glu Asn Asp Leu Ile Gln Leu Ile Gln Tyr Thr Pro Thr Thr
225                 230                 235                 240

Ala Thr Val Phe Glu Arg Pro Leu Leu Ile Val Pro Pro Cys Ile Asn
                245                 250                 255

Lys Phe Tyr Ile Leu Asp Leu Gln Pro Glu Asn Ser Leu Val Ala His
            260                 265                 270

Ala Leu Ser Cys Gly His Gln Val Phe Leu Val Ser Trp Arg Asn Ala
        275                 280                 285

Asp Ala Ser Val Ala His Lys Thr Trp Asp Asp Tyr Ile Asp Glu Gly
    290                 295                 300

Leu Leu Ala Ala Ile Asp Val Val Gln Gln Val Ser Gly Arg Glu Gln
305                 310                 315                 320

Ile Asn Thr Leu Gly Phe Cys Val Gly Gly Thr Met Leu Ala Thr Ala
                325                 330                 335

Leu Ala Val Leu Ala Ala Arg Gly Glu His Pro Ala Ala Ser Met Thr
            340                 345                 350

Leu Leu Thr Ser Met Leu Asp Phe Ser Asp Thr Gly Ile Leu Asp Val
        355                 360                 365

Phe Val Asp Glu Ala His Val Gln Met Arg Glu Gln Thr Ile Gly Gly
    370                 375                 380

Lys Gly Gly Ala Pro Ala Gly Leu Met Arg Gly Val Glu Phe Ala Asn
```

```
            385                 390                 395                 400
        Thr Phe Ser Phe Leu Arg Pro Asn Asp Leu Val Trp Asn Tyr Val Val
                        405                 410                 415

Asp Asn Tyr Leu Lys Gly Arg Thr Pro Ala Pro Phe Asp Leu Leu Tyr
                        420                 425                 430

Trp Asn Gly Asp Ser Thr Ser Leu Pro Gly Pro Met Tyr Ala Trp Tyr
                        435                 440                 445

Leu Arg Asn Thr Tyr Leu Glu Asn Lys Leu Arg Glu Pro Asp Ala Leu
                        450                 455                 460

Thr Val Cys Gly Glu Pro Val Asp Leu Ser Arg Ile Asp Val Pro Thr
        465                 470                 475                 480

Phe Ile Tyr Gly Ser Arg Glu Asp His Ile Val Pro Trp Gln Thr Ala
                        485                 490                 495

Tyr Ala Ser Thr Ser Leu Leu Thr Gly Pro Leu Lys Phe Val Leu Gly
                        500                 505                 510

Ala Ser Gly His Ile Ala Gly Val Ile Asn Pro Pro Ala Lys Arg Lys
                        515                 520                 525

Arg Ser Tyr Trp Ser Tyr Asp Ala Ser Ala Lys Glu Leu Pro Glu Ser
                        530                 535                 540

Ala Asn Asp Trp Leu Asp Ala Ala Val Glu His Pro Gly Ser Trp Trp
        545                 550                 555                 560

Pro Val Trp Ile Glu Trp Leu Asp Gln Tyr Gly Gly Lys Lys Val Lys
                        565                 570                 575

Pro Arg Ala His Leu Gly Cys Ala Arg Phe Pro Val Ile Glu Pro Ala
                        580                 585                 590

Pro Gly Arg Tyr Val Leu Gln Arg Asp
                        595                 600

<210> SEQ ID NO 55
<211> LENGTH: 771
<212> TYPE: PRT
<213> ORGANISM: Methylosinus trichosporium

<400> SEQUENCE: 55

Met Thr Ala Gly Arg Arg Ser Thr Ala Gly Ala Lys Arg Arg Pro Pro
        1               5                   10                  15

His Leu Arg Asp Ala Ala Glu Thr Lys Leu Val Val Glu Glu Pro Pro
                        20                  25                  30

Pro Ala Glu Asn Ala Asp Val Ser Leu Leu Glu Ala Pro Arg Val Asn
                        35                  40                  45

Gly Ala Arg Val Ala Ala Ala Pro Ala Gln Lys Lys Thr Gly
                        50                  55                  60

Lys Val Arg Ala Lys Pro Arg Ala Pro Val Gln Glu Pro Pro Val Gln
        65                  70                  75                  80

Glu Pro Pro Val Arg Glu Pro Thr Ala Glu Ala Pro Arg Glu Ala Met
                        85                  90                  95

Ile Ala Ile Ala Thr Pro Pro Ala Ala Pro Thr Ala Glu Glu Arg Arg
                        100                 105                 110

Leu Glu Leu Gln Ala Ala Ala Leu Val Ala Gly Ala Ala Ala Glu
                        115                 120                 125

Leu Thr Glu Ala Gln Arg Arg Ser Leu Met Gly Gln Leu Gln Ala Leu
                        130                 135                 140

Glu Pro Ala Pro Pro Ala Pro Ala Pro Val Leu Thr Pro Ala Ala Pro
        145                 150                 155                 160
```

Pro Glu Ile Pro Ala Ala Pro Gln Arg Lys Pro Ala Arg Asp Tyr Gln
            165                 170                 175

Ala Gly Ala Ala Glu Ser Thr Ala His Asp Phe Glu Ile Ile Ala Glu
            180                 185                 190

Asn Leu Ala Arg Leu Val Asp Gln Gly Arg Lys Ala Leu Ala Ala Ala
            195                 200                 205

Val Gly Gly Met Glu Pro Gly Asp Thr Arg Ser Glu Leu Ala Ser Asn
            210                 215                 220

Val Ala Asp Ala Thr Lys Thr Leu Gly Ala Val Ala Glu Arg Trp Met
225                 230                 235                 240

Ala Lys Pro Glu Gln Ala Val Ala Gln Ala Asp Leu Leu Thr Gly
            245                 250                 255

Leu Ser Ala Ile Trp Ser Gln Thr Leu Arg Arg Phe Ser Gly Ala Asp
            260                 265                 270

Val Pro Pro Val Val Pro Ala Asp Pro Ser Asp Lys Arg Phe Ser Ala
            275                 280                 285

Pro Glu Trp Arg Asp Asn Pro Phe Phe Asp Cys Leu Arg Gln Ser Tyr
            290                 295                 300

Ala Leu Thr Thr His Trp Ala Ser Glu Ala Val Glu Arg Thr Asp Gly
305                 310                 315                 320

Leu Asp Pro Gln Thr Lys Ser Lys Ala Ala Phe Tyr Thr Arg Leu Ile
            325                 330                 335

Ala Ser Ala Leu Ser Pro Ser Asn Phe Val Ala Thr Asn Pro Glu Leu
            340                 345                 350

Leu Arg Ala Thr Leu Asp Ala Arg Gly Glu Asn Leu Val Arg Gly Met
            355                 360                 365

Lys Met Leu Thr Glu Asp Leu Ser Ala Gly Arg Gly Met Leu Lys Leu
            370                 375                 380

Arg Gln Ser Asp Glu Ser Lys Phe Glu Leu Gly Val Asp Met Ala Ser
385                 390                 395                 400

Thr Pro Gly Lys Val Val Tyr Arg Thr Pro Val Met Glu Leu Ile Gln
            405                 410                 415

Tyr Ala Pro Ser Thr Glu Thr Val Tyr Glu Arg Pro Leu Leu Ile Val
            420                 425                 430

Pro Pro Trp Ile Asn Lys Phe Tyr Val Leu Asp Leu Asn Arg Glu Lys
            435                 440                 445

Ser Phe Val Arg Trp Ala Thr Gly Lys Gly Leu Thr Val Phe Val Val
            450                 455                 460

Ser Trp Val Asn Pro Asp Glu Ser Gln Ala Asp Lys Gly Phe Asp Ala
465                 470                 475                 480

Tyr Met Lys Glu Gly Val Leu Ala Ala Leu Asp Ala Val Gln Lys Ala
            485                 490                 495

Thr Gly Ala Pro His Val Ala Ala Gly Tyr Cys Val Gly Gly Thr
            500                 505                 510

Met Leu Ala Ala Thr Leu Ala Tyr Leu Ala Glu Lys Gly Asp Asp Arg
            515                 520                 525

Ile Asp Ser Val Thr Phe Leu Ala Thr Gln Val Asp Phe Thr Asp Ala
            530                 535                 540

Gly Asp Met Gln Val Phe Ile Asp Glu Ala Arg Leu Ala Ala Leu Asp
545                 550                 555                 560

Glu Ala Met Ser Arg Thr Gly Tyr Leu Glu Gly Val Lys Met Ala Thr
            565                 570                 575

Thr Phe Asn Met Leu Arg Pro Asn Glu Leu Phe Trp Thr Tyr Phe Val

```
            580             585             590
Asn Asn Tyr Met Lys Gly Val Glu Pro Ala Ala Phe Asp Leu Leu Thr
        595             600             605

Trp Asn Ser Asp Cys Thr Arg Ile Pro Arg Ala Asn His Leu Phe Tyr
610             615             620

Leu Arg Tyr Cys Tyr Ile Glu Asn Ala Leu Ser Gln Gly Arg Met Val
625             630             635             640

Ile Asp Gly Val Thr Leu Asn Leu Arg Lys Val Lys Ile Pro Ile Tyr
                645             650             655

Glu Leu Ala Ala Lys Glu Asp His Ile Ala Pro Ala Arg Ser Val Phe
            660             665             670

Thr Gly Ala Lys Tyr Phe Gly Gly Glu Val Arg Tyr Val Leu Ala Gly
        675             680             685

Ala Gly His Ile Ala Gly Val Val Asn Pro Pro Asp Lys His Lys Tyr
    690             695             700

Gln Tyr Trp Thr Gly Gly Pro Pro Met Gly Ala Tyr Glu Asp Trp Val
705             710             715             720

Lys Ala Ala Lys Glu Ser Lys Gly Ser Trp Trp Asp Trp His Asp
                725             730             735

Trp Ile Thr Ser Gln Ala Pro Glu Gln Val Ala Ala Arg Ile Pro Gly
            740             745             750

Glu Gly Gly Leu Lys Ala Leu Cys Asp Ala Pro Gly Asp Tyr Val Arg
        755             760             765

Val Arg Ala
    770

<210> SEQ ID NO 56
<211> LENGTH: 610
<212> TYPE: PRT
<213> ORGANISM: Methylosinus trichosporium

<400> SEQUENCE: 56

Met Val Val Val Asp Phe Ala Gly Arg Ala Gly Arg Leu Gln Glu Pro
1               5               10              15

Ala Ala Glu Ala Ser Pro Asn Pro Ala Pro Val Glu Glu Pro Pro
            20              25              30

Arg Arg Ala Tyr Pro Ile Gly Glu Val Pro Ser Phe Asp Thr Leu Asp
        35              40              45

Arg Ala Ala Arg Ala Val Ala Ala Arg Phe Thr Gln Gly Val Ser Pro
    50              55              60

Leu Ala Gln Met Ser Ala Trp Leu Asp Phe Ala Thr His Leu Ala Leu
65              70              75              80

Ala Pro Gly Arg Gln Ile Glu Leu Gly Leu Ala Ala Gln Ser Ala
            85              90              95

Ala Ala Leu Ala Tyr Phe Ser Ala Glu Thr Leu Ala Gly Arg Ala Glu
            100             105             110

Ala Gly Pro Phe Val Ser Glu Pro His Asp Arg Arg Phe Val Asp Pro
        115             120             125

Gly Trp Asp Ala Pro Pro Phe Ser Leu Trp Lys Gln Gly Phe Leu Ala
    130             135             140

Thr Glu His Trp Trp Arg Leu Ala Thr Arg Glu Thr Arg Gly Met Thr
145             150             155             160

Arg Ser Asp Ala Ala Arg Val Gly Phe Met Ala Glu Gln Trp Leu Gly
            165             170             175
```

```
Ala Phe Ser Pro Ser Asn Ile Ala Trp Ala Asn Pro Ala Val Val Glu
                180                 185                 190

Arg Thr Arg Glu Glu Gly Gly Ala Asn Leu Val Arg Gly Ala Glu Asn
            195                 200                 205

Phe Ala Glu Asp Leu Leu Arg Leu Val Leu Arg Ala Pro Asn Gly His
        210                 215                 220

Gly Glu Phe Glu Val Gly Val Asp Val Ala Ala Thr Pro Gly Glu Val
225                 230                 235                 240

Ile Phe Arg Asn Glu Leu Ile Glu Leu Ile Gln Tyr Gly Pro Ser Thr
                245                 250                 255

Glu Thr Val His Ala Glu Pro Ile Leu Ile Val Pro Ala Trp Ile Met
                260                 265                 270

Lys Tyr Tyr Val Leu Asp Leu Arg Pro Gln Asn Ser Leu Val Arg Tyr
            275                 280                 285

Leu Thr Ala Gln Gly Phe Thr Val Phe Met Ile Ser Trp Arg Asn Pro
        290                 295                 300

Gly Pro Glu Asp Arg Asp Leu Thr Phe Asp Asp Tyr Arg Val Ser Gly
305                 310                 315                 320

Val Leu Ala Ala Leu Ser Ala Ile Asp Ala Val Arg Pro Gly Ser Lys
                325                 330                 335

Val His Ala Cys Gly Tyr Cys Leu Gly Gly Thr Leu Leu Ser Ile Ala
                340                 345                 350

Ala Ala Ala Met Ala Arg Asp Gly Asp Ala Arg Leu Ala Ser Ile Ser
            355                 360                 365

Leu Leu Ala Ala Gln Thr Asp Phe Ser Glu Pro Gly Glu Leu Met Leu
        370                 375                 380

Phe Val Asp Ala Ala Gln Val Ala Phe Leu Glu Asp Met Met Trp Asp
385                 390                 395                 400

Gln Gly Val Leu Asp Thr Arg Gln Met Ala Gly Ala Phe Ala Ala Leu
                405                 410                 415

Arg Ser Asn Asp Leu Val Trp Gly Lys Ala Val Gln Asp Tyr Leu Leu
            420                 425                 430

Gly Glu Arg Arg Lys Pro Asn Asp Leu Met Ala Trp Ser Ala Asp Gln
        435                 440                 445

Thr Arg Met Pro Tyr Arg Met His Ser Gln Tyr Leu Arg Gly Leu Phe
450                 455                 460

Leu Glu Asn Arg Leu Thr Ala Gly Arg Tyr Ala Val Glu Gly Glu Val
465                 470                 475                 480

Val Ala Leu Lys Asp Ile Ser Ala Pro Met Phe Val Gly Thr Thr
                485                 490                 495

Ser Asp His Ile Ala Pro Trp Arg Ser Val Lys Ala Ser Leu Phe
            500                 505                 510

Thr Asp Cys Glu Leu Thr Phe Val Leu Thr Ser Gly Gly His Asn Ala
        515                 520                 525

Gly Val Val Ser Glu Pro Gly Arg Ser Gly Arg Ser Tyr His Val Gly
530                 535                 540

Leu Arg Arg Pro Gly Asp Phe Tyr Val Gly Pro Asp Lys Trp Leu Ala
545                 550                 555                 560

Ala Ala Arg Leu Ala Glu Gly Ser Trp Trp Pro Glu Trp Ala Ala Trp
                565                 570                 575

Leu Ala Ala Arg Ser Gly Asp Glu Arg Val Ala Pro Pro Thr Met Gly
            580                 585                 590

Ala Arg Gly Tyr Pro Pro Leu Tyr Pro Ala Pro Gly Arg Tyr Val His
```

```
        595                 600                 605

Gln Ala
    610

<210> SEQ ID NO 57
<211> LENGTH: 600
<212> TYPE: PRT
<213> ORGANISM: Legionella pneumophila subsp. pneumophila str.

<400> SEQUENCE: 57

Met Ser Ala Met Lys Gly Leu Glu Lys Gln Cys Cys Pro Lys Lys Arg
 1               5                  10                  15

Ile Leu Thr Gln Ser Gln Glu Leu Gln Glu Gly Val Asp Phe Ser Cys
            20                  25                  30

Cys Ala Pro Ala Asp Arg Gly Thr Ser Asp Asn Phe Phe Pro Phe Phe
        35                  40                  45

Thr Arg Leu Val Gln Ala Asn Leu Ala Lys Trp Thr Ala Gly Ile Ser
    50                  55                  60

Pro Ala Ala Ile Gly Ser Ser Tyr Ser Thr Trp Leu Trp Gln Leu Ala
65                  70                  75                  80

Gln Ser Pro Gly Val Leu Trp Glu Leu Ala Phe Tyr Pro Val Phe His
                85                  90                  95

Ala Lys Asp Cys Ile Asn Asn Ile Val Cys Val Glu Arg Ala Ala Asp
            100                 105                 110

Gly Lys Asp Val Arg Phe Lys Lys Asp Ser Trp Gln Pro Met Pro Trp
        115                 120                 125

Arg Leu Phe Ala Glu Gly Phe Leu Gln Met Glu Asp Trp Trp Arg Arg
    130                 135                 140

Ala Thr Thr Asp Val Pro Gly Leu Pro Asn Gln Val Glu Arg Thr Val
145                 150                 155                 160

Ser Phe Trp Ala Arg Gln Cys Leu Asp Ala Leu Ser Pro Ser Asn Phe
                165                 170                 175

Val Trp Ser Asn Pro Asp Leu Phe His Glu Ala Met Arg Thr Gly Gly
            180                 185                 190

Leu Asn Leu Ile Gln Gly Gly Gln Ile Ala Leu Glu Asp Trp Leu Glu
        195                 200                 205

Lys Leu Thr Gly Ala Pro Pro Thr Gly Ser Glu His Phe Ile Pro Gly
    210                 215                 220

Lys Gln Val Ala Ile Thr Pro Gly Arg Val Val Phe Gln Asn His Leu
225                 230                 235                 240

Ile Glu Leu Ile Gln Tyr Glu Ala Gln Thr Lys Thr Val Tyr Lys Glu
                245                 250                 255

Pro Ile Leu Ile Leu Pro Ala Trp Ile Met Lys Tyr Tyr Ile Leu Asp
            260                 265                 270

Leu Ser Pro His Asn Ser Leu Val Lys Trp Leu Val Ser Gln Gly His
        275                 280                 285

Thr Val Phe Ile Ile Ser Trp Arg Asn Pro Asp Lys Glu Asp Gln Asp
    290                 295                 300

Leu Gly Met Asp Asp Tyr Tyr Arg Gln Gly Ala Met Ala Ala Ile Asp
305                 310                 315                 320

Ala Val Ser Thr Leu Phe Pro Glu Thr Lys Ile Asn Leu Met Gly Tyr
                325                 330                 335

Cys Leu Gly Gly Thr Leu Ala Met Ile Thr Ala Ala Ala Met Gly Arg
            340                 345                 350
```

```
Asp Lys Asp Glu Arg Leu Asn Ser Leu Thr Leu Leu Ala Ala Gln Gly
        355                 360                 365

Asp Phe Thr Glu Ala Gly Glu Leu Met Leu Phe Val Thr Glu Ser Gln
    370                 375                 380

Val Asp Phe Leu Lys Ser Met Met Arg Glu Gln Gly Tyr Leu Asp Thr
385                 390                 395                 400

Lys Gln Met Ala Gly Ser Phe Gln Met Leu Arg Ala Tyr Asp Leu Ile
                405                 410                 415

Trp Ser Lys Met Val Gln Asp Tyr Met His Gly Met Arg Arg Gly Met
            420                 425                 430

Ile Asp Leu Thr Ala Trp Asn Ala Asp Ala Thr Arg Met Pro Tyr Lys
        435                 440                 445

Met His Ser Glu Tyr Leu Glu Lys Leu Phe Leu Arg Asn Asp Phe Ala
    450                 455                 460

Glu Gly Arg Tyr Thr Val Glu Gly Lys Pro Val Ala Ala Glu Asn Ile
465                 470                 475                 480

Lys Leu Pro Val Phe Ala Val Ser Thr Glu Lys Asp His Val Ala Pro
                485                 490                 495

Trp Gln Ser Val Tyr Lys Ile His Leu Met Thr Glu Gly Asp Val Thr
            500                 505                 510

Phe Val Leu Thr Gly Gly Gly His Asn Ala Gly Ile Ile Ser Glu Pro
        515                 520                 525

Gly His Pro Gly Arg Ser Tyr Arg Val His Glu Gln Lys Gln Gly Glu
    530                 535                 540

Ala Tyr Leu Asn Pro Glu Ser Trp Leu Ala Met Ala Glu Arg Arg Glu
545                 550                 555                 560

Gly Ser Trp Trp Arg Glu Trp Asn Glu Trp Leu Val Gln Gln Asn Thr
                565                 570                 575

Lys Lys Arg Ile Ala Ser Ser Val Met Asn Pro Ser Leu Pro Glu Ala
            580                 585                 590

Pro Gly Thr Tyr Val Leu Gln Lys
        595                 600

<210> SEQ ID NO 58
<211> LENGTH: 595
<212> TYPE: PRT
<213> ORGANISM: Legionella pneumophila str. Corby

<400> SEQUENCE: 58

Met Lys Lys Thr Thr Glu Lys Pro Ile Asn Lys Thr Lys Glu Met Pro
 1               5                  10                  15

Ala Ser Ser Lys Lys Glu Ile Leu Asn Pro Leu Glu Gln Thr Pro Ser
            20                  25                  30

Pro Glu Gln Ser Asp Pro Ile Phe Arg Phe Ile Asp Lys Leu Tyr Gln
        35                  40                  45

Ala Asn Leu Gly Lys Leu Thr Ala Gly Ile Ser Pro Ala Ala Leu Gly
    50                  55                  60

Thr Ala Tyr Tyr Ser Trp Phe Ala Gln Leu Leu Gln Ser Pro Gly Ser
65                  70                  75                  80

Met Leu Arg Leu Ala Tyr Tyr Pro Leu Leu His Ala Asn Asp Tyr Leu
                85                  90                  95

Ser Asn Leu Phe Lys Tyr Asp Lys Pro Arg Asp Gly Lys Asp Val Arg
            100                 105                 110

Phe His Thr Glu Asn Trp Ser Tyr Tyr Pro Trp Arg Leu Trp Ala Glu
        115                 120                 125
```

-continued

Gln Phe Leu Gln Phe Glu Asp Trp Cys Leu Gln Ala Ser Ser Lys Val
130                 135                 140

Pro Gly Ile Pro Leu His Val Lys Arg Thr Val Thr Phe Ser Thr Arg
145                 150                 155                 160

Gln Ile Leu Asp Ala Leu Ser Pro Ser Asn Phe Val Leu Thr Asn Pro
                165                 170                 175

Asp Leu Leu Gln Glu Thr Ile Arg Ser Asn Gly Gln Asn Leu Ile Arg
                180                 185                 190

Gly Thr Glu Leu Ala Phe Gln Asp Phe Val Glu Lys Ile Thr Gly Ser
            195                 200                 205

Pro Pro Ala Gly Val Glu Asn Phe Ile Pro Gly Lys Gln Val Ala Val
210                 215                 220

Thr Lys Gly Lys Val Val Tyr Ser Asn His Leu Ile Glu Leu Ile Gln
225                 230                 235                 240

Tyr Thr Pro Gln Thr Glu Lys Val Tyr Lys Glu Pro Ile Leu Ile Leu
                245                 250                 255

Pro Ala Trp Ile Met Lys Tyr Tyr Ile Leu Asp Leu Leu Pro Glu Asn
                260                 265                 270

Ser Leu Val Asn Trp Leu Val Arg Gln Gly His Thr Val Phe Ile Val
            275                 280                 285

Ser Trp Arg Asn Pro Thr Lys Glu Asp Arg Asn Leu Gly Leu Asp Asp
290                 295                 300

Tyr Tyr Lys Leu Gly Ala Met Asp Ala Ile Asn Ala Val Ser Asn Ala
305                 310                 315                 320

Ile Pro His Thr Lys Ile His Leu Met Gly Tyr Cys Leu Gly Gly Thr
                325                 330                 335

Leu Ala Leu Leu Thr Ala Ala Met Ala His Asp His Asp Asn Arg
                340                 345                 350

Leu Lys Thr Leu Ser Leu Leu Ala Ala Gln Gly Asp Phe Ile Asp Ala
            355                 360                 365

Gly Glu Leu Leu Leu Phe Ile Thr Lys Ser Glu Val Ser Phe Leu Lys
370                 375                 380

Ser Met Met Trp Glu Gln Gly Tyr Leu Asp Thr Lys Gln Met Ser Gly
385                 390                 395                 400

Thr Phe Gln Met Leu Arg Ser Tyr Asp Leu Ile Trp Ser Lys Met Val
                405                 410                 415

Gln Asp Tyr Met His Gly Thr Gln Arg Gly Met Ile Pro Leu Leu Ala
                420                 425                 430

Trp Asn Ala Asp Ala Thr Arg Met Pro Tyr Lys Met His Ser Glu Tyr
            435                 440                 445

Leu Glu Lys Leu Phe Leu Asn Asn Asp Phe Ala Glu Gly Arg Phe Ile
450                 455                 460

Leu Asp Gly Lys Pro Val Val Gly Glu Asn Ile Arg Ile Pro Ala Phe
465                 470                 475                 480

Val Val Ser Thr Glu Lys Asp His Val Ala Pro Trp Lys Ser Val Tyr
                485                 490                 495

Lys Thr His Leu Leu Ile Asn Ser Asp Ile Thr Phe Val Leu Thr Asn
                500                 505                 510

Gly Gly His Asn Ala Gly Ile Val Ser Glu Pro Gly His Glu Gly Arg
            515                 520                 525

Tyr Tyr Arg Ile Arg Glu Arg Lys Met Asp Ser Thr Tyr Leu Asp Pro
530                 535                 540

```
Thr Asn Trp Leu Lys Lys Ala Glu Leu Arg Glu Gly Ser Trp Trp Ile
545                 550                 555                 560

Ala Trp His Asp Trp Leu Val Asn His Ser Ser Gln Lys Gln Val Ser
            565                 570                 575

Ala Pro Lys Leu Asp Lys Lys Leu Pro Asn Ala Pro Gly Lys Tyr Val
            580                 585                 590

Leu Gln Lys
        595

<210> SEQ ID NO 59
<211> LENGTH: 573
<212> TYPE: PRT
<213> ORGANISM: Acidiphilium multivorum

<400> SEQUENCE: 59

Met Pro Gly Phe Ala Thr Phe Asp Arg Leu Ser Arg Ala Met Phe Ala
1               5                   10                  15

Arg Ile Ser Gln Gly Val Ser Pro Leu Ala Val Ala Asp Ala Trp Thr
            20                  25                  30

Asp Trp Ala Leu His Leu Glu Leu Ala Leu Gly Lys Gln Glu Ala Leu
            35                  40                  45

Ala Met Arg Ala Ala Thr Phe Leu Leu Arg Leu Gly Phe Trp Leu Pro
50                  55                  60

Arg Ala Ala Ile Gly Glu Pro Glu Asn Pro Pro Leu Arg Pro Pro Glu
65                  70                  75                  80

Gly Asp Arg Arg Phe Ala Asp Glu Gly Trp Ser Ala Tyr Pro Phe Asn
                85                  90                  95

Ala Ile Val Gln Gly Phe Leu Val Ala Asp Asp Trp Trp Arg Glu Ala
            100                 105                 110

Thr Arg Gln Val Pro Gly Leu Val Arg Arg His Glu Ala Glu Val Ala
            115                 120                 125

Phe Met Ala Arg Gln Ile Leu Asp Ile Ala Ala Pro Thr Asn Ile Pro
130                 135                 140

Trp Leu Asn Pro Glu Ile Ile Arg Arg Thr Leu Gln Glu Gly Gly Phe
145                 150                 155                 160

Asn Leu Leu Arg Gly Trp Ser Asn Trp Ile Glu Asp Ala Glu Arg Leu
                165                 170                 175

Leu Ala Gly Gln Gly Pro Tyr Gly Ala Glu Ala Phe Pro Val Gly Glu
            180                 185                 190

Val Val Ala Thr Thr Ala Gly Lys Val Val Tyr Arg Asn Glu Leu Met
            195                 200                 205

Glu Leu Ile Gln Tyr Ala Pro Ala Thr Ala Lys Val Thr Ala Glu Pro
210                 215                 220

Val Leu Ile Val Pro Ala Trp Ile Met Lys Tyr Tyr Ile Leu Asp Leu
225                 230                 235                 240

Thr Pro Glu Thr Ser Leu Val Arg Tyr Leu Val Thr Asn Gly His Thr
                245                 250                 255

Val Phe Ile Ile Ser Trp Ile Asn Pro Asp Arg His Asp Arg Asn Val
            260                 265                 270

Gly Leu Asp Asp Tyr Arg Arg His Gly Val Met Ala Ala Leu Asp Ala
            275                 280                 285

Val Ser Arg Ile Val Pro Asp Arg Ala Ile His Ala Cys Gly Tyr Cys
290                 295                 300

Leu Gly Gly Thr Ile Leu Ala Ile Ala Ala Ala Thr Met Ala Arg Asp
305                 310                 315                 320
```

His Asp Asp Arg Leu Ala Ser Leu Thr Leu Leu Ala Ala Gln Thr Asp
                325                 330                 335

Phe Ala Asp Ala Gly Asp Leu Met Leu Phe Leu Asp Glu Arg Gln Phe
                340                 345                 350

Leu Leu Leu Glu Asp Leu Met Trp Asp Gln Gly Tyr Leu Asp Thr Arg
            355                 360                 365

Gln Met Ala Gly Ala Phe Gln Ala Leu Arg Ser Asn Glu Leu Val Trp
        370                 375                 380

Ser Arg Leu Ile Arg Asn Tyr Met Leu Gly Glu Arg Asp Arg Met Thr
385                 390                 395                 400

Pro Leu Ser Ala Trp Asn Ser Asp Gln Thr Arg Met Pro Ala Arg Met
                405                 410                 415

His Ser Glu Tyr Leu Arg Gly Leu Phe Leu Glu Asn Arg Leu Ser Ala
                420                 425                 430

Gly Arg Phe Ala Val Glu Gly Arg Val Ile Ala Leu Arg Asp Ile Arg
            435                 440                 445

Val Pro Leu Phe Ala Val Ala Thr Thr Arg Asp His Ile Ala Pro Trp
        450                 455                 460

Arg Ser Val Tyr Lys Ile Ala Leu Phe Ala Asp Thr Asp Ile Thr Phe
465                 470                 475                 480

Val Leu Ala Ser Gly Gly His Asn Val Gly Val Val Asn Pro Pro Asn
                485                 490                 495

Gln Ser Ile Gly Thr Phe Gln Ile Leu Thr Arg Arg His Gly Glu Arg
                500                 505                 510

Tyr Val Asp Pro Asp Thr Trp Ala Thr Leu Ala Pro Glu Arg Gln Gly
            515                 520                 525

Ser Trp Trp Pro Ala Trp Arg Asp Trp Ile Gly Gly Val Gly Thr Gly
        530                 535                 540

Cys Ala Ala Asp Pro Pro Met Ala Ala Pro Ser Arg Gly Leu Pro
545                 550                 555                 560

Val Leu Gly Asp Ala Pro Gly Ala Tyr Val His Glu Arg
                565                 570

<210> SEQ ID NO 60
<211> LENGTH: 580
<212> TYPE: PRT
<213> ORGANISM: Alicycliphilus denitrificans

<400> SEQUENCE: 60

Met Pro Asp Thr Phe Ser Ala Ala Leu Ala Asp Gln Leu Asp Thr
1               5                   10                  15

Gln Phe His Ala Ala Leu Ala Arg Arg Phe Ser Leu Ser Pro Ala
                20                  25                  30

Ala Gly Met Leu Ala Ala Ser Asp Trp Ala Leu His Leu Ala Val Ser
            35                  40                  45

Pro Gly Lys Cys Met Ala Leu Ala Arg Leu Ala Leu Arg Gln Ser Glu
        50                  55                  60

Glu Leu Ala Gly Tyr Ala Arg Glu Arg Met Thr Ala Gly Ala Asp Pro
65                  70                  75                  80

Gln Leu Arg His Gly Val Gln Pro Pro Ala Gln Asp Arg Arg Phe Ala
                85                  90                  95

Ala Pro Glu Trp Gln Gln Trp Pro Phe Asn Tyr Met His Gln Ser Phe
                100                 105                 110

Leu Leu Thr Gln Gln Trp Trp Ala Ala Ala Thr His Gly Val Lys Gly

```
            115                 120                 125
Val Glu Lys His His Glu Asn Val Ala Phe Ala Ala Arg Gln Leu
130                 135                 140
Leu Asp Val Phe Ser Pro Gly Asn Gln Leu Ala Thr Asn Pro Val Val
145                 150                 155                 160
Leu Gln Arg Thr Leu Gln Gln Gly Gly Ala Asn Leu Leu Arg Gly Ala
                165                 170                 175
Leu Asn Ala Ala Asp Asp Leu Gln Arg Leu Ala Ala Gly Lys Pro Pro
                180                 185                 190
Ala Gly Thr Glu Asp Phe Val Val Gly Arg Asp Val Ala Val Thr Pro
                195                 200                 205
Gly Lys Val Val Leu Arg Asn Arg Leu Val Glu Leu Ile Gln Tyr Thr
        210                 215                 220
Pro Thr Thr Glu Ala Val His Pro Glu Pro Val Leu Ile Val Pro Ala
225                 230                 235                 240
Trp Ile Met Lys Tyr Tyr Ile Leu Asp Leu Ser Pro His Asn Ser Leu
                245                 250                 255
Ile Arg Tyr Leu Val Asp Gln Gly His Thr Val Phe Cys Leu Ser Trp
                260                 265                 270
Lys Asn Pro Gly Tyr Glu Asp Arg Asp Leu Gly Leu Asp Asp Tyr Leu
                275                 280                 285
Lys Leu Gly Phe His Ala Ala Leu Asp Ala Val Asn Ala Ile Val Pro
                290                 295                 300
Lys Arg Lys Val His Ala Thr Gly Tyr Cys Leu Gly Gly Thr Leu Leu
305                 310                 315                 320
Ala Ile Ala Ala Ala Ala Met Ala Arg Asp Gly Asp Ala Arg Leu Ala
                325                 330                 335
Ser Leu Ser Leu Phe Ala Ala Gln Thr Asp Phe Ser Glu Pro Gly Glu
                340                 345                 350
Leu Gly Leu Phe Ile Asp Glu Ser Gln Val Asn Leu Leu Glu Ala Gln
                355                 360                 365
Met Thr Gln Thr Gly Tyr Leu Lys Ala Ser Gln Met Ala Gly Ala Phe
        370                 375                 380
Gln Met Leu Arg Ser Tyr Asp Leu Leu Trp Ser Arg Leu Val Asn Glu
385                 390                 395                 400
Tyr Leu Leu Gly Glu Arg Thr Pro Met Asn Asp Leu Met Ala Trp Asn
                405                 410                 415
Ala Asp Ala Thr Arg Met Pro Ala Arg Met His Ala Gln Tyr Leu Arg
                420                 425                 430
Arg Leu Leu Leu Asp Asp Leu Ser Arg Gly Arg Tyr Pro Val Gly
        435                 440                 445
Gly Lys Pro Val Ser Leu Ser Asp Ile Thr Leu Pro Ile Phe Met Val
        450                 455                 460
Gly Thr Leu Thr Asp His Val Ala Pro Trp Arg Ser Val His Lys Leu
465                 470                 475                 480
His His Leu Thr Thr Thr Glu Ile Thr Phe Ala Leu Thr Ser Gly Gly
                485                 490                 495
His Asn Ala Gly Ile Val Asn Pro Pro Gly Asn Pro Arg Arg His Tyr
                500                 505                 510
Gln Leu Arg Thr Arg Pro Ala Gly Gly Asn Tyr Met Ala Pro Asp Asp
                515                 520                 525
Trp Leu Ala Ala Ala Pro Ala Ala Gln Gly Ser Trp Trp Pro Ala Trp
                530                 535                 540
```

```
Gln Glu Trp Leu Gln Ala Arg Ser Gly Lys Pro Val Ala Pro Pro His
545                 550                 555                 560

Met Gly Ala Arg Gly Tyr Lys Ala Gly Ala Asp Ala Pro Gly His Tyr
                565                 570                 575

Val Leu Glu Lys
            580

<210> SEQ ID NO 61
<211> LENGTH: 585
<212> TYPE: PRT
<213> ORGANISM: Acidovorax ebreus TPSY

<400> SEQUENCE: 61

Met Ser Asn Val Ala Thr His Gly Lys Ala Asp Leu Ala Gln Pro Glu
1               5                   10                  15

Ala Cys Arg Pro Asp Thr Leu Asp Thr Leu Ala Asn Ala Trp Arg Ala
            20                  25                  30

Arg Ser Thr Gly Gly Leu Ser Pro Ala Ala Gly Leu Leu Ala Trp Tyr
        35                  40                  45

Asp Trp Ala Leu His Leu Ser Leu Ser Pro Gly Lys Gln Arg Ser Leu
    50                  55                  60

Ile Glu Lys Gly Leu His Lys Gln Gln Arg Leu Ala Arg Tyr Ala Leu
65              70                  75                  80

Arg Val Ala Ser Ala His Asp Cys Pro Thr Cys Ile Glu Pro Leu Glu
                85                  90                  95

Gln Asp Arg Arg Phe Ala Ala Pro Ala Trp Gln Gln Trp Pro Phe Asn
            100                 105                 110

Val Ile His Gln Gly Phe Leu Leu Gln Gln Gln Trp Trp His Asn Ala
        115                 120                 125

Thr Thr Gly Val Arg Gly Val Ser Arg His His Glu Asn Met Val Thr
    130                 135                 140

Phe Ala Gly Arg Gln Trp Leu Asp Met Trp Ser Pro Ser Asn Phe Ile
145                 150                 155                 160

Trp Thr Asn Pro Glu Val Leu His Ala Ile Thr Gln Ser Gly Gly Ala
                165                 170                 175

Asn Leu Trp Arg Gly Ala Met Asn Phe Leu Glu Asp Ala Arg Arg Leu
            180                 185                 190

Ala Leu Asp Asp Ala Pro Ala Gly Val Glu Gly Phe Glu Val Gly Lys
        195                 200                 205

Asp Val Ala Val Thr Pro Gly Lys Val Val Phe Arg Asn His Leu Ile
    210                 215                 220

Glu Leu Ile Gln Tyr Ser Pro Thr Thr Pro Asp Val His Ala Glu Pro
225                 230                 235                 240

Val Leu Ile Val Pro Ser Trp Ile Met Lys Tyr Tyr Ile Leu Asp Leu
                245                 250                 255

Ser Pro His Asn Ser Met Val Lys Tyr Leu Val Asp Gln Gly His Thr
            260                 265                 270

Val Phe Ile Leu Ser Trp Lys Asn Pro Thr Ala Ala Asp Arg Asp Leu
        275                 280                 285

Gly Leu Glu Asp Tyr Arg Trp Leu Gly Val Met Asp Ala Leu Asp Ala
    290                 295                 300

Val Thr Ala Ile Val Pro Glu Arg Lys Val Gln Ala Val Gly Tyr Cys
305                 310                 315                 320

Leu Gly Gly Thr Leu Leu Ala Ile Ala Ala Ala Ala Met Ala Arg Asp
```

```
                    325                 330                 335
Gly Asp Glu Arg Leu Gln Ser Leu Thr Leu Ala Ser Glu Thr Asp
                340                 345                 350

Phe Arg Glu Ser Gly Glu Ile Ala Leu Phe Ile Asp Ser Gln Leu
                355                 360                 365

Ala Trp Leu Glu Ala Gly Met Trp Asp Lys Gly Tyr Leu Asp Gly Lys
        370                 375                 380

Gln Met Ala Gly Ala Phe Gln Met Leu Asn Ser Arg Asp Leu Ile Trp
385                 390                 395                 400

Ser Arg Arg Val Arg Glu Tyr Leu Leu Gly Glu Arg Gln Thr Phe Asn
                405                 410                 415

Asp Leu Met Ala Trp Asn Ala Asp Val Thr Arg Met Pro Tyr Arg Met
                420                 425                 430

His Ser Glu Tyr Leu Arg Arg Leu Tyr Leu Asp Asn Asp Leu Ala Glu
                435                 440                 445

Gly Arg Tyr Arg Val Gly Gly Arg Pro Val Ala Leu Ala Asp Ile Glu
        450                 455                 460

Val Pro Met Phe Ile Val Gly Thr Val Arg Asp His Val Ala Pro Trp
465                 470                 475                 480

Pro Ser Val Tyr Lys Met His Leu Leu Ser Asp Ala Glu Leu Thr Phe
                485                 490                 495

Val Leu Thr Ser Gly Gly His Asn Ala Gly Val Val Ser Glu Pro Gly
                500                 505                 510

His Pro Arg Arg Ser Phe Gln Ile Ala Thr Arg Ala Ala Gly Asp Arg
        515                 520                 525

Tyr Ile Asp Pro Gln Leu Trp Arg Ala Glu Thr Pro Met Asn Glu Gly
        530                 535                 540

Ser Trp Trp Pro Ala Trp Gln Gln Trp Leu Ala Gln Arg Ser Ala Gly
545                 550                 555                 560

Arg Val Ala Pro Ala Met Gly Gly Thr Gln Ala Pro Leu Gly Asp
                565                 570                 575

Ala Pro Gly Thr Tyr Val Ala Met Arg
                580                 585

<210> SEQ ID NO 62
<211> LENGTH: 588
<212> TYPE: PRT
<213> ORGANISM: Rhodopseudomonas palustris

<400> SEQUENCE: 62

Met Met Leu Gln Thr Ser Pro Pro Ala Pro Ser Ala Ala Ser Gln Gln
  1               5                  10                  15

Ile Gln Ser Pro Ala Arg His His Gly Pro Ser Asp Ser Asp Arg Thr
                20                  25                  30

Leu His Ala Thr Leu Ala Pro Leu Thr Gly Gly Leu Ser Pro Thr Ala
            35                  40                  45

Leu Thr Leu Ala Tyr Ala Asp Trp Leu Ser His Leu Phe Trp Ala Pro
        50                  55                  60

Thr Gln Arg Met Asp Leu Val Asn Asp Ala Leu Arg Arg Gly Thr Gln
65                  70                  75                  80

Leu Ala Glu Ala Ser Ile Gly Gln Thr Ala Pro Trp Ser Leu Ile Ala
                85                  90                  95

Pro Gln Pro Gln Asp Arg Arg Phe Ser Ala Pro Glu Trp Arg Glu Pro
            100                 105                 110
```

```
Pro Phe Asn Leu Met Ala Gln Gly Phe Leu Leu Ala Glu Gln Trp Trp
            115                 120                 125

His Asp Ala Thr Thr Asn Ile Arg Gly Val Ser Glu Gln Asn Glu Lys
        130                 135                 140

Ile Val Glu Phe Ala Thr Arg Gln Met Leu Asp Val Trp Ala Pro Ser
145                 150                 155                 160

Asn Phe Ala Leu Thr Asn Pro Glu Val Leu Arg Arg Thr Val Ser Thr
                165                 170                 175

Glu Gly Arg Asn Leu Ala Asp Gly Phe Arg Asn Trp Trp Glu Asp Leu
            180                 185                 190

Leu Glu Leu Met Ala His Glu Pro Lys His Asp Phe Val Val Gly Lys
        195                 200                 205

Asp Val Ala Val Thr Pro Gly Lys Val Val Tyr Ser Asn Lys Leu Ile
210                 215                 220

Glu Leu Ile Gln Tyr Ala Pro Ala Thr Glu Thr Val Arg Pro Glu Pro
225                 230                 235                 240

Ile Leu Ile Val Pro Ala Trp Ile Met Lys Tyr Tyr Ile Leu Asp Leu
                245                 250                 255

Ser Pro His Asn Ser Leu Val Lys Tyr Leu Thr Glu Gln Gly Tyr Thr
            260                 265                 270

Val Phe Met Ile Ser Trp Arg Asn Pro Thr Ala Ala Asp Arg Asp Val
        275                 280                 285

Ser Leu Glu Asp Tyr Arg Arg Leu Gly Val Met Ala Ala Leu Asp Thr
        290                 295                 300

Ile Gly Ala Ile Leu Pro Asp Arg Pro Val His Ala Val Gly Tyr Cys
305                 310                 315                 320

Leu Gly Gly Thr Met Leu Ser Ile Ala Ala Ala Met Gly Arg Asp
                325                 330                 335

Gly Asp Ser Arg Leu Lys Ser Ile Thr Leu Phe Ala Ala Gln Thr Asp
            340                 345                 350

Phe Thr Glu Ala Gly Glu Leu Thr Leu Phe Ile Asn Glu Ser Gln Val
        355                 360                 365

Ala Phe Leu Glu Asp Met Met Trp Asn Arg Gly Val Leu Asp Thr Thr
        370                 375                 380

Gln Met Ser Gly Ala Phe Gln Ile Leu Arg Ser Asn Asp Leu Ile Trp
385                 390                 395                 400

Ser Arg Leu Val His Glu Tyr Leu Met Gly Val Arg Ser Glu Pro Asn
                405                 410                 415

Asp Leu Met Ala Trp Asn Ala Asp Ala Thr Arg Met Pro Tyr Arg Met
            420                 425                 430

His Ser Glu Tyr Leu Arg Lys Leu Phe Leu Asp Asn Asp Leu Ala Glu
        435                 440                 445

Gly Arg Tyr Val Val Asp Gly Arg Pro Ile Ala Leu Ser Asp Ile His
        450                 455                 460

Thr Pro Ile Phe Val Val Gly Thr Gln Arg Asp His Val Ala Pro Trp
465                 470                 475                 480

Arg Ser Thr Phe Lys Ile His Leu Leu Ala Asp Ala Asp Val Thr Phe
                485                 490                 495

Cys Leu Thr Gly Gly His Asn Ala Gly Ile Val Ser Pro Pro Ser
            500                 505                 510

Pro Lys Ala His Gly Tyr Gln Val Met Thr Lys Glu Ala Asp Gly Pro
        515                 520                 525

Tyr Val Gly Pro Asp Asp Trp Leu Lys Gln Ala Pro His Ala Glu Gly
```

```
                    530              535             540
Ser Trp Trp Thr Glu Trp Val His Trp Leu Gly Thr Arg Ser Gly Glu
545                 550             555             560

Pro Val Ala Pro Pro Arg Ile Gly Leu Pro Asp Val Asp Pro Gly Ala
                565             570             575

Leu Pro Asn Ala Pro Gly Ser Tyr Val Leu Gln Thr
            580             585
```

<210> SEQ ID NO 63
<211> LENGTH: 606
<212> TYPE: PRT
<213> ORGANISM: Burkholderia ambifaria

<400> SEQUENCE: 63

```
Met Lys Ala Ser Val Thr Arg Ala Pro Arg Gly Asn Glu Ser Ile Arg
1               5                   10                  15

Pro Ser Gly Ala Val Glu Pro Glu Ser Ser Met Thr Gln Cys Pro Gln
                20                  25                  30

Ala Gly Thr Thr Pro Ala Glu Gln Trp Asn Arg Ala Ala His Ala Asn
            35                  40                  45

Val Ala Ala Met Thr Phe Gly Leu Ser Pro Val Ser Leu Ala Leu Ala
    50                  55                  60

Met Leu Asp Trp Gly Ala His Leu Ala Val Ser Pro Gly Lys Cys Phe
65                  70                  75                  80

Asp Leu Ala Met Gln Ala Cys Val Ala Ala Val Ala Pro Ala Ala Asp
                85                  90                  95

Gln Cys Glu Ala Glu Ala Gly Glu Ala Asp Pro Thr Gly Leu Ala Val
            100                 105                 110

His Ala Gly Gln Ala Asp Pro Arg Phe Ala Ala Pro Ala Trp Ala Gly
        115                 120                 125

Trp Pro Phe His Val Tyr Arg Asp Ser Phe Leu Ser Ile Gln Arg Trp
    130                 135                 140

Trp Arg Asp Ala Thr His Gly Val Pro Gly Val Glu Arg His His Glu
145                 150                 155                 160

Glu Leu Val Gly Phe Ala Ala Arg Gln Trp Leu Asp Ala Cys Ser Pro
                165                 170                 175

Gly Asn Phe Leu Ala Thr Asn Pro Val Val Leu Asp Ala Thr Met Cys
            180                 185                 190

Ser Gly Gly Ala Asn Leu Ala Ala Gly Ala Leu Asn Trp Leu Glu Asp
        195                 200                 205

Ala Lys Ala Leu Leu Glu Arg Ala Gly Gly Thr His Ala His Asp Ala
    210                 215                 220

Arg Thr Tyr Leu Pro Gly Arg Asp Val Ala Ile Thr Pro Gly Arg Val
225                 230                 235                 240

Val Trp Arg Asn Ala Leu Cys Glu Leu Leu Gln Tyr Glu Pro Thr Thr
                245                 250                 255

Ala Arg Val Ala Arg Glu Pro Ile Leu Ile Val Pro Ser Trp Ile Met
            260                 265                 270

Lys Tyr Tyr Ile Leu Asp Leu Gln Pro His Asn Ser Leu Ile Arg Phe
        275                 280                 285

Leu Val Asp Ala Gly Tyr Thr Val Phe Ala Val Ser Trp Arg Asn Pro
    290                 295                 300

Gly Ala Glu Ala Arg Asp Leu Gly Leu Asp Asp Tyr Leu Arg Asp Gly
305                 310                 315                 320
```

```
Cys Met Ala Ala Leu Asp Ala Arg Ser Val Cys Gly Gly Ala Val
            325                 330                 335

His Thr Val Gly Tyr Cys Leu Gly Gly Thr Leu Leu Ala Ile Val Ala
            340                 345                 350

Ala Ala Leu Ala Arg Asp Gly Arg Gln His Glu Ala Leu Arg Ser Val
            355                 360                 365

Thr Leu Leu Ala Ala Gln Thr Asp Phe Ser Glu Pro Gly Glu Leu Gly
            370                 375                 380

Leu Phe Ile Asp Ala Ser Glu Leu Ser Ala Leu Asp Ala Leu Met Trp
385                 390                 395                 400

Arg Gln Gly Tyr Leu Asp Gly Ala Gln Met Ser Ala Ala Phe Gln Leu
                405                 410                 415

Leu Asn Ala Arg Asp Leu Ile Trp Ser Arg Met Met Ser Glu Tyr Leu
                420                 425                 430

Leu Gly Thr Arg Thr Lys Pro Asn Asp Leu Met Ser Trp Asn Ala Asp
                435                 440                 445

Thr Thr Arg Met Pro Tyr Arg Met His Ser Glu Tyr Leu Thr Arg Leu
                450                 455                 460

Phe Leu Asp Asn Asp Leu Ala Val Gly Arg Tyr Cys Val Asp Gly Arg
465                 470                 475                 480

Pro Val Ala Leu Ser Asp Ile Asp Val Pro Thr Phe Val Val Gly Thr
                485                 490                 495

Glu Arg Asp His Val Ser Pro Trp Gly Ser Val Tyr Lys Leu His Leu
                500                 505                 510

Leu Thr His His Ala Leu Thr Phe Val Leu Thr Ser Gly Gly His Asn
                515                 520                 525

Ala Gly Ile Val Ser Glu Pro Gly His Pro Gly Arg His Tyr Arg Arg
            530                 535                 540

Ala Thr Arg Glu Pro Gly Ala Pro Tyr Arg Ser Arg His Asp Phe Val
545                 550                 555                 560

Arg Gly Thr Thr Ala Val Asp Gly Ser Trp Trp Thr Cys Trp Arg Asp
                565                 570                 575

Trp Leu His Glu Arg Ser Ser Gly Asp Val Pro Ala Arg Thr Pro Ala
                580                 585                 590

Ala Gly Phe Asp Ala Ala Pro Gly Thr Tyr Val Leu Glu Thr
            595                 600                 605

<210> SEQ ID NO 64
<211> LENGTH: 605
<212> TYPE: PRT
<213> ORGANISM: Methylobacterium extorquens

<400> SEQUENCE: 64

Met Gly Thr Glu Arg Thr Asn Pro Ala Ala Pro Asp Phe Glu Thr Ile
  1               5                  10                  15

Ala Arg Asn Ala Asn Gln Leu Ala Glu Val Phe Arg Gln Ser Ala Ala
                20                  25                  30

Ala Ser Leu Lys Pro Phe Glu Pro Ala Gly Gln Gly Ala Leu Leu Pro
            35                  40                  45

Gly Ala Asn Leu Gln Gly Ala Ser Glu Ile Asp Glu Met Thr Arg Thr
        50                  55                  60

Leu Thr Arg Val Ala Glu Thr Trp Leu Lys Asp Pro Glu Lys Ala Leu
 65                  70                  75                  80

Gln Ala Gln Thr Lys Leu Gly Gln Ser Phe Ala Ala Leu Trp Ala Ser
                85                  90                  95
```

```
Thr Leu Thr Arg Met Gln Gly Ala Val Thr Glu Pro Val Val Gln Pro
            100                 105                 110

Pro Pro Thr Asp Lys Arg Phe Ala His Ala Asp Trp Ser Ala Asn Pro
            115                 120                 125

Val Phe Asp Leu Ile Lys Gln Ser Tyr Leu Leu Gly Arg Trp Ala
            130                 135                 140

Glu Glu Met Val Glu Thr Ala Glu Gly Ile Asp Glu His Thr Arg His
145                 150                 155                 160

Lys Ala Glu Phe Tyr Leu Arg Gln Leu Leu Ser Ala Tyr Ser Pro Ser
                165                 170                 175

Asn Phe Val Met Thr Asn Pro Glu Leu Leu Arg Gln Thr Leu Glu Glu
            180                 185                 190

Gly Gly Ala Asn Leu Met Arg Gly Met Lys Met Leu Gln Glu Asp Leu
            195                 200                 205

Glu Ala Gly Gly Gly Gln Leu Arg Val Arg Gln Thr Asp Leu Ser Ala
210                 215                 220

Phe Thr Phe Gly Lys Asp Val Ala Val Thr Pro Gly Glu Val Ile Phe
225                 230                 235                 240

Arg Asn Asp Leu Met Glu Leu Ile Gln Tyr Ala Pro Thr Thr Glu Thr
                245                 250                 255

Val Leu Lys Arg Pro Leu Leu Ile Val Pro Pro Trp Ile Asn Lys Phe
            260                 265                 270

Tyr Ile Leu Asp Leu Asn Pro Gln Lys Ser Leu Ile Gly Trp Met Val
            275                 280                 285

Ser Gln Gly Ile Thr Val Phe Val Ile Ser Trp Val Asn Pro Asp Glu
            290                 295                 300

Arg His Arg Asp Lys Asp Phe Glu Ser Tyr Met Arg Glu Gly Ile Glu
305                 310                 315                 320

Thr Ala Ile Asp Met Ile Gly Val Ala Thr Gly Glu Thr Asp Val Ala
                325                 330                 335

Ala Ala Gly Tyr Cys Val Gly Gly Thr Leu Leu Ala Val Thr Leu Ala
            340                 345                 350

Tyr Gln Ala Ala Thr Gly Asn Arg Arg Ile Lys Ser Ala Thr Phe Leu
            355                 360                 365

Thr Thr Gln Val Asp Phe Thr His Ala Gly Asp Leu Lys Val Phe Ala
370                 375                 380

Asp Glu Gly Gln Ile Lys Ala Ile Glu Glu Arg Met Ala Glu His Gly
385                 390                 395                 400

Tyr Leu Glu Gly Ala Arg Met Ala Asn Ala Phe Asn Met Leu Arg Pro
                405                 410                 415

Asn Asp Leu Ile Trp Ser Tyr Val Val Asn Tyr Val Arg Gly Lys
            420                 425                 430

Ala Pro Ala Ala Phe Asp Leu Leu Tyr Trp Asn Ala Asp Ala Thr Arg
            435                 440                 445

Met Pro Ala Ala Asn His Ser Phe Tyr Leu Arg Asn Cys Tyr Leu Asn
            450                 455                 460

Asn Thr Leu Ala Lys Gly Gln Met Val Leu Gly Asn Val Arg Leu Asp
465                 470                 475                 480

Leu Lys Lys Val Lys Val Pro Val Phe Asn Leu Ala Thr Arg Glu Asp
                485                 490                 495

His Ile Ala Pro Ala Leu Ser Val Phe Glu Gly Ser Ala Lys Phe Gly
            500                 505                 510
```

```
Gly Lys Val Asp Tyr Val Leu Ala Gly Ser Gly His Ile Ala Gly Val
        515                 520                 525

Val Ala Pro Gly Pro Lys Ala Lys Tyr Gly Phe Arg Thr Gly Gly
    530                 535                 540

Pro Ala Arg Gly Arg Phe Glu Asp Trp Val Ala Ala Thr Glu His
545                 550                 555                 560

Pro Gly Ser Trp Trp Pro Tyr Trp Tyr Lys Trp Leu Glu Glu Gln Ala
                565                 570                 575

Pro Glu Arg Val Pro Ala Arg Ile Pro Gly Thr Gly Ala Leu Pro Ser
                580                 585                 590

Leu Ala Pro Ala Pro Gly Thr Tyr Val Arg Met Lys Ala
                595                 600                 605

<210> SEQ ID NO 65
<211> LENGTH: 587
<212> TYPE: PRT
<213> ORGANISM: Caulobacter crescentus

<400> SEQUENCE: 65

Met Val Glu Thr Leu Ser Ala Asn Leu Ala Arg Ala Ala Val Thr Ala
 1               5                  10                  15

Gln Gly Ala Ile Ala Glu Ala Ala Leu Arg Gln Ala Asp Arg Pro Ala
                20                  25                  30

Ala Leu Thr Pro Asp Pro Phe His Val Ala Pro Ala Leu Asn Glu Val
                35                  40                  45

Met Thr Arg Leu Ala Ala Gln Pro Asp Arg Leu Met Arg Ala Gln Ala
            50                  55                  60

Asp Leu Phe Gly Gln Tyr Met Glu Leu Trp Gln Thr Ala Ala Arg Arg
65                  70                  75                  80

Ala Ala Gly Glu Asp Val Ala Pro Val Ala Pro Ala Gly Asp
                    85                  90                  95

Lys Arg Phe Asn Asp Pro Asp Trp Ala Ser Asn Pro Met Phe Asp Leu
                100                 105                 110

Met Lys Gln Ser Tyr Leu Leu Ser Ser Asn Trp Leu Asn Gly Leu Ile
            115                 120                 125

Ala Glu Val Asp Gly Val Asp Pro Ala Thr Lys Arg Arg Val Glu Phe
        130                 135                 140

Phe Thr Lys Met Leu Thr Asp Ala Phe Ser Pro Ser Asn Phe Leu Ile
145                 150                 155                 160

Ser Asn Pro Ala Ala Leu Arg Glu Val Gln Thr Gln Gly Gln Ser
                165                 170                 175

Leu Val Arg Gly Met Glu Asn Phe Ala Ala Asp Leu Glu Arg Gly Gly
                180                 185                 190

Gly Gln Leu Ala Ile Ser Gln Thr Asp Leu Ala Lys Phe Lys Val Gly
            195                 200                 205

Glu Asn Val Ala Thr Ala Pro Gly Lys Val Val Tyr Gln Asn Asp Ile
        210                 215                 220

Leu Gln Leu Leu Gln Phe Asp Pro Thr Thr Asp Thr Val Cys Glu Ile
225                 230                 235                 240

Pro Leu Leu Ile Phe Pro Pro Trp Ile Asn Lys Phe Tyr Ile Met Asp
                245                 250                 255

Leu Arg Pro Glu Asn Ser Met Ile Arg Trp Leu Thr Ala Gln Gly Phe
                260                 265                 270

Thr Val Phe Val Ala Ser Trp Val Asn Pro Asp Gln Thr Leu Ala Ala
            275                 280                 285
```

```
Lys Thr Phe Glu Asp Tyr Met Val Glu Gly Ile Tyr Asp Ala Ala Gln
            290                 295                 300

Gln Val Met Thr Gln Cys Gly Val Asp Arg Val Asn Thr Val Gly Tyr
305                 310                 315                 320

Cys Ile Gly Gly Thr Leu Leu Ser Val Ala Leu Ala His Met Ala Ala
                325                 330                 335

Arg Gly Asp Lys Arg Ile Asn Ser Ala Thr Phe Phe Ala Ala Gln Gln
            340                 345                 350

Asp Phe Ala Glu Ala Gly Asp Leu Leu Leu Phe Thr Asn Glu Glu Trp
        355                 360                 365

Leu Gln Ser Ile Glu Gln Gln Met Asp Gln Ala Gly Gly Phe Leu Pro
    370                 375                 380

Ser Gln Ser Met Ala Asp Thr Phe Asn Ala Leu Arg Gly Asn Asp Leu
385                 390                 395                 400

Ile Trp Ser Phe Phe Val Ser Asn Tyr Leu Met Gly Lys Glu Pro Arg
                405                 410                 415

Pro Phe Asp Leu Leu Phe Trp Asn Ala Asp Gln Thr Arg Met Pro Lys
            420                 425                 430

Ala Leu His Leu Phe Tyr Leu Arg Asn Phe Tyr Lys Asp Asn Ala Leu
        435                 440                 445

Thr Thr Gly Lys Leu Ser Leu Gly Gly Glu Arg Leu Asp Leu Ser Lys
    450                 455                 460

Val Lys Ile Pro Ile Tyr Val Gln Ser Ser Lys Asp Asp His Ile Ala
465                 470                 475                 480

Pro Tyr Arg Ser Val Tyr Arg Gly Ala Arg Ala Phe Gly Gly Pro Val
                485                 490                 495

Thr Phe Thr Met Ala Gly Ser Gly His Ile Ala Gly Val Ile Asn His
            500                 505                 510

Pro Asp Ala Arg Lys Tyr Gln His Trp Thr Asn Ser Glu Leu Pro Ala
        515                 520                 525

Asp Val Ser Glu Trp Ile Ala Gly Ala His Glu His Pro Gly Ser Trp
    530                 535                 540

Trp Pro His Trp Ala Ala Trp Leu Lys Ala Arg Ser Gly Asp Gln Val
545                 550                 555                 560

Pro Ala Arg Asp Pro Ala Lys Gly Lys Leu Lys Pro Leu Glu Asp Ala
                565                 570                 575

Pro Gly Ser Phe Val Leu Val Lys Ser Gln Pro
            580                 585

<210> SEQ ID NO 66
<211> LENGTH: 613
<212> TYPE: PRT
<213> ORGANISM: Methylobacterium sp.

<400> SEQUENCE: 66

Met Leu Ala Thr Ser Pro Thr Gln Ser Ser Ala Ala Ile Pro Ala Arg
 1               5                  10                  15

Pro Pro Ala Leu Arg Leu Val Pro Val Ala Ala Gly Pro Val
            20                  25                  30

Arg Asp Ala Ala Glu Pro Gly Asp Asp Leu His Asp Ala Gly Gln Ala
        35                  40                  45

Ile Asp Gln Ala Ala His Ala Ala Val Ala Arg Leu Thr Gly Gly Leu
    50                  55                  60

Ser Pro Ala Ala Leu Ala Asn Ala Trp Leu Asp Trp Ser Val His Ala
```

-continued

```
                65                  70                  75                  80
Ala Phe Ser Pro Gly Lys Gln Ala Glu Leu Ala Ala Lys Ala Phe Arg
                    85                  90                  95

Lys Gly Gln Arg Leu Gln Ser Phe Leu Trp Arg Asn Leu Leu Val Gly
                100                 105                 110

Ala Gln Ala Glu Pro Cys Ile Glu Pro Leu Pro Gln Asp His Arg Phe
                115                 120                 125

Asp Asp Pro Ala Trp Arg Thr Trp Pro Phe Cys Leu Tyr Gln Gln Gly
130                 135                 140

Phe Leu Leu Thr Gln Gln Trp Trp His Asn Ala Thr Thr Gly Val Arg
145                 150                 155                 160

Gly Val Ala Arg Ala His Glu Glu Ile Val Ala Phe Thr Ala Arg Gln
                165                 170                 175

Met Leu Asp Gly Val Ser Pro Ser Asn His Pro Leu Thr Asn Pro Val
                180                 185                 190

Val Leu Asn Ala Thr Leu Ala Ser Gly Gly Ala Asn Leu Val Leu Gly
                195                 200                 205

Ala Leu Asn Ala Leu Glu Asp Ala Arg Arg Gly Leu Ala Gly Leu Lys
                210                 215                 220

Pro Ala Gly Ala Glu Arg Phe Ala Val Gly Arg Glu Val Ala Val Thr
225                 230                 235                 240

Glu Gly Glu Val Val Tyr Arg Asn Asp Leu Ile Glu Leu Ile Gln Tyr
                245                 250                 255

Ala Pro Lys Thr Gly Ala Val Arg Pro Glu Pro Val Leu Ile Val Pro
                260                 265                 270

Ala Trp Ile Met Lys Tyr Tyr Ile Leu Asp Leu Ser Pro Glu Asn Ser
                275                 280                 285

Leu Val Arg His Leu Val Gly Gln Gly Phe Thr Val Phe Met Ile Ser
                290                 295                 300

Trp Arg Asn Pro Gly Pro Ala Asp Arg Asp Val Ser Phe Asp Asp Tyr
305                 310                 315                 320

Arg Arg Leu Gly Val Met Ala Ala Leu Asp Ala Val Ser Ala Ile Arg
                325                 330                 335

Pro Gly Arg Ala Val His Ala Ala Gly Tyr Cys Leu Gly Gly Thr Leu
                340                 345                 350

Leu Ser Ile Ala Ala Thr Met Ala Arg Asp Gly Asp Ala Arg Leu
                355                 360                 365

Ala Ser Leu Thr Leu Phe Ala Ala Gln Val Asp Phe Thr Glu Ala Gly
                370                 375                 380

Glu Leu Thr Leu Phe Ile Asn Glu Ser Gln Ile Ser Phe Leu Glu Ser
385                 390                 395                 400

Leu Met Arg Ser Glu Gly Val Leu Asp Ser Lys Gln Met Ala Gly Ala
                405                 410                 415

Phe Gln Leu Leu Arg Ser Asn Asp Leu Ile Trp Ser Arg Ile Val Asn
                420                 425                 430

Ser Tyr Leu Leu Gly Arg Arg Glu Ala Val Thr Asp Leu Met Ala Trp
                435                 440                 445

Asn Ala Asp Ala Thr Arg Met Pro Ala Arg Met His Ala Glu Tyr Leu
                450                 455                 460

Arg Arg Leu Phe Leu Asp Asn Asp Leu Ala Glu Gly Arg Leu Arg Val
465                 470                 475                 480

Glu Gly Arg Pro Val Ala Leu Thr Asp Ile Arg Ala Pro Ile Phe Ala
                485                 490                 495
```

```
Val Gly Thr Glu Lys Asp His Val Ala Pro Trp Arg Ser Val Phe Lys
            500                 505                 510

Leu Thr Leu Met Thr Asp Ala Asp Val Thr Phe Leu Leu Ala Ser Gly
        515                 520                 525

Gly His Asn Ala Gly Ile Val Ser Glu Pro Gly His Arg Gly Arg His
    530                 535                 540

Tyr Arg Val His Ser Arg Ala Ala Thr Asp Arg Tyr Val Asp Pro Asp
545                 550                 555                 560

Ser Trp Leu Asp Leu Ala Arg Leu Glu Gln Gly Ser Trp Pro Glu
                565                 570                 575

Trp Ala Ser Trp Leu Ala Glu Arg Ser Gly Pro Glu Pro Pro
            580                 585                 590

Pro Met Gly Leu Pro Gly Ala Pro Thr Leu Gly Pro Ala Pro Gly Arg
        595                 600                 605

Tyr Val Arg Glu Ala
        610

<210> SEQ ID NO 67
<211> LENGTH: 601
<212> TYPE: PRT
<213> ORGANISM: Bradyrhizobium sp.

<400> SEQUENCE: 67

Met Thr Asp Val Pro Asn Asn Thr Asn Pro Gln Lys Thr Phe Asp Ala
1               5                   10                  15

Glu Ala Phe Ala Thr Asn Ile Ala Arg Ala Met Glu Ser Ser Gly Lys
            20                  25                  30

Ala Leu Ala Ala Tyr Leu Lys Pro Arg Glu Thr Gly Glu Val Gln Asp
        35                  40                  45

Arg Pro Pro Thr Glu Leu Thr Glu Val Val Lys Ser Phe Thr Ala Val
    50                  55                  60

Ala Asp Tyr Trp Leu Ser Asp Lys Asp Arg Ala Ser Asp Ile Gln Thr
65                  70                  75                  80

Lys Leu Ala Lys Gly Tyr Leu Asp Leu Trp Gly Ser Ala Ala Arg Arg
                85                  90                  95

Leu Ala Gly Glu Glu Ala Pro Ala Ile Ser Pro Ser Pro Arg Asp
            100                 105                 110

Lys Arg Phe Ala Asp Pro Glu Trp Lys Ser Asn Gln Phe Tyr Asp Phe
        115                 120                 125

Val Met Gln Ala Tyr Leu Leu Thr Thr Gln Trp Ala Gln Asp Leu Val
    130                 135                 140

His Asn Ala Glu Gly Leu Asp Pro His Thr Arg Lys Lys Ala Glu Phe
145                 150                 155                 160

Tyr Val Asn Gln Ile Thr Asn Ala Leu Ala Pro Ser Asn Phe Val Met
                165                 170                 175

Thr Asn Pro Glu Val Met Arg Gln Thr Val Ala Ser Ser Gly Asp Asn
            180                 185                 190

Leu Val Arg Gly Met Gln Met Leu Ala Glu Asp Ile Glu Ala Gly Lys
        195                 200                 205

Gly Thr Leu Lys Ile Arg Gln Ser Asp Pro Ala Asn Leu Glu Val Gly
    210                 215                 220

Val Asn Met Ala Thr Thr Pro Gly Lys Val Ile Phe Gln Asn Glu Met
225                 230                 235                 240

Met Gln Leu Ile Gln Tyr Ala Pro Thr Thr Glu Thr Val Leu Arg Thr
```

```
                245                 250                 255
Pro Leu Leu Ile Val Pro Pro Trp Ile Asn Lys Phe Tyr Ile Leu Asp
            260                 265                 270

Leu Arg Pro Glu Lys Ser Phe Ile Lys Trp Cys Val Asp Gln Gly Leu
            275                 280                 285

Thr Val Phe Val Ile Ser Trp Val Asn Pro Asp Lys Lys Leu Gly Thr
            290                 295                 300

Lys Thr Trp Glu Asp Tyr Met Lys Glu Gly Pro Leu Thr Ala Met Asp
305                 310                 315                 320

Val Ile Glu Lys Val Thr Gly Glu Met Lys Val His Thr Met Gly Tyr
                325                 330                 335

Cys Val Gly Gly Thr Met Leu Ala Thr Thr Leu Ala Trp Leu Ala Asp
            340                 345                 350

Lys Arg Arg Gln Arg Val Thr Ser Ala Thr Phe Leu Ala Ala Gln Val
            355                 360                 365

Asp Phe Thr His Ala Gly Asp Leu Leu Val Phe Val Asp Glu Thr Gln
            370                 375                 380

Ile Ser Ala Leu Glu Arg Asp Met Gln Ala Ser Gly Val Leu Glu Gly
385                 390                 395                 400

Ser Lys Met Ala Met Ala Phe Asn Met Leu Arg Ser Asn Asp Leu Ile
                405                 410                 415

Trp Ser Tyr Val Val Asn Asn Tyr Leu Lys Gly Gln Pro Pro Gln Ala
            420                 425                 430

Phe Asp Leu Leu His Trp Asn Ser Asp Ala Thr Arg Met Ser Ala Ala
            435                 440                 445

Asn His Ser Tyr Tyr Leu Arg Asn Cys Tyr Leu Glu Asn Arg Leu Thr
450                 455                 460

Thr Gly Thr Met Val Leu Asp Asn Thr Leu Leu Asp Leu Ser Lys Val
465                 470                 475                 480

Lys Val Pro Val Tyr Asn Leu Ala Thr Arg Glu Asp His Ile Ala Pro
                485                 490                 495

Ala Asp Ser Val Leu Tyr Gly Ser Gln Phe Phe Gly Gly Pro Val Lys
            500                 505                 510

Tyr Val Leu Ser Gly Ser Gly His Ile Ala Gly Val Val Asn Pro Pro
            515                 520                 525

Ser Ser Gly Lys Tyr Gln Tyr Trp Thr Asn Asp Gln Ile His Asp Ile
            530                 535                 540

Ser Leu Lys Asp Trp Met Lys Gly Ala Gln Glu His Lys Gly Ser Trp
545                 550                 555                 560

Trp Pro Asp Trp Arg Glu Trp Leu Gly Gln Leu Asp Pro Glu Gln Val
                565                 570                 575

Pro Ala Arg Ser Val Gly Ser Glu Ala Tyr Pro Pro Ile Glu Asp Ala
            580                 585                 590

Pro Gly Ser Tyr Val Arg Val Arg Ala
            595                 600

<210> SEQ ID NO 68
<211> LENGTH: 573
<212> TYPE: PRT
<213> ORGANISM: Rhodobacter sphaeroides

<400> SEQUENCE: 68

Met Ser Asp Met Lys Trp Asn Ala Glu Gly Ala Pro Ala Tyr Gly Gln
1               5                   10                  15
```

Ala Leu Asp Arg Ala Ala Arg Ala Ala Ile Ala Gly Met Thr Arg Gly
            20                  25                  30

Leu Ala Pro Ser Val Leu Ala Thr Ala Ala Leu Asp Trp Met Met His
        35                  40                  45

Leu Ala Ala Ala Pro Gly Lys Gln Ala Glu Leu Trp Glu Lys Ala Ala
    50                  55                  60

Thr Ala Ser Ala Ala Leu Met Gln Ala Gly Leu Gln Pro His Glu Ala
65                  70                  75                  80

Pro Val Arg Asp Arg Arg Tyr Ala Ser Glu Ala Trp Asn Arg Gln Pro
                85                  90                  95

Phe Ala Ala Leu Arg Asp Ser Phe Leu Leu Thr Glu Asp Trp Trp Gln
            100                 105                 110

Thr Ala Thr Thr Gly Leu Arg Gly Met Asp Arg Ala His Glu Ala Ala
        115                 120                 125

Leu Ser Phe Ser Val Arg Gln Met Leu Asp Val Trp Ser Pro Ser Asn
    130                 135                 140

Asn Pro Phe Leu Asn Pro Glu Val Leu Ala Arg Thr Thr Glu Thr Arg
145                 150                 155                 160

Gly Ala Asn Leu Met Gln Gly Ala Met Asn Phe Ala Gly Asp Met Ala
                165                 170                 175

Arg Leu Ala Thr Gly Val Pro Met Asp Glu Gly Gly Phe Arg Ile Gly
            180                 185                 190

Glu Thr Leu Ala Ala Thr Pro Gly Lys Val Val Leu Arg Thr His Leu
        195                 200                 205

Met Glu Leu Ile Gln Tyr Ser Pro Thr Thr Arg Glu Val His Pro Glu
210                 215                 220

Pro Val Leu Ile Val Pro Ala Trp Ile Met Lys Tyr Tyr Ile Leu Asp
225                 230                 235                 240

Leu Ser Glu Gln Asn Ser Leu Val Arg Trp Leu Val Ala Gln Gly Phe
                245                 250                 255

Thr Val Phe Met Ile Ser Trp Arg Asn Pro Glu Ser Glu Asp Arg Asp
            260                 265                 270

Leu Gly Leu Ile Asp Tyr Leu Asp Gln Gly Pro Arg Ala Ala Leu Lys
        275                 280                 285

Ala Ile Gln Thr Ile Thr Gly Ala Pro Lys Val His Ala Ala Gly Tyr
    290                 295                 300

Cys Leu Gly Gly Thr Leu Leu Ser Ile Met Ala Ala Arg Met Ala His
305                 310                 315                 320

Asp His Asp Glu Arg Leu Ala Ser Met Thr Leu Phe Ala Ala Gln Val
                325                 330                 335

Asp Phe Ser Glu Ala Gly Glu Leu Ala Leu Phe Ile Ser Glu Ala Gln
            340                 345                 350

Val Ala Leu Leu Glu Asp Met Met Trp His Gln Gly Tyr Leu Asp Ser
        355                 360                 365

Asp Gln Met Ser Gly Ala Phe Thr Leu Leu Arg Ser Asn Asp Leu Ile
    370                 375                 380

Trp Ser Arg Met Ile His Glu Tyr Met Met Gly Glu Arg Pro His Pro
385                 390                 395                 400

Asn Asp Leu Met Thr Trp Asn Ala Asp Ser Thr Arg Met Pro Tyr Arg
                405                 410                 415

Met His Ser Glu Tyr Leu Arg Gln Leu Phe Leu Glu Asn Arg Phe Ala
            420                 425                 430

Glu Gly Lys Phe Glu Leu Glu Gly His Ala Leu Ser Leu Thr Glu Leu

```
            435                 440                 445
Arg Leu Pro Ile Leu Ala Val Gly Thr Glu Thr Asp His Val Ala Pro
450                 455                 460

Trp Arg Ser Val Phe Lys Ile Gln Arg Leu Thr Glu Thr Glu Thr Thr
465                 470                 475                 480

Phe Val Leu Thr Ser Gly Gly His Asn Ala Gly Ile Val Ser Glu Pro
                485                 490                 495

Gly His Pro Arg Arg His Phe Arg Ile Ala Thr Thr Gly Arg Asp Asp
                500                 505                 510

Pro Tyr Arg Asp Ala Asp Glu Trp Phe Ala Glu Thr Ala Pro Val Glu
                515                 520                 525

Gly Ser Trp Trp Pro Ala Trp Gly Ala Trp Leu Ala Glu Arg Ser Thr
                530                 535                 540

Pro Lys Gly Lys Leu Pro Pro Met Gly Asn Ala Arg Gly Gly Tyr Pro
545                 550                 555                 560

Ala Leu Cys Glu Ala Pro Gly Thr Tyr Ile Leu Gln Arg
                565                 570

<210> SEQ ID NO 69
<211> LENGTH: 591
<212> TYPE: PRT
<213> ORGANISM: Novosphingobium pentaromativorans

<400> SEQUENCE: 69

Met Lys Gly Leu Lys Ile Met Val Glu Ala Gln Ile Pro Gly Val Gly
1               5                   10                  15

Asp Pro Leu Asp Gly Leu Ala Glu Thr Met Asp Arg Ala Ala Gly Ala
                20                  25                  30

Met Ile Ala Gln Ala Thr Phe Gly Leu Ser Pro Ala Thr Leu Ala Gln
                35                  40                  45

Ala Val Ser Asp Trp Met Leu His Leu Ala Ala Ser Pro Gly Lys Gln
            50                  55                  60

Thr Gln Leu Ala Ala Lys Ala Leu Arg Lys Met Thr Arg Leu Gly Asp
65                  70                  75                  80

Tyr Ala Met Arg Ser Ala Thr Asp Ala Gln Ala Arg Ala Ile Glu
                85                  90                  95

Pro Leu Pro Gln Asp Arg Arg Phe Ala Asp Pro Ala Trp Ala Ser Ala
                100                 105                 110

Pro Phe Asn Leu Val Ser Gln Ala Phe Leu Leu Asn Gln Gln Trp Trp
                115                 120                 125

His Ala Thr Thr Gly Ile Thr Gly Val Thr Ala His His Glu Glu
                130                 135                 140

Met Val Ala Phe Ala Val Arg Gln Trp Leu Asp Thr Val Ala Pro Thr
145                 150                 155                 160

Asn Phe Leu Ala Thr Asn Pro Val Leu Gln Gln Arg Ile Leu Glu Thr
                165                 170                 175

Gly Gly Gln Cys Leu Ala Asp Gly Leu Arg Asn Trp Met Thr Asp Val
                180                 185                 190

Glu Ala Leu Met Arg Gly Leu Pro Pro Ala Gly Thr Glu Ala Phe Gln
                195                 200                 205

Val Gly Glu Thr Leu Ala Thr Ala Glu Gly Lys Val Val Tyr Arg Asn
                210                 215                 220

Arg Leu Met Glu Leu Ile Gln Tyr Ala Pro Thr Thr Glu Gln Ala Arg
225                 230                 235                 240
```

```
Pro Glu Pro Ile Leu Ile Val Pro Ala Trp Ile Met Lys Tyr Tyr Ile
                245                 250                 255

Leu Asp Leu Ser Pro Glu Asn Ser Leu Val Gln Trp Leu Thr Ala Gln
            260                 265                 270

Gly Phe Thr Val Phe Met Ile Ser Trp His Asn Pro Gly Ser Thr Asp
        275                 280                 285

Arg Asp Leu Glu Met Ala Asp Tyr Leu Gln Leu Gly Pro Met Ala Ala
    290                 295                 300

Leu Asp Ala Val Ala Ala Ile Thr Gly Gly Ala Ser Val His Ala Ala
305                 310                 315                 320

Gly Tyr Cys Leu Gly Gly Thr Leu Leu Ala Ile Ala Ala Ala Ala Met
                325                 330                 335

Ala Arg Asp Gly Asp Arg Leu Ala Ser Leu Thr Leu Leu Ala Ala
                340                 345                 350

Gln Thr Glu Phe Cys Glu Pro Gly Glu Leu Gly Leu Phe Ile Asp Glu
            355                 360                 365

Gly Gln Leu Ser Leu Leu Glu Asn Met Met Trp Gly Arg Gly Tyr Leu
        370                 375                 380

Asp Ser Ala Gln Met Gly Gly Ala Phe Gln Met Leu Arg Ser Asn Asp
385                 390                 395                 400

Leu Val Trp Ser Arg Val Leu Thr Thr Tyr Leu Met Gly Glu Arg Glu
                405                 410                 415

Pro Met Asn Asp Leu Met Ala Trp Asn Ala Asp Gly Thr Arg Met Pro
            420                 425                 430

Tyr Ala Met His Ser Gln Tyr Leu Arg Arg Leu Phe Leu Glu Asp Asp
        435                 440                 445

Leu Ala Glu Gly Arg Phe Gln Val Asn Gly Arg Pro Ile Ala Leu Ser
450                 455                 460

Val Leu Arg Trp Pro Met Phe Val Val Gly Thr Glu Arg Asp His Val
465                 470                 475                 480

Ala Pro Trp Arg Ser Val Phe Lys Ile His Arg Leu Thr Gly Ala Pro
                485                 490                 495

Ile Asp Phe Val Leu Thr Ser Gly His Asn Ala Gly Ile Val Ser
        500                 505                 510

Glu Pro Gly His Pro Gly Arg Ser Tyr Arg Leu Leu Thr Arg Glu Ala
    515                 520                 525

Asp Gly Ala Ala Leu Asp Pro Asp Ala Trp Leu Asp Ala Ala Pro Arg
530                 535                 540

His Glu Gly Ser Trp Trp Thr Ala Trp Gly Asp Trp Leu Ala Lys Leu
545                 550                 555                 560

Ser Gly Asn Ala Gly Thr Pro Pro Met Gly Ala Thr Asp Lys Gly
                565                 570                 575

Tyr Ala Pro Leu Ala Asp Ala Pro Gly His Phe Val Leu Glu Arg
            580                 585                 590

<210> SEQ ID NO 70
<211> LENGTH: 562
<212> TYPE: PRT
<213> ORGANISM: Rhodococcus ruber

<400> SEQUENCE: 70

Met Leu Asp His Val His Lys Lys Leu Lys Ser Thr Leu Asp Pro Ile
1               5                   10                  15

Gly Trp Gly Pro Ala Val Thr Ser Val Ala Gly Arg Ala Val Arg Asn
            20                  25                  30
```

```
Pro Gln Ala Val Thr Ala Ala Thr Ala Glu Tyr Ala Gly Arg Leu Ala
        35                  40                  45

Lys Ile Pro Ala Ala Ala Thr Arg Val Phe Asn Ala Asn Asp Pro Asp
50                      55                  60

Ala Pro Met Pro Val Asp Pro Arg Asp Arg Phe Ser Asp Thr Ala
65              70                  75                  80

Trp Gln Glu Asn Pro Ala Tyr Phe Ser Leu Leu Gln Ser Tyr Leu Ala
                85                  90                  95

Thr Arg Ala Tyr Val Glu Glu Leu Thr Glu Ala Gly Ser Gly Asp Pro
            100                 105                 110

Leu Gln Asp Gly Lys Ala Arg Gln Phe Ala Asn Leu Met Phe Asp Ala
            115                 120                 125

Leu Ala Pro Ser Asn Phe Leu Trp Asn Pro Gly Val Leu Thr Arg Ala
            130                 135                 140

Phe Glu Thr Gly Gly Ala Ser Leu Leu Arg Gly Ala Arg Tyr Ala Ala
145                 150                 155                 160

His Asp Ile Leu Asn Arg Gly Gly Leu Pro Leu Lys Val Asp Ser Asp
                165                 170                 175

Ala Phe Thr Val Gly Glu Asn Leu Ala Ala Thr Pro Gly Lys Val Val
            180                 185                 190

Phe Arg Asn Asp Leu Ile Glu Leu Ile Gln Tyr Ala Pro Gln Thr Glu
            195                 200                 205

Gln Val His Ala Val Pro Ile Leu Ala Ala Pro Pro Trp Ile Asn Lys
            210                 215                 220

Tyr Tyr Ile Leu Asp Leu Ala Pro Gly Arg Ser Leu Ala Glu Trp Ala
225                 230                 235                 240

Val Gln His Gly Arg Thr Val Phe Met Ile Ser Tyr Arg Asn Pro Asp
                245                 250                 255

Glu Ser Met Arg His Ile Thr Met Asp Asp Tyr Tyr Val Asp Gly Ile
            260                 265                 270

Ala Thr Ala Leu Asp Val Val Glu Glu Ile Thr Gly Ser Pro Lys Ile
            275                 280                 285

Glu Val Leu Ser Ile Cys Leu Gly Gly Ala Met Ala Ala Met Ala Ala
            290                 295                 300

Ala Arg Ala Phe Ala Val Gly Asp Lys Arg Val Ser Ala Phe Thr Met
305                 310                 315                 320

Leu Asn Thr Leu Leu Asp Tyr Ser Gln Val Gly Glu Leu Gly Leu Leu
                325                 330                 335

Thr Asp Pro Ala Thr Leu Asp Leu Val Glu Phe Arg Met Arg Gln Gln
            340                 345                 350

Gly Phe Leu Ser Gly Lys Glu Met Ala Gly Ser Phe Asp Met Ile Arg
            355                 360                 365

Ala Lys Asp Leu Val Phe Asn Tyr Trp Val Ser Arg Trp Met Lys Gly
            370                 375                 380

Glu Lys Pro Ala Ala Phe Asp Ile Leu Ala Trp Asn Glu Asp Ser Thr
385                 390                 395                 400

Ser Met Pro Ala Glu Met His Ser His Tyr Leu Arg Ser Leu Tyr Gly
                405                 410                 415

Arg Asn Glu Leu Ala Glu Gly Leu Tyr Val Leu Asp Gly Gln Pro Leu
            420                 425                 430

Asn Leu His Asp Ile Ala Cys Asp Thr Tyr Val Val Gly Ala Ile Asn
            435                 440                 445
```

```
Asp His Ile Val Pro Trp Thr Ser Ser Tyr Gln Ala Val Asn Leu Leu
    450                 455                 460

Gly Gly Asp Val Arg Tyr Val Leu Thr Asn Gly Gly His Val Ala Gly
465                 470                 475                 480

Ala Val Asn Pro Pro Gly Lys Arg Val Trp Phe Lys Ala Val Gly Ala
                485                 490                 495

Pro Asp Ala Glu Ser Gly Thr Pro Leu Pro Ala Asp Pro Gln Val Trp
                500                 505                 510

Asp Glu Ala Ala Thr Arg Tyr Glu His Ser Trp Trp Glu Asp Trp Thr
                515                 520                 525

Ala Trp Ser Asn Lys Arg Ala Gly Glu Leu Val Ala Pro Pro Ala Met
530                 535                 540

Gly Ser Thr Ala His Pro Pro Leu Glu Asp Ala Pro Gly Thr Tyr Val
545                 550                 555                 560

Phe Ser

<210> SEQ ID NO 71
<211> LENGTH: 610
<212> TYPE: PRT
<213> ORGANISM: Sinorhizobium fredii

<400> SEQUENCE: 71

Met Lys Thr Gly Asp Arg Pro Val Leu Ala Ala Asp Arg Ala Arg Gln
1               5                   10                  15

Ala Gly Ser Ala Arg Ala Ile Ala Ala Gln Ser Ala Leu Pro Cys Glu
                20                  25                  30

Asn Asp Gly Ala Asp Gly Glu Ala Phe Arg Ala Ile Asp Arg Met Arg
            35                  40                  45

Glu Ala Leu Ser Ala Thr Ala Thr Gly Gly Leu Ser Pro Ala Ala Leu
    50                  55                  60

Thr Leu Ala Phe Phe Asp Trp Ser Ile His Leu Ala Ser Ala Pro Gly
65                  70                  75                  80

Lys Arg Met Glu Leu Ala His Met Ala Ala Gln Asn Trp Gly Leu Leu
                85                  90                  95

Leu Thr Tyr Met Ala Ala Ala Ala Thr Arg Pro Asp Ala Pro Pro Cys
                100                 105                 110

Ile Glu Ala Leu Pro Gly Asp Asn Arg Phe Arg Ala Glu Gly Trp Gln
            115                 120                 125

Lys Gln Pro Tyr Thr Val Trp Ala Gln Ala Phe Leu Leu Gly Gln Gln
130                 135                 140

Trp Trp His Asn Val Thr Arg Asn Val Pro Gly Met Thr Pro His His
145                 150                 155                 160

Glu Asp Val Val Ser Phe Thr Ala Arg Gln Trp Leu Asp Val Phe Ser
                165                 170                 175

Pro Ser Asn Ile Pro Phe Ala Asn Pro Glu Val Ile His Lys Ala Met
                180                 185                 190

Glu Thr Gly Gly Ala Asn Phe Thr Gln Gly Phe Arg Asn Trp Leu Glu
            195                 200                 205

Asp Val Gly Arg Leu Ala Thr Lys Gln Arg Pro Val Gly Thr Glu Ala
    210                 215                 220

Phe Arg Val Gly His Asp Thr Ala Ala Thr Pro Gly Lys Val Val Tyr
225                 230                 235                 240

Arg Asn His Leu Ile Glu Leu Ile Gln Tyr Ala Pro Ala Thr Glu Glu
                245                 250                 255
```

Val Leu Ala Glu Pro Ile Leu Ile Val Pro Ala Trp Ile Met Lys Tyr
            260                 265                 270

Tyr Ile Leu Asp Leu Ser Pro His Asn Ser Leu Ile Arg Tyr Leu Val
            275                 280                 285

Ala Gln Gly His Thr Val Phe Cys Ile Ser Trp Arg Asn Pro Ser Ala
        290                 295                 300

Lys Asp Arg Asp Leu Thr Leu Asp Asp Tyr Arg Arg Leu Gly Ile Leu
305                 310                 315                 320

Ala Ala Leu Asp Ala Val Ser Ala Ile Val Pro Glu Arg Lys Ile His
                325                 330                 335

Ala Thr Gly Tyr Cys Leu Gly Gly Thr Leu Leu Ala Ile Ala Ala Ala
            340                 345                 350

Ala Met Ala Arg Thr Glu Asp Gln Arg Leu Ala Ser Val Thr Leu Phe
            355                 360                 365

Ala Ala Gln Thr Asp Phe Ser Glu Pro Gly Glu Leu Ala Leu Phe Ile
        370                 375                 380

Asp His Ser Gln Leu His Phe Leu Asp Ser Leu Met Trp His Ser Gly
385                 390                 395                 400

Cys Leu Ser Ala Asp Gln Met Ala Gly Ala Phe Gln Leu Leu Arg Thr
                405                 410                 415

Asn Asp Leu Val Trp Ser Arg Leu Val His Asp Tyr Leu Ile Gly Lys
            420                 425                 430

Arg Thr Pro Met Thr Asp Leu Met Ala Trp Asn Ala Asp Pro Thr His
            435                 440                 445

Met Pro Tyr Arg Met His Ala Glu Tyr Leu Gln Arg Leu Tyr Leu Asp
        450                 455                 460

Asn Glu Leu Ala Ala Gly Arg Phe Ile Val Asp Gly Arg Pro Ala His
465                 470                 475                 480

Leu Gln Asn Ile Arg Val Pro Met Phe Val Val Gly Thr Glu Arg Asp
                485                 490                 495

His Val Ala Pro Trp His Ser Val Tyr Lys Ile His Tyr Leu Thr Asp
            500                 505                 510

Thr Asp Val Thr Phe Val Leu Thr Ser Gly Gly His Asn Ala Gly Ile
        515                 520                 525

Val Ser Glu Pro Asp His Pro Gly Arg Gly Phe Arg Ile Ala Leu Thr
        530                 535                 540

Arg Glu Ser Asp Ser Ser Val Ser Ala Asp Glu Trp Val Ala Ala Ala
545                 550                 555                 560

Thr Ser Lys Asp Gly Ser Trp Trp Pro Asp Trp Val Glu Trp Leu Ala
                565                 570                 575

Gly His Ser Ala Pro Lys Arg Val Thr Pro Pro Val Ile Gly Ala Pro
            580                 585                 590

Glu Arg Gly Tyr Pro Pro Ile Asp Asp Ala Pro Gly Thr Tyr Val His
            595                 600                 605

Gln Arg
    610

<210> SEQ ID NO 72
<211> LENGTH: 589
<212> TYPE: PRT
<213> ORGANISM: Rubrivivax benzoatilyticus

<400> SEQUENCE: 72

Met His Asn Pro Asn Val Ala Ala Val Leu Ala Asp Pro Ala Leu
1               5                   10                  15

```
Asp Pro Ala Leu Ala Ala Ala Arg Arg Leu Asp Ser His Phe His Ala
         20                  25                  30

Ala Val Ala Pro Ala Phe Ser Gly Leu Ser Pro Ile Ser Leu Ala Leu
         35                  40                  45

Ala Trp Gln Asp Trp Ala Leu His Leu Ala Thr Gln Pro Ala Thr Ala
 50                  55                  60

Leu Ala Leu Val Ala Arg Ala Gln Gln Ser Trp Leu Gln Ala Trp Gly
 65                  70                  75                  80

Glu Met Leu Gly Gln Ala Glu Pro Gly Asn Gly Asp Ala Arg Phe Ala
                 85                  90                  95

Ala Pro Ala Trp Arg Gln Trp Pro Trp Ala Pro Val Val His Gly Trp
                100                 105                 110

His Ala Thr Glu Arg Trp Trp Gln Asp Ala Thr Asp Leu Arg Gly Val
            115                 120                 125

Asp Pro His His Arg Glu Val Val Arg Phe Phe Ala Arg Gln Trp Leu
130                 135                 140

Asp Met Leu Ala Pro Ser Asn Ala Gly Leu Ala Asn Pro Glu Val Leu
145                 150                 155                 160

Gln Arg Thr Ala Glu Arg Gly Gly Ala Asn Leu Val Asp Gly Thr Leu
                165                 170                 175

His Ala Leu Asp Gly Trp Arg Arg Gln His Gly Leu Glu Pro Leu Arg
            180                 185                 190

Thr Pro Glu Arg Arg Tyr Glu Pro Gly Val Asp Val Ala Val Thr Pro
        195                 200                 205

Gly Gln Val Val Trp Arg Asn His Leu Val Glu Leu Ile Gln Tyr Leu
    210                 215                 220

Pro Leu Thr Ala Ser Val Gln Ala Glu Pro Val Phe Ile Val Pro Ser
225                 230                 235                 240

Trp Ile Met Lys Tyr Tyr Ile Leu Asp Leu Ser Pro His Asn Ser Phe
                245                 250                 255

Val Lys Trp Leu Val Glu Gln Gly His Thr Val Phe Ile Leu Ser Trp
            260                 265                 270

Arg Asn Pro Asp Glu Ser Asp Ala Leu Leu Ala Met Gln Asp Tyr Leu
        275                 280                 285

Glu Leu Gly Ile Phe Asp Pro Leu Ala Gln Ile Ala Arg Met Ile Pro
    290                 295                 300

Gly Arg Arg Val His Ala Cys Gly Tyr Cys Leu Gly Gly Thr Leu Leu
305                 310                 315                 320

Ser Leu Ala Ala Ala Leu Ala Arg Pro Gly Arg Ile Ala Arg Ala
                325                 330                 335

Glu Leu Leu Pro Glu Leu Ala Ser Val Ser Leu Leu Ala Ala Glu Thr
            340                 345                 350

Asp Phe Thr Glu Pro Gly Glu Met Gly Val Leu Ile Asp Glu Ser Gln
        355                 360                 365

Val Thr Leu Leu Glu Asp Met Met Ala Glu Arg Gly Phe Leu Thr Gly
    370                 375                 380

Ala Gln Met Ala Gly Ser Phe Ala Tyr Leu His Ser Arg Asp Gln Val
385                 390                 395                 400

Trp Ser Arg Arg Leu Arg Glu Phe Trp Leu Gly Glu Pro Asp Ser Pro
                405                 410                 415

Asn Asp Leu Met Ala Trp Asn Asp Leu Thr Arg Met Pro Ala Ala
            420                 425                 430
```

```
Met His Ser Glu Tyr Leu Arg Arg Cys Tyr Leu Arg Asn Glu Ile Ala
            435                 440                 445

Glu Gly Arg Phe Pro Val Glu Gly Arg Ala Val Ser Leu Ser Asp Ile
450                 455                 460

Ala Ala Pro Met Phe Val Val Gly Thr Glu Lys Asp His Val Ser Pro
465                 470                 475                 480

Trp Lys Ser Val Tyr Lys Ile His Arg Leu Ala Asp Thr Thr Ile Thr
                485                 490                 495

Phe Val Leu Thr Ser Gly Gly His Asn Ala Gly Ile Val Ser Glu Pro
            500                 505                 510

Gly His Ala Asn Arg Arg Tyr Arg Met Ala Thr Arg Glu Val Asp Gly
        515                 520                 525

Ala Trp Val Asp Pro Glu Ala Trp Ala Glu Gln Ala Pro Arg His Glu
530                 535                 540

Gly Ser Trp Trp Thr Ala Trp His Glu Trp Leu Leu Ala Gln Gly Ser
545                 550                 555                 560

Gly Glu Thr Ala Lys Ala Arg Thr Pro Ala Lys Ala Asp Val Val Cys
                565                 570                 575

Ala Ala Pro Gly Thr Tyr Val Tyr Gln Cys Trp Arg Asp
            580                 585

<210> SEQ ID NO 73
<211> LENGTH: 583
<212> TYPE: PRT
<213> ORGANISM: Parvibaculum lavamentivorans

<400> SEQUENCE: 73

Met Thr Lys Asn Lys Lys Gly Asn Thr Ser Thr Ile Val Pro Ala
 1               5                  10                  15

Leu Asp Met Gln Ala His Met Ala Trp Ala Gln Ala Trp Ser Ser Ile
                20                  25                  30

Ser Pro Glu Ser Ser Leu Leu Ala Trp Thr Asp Trp Ala Ser His Leu
            35                  40                  45

Ala Asn Ser Pro Gly Lys Gln Ser Glu Leu Leu Ala Phe Ala Gly Ser
50                  55                  60

Leu Ser Glu Gln Trp Met Ser Leu Leu Lys Lys Ser Leu Val Ser Pro
65                  70                  75                  80

Asp Gln Glu Val Ala Ser Pro Glu Pro Ser Pro Thr Asn Asp Arg Arg
                85                  90                  95

Phe Asn Asp Pro Ala Trp Asp Gln Trp Pro Tyr Asn Leu Phe Arg Ser
            100                 105                 110

Ser Phe Leu Ile Gln Ser Lys Trp Trp Glu Gln Ala Thr Gln Gly Val
        115                 120                 125

Trp Gly Val Asp Pro Gln His Glu Arg Leu Leu Ala Phe Gly Ala Lys
    130                 135                 140

Gln Trp Leu Glu Met Val Ser Pro Thr Asn Ser Ala Leu Phe Asn Pro
145                 150                 155                 160

Val Val Leu Lys Lys Thr Ile Glu Glu Gln Gly Ala Asn Leu Ala Arg
                165                 170                 175

Gly Met Ser Asn Phe Leu Asp Asp Leu Arg Arg Gln Leu Ser Gly Glu
            180                 185                 190

Pro Pro Ala Gly Thr Glu Asn Phe Val Val Gly Arg Asp Val Ala Val
        195                 200                 205

Thr Glu Gly Lys Val Val Leu Arg Asn Gln Leu Ile Glu Leu Ile Gln
    210                 215                 220
```

Tyr Thr Pro Thr Thr Glu Lys Val His Pro Glu Pro Ile Leu Ile Ile
225                 230                 235                 240

Pro Ala Trp Ile Met Lys Tyr Tyr Val Leu Asp Leu Ser Pro His Asn
            245                 250                 255

Ser Leu Ile Arg Tyr Leu Val Ala Gln Gly His Thr Val Phe Cys Ile
        260                 265                 270

Ser Trp Lys Asn Pro Asp Ala Gly Asp Arg Asp Leu Gly Met Asp Glu
        275                 280                 285

Tyr Leu Glu Phe Gly Leu Arg Ala Ala Leu Asp Ala Val Thr Ser Ile
    290                 295                 300

Val Pro Glu Gln Gly Ile His Ala Ala Gly Tyr Cys Leu Gly Gly Thr
305                 310                 315                 320

Leu Leu Ala Ile Gly Ala Ser Ala Met Ala Arg Asp Gly Asp Thr Arg
            325                 330                 335

Leu Val Ser Val Ser Leu Leu Ala Ala Gln Thr Asp Phe Ser Glu Pro
        340                 345                 350

Gly Glu Leu Ser Leu Phe Ile Asn Glu Ser Gln Val Ala Leu Leu Glu
        355                 360                 365

Ala Ser Met Ala Gln Thr Gly Tyr Leu Thr Ser Asp Gln Met Ser Gly
    370                 375                 380

Ala Phe Gln Leu Leu Arg Ser Tyr Asp Leu Ile Trp Ser Arg Met Ile
385                 390                 395                 400

Asp Glu Tyr Leu Leu Gly Asp Arg Arg Pro Met Thr Asp Leu Met Ala
            405                 410                 415

Trp Asn Ala Asp Gly Thr Arg Leu Pro Ala Lys Met His Ser Gln Tyr
        420                 425                 430

Leu Arg Arg Leu Tyr Leu Asn Asn Asp Leu Ser Ala Gly Arg Tyr Pro
    435                 440                 445

Val Thr Gly Arg Pro Val Ser Val Gly Asp Ile Ala Val Pro Val Phe
450                 455                 460

Cys Val Gly Thr Ala Ser Asp His Ile Ala Pro Trp Arg Ser Val Tyr
465                 470                 475                 480

Lys Leu His Leu Leu Ser Ser Ala Glu Leu Thr Phe Val Leu Thr Thr
            485                 490                 495

Gly Gly His Asn Gly Gly Ile Val Ser Glu Pro Gly Arg Gly Lys Arg
        500                 505                 510

Gln Tyr Gln Ile His Thr Arg Ala Ala Gly Asp Gly Tyr Met Ala Pro
    515                 520                 525

Asp Glu Trp Gln Ala Thr Ala Gln Thr His Leu Asp Ser Trp Trp Pro
    530                 535                 540

Ala Trp Ser Ala Trp Leu Arg Glu Arg Ser Gly Glu Gly Val Ala Pro
545                 550                 555                 560

Pro Leu Met Gly Ala Glu Ser Arg Gly Tyr Pro Thr Ile Cys Asp Ala
            565                 570                 575

Pro Gly Lys Tyr Val Arg Ser
            580

<210> SEQ ID NO 74
<211> LENGTH: 597
<212> TYPE: PRT
<213> ORGANISM: Burkholderia mallei

<400> SEQUENCE: 74

Met Asp Thr Arg His Ala Pro Glu Ser Gly Ala Pro Asp Ala Pro Leu

-continued

```
            1               5              10              15
          Pro Ala His Pro Pro Ala Ser Tyr Ala Pro Glu Ser Pro Tyr Arg Ile
                          20                  25                  30

Phe Asp Leu Ala Lys Glu Ala Ser Val Ala Lys Leu Thr Ser Gly Leu
                          35                  40                  45

Ser Pro Ala Ser Leu Gln Leu Ala Leu Ala Asp Trp Leu Ile His Leu
                  50                  55                  60

Ala Ala Ala Pro Gly Lys Arg Ala Glu Leu Ala Thr Leu Ala Leu Arg
          65                  70                  75                  80

His Ala Ala Leu Leu Gly Gln Tyr Leu Leu Glu Ala Ala Thr Gly Arg
                          85                  90                  95

Thr Pro Ala Ala Pro Ala Gln Pro Ser Pro Gly Asp Arg Arg Phe Arg
                          100                 105                 110

Ala Gly Ala Trp Gln Leu Glu Pro Tyr Arg Phe Trp His Gln Ser Phe
                          115                 120                 125

Leu Leu Ala Glu Gln Trp Trp Arg Ala Ala Thr Arg Asp Val Pro Gly
                          130                 135                 140

Val Ser Pro His His Glu Asp Val Val Ala Phe Ser Ala Arg Gln Met
          145                 150                 155                 160

Leu Asp Thr Phe Ala Pro Ala Asn Tyr Val Ala Thr Asn Pro Glu Ile
                          165                 170                 175

Ala Gln Arg Thr Ala Leu Thr Gly Gly Ala Asn Leu Ala Gln Gly Val
                          180                 185                 190

Trp Asn Tyr Leu Asp Asp Val Arg Arg Leu Ile Thr Lys Gln Pro Pro
                          195                 200                 205

Ala Gly Ala Glu Gln Phe Glu Leu Gly Arg Asn Leu Ala Thr Thr Pro
                          210                 215                 220

Gly Arg Val Val Phe Arg Asn His Leu Ile Glu Leu Leu Gln Tyr Ser
          225                 230                 235                 240

Pro Thr Thr Pro Asp Val Tyr Ala Gln Pro Val Leu Ile Val Pro Ala
                          245                 250                 255

Trp Ile Met Lys Tyr Tyr Ile Leu Asp Leu Ser Ala His Asn Ser Leu
                          260                 265                 270

Ile Arg Tyr Leu Val Gly Glu Gly His Thr Val Phe Cys Ile Ser Trp
                          275                 280                 285

Arg Asn Val Asp Ala Ser Asp Arg Asp Leu Ser Leu Asp Asp Tyr Arg
                          290                 295                 300

Lys Leu Gly Val Met Asp Ala Leu Asp Thr Ile Gly Ala Ile Val Pro
          305                 310                 315                 320

Gly Glu Lys Ile His Ala Thr Gly Tyr Cys Leu Gly Gly Thr Leu Leu
                          325                 330                 335

Ser Ile Ala Ala Ala Met Ala Asn Thr Gly Asp Asp Arg Leu Ala
                          340                 345                 350

Ser Ile Thr Leu Leu Ala Ala Gln Thr Asp Phe Ala Glu Pro Gly Glu
                          355                 360                 365

Leu Gln Leu Phe Ile Asp Asp Ser Glu Ile His Phe Leu Glu Ser Met
                          370                 375                 380

Met Trp Glu Arg Gly Tyr Leu Gly Ala His Gln Met Ala Gly Ser Phe
          385                 390                 395                 400

Gln Leu Leu Met Ser Asn Asp Leu Ile Trp Ser Arg Val Ile His Asp
                          405                 410                 415

Tyr Leu Leu Gly Glu Arg Thr Pro Met Ile Asp Leu Met Ala Trp Asn
                          420                 425                 430
```

Ala Asp Ser Thr Arg Met Pro Tyr Arg Met His Ser Glu Tyr Leu Arg
            435                 440                 445

His Leu Phe Leu Asp Asn Asp Leu Ala Thr Asn Arg Tyr Val Ile Asp
        450                 455                 460

Gly Gln Thr Val Ser Val His Asn Ile Arg Ala Pro Phe Phe Val Val
465                 470                 475                 480

Gly Thr Glu His Asp His Ile Ala Pro Trp Arg Ser Val Tyr Lys Ile
                485                 490                 495

His Tyr Leu Ser Gly Ser Asp Val Thr Phe Val Leu Thr Ala Gly Gly
                500                 505                 510

His Asn Ala Gly Ile Val Ser Glu Pro Gly His Ala Lys Arg His Tyr
            515                 520                 525

Arg Met Lys Met Thr Ala Ala Ala Pro Ser Ile Ser Pro Asp Glu
        530                 535                 540

Trp Leu Ala Gly Ala Thr Asp Phe Glu Gly Ser Trp Pro Ala Trp
545                 550                 555                 560

His Ala Trp Leu Ala Arg His Ser Ser Pro Gln Arg Val Ala Pro Pro
                565                 570                 575

Pro Leu Gly Lys Pro Gly Ala His Thr Leu Gly Asp Ala Pro Gly Thr
            580                 585                 590

Tyr Val Phe Gln Lys
        595

<210> SEQ ID NO 75
<211> LENGTH: 588
<212> TYPE: PRT
<213> ORGANISM: Bradyrhizobium sp.

<400> SEQUENCE: 75

Met Ser Asp Ala Lys Ser Ala Ala Glu Asp Ala Asn Ser Val Ala Arg
1               5                   10                  15

Glu Phe Val Arg Glu Asp His Glu Leu Asp Lys Ala Phe Ser Ala Val
            20                  25                  30

Leu Ala Arg Leu Thr Gly Gly Ile Ser Pro Ala Ala Leu Ser Met Ala
        35                  40                  45

Tyr Leu Asp Trp Ala Cys His Leu Ala Ala Pro Gln Arg Gln Leu
    50                  55                  60

Asp Ile Ala Arg Asp Ala Trp Gln Gly Ala Arg Gln Leu Ala Glu Arg
65                  70                  75                  80

Ser Leu His Phe Ala Asp Ser Asn Arg Val Pro Trp Asp Leu Ile Lys
                85                  90                  95

Pro Gln Ala Asn Asp His Arg Phe Ser Lys Pro Gln Trp Gly Met Gln
            100                 105                 110

Pro Phe Asn Leu Phe Ala Gln Ala Phe Leu Leu Gly Glu Asp Trp Trp
        115                 120                 125

His Lys Ala Thr Thr Asn Ile Arg Gly Val Asp Pro Ala Asn Glu Ala
    130                 135                 140

Val Val Asp Phe Ser Leu Arg Gln Leu Leu Asp Met Phe Ala Pro Ser
145                 150                 155                 160

Asn Phe Ala Ala Thr Asn Pro Glu Val Val Glu Lys Ile Phe Gln Ser
                165                 170                 175

Gly Gly Glu Asn Leu Val Phe Gly Trp Gln Asn Trp Leu Ser Asp Leu
            180                 185                 190

Met Gln Val Leu Gln Pro Gly Gln Ala Ser Arg Ser Ala Glu Phe Val

```
            195                 200                 205
Pro Gly Glu Thr Val Ala Thr Ala Pro Gly Lys Val Val Phe Arg Asn
210                 215                 220

Gln Leu Ile Glu Leu Ile Gln Tyr Ala Pro Thr Thr Ala Glu Val Arg
225                 230                 235                 240

Pro Glu Pro Ile Leu Ile Val Pro Ala Trp Ile Met Lys Tyr Tyr Ile
                245                 250                 255

Leu Asp Leu Ser Gln His Asn Ser Leu Val Arg Tyr Leu Thr Asp Gln
            260                 265                 270

Gly Phe Thr Val Phe Met Ile Ser Trp Arg Asn Pro Asp Ala Lys Asp
        275                 280                 285

Arg Asp Ile Ala Phe Asp Asp Tyr Arg Ser Met Gly Val Met Ala Ala
        290                 295                 300

Leu Ser Glu Ile Gly Lys Ile Val Pro Gly Ala Gln Ile His Ala Ala
305                 310                 315                 320

Gly Tyr Cys Leu Gly Gly Thr Leu Leu Ser Ile Thr Ala Ala Ala Met
                325                 330                 335

Ala Arg Glu Gly Asp Thr Arg Leu Lys Thr Ile Thr Leu Phe Ala Ala
            340                 345                 350

Gln Thr Asp Phe Thr Glu Ala Gly Glu Leu Thr Leu Phe Ile Asn Glu
        355                 360                 365

Ser Gln Val Ala Phe Leu Glu Asp Met Met Trp Glu Arg Gly Tyr Leu
    370                 375                 380

Asp Thr Thr Gln Met Ala Gly Ala Phe Gln Leu Leu Arg Ser Asn Asp
385                 390                 395                 400

Leu Ile Trp Ser Arg Val Ser Arg Asp Tyr Leu Leu Gly Glu Arg Ala
                405                 410                 415

His Pro Ser Asp Leu Met Ala Trp Asn Ala Asp Ala Thr Arg Leu Pro
            420                 425                 430

Tyr Arg Met His Ser Glu Tyr Leu Arg Lys Leu Phe Leu Asn Asn Asp
        435                 440                 445

Leu Ala Glu Gly Arg Tyr Arg Val Glu Gly Lys Pro Val Ser Leu Ser
    450                 455                 460

Asp Ile His Thr Pro Met Phe Val Val Gly Thr Leu Arg Asp His Val
465                 470                 475                 480

Ala Pro Trp Lys Ser Thr Tyr Lys Ile His Tyr Glu Val Asp Ala Asp
                485                 490                 495

Val Thr Phe Val Leu Ala Ser Gly His Asn Ala Gly Ile Val Ala
            500                 505                 510

Pro Pro His Glu Gln Gly His Ser His Gln Val Arg Thr Lys Ala Ala
        515                 520                 525

Asp Ala Pro Tyr Leu Gly Pro Asp Glu Trp Gln Ser Thr Ser Pro Arg
    530                 535                 540

Ile Glu Gly Ser Trp Trp Pro Thr Trp Leu Asp Trp Leu Ala Gln Arg
545                 550                 555                 560

Ser Gly Pro Leu Asp Ala Pro Pro Arg Leu Gly Thr Glu Gly Ser His
                565                 570                 575

Glu Leu Gly Asn Ala Pro Gly Glu Tyr Val His Ser
            580                 585

<210> SEQ ID NO 76
<211> LENGTH: 599
<212> TYPE: PRT
<213> ORGANISM: Acidiphilium sp. PM
```

<400> SEQUENCE: 76

Met Ala Glu Gln Gln Asn Pro Arg Thr Glu Pro Asn Leu Pro Asp
1               5                   10                  15

Pro Ala Ala Phe Ser Arg Thr Met Ala Asp Ile Ala Ala Arg Ser Gln
            20                  25                  30

Arg Ile Val Ala Glu Trp Leu Gln Arg Gln His Glu Ala Asp Val Ala
        35                  40                  45

Ile Asp Pro Leu Asn Ile Gly Ser Ala Phe Met Glu Met Met Ala Arg
    50                  55                  60

Leu Met Ala Asn Pro Ala Ser Leu Ile Glu Ala Gln Ile Gly Phe Trp
65                  70                  75                  80

Gln Asp Tyr Val Thr Leu Trp Gln His Ser Thr Arg Arg Ile Met Gly
            85                  90                  95

Ile Glu Thr Gln Pro Val Val Pro Asp Pro Arg Asp Lys Arg Phe
        100                 105                 110

Gln His Glu Glu Trp Lys Glu Asn Glu Ile Phe Asp Phe Ile Arg Gln
    115                 120                 125

Ser Tyr Leu Leu Ser Ala Arg Phe Val Gln Asp Val Val Arg Arg Val
130                 135                 140

Asp Gly Leu Asp Pro Lys Thr Ala Gln Lys Val Asp Phe Tyr Ala Arg
145                 150                 155                 160

Gln Phe Val Asp Ala Met Ser Pro Ser Asn Phe Ala Leu Thr Asn Pro
            165                 170                 175

Gln Val Leu Arg Lys Thr Ala Glu Thr Gly Gly Glu Asn Leu Leu Arg
        180                 185                 190

Gly Leu Ser Asn Leu Leu Arg Asp Leu Glu Ala Gly Arg Gly Gln Leu
    195                 200                 205

His Ile Arg Met Thr Asp Ala Glu Ala Phe Ser Val Gly Gly Asn Ile
    210                 215                 220

Ala Val Thr Pro Gly Lys Val Val Tyr Arg Asn Glu Leu Met Glu Leu
225                 230                 235                 240

Ile Gln Tyr Ala Pro Ala Thr Thr Thr Ala His Lys Thr Pro Leu Val
            245                 250                 255

Ile Phe Pro Pro Trp Ile Asn Lys Phe Tyr Ile Leu Asp Leu Arg Pro
        260                 265                 270

Lys Asn Ser Phe Ile Arg Trp Ala Val Glu Gln Gly His Thr Val Phe
    275                 280                 285

Val Ala Ser Trp Val Asn Pro Asp Glu Arg Leu Ala Glu Lys Asp Phe
290                 295                 300

Ala Asp Tyr Met Lys Leu Gly Val Phe Ala Ala Leu Asp Ala Ile Glu
305                 310                 315                 320

Gln Ala Thr Gly Glu Arg Gln Val Asn Ala Ile Gly Tyr Cys Leu Gly
            325                 330                 335

Gly Thr Leu Leu Ala Ala Thr Leu Ala Val Met Ala Arg Arg Asp
        340                 345                 350

Ser Arg Ile Lys Ser Ala Thr Phe Leu Val Thr Leu Thr Asp Phe Ala
    355                 360                 365

Asp Val Gly Glu Leu Gly Val Phe Ile Asp Glu Gln Leu Ala Ala
    370                 375                 380

Leu Glu Asp Arg Met Asn Arg Arg Gly Tyr Leu Glu Gly Ser Ala Met
385                 390                 395                 400

Ala Thr Thr Phe Asn Met Leu Arg Ser Asn Asp Leu Ile Trp Ser Phe

```
            405                 410                 415
Val Val Asn Asn Tyr Leu Leu Gly Asn Glu Thr Phe Pro Phe Asp Leu
            420                 425                 430

Leu Tyr Trp Asn Ser Asp Ser Thr Arg Met Pro Ala Ala Met His Ser
            435                 440                 445

Phe Tyr Leu Arg Asn Met Tyr Gln Lys Asn Leu Leu Ser Gln Ala Asp
            450                 455                 460

Ala Ile Thr Leu Asp Gly Thr Pro Val Asp Leu Arg Arg Ile Lys Val
465                 470                 475                 480

Pro Val Tyr Phe Leu Ser Cys Arg Glu Asp His Ile Ala Pro Trp Ala
                485                 490                 495

Ser Thr Tyr Arg Ala Thr Gln Leu Met Ala Gly Pro Lys Arg Phe Val
                500                 505                 510

Leu Ala Ala Ser Gly His Ile Ala Gly Val Ile Asn Pro Pro Gly Ser
                515                 520                 525

Gly Lys Tyr Asn His Phe Val Asn Ala Thr Leu Pro Ala Asn Ala Glu
        530                 535                 540

Asp Trp Phe Ala Gly Ala Thr Glu Val Ala Gly Ser Trp Trp Pro Asp
545                 550                 555                 560

Trp Gln Arg Trp Ile Ala Ala Gln Gly Arg Gly Glu Val Pro Ala Arg
                    565                 570                 575

Thr Pro Gly Asp Gly Ala Leu Pro Ala Leu Asp Ala Pro Gly Asp
                580                 585                 590

Tyr Val Lys Val Arg Ser Ala
            595

<210> SEQ ID NO 77
<211> LENGTH: 393
<212> TYPE: PRT
<213> ORGANISM: Burkholderia pseudomallei

<400> SEQUENCE: 77

Met Thr Asp Val Val Ile Val Ser Ala Ala Arg Thr Ala Val Gly Lys
1               5                   10                  15

Phe Gly Gly Ser Leu Ala Lys Ile Ala Ala Pro Glu Leu Gly Ala Ser
                20                  25                  30

Val Ile Arg Ala Val Leu Glu Arg Ala Gly Val Lys Pro Glu Gln Val
            35                  40                  45

Ser Glu Val Ile Leu Gly Gln Val Leu Thr Ala Gly Ser Gly Gln Asn
        50                  55                  60

Pro Ala Arg Gln Ala Leu Ile Ala Ala Gly Leu Pro Asn Ala Val Pro
65                  70                  75                  80

Gly Met Thr Ile Asn Lys Val Cys Gly Ser Gly Leu Lys Ala Val Met
                85                  90                  95

Leu Ala Ala Asn Ala Val Val Ala Gly Asp Ala Glu Ile Val Val Ala
                100                 105                 110

Gly Gly Gln Glu Asn Met Ser Ala Ala Pro His Val Leu Pro Gly Ser
            115                 120                 125

Arg Asp Gly Phe Arg Met Gly Asp Ala Lys Leu Val Asp Ser Met Ile
        130                 135                 140

Val Asp Gly Leu Trp Asp Val Tyr Asn Lys Tyr His Met Gly Ile Thr
145                 150                 155                 160

Ala Glu Asn Val Ala Lys Glu Tyr Gly Ile Thr Arg Glu Ala Gln Asp
                165                 170                 175
```

```
Gln Phe Ala Ala Leu Ser Gln Asn Lys Ala Glu Ala Ala Gln Lys Ala
            180                 185                 190

Gly Arg Phe Asp Asp Glu Ile Val Pro Ile Glu Ile Pro Gln Arg Lys
        195                 200                 205

Gly Glu Pro Leu Arg Phe Ala Thr Asp Glu Phe Val Arg His Gly Val
    210                 215                 220

Thr Ala Glu Ser Leu Ala Ser Leu Lys Pro Ala Phe Ala Lys Glu Gly
225                 230                 235                 240

Thr Val Thr Ala Ala Asn Ala Ser Gly Ile Asn Asp Gly Ala Ala Ala
                245                 250                 255

Val Leu Val Met Ser Ala Lys Lys Ala Glu Ala Leu Gly Leu Glu Pro
            260                 265                 270

Leu Ala Arg Ile Lys Ala Tyr Ala Asn Ala Gly Val Asp Pro Ser Val
        275                 280                 285

Met Gly Met Gly Pro Val Pro Ala Ser Arg Arg Cys Leu Glu Arg Ala
    290                 295                 300

Gly Trp Ser Val Gly Asp Leu Asp Leu Met Glu Ile Asn Glu Ala Phe
305                 310                 315                 320

Ala Ala Gln Ala Leu Ala Val His Lys Gln Met Gly Trp Asp Thr Ser
                325                 330                 335

Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Leu Lys
        355                 360                 365

Arg Asp Ala Lys Arg Gly Leu Ala Ser Leu Cys Ile Gly Gly Met
    370                 375                 380

Gly Val Ala Leu Ala Leu Glu Arg Pro
385                 390

<210> SEQ ID NO 78
<211> LENGTH: 391
<212> TYPE: PRT
<213> ORGANISM: Methylosinus trichosporium

<400> SEQUENCE: 78

Met Thr Thr Glu Ile Val Ile Val Ser Ala Ala Arg Thr Ala Val Gly
1               5                   10                  15

Ser Phe Asn Gly Ala Phe Gly Ala Thr Pro Ala His Glu Leu Gly Ala
            20                  25                  30

Val Ala Val Lys Ala Ala Ile Glu Arg Ala Gly Leu Ala Pro Ala Asp
        35                  40                  45

Ile Asp Glu Val Ile Leu Gly Gln Val Leu Gly Ala Ala Gln Gly Gln
    50                  55                  60

Asn Pro Ala Arg Gln Ala Ala Ile Lys Ala Gly Val Pro Gln Glu Lys
65                  70                  75                  80

Thr Ala Phe Gly Ile Asn Gln Val Cys Gly Ser Gly Leu Arg Ala Val
                85                  90                  95

Ala Leu Ala Ala Gln Gln Ile Gln Ala Gly Asp Ala Ser Val Ile Val
            100                 105                 110

Ala Gly Gly Gln Glu Ser Met Ser Leu Ser Gln His Ser Ala His Met
        115                 120                 125

Arg Ala Gly Thr Lys Met Gly Asp Val Lys Phe Val Asp Thr Met Ile
    130                 135                 140

Val Asp Gly Leu Thr Asp Ala Phe Asn Asn Tyr His Met Gly Ile Thr
145                 150                 155                 160
```

```
Ala Glu Asn Val Ala Ala Lys Trp Gln Ile Ser Arg Ala Glu Gln Asp
            165                 170                 175

Ala Phe Ala Val Ala Ser Gln Asn Lys Ala Glu Ala Ala Gln Lys Ala
            180                 185                 190

Gly Lys Phe Lys Asp Glu Ile Val Pro Phe Thr Val Ser Thr Arg Lys
            195                 200                 205

Gly Asp Val Ile Val Asp Gln Asp Glu Tyr Ile Lys His Gly Val Thr
            210                 215                 220

Leu Glu Gly Val Ala Lys Leu Lys Pro Ala Phe Thr Lys Glu Gly Thr
225                 230                 235                 240

Val Thr Ala Ala Asn Ala Ser Gly Leu Asn Asp Gly Ala Ala Ala Leu
            245                 250                 255

Val Val Met Ser Ala Ala Glu Ala Arg Arg Gly Leu Thr Pro Leu
            260                 265                 270

Ala Arg Ile Ala Ser Trp Ala Thr Ala Gly Val Asp Pro Ser Val Met
            275                 280                 285

Gly Ser Gly Pro Ile Pro Ala Ser Arg Lys Ala Leu Glu Lys Ala Gly
            290                 295                 300

Trp Lys Ile Gly Asp Leu Asp Leu Val Glu Ala Asn Glu Ala Phe Ala
305                 310                 315                 320

Ala Gln Ala Leu Ala Val Asn Lys Asp Leu Gly Trp Asp Pro Ala Ile
            325                 330                 335

Val Asn Val Asn Gly Gly Ala Ile Ala Ile Gly His Pro Ile Gly Ala
            340                 345                 350

Ser Gly Ala Arg Val Leu Thr Thr Leu Leu Tyr Glu Leu Ala Arg Arg
            355                 360                 365

Gly Gly Lys Arg Gly Leu Ala Thr Leu Cys Ile Gly Gly Gly Met Gly
            370                 375                 380

Val Ala Leu Thr Ile Glu Arg
385                 390

<210> SEQ ID NO 79
<211> LENGTH: 396
<212> TYPE: PRT
<213> ORGANISM: Methylosinus trichosporium

<400> SEQUENCE: 79

Met Ser Ala Val Asp Pro Ile Val Ile Val Gly Ala Ala Arg Thr Pro
1               5                   10                  15

Ile Gly Ala Leu Leu Gly Glu Leu Lys Asn Ala Thr Ala Pro Gln Leu
            20                  25                  30

Gly Ala Ala Ala Ile Arg Ala Ala Thr Glu Arg Ala Gly Leu Ala Pro
            35                  40                  45

Glu Arg Val Asp Asp Val Leu Met Gly Cys Val Leu Ser Ala Gly Leu
        50                  55                  60

Gly Gln Ala Pro Ala Arg Gln Ala Leu Gly Ala Gly Leu Ala Asp
65                  70                  75                  80

Thr Thr Gly Cys Val Thr Ile Asn Lys Met Cys Gly Ser Gly Met Lys
            85                  90                  95

Ala Leu Met Leu Ala His Asp Gln Leu Leu Ala Gly Ser Ser Arg Ala
            100                 105                 110

Ile Val Ala Gly Gly Met Glu Ser Met Ser Asn Ala Pro Tyr Leu Leu
            115                 120                 125

Gly Arg Ala Arg Val Gly Tyr Arg Met Gly His Gly Arg Leu Ile Asp
```

```
            130                 135                 140
His Met Phe Leu Asp Gly Leu Glu Asp Ala Tyr Asp Glu Gly Lys Leu
145                 150                 155                 160

Met Gly Ala Phe Ala Glu Asp Cys Ala Thr Thr His Gln Phe Thr Arg
                165                 170                 175

Glu Lys Gln Asp Asp Tyr Ala Thr Ala Ser Leu Arg Arg Ala Gln Gln
            180                 185                 190

Ala Ala Ala Ser Gly Ala Phe Asp Trp Glu Thr Thr Pro Val Ala Thr
        195                 200                 205

His Asp Arg Lys Thr Ser Ala Thr Val Thr Arg Asp Glu Leu Pro Ala
    210                 215                 220

Ser Ala Lys Ile Glu Asn Ile Ala Ser Leu Lys Pro Ala Phe Arg Asp
225                 230                 235                 240

Gly Gly Thr Val Thr Ala Ala Asn Ser Ser Ala Ile Ser Asp Gly Ala
                245                 250                 255

Ala Ala Leu Ala Leu Met Arg Arg Ser Glu Ala Glu Arg Ala Ser Leu
            260                 265                 270

Ala Pro Leu Ala Ile Val Arg Ala His Ala Thr His Ala Gly Pro Pro
        275                 280                 285

His Leu Phe Pro Ile Ala Pro Ile Gly Ala Ile Ala Lys Leu Cys Glu
    290                 295                 300

Arg Ala Gly Trp Pro Leu Thr Ser Val Asp Leu Phe Glu Ile Asn Glu
305                 310                 315                 320

Ala Phe Ala Val Val Leu Ala Ala Met Arg Glu Leu Tyr Leu Pro
                325                 330                 335

His Glu Lys Val Asn Val His Gly Gly Ala Cys Ala Leu Gly His Pro
            340                 345                 350

Ile Gly Ala Ser Gly Ala Arg Ile Val Val Thr Leu Leu Ala Ala Leu
        355                 360                 365

Arg Lys Tyr Asp Leu Arg Arg Gly Val Ala Ala Leu Cys Ile Gly Gly
    370                 375                 380

Gly Glu Ala Thr Ala Met Ala Ile Glu Thr Ile Val
385                 390                 395

<210> SEQ ID NO 80
<211> LENGTH: 402
<212> TYPE: PRT
<213> ORGANISM: Methylosinus trichosporium

<400> SEQUENCE: 80

Met Pro Glu Ala Tyr Ile Tyr Asp Ala Val Arg Thr Pro Arg Gly Arg
1               5                   10                  15

Gly Lys Pro Asn Gly Ser Leu His Glu Val Ser Ser Leu Gly Leu Ala
            20                  25                  30

Val Ala Ala Leu Ser Ala Leu Lys Gln Arg Asn Arg Leu Asp Gly Ala
        35                  40                  45

Pro Val Asp Asp Val Ile Leu Gly Cys Val Asp Pro Val Gly Glu Ala
    50                  55                  60

Gly Gly Asp Ile Ala Arg Ala Ala Ile Ala Ser Gly Phe Gly Tyr
65                  70                  75                  80

Glu Val Pro Gly Val Gln Ile Asn Arg Phe Cys Ala Ser Gly Leu Asp
                85                  90                  95

Ala Val Asn Phe Ala Ala Gln Ile Met Ser Gly Gln His Glu Leu
            100                 105                 110
```

Thr Ile Gly Gly Gly Val Glu Ser Met Ser Arg Val Gly Ile Gly Ala
            115                 120                 125

Ser Gly Gly Ala Trp Pro Ala Asp Pro Ala Ile Ala Ile Pro Ser Tyr
130                 135                 140

Phe Met Pro Gln Gly Val Ser Ala Asp Leu Ile Ala Thr Lys Tyr Gly
145                 150                 155                 160

Phe Ser Arg Asn Asp Val Asp Ala Tyr Ala Met Gln Ser Gln Gln Arg
                165                 170                 175

Ala Ala Arg Ala Trp Glu Glu Gln Arg Phe Ala Arg Ser Val Thr Pro
            180                 185                 190

Val Lys Asp Val Asn Gly Leu Thr Ile Leu Asp His Asp Glu His Met
        195                 200                 205

Arg Pro Ser Thr Asp Met Gln Ser Leu Gly Ala Leu Lys Pro Ala Phe
210                 215                 220

Ala Phe Leu Ala Glu Gln Ala Gly Phe Asp Ala Val Ala Ile Gln Ala
225                 230                 235                 240

His Pro Asp Val Glu Lys Ile Asn Tyr Val His His Ala Gly Asn Ser
                245                 250                 255

Ser Gly Ile Val Asp Gly Ala Ala Val Leu Leu Gly Ser Lys Glu
            260                 265                 270

Ala Gly Glu Lys Ala Gly Leu Thr Pro Arg Ala Arg Ile Arg Ala Phe
    275                 280                 285

Ala Asn Ile Gly Ser Glu Pro Ala Leu Met Leu Thr Gly Pro Val Asp
290                 295                 300

Val Thr Lys Lys Leu Leu Ala Lys Ala Gly Met Thr Phe Gly Asp Ile
305                 310                 315                 320

Asp Leu Val Glu Val Asn Glu Ala Phe Ala Ala Val Val Leu Arg Phe
                325                 330                 335

Leu Gln Ala Phe Ser Leu Asp Asp Ser Lys Val Asn Val Asn Gly Gly
            340                 345                 350

Ala Ile Ala Leu Gly His Pro Leu Gly Ala Thr Gly Ala Met Leu Val
        355                 360                 365

Gly Thr Ala Leu Asp Glu Leu Glu Arg Ser Lys Gly Val Ala Leu
370                 375                 380

Val Thr Leu Cys Ile Gly Ala Gly Met Gly Thr Ala Thr Ile Ile Glu
385                 390                 395                 400

Arg Val

<210> SEQ ID NO 81
<211> LENGTH: 394
<212> TYPE: PRT
<213> ORGANISM: Brucella suis

<400> SEQUENCE: 81

Met Ser Asp Pro Lys Ser Ile Val Ile Ala Ser Ala Ala Arg Thr Ala
1               5                   10                  15

Val Gly Ala Phe Asn Gly Ala Phe Ala Asn Val Pro Ala His Glu Leu
            20                  25                  30

Gly Ala Val Ala Ile Lys Ala Ala Leu Glu Arg Ala Gly Val Asp Ala
        35                  40                  45

Ala Asp Val Asp Glu Val Ile Leu Gly Gln Val Leu Thr Ala Gly Glu
    50                  55                  60

Gly Gln Asn Pro Ala Arg Gln Ala Ala Met Gly Ala Gly Cys Pro Lys
65                  70                  75                  80

```
Glu Thr Thr Ala Phe Ala Ile Asn Gln Leu Cys Gly Ser Gly Leu Arg
                85                  90                  95

Ala Val Ala Leu Gly Met Gln Gln Ile Val Ser Gly Asp Ala Lys Ile
            100                 105                 110

Ile Val Ala Gly Gly Gln Glu Ser Met Ser Met Ala Pro His Cys Ala
        115                 120                 125

Tyr Leu Arg Ser Gly Val Lys Met Gly Asp Phe Lys Met Ile Asp Thr
    130                 135                 140

Met Leu Lys Asp Gly Leu Thr Asp Ala Phe His Gly Tyr His Met Gly
145                 150                 155                 160

Ile Thr Ala Glu Asn Ile Ala Arg Gln Trp Gln Leu Ser Arg Ser Glu
                165                 170                 175

Gln Asp Glu Phe Ala Leu Ala Ser Gln His Lys Ala Glu Ala Ala Gln
            180                 185                 190

Lys Ala Gly Arg Phe Asp Glu Glu Ile Val Pro Phe Thr Val Lys Ala
        195                 200                 205

Arg Lys Gly Asp Val Val Ser Ala Asp Glu Tyr Ile Arg Pro Gly
    210                 215                 220

Thr Thr Met Glu Val Leu Ala Lys Leu Lys Pro Ala Phe Asp Lys Glu
225                 230                 235                 240

Gly Thr Val Thr Ala Gly Asn Ala Ser Gly Ile Asn Asp Gly Ala Ala
                245                 250                 255

Ala Val Val Leu Met Asp Ala Gly Glu Ala Ala Arg Arg Gly Val Lys
            260                 265                 270

Pro Leu Ala Arg Ile Val Ser Trp Ala Thr Ala Gly Val Asp Pro Ser
        275                 280                 285

Ile Met Gly Thr Gly Pro Ile Pro Ala Thr Arg Lys Ala Leu Glu Lys
    290                 295                 300

Ala Gly Trp Ser Val Gly Asp Leu Asp Leu Val Glu Ala Asn Glu Ala
305                 310                 315                 320

Phe Ala Ala Gln Ser Cys Ala Val Val Arg Asp Leu Gly Leu Asn Pro
                325                 330                 335

Glu Ile Val Asn Val Asn Gly Gly Ala Ile Ala Ile Gly His Pro Ile
            340                 345                 350

Gly Ala Ser Gly Ala Arg Val Leu Thr Thr Leu Leu Tyr Glu Met Glu
        355                 360                 365

Arg Arg Asp Ala Lys Arg Gly Leu Ala Thr Leu Cys Ile Gly Gly Gly
    370                 375                 380

Met Gly Val Ala Leu Cys Val Glu Arg Asp
385                 390

<210> SEQ ID NO 82
<211> LENGTH: 396
<212> TYPE: PRT
<213> ORGANISM: Clostridium difficile

<400> SEQUENCE: 82

Met Gly Val Met Asn Met Arg Glu Val Val Ile Ala Ser Ala Ala Arg
  1               5                  10                  15

Thr Ala Val Gly Ser Phe Gly Gly Ala Phe Lys Ser Val Ser Ala Val
            20                  25                  30

Glu Leu Gly Val Thr Ala Ala Lys Glu Ala Ile Lys Arg Ala Asn Ile
        35                  40                  45

Thr Pro Asp Met Ile Asp Glu Ser Leu Leu Gly Gly Val Leu Thr Ala
    50                  55                  60
```

Gly Leu Gly Gln Asn Ile Ala Arg Gln Ile Ala Leu Gly Ala Gly Ile
65                  70                  75                  80

Pro Val Glu Lys Pro Ala Met Thr Ile Asn Ile Val Cys Gly Ser Gly
            85                  90                  95

Leu Arg Ser Val Ser Met Ala Ser Gln Leu Ile Ala Leu Gly Asp Ala
            100                 105                 110

Asp Ile Met Leu Val Gly Gly Ala Glu Asn Met Ser Met Ser Pro Tyr
            115                 120                 125

Leu Val Pro Ser Ala Arg Tyr Gly Ala Arg Met Gly Asp Ala Ala Phe
            130                 135                 140

Val Asp Ser Met Ile Lys Asp Gly Leu Ser Asp Ile Phe Asn Asn Tyr
145                 150                 155                 160

His Met Gly Ile Thr Ala Glu Asn Ile Ala Glu Gln Trp Asn Ile Thr
                165                 170                 175

Arg Glu Glu Gln Asp Glu Leu Ala Leu Ala Ser Gln Asn Lys Ala Glu
            180                 185                 190

Lys Ala Gln Ala Glu Gly Lys Phe Asp Glu Glu Ile Val Pro Val Val
            195                 200                 205

Ile Lys Gly Arg Lys Gly Asp Thr Val Val Asp Lys Asp Glu Tyr Ile
210                 215                 220

Lys Pro Gly Thr Thr Met Glu Lys Leu Ala Lys Leu Arg Pro Ala Phe
225                 230                 235                 240

Lys Lys Asp Gly Thr Val Thr Ala Gly Asn Ala Ser Gly Ile Asn Asp
                245                 250                 255

Gly Ala Ala Met Leu Val Val Met Ala Lys Glu Lys Ala Glu Glu Leu
                260                 265                 270

Gly Ile Glu Pro Leu Ala Thr Ile Val Ser Tyr Gly Thr Ala Gly Val
            275                 280                 285

Asp Pro Lys Ile Met Gly Tyr Gly Pro Val Pro Ala Thr Lys Lys Ala
            290                 295                 300

Leu Glu Ala Ala Asn Met Thr Ile Glu Asp Ile Asp Leu Val Glu Ala
305                 310                 315                 320

Asn Glu Ala Phe Ala Ala Gln Ser Val Ala Val Ile Arg Asp Leu Asn
                325                 330                 335

Ile Asp Met Asn Lys Val Asn Val Asn Gly Gly Ala Ile Ala Ile Gly
                340                 345                 350

His Pro Ile Gly Cys Ser Gly Ala Arg Ile Leu Thr Thr Leu Leu Tyr
            355                 360                 365

Glu Met Lys Arg Arg Asp Ala Lys Thr Gly Leu Ala Thr Leu Cys Ile
            370                 375                 380

Gly Gly Gly Met Gly Thr Thr Leu Ile Val Lys Arg
385                 390                 395

<210> SEQ ID NO 83
<211> LENGTH: 398
<212> TYPE: PRT
<213> ORGANISM: Xenopus laevis

<400> SEQUENCE: 83

Met Asn Ser Gly Glu Glu Thr Val Val Ile Ile Ser Ala Ala Arg Thr
  1               5                  10                  15

Pro Ile Gly Ser Phe Asn Gly Ala Leu Ser Thr Leu Pro Ala His Thr
             20                  25                  30

Leu Gly Ser Thr Val Ile Lys Glu Val Leu Lys Arg Ala Thr Ile Lys

```
            35                  40                  45
Pro Glu Glu Val Ser Glu Val Ile Phe Gly Gln Val Leu Thr Ala Gly
         50                  55                  60

Ala Gly Gln Asn Pro Ala Arg Gln Ala Ser Val Ala Ala Gly Val Pro
 65                  70                  75                  80

Tyr Ser Ile Pro Ala Trp Ser Cys Gln Met Ile Cys Gly Ser Gly Leu
                 85                  90                  95

Lys Ala Val Ser Leu Gly Ala Gln Ser Ile Lys Thr Gly Glu Ala Asp
                100                 105                 110

Ile Val Val Ala Gly Gly Met Glu Asn Met Ser Gln Ala Pro His Leu
            115                 120                 125

Val His Met Arg Ala Gly Val Lys Ala Gly Asp Val Ser Leu Gln Asp
        130                 135                 140

Ser Ile Ile Cys Asp Gly Leu Asn Asp Ala Phe Tyr Lys Tyr His Met
145                 150                 155                 160

Gly Ile Thr Ala Glu Asn Val Ala Lys Gln Trp Gln Ile Thr Arg Glu
                165                 170                 175

Glu Gln Asp Gln Leu Ala Val Gln Ser Gln Asn Arg Thr Glu Ala Ala
            180                 185                 190

Gln Lys Ala Gly Tyr Phe Asp Lys Glu Ile Val Pro Val Ser Val Pro
        195                 200                 205

Ser Arg Lys Gly Pro Val Glu Val Lys Val Asp Glu Phe Pro Arg His
210                 215                 220

Gly Ser Asn Val Glu Ala Met Ser Lys Leu Lys Pro Tyr Phe Leu Lys
225                 230                 235                 240

Asp Gly Ser Gly Thr Val Thr Pro Ala Asn Ala Ser Gly Ile Asn Asp
                245                 250                 255

Gly Ala Ala Ala Val Val Leu Ile Lys Glu Ser Glu Ala Arg Arg Arg
            260                 265                 270

Gly Leu Thr Pro Met Ala Arg Ile Val Ala Ser Ala Gln Ala Gly Leu
        275                 280                 285

Asp Pro Ser Ile Met Gly Val Gly Pro Ile Ala Ala Ile Arg Lys Ala
290                 295                 300

Val Glu Lys Ala Gly Trp Ser Leu Asp Asp Ile Asp Leu Phe Glu Ile
305                 310                 315                 320

Asn Glu Ala Phe Ala Ala Gln Ala Leu Ala Val Val Lys Asp Leu Gly
                325                 330                 335

Leu Asn Pro Glu Lys Val Asn Cys Gln Gly Gly Ala Val Ala Leu Gly
            340                 345                 350

His Pro Leu Gly Met Ser Gly Cys Arg Ile Leu Val Thr Leu Leu Tyr
        355                 360                 365

Ala Leu Glu Arg Thr Gly Leu Lys Gly Val Ala Ala Leu Cys Ile
    370                 375                 380

Gly Gly Gly Met Gly Ile Ala Met Cys Val Glu Arg Thr Ser
385                 390                 395

<210> SEQ ID NO 84
<211> LENGTH: 392
<212> TYPE: PRT
<213> ORGANISM: Marinobacter manganoxydans

<400> SEQUENCE: 84

Met Arg Asp Val Val Ile Val Ala Ala Arg Arg Thr Ala Ile Gly Thr
  1               5                  10                  15
```

Phe Gly Gly Gly Leu Ser Ser Leu Ser Ala Asp Gln Leu Gly Thr Ala
            20                  25                  30

Val Ile Lys Ala Leu Met Glu Glu Thr Gly Val Ala Gly Asp Gln Ile
        35                  40                  45

Asn Glu Val Val Leu Gly Gln Val Leu Thr Ala Gly Val Gly Gln Asn
    50                  55                  60

Pro Ala Arg Gln Ser Ala Ile Asn Ala Gly Ile Pro Ala Ser Val Pro
65                  70                  75                  80

Ala Met Thr Ile Asn Lys Val Cys Gly Ser Gly Leu Lys Ala Val His
                85                  90                  95

Met Ala Val Gln Ala Ile Arg Cys Gly Asp Ala Glu Met Met Ile Ala
            100                 105                 110

Gly Gly Gln Glu Ser Met Ser Gln Ala Pro His Val Leu Pro Asn Ser
        115                 120                 125

Arg Asn Gly Gln Arg Met Gly Asn Trp Ser Met Val Asp Thr Met Ile
    130                 135                 140

Lys Asp Gly Leu Trp Asp Ala Phe Asn Asp Tyr His Met Gly Ile Thr
145                 150                 155                 160

Ala Glu Asn Ile Val Glu Lys Tyr Gly Ile Ser Arg Asp Glu Gln Asp
                165                 170                 175

Glu Phe Ala Ala Ala Ser Gln Gln Lys Ala Ala Ala Arg Glu Ala
            180                 185                 190

Gly Tyr Phe Asp Gly Gln Ile Val Pro Val Ser Ile Pro Gln Arg Lys
        195                 200                 205

Gly Asp Pro Ile Val Val Asp Arg Asp Glu Pro Arg Asp Gly Val
    210                 215                 220

Thr Ala Glu Gly Leu Gly Lys Leu Arg Ala Ala Phe Lys Lys Asp Gly
225                 230                 235                 240

Thr Val Thr Ala Gly Asn Ala Ser Ser Leu Asn Asp Gly Ala Ala Ala
                245                 250                 255

Val Met Val Cys Ser Ala Glu Lys Ala Lys Glu Leu Gly Leu Thr Pro
            260                 265                 270

Ile Ala Thr Ile Lys Ala Tyr Ala Asn Ala Gly Val Asp Pro Thr Ile
        275                 280                 285

Met Gly Thr Gly Pro Ile Pro Ala Ser Gln Arg Cys Leu Lys Leu Ala
    290                 295                 300

Gly Trp Ser Thr Glu Asp Leu Asp Leu Val Glu Ala Asn Glu Ala Phe
305                 310                 315                 320

Ala Ala Gln Ala Ile Ser Val Asn Arg Asp Met Gly Trp Asp Thr Gly
                325                 330                 335

Lys Val Asn Val Asn Gly Gly Ala Ile Ala Leu Gly His Pro Ile Gly
            340                 345                 350

Ala Ser Gly Cys Arg Ile Leu Val Ser Leu Leu His Glu Met Val Arg
        355                 360                 365

Arg Asp Val His Lys Gly Leu Ala Thr Leu Cys Ile Gly Gly Gly Met
    370                 375                 380

Gly Val Ala Leu Ala Val Glu Arg
385                 390

<210> SEQ ID NO 85
<211> LENGTH: 392
<212> TYPE: PRT
<213> ORGANISM: Sphingobium japonicum

<400> SEQUENCE: 85

```
Met Pro Leu Ser Asp Ile Val Ile Thr Ala Ala Lys Arg Thr Ala Val
 1               5                  10                  15

Gly Gly Phe Met Gly Ala Phe Gly Ser Thr Pro Ala His Glu Leu Gly
             20                  25                  30

Arg Thr Ala Ile Leu Ala Ala Leu Ala Gln Ala Gly Val Ala Pro Glu
             35                  40                  45

Glu Val Asp Glu Val Ile Leu Gly Gln Val Leu Thr Ala Gly Gln Gly
 50                  55                  60

Gln Asn Pro Ala Arg Gln Ala Ala Val Asn Ala Gly Ile Pro Val Glu
 65                  70                  75                  80

Arg Thr Ala Ile Gly Val Asn Gln Leu Cys Gly Ser Gly Leu Arg Ala
                 85                  90                  95

Val Ala Leu Ala Ala Gln Ala Ile Arg Ala Gly Asp Ala Arg Ile Met
                100                 105                 110

Val Ala Gly Gly Gln Glu Ser Met Ser Leu Ala Pro His Ala Gln Tyr
            115                 120                 125

Leu Arg Gly Gly Ala Lys Met Gly Pro Ile Ser Leu Val Asp Thr Met
        130                 135                 140

Thr His Asp Gly Leu Thr Asp Ala Phe Asn Asn Tyr His Met Gly Ile
145                 150                 155                 160

Thr Ala Glu Asn Leu Ala Glu Lys Tyr Gln Ile Ser Arg Glu Ala Gln
                165                 170                 175

Asp Val Phe Ser Val Gly Ser Gln Asn Lys Ala Glu Ala Ala Arg Ala
            180                 185                 190

Ser Gly Arg Phe Lys Asp Glu Ile Ala Pro Val Thr Val Lys Gly Arg
        195                 200                 205

Lys Gly Asp Thr Ile Val Asp Thr Asp Glu Tyr Ile Arg Ala Gly Ala
210                 215                 220

Thr Leu Glu Ala Met Gln Ser Leu Arg Pro Ala Phe Arg Lys Asp Gly
225                 230                 235                 240

Thr Val Thr Ala Ala Asn Ala Ser Gly Ile Asn Asp Gly Ala Ala Ala
                245                 250                 255

Leu Val Leu Met Ser Ala Glu Glu Ala Lys Arg Asp Ala Leu Val
                260                 265                 270

Leu Ala Arg Ile Ala Ser Phe Ala Thr Cys Gly Val Asp Pro Ser Ile
        275                 280                 285

Met Gly Ile Gly Pro Ala Pro Ala Ser Arg Gln Ala Leu Ala Lys Ala
290                 295                 300

Gly Trp Ser Leu Ala Asp Leu Asp Leu Ile Glu Ala Asn Glu Ala Phe
305                 310                 315                 320

Ala Ala Gln Ala Leu Ala Val Gly Gln Glu Leu Gly Trp Asp Ala Glu
                325                 330                 335

Lys Val Asn Val Asn Gly Gly Ala Ile Ala Ile Gly His Pro Ile Gly
            340                 345                 350

Ala Ser Gly Ala Arg Val Leu Thr Thr Leu Ile Tyr Glu Met Gln Lys
        355                 360                 365

Arg Asp Ala Lys Lys Gly Leu Ala Thr Leu Cys Ile Gly Gly Gly Met
370                 375                 380

Gly Val Ala Met Cys Ile Glu Arg
385                 390
```

<210> SEQ ID NO 86
<211> LENGTH: 393

<212> TYPE: PRT
<213> ORGANISM: Anaerococcus hydrogenalis

<400> SEQUENCE: 86

```
Met Thr Arg Lys Val Val Ile Ala Ser Ala Ala Arg Thr Pro Val Gly
 1               5                  10                  15

Ser Phe Gly Gly Ala Leu Lys Ser Gln Ser Ala Ala Asp Leu Gly Ile
             20                  25                  30

Val Ala Ala Lys Ala Ala Ile Glu Arg Ala Gly Ile Lys Pro Glu Asp
         35                  40                  45

Ile Asp Glu Thr Val Leu Gly Cys Val Leu Gln Ala Gly Leu Gly Gln
     50                  55                  60

Asn Val Ala Arg Gln Ile Ser Leu Gly Ala Gly Ile Pro Glu Thr Thr
 65                  70                  75                  80

Pro Ala Met Thr Ile Asn Lys Val Cys Gly Ser Gly Leu Arg Thr Val
                 85                  90                  95

Ser Leu Ala Ala Gln Met Ile Leu Ala Gly Asp Val Asp Val Val Leu
            100                 105                 110

Ala Gly Gly Ala Glu Ser Met Ser Asn Ala Pro Phe Leu Leu Asn Glu
        115                 120                 125

Ala Arg Trp Gly Ala Arg Met Gly Asn Lys Lys Leu Val Asp Glu Met
    130                 135                 140

Ile Thr Asp Gly Leu Trp Asp Val Tyr Asn Asp Tyr His Met Gly Val
145                 150                 155                 160

Thr Ala Glu Asn Val Ala Glu Lys Tyr Gly Ile Thr Arg Glu Met Gln
                165                 170                 175

Asp Asp Leu Ala Ala Val Ser Gln Gln Arg Ala Ser Lys Ala Arg Ala
            180                 185                 190

Glu Gly Arg Phe Lys Asp Glu Ile Ala Pro Val Glu Ile Lys Asp Arg
        195                 200                 205

Lys Gly Asn Val Thr Val Glu Asp Glu Tyr Ile Arg Asp Gly
    210                 215                 220

Val Thr Gln Glu Gly Ile Ser Lys Leu Arg Pro Ala Phe Ile Lys Asp
225                 230                 235                 240

Gly Thr Val Thr Ala Ala Asn Ala Ser Gly Ile Asn Asp Gly Ala Ala
                245                 250                 255

Cys Leu Val Val Met Ser Glu Glu Lys Ala Lys Glu Leu Gly Val Lys
            260                 265                 270

Pro Leu Ala Thr Ile Val Ser Tyr Ala Ser Ala Gly Val Asp Pro Lys
        275                 280                 285

Val Met Gly Thr Gly Pro Ile Pro Ser Ser Lys Lys Ala Leu Glu Lys
    290                 295                 300

Ala Gly Trp Lys Val Glu Asp Leu Asp Leu Val Glu Ser Asn Glu Ala
305                 310                 315                 320

Phe Ala Ala Gln Ser Tyr Ala Val Arg Asn Glu Met Gly Phe Asp Pro
                325                 330                 335

Glu Lys Thr Asn Val Asn Gly Gly Ala Ile Ala Ile Gly His Pro Ile
            340                 345                 350

Gly Gly Ser Gly Ala Arg Ile Leu Thr Thr Leu Leu Phe Glu Met Gln
        355                 360                 365

Lys Arg Asp Ser Lys Lys Gly Leu Ala Thr Leu Cys Ile Gly Gly Gly
    370                 375                 380

Met Gly Thr Ala Leu Val Val Glu Arg
385                 390
```

<210> SEQ ID NO 87
<211> LENGTH: 392
<212> TYPE: PRT
<213> ORGANISM: Acidovorax radicis

<400> SEQUENCE: 87

| | | | | | | | | | | | | | | |
|---|---|---|---|---|---|---|---|---|---|---|---|---|---|---|
| Met | Glu | Asp | Ile | Val | Ile | Val | Ser | Ala | Ala | Arg | Thr | Ala | Val | Gly | Lys |
| 1 | | | | 5 | | | | | 10 | | | | | 15 | |
| Phe | Gly | Gly | Ala | Leu | Ala | Lys | Thr | Pro | Ala | Thr | Glu | Leu | Gly | Ala | Ile |
| | | | 20 | | | | | 25 | | | | | 30 | | |
| Val | Ile | Arg | Glu | Ala | Ile | Ala | Arg | Ala | Gly | Leu | Ser | Ser | Asp | Gln | Ile |
| | | 35 | | | | | 40 | | | | | 45 | | | |
| Gly | Glu | Val | Ile | Met | Gly | Gln | Val | Leu | Ala | Ala | Gly | Val | Gly | Gln | Asn |
| | 50 | | | | | 55 | | | | | 60 | | | | |
| Pro | Ala | Arg | Gln | Ala | Ser | Met | Lys | Ala | Gly | Val | Ala | Lys | Glu | Thr | Pro |
| 65 | | | | | 70 | | | | | 75 | | | | | 80 |
| Ala | Leu | Thr | Ile | Asn | Ala | Val | Cys | Gly | Ser | Gly | Leu | Lys | Ala | Val | Met |
| | | | | 85 | | | | | 90 | | | | | 95 | |
| Leu | Ala | Ala | Gln | Ala | Val | Ala | Trp | Gly | Asp | Ser | Glu | Ile | Val | Val | Ala |
| | | | 100 | | | | | 105 | | | | | 110 | | |
| Gly | Gly | Gln | Glu | Ser | Met | Ser | Leu | Ala | Pro | His | Val | Leu | Pro | Gly | Ser |
| | | 115 | | | | | 120 | | | | | 125 | | | |
| Arg | Asp | Gly | Gln | Arg | Met | Gly | Asp | Trp | Lys | Leu | Ile | Asp | Thr | Met | Ile |
| | 130 | | | | | 135 | | | | | 140 | | | | |
| Val | Asp | Gly | Leu | Trp | Asp | Val | Tyr | Asn | Gln | Tyr | His | Met | Gly | Ile | Thr |
| 145 | | | | | 150 | | | | | 155 | | | | | 160 |
| Ala | Glu | Asn | Val | Ala | Lys | Ala | His | Gly | Ile | Thr | Arg | Glu | Met | Gln | Asp |
| | | | | 165 | | | | | 170 | | | | | 175 | |
| Ala | Leu | Ala | Leu | Gly | Ser | Gln | Gln | Lys | Ala | Ala | Ala | Gln | Asp | Ala |
| | | | 180 | | | | | 185 | | | | | 190 | | |
| Gly | Lys | Phe | Val | Asp | Glu | Ile | Val | Gly | Val | Ser | Leu | Ala | Gln | Lys | Lys |
| | | 195 | | | | | 200 | | | | | 205 | | | |
| Gly | Asp | Pro | Ile | Leu | Phe | Asn | Ala | Asp | Glu | Tyr | Leu | Asn | Arg | Lys | Thr |
| | 210 | | | | | 215 | | | | | 220 | | | | |
| Asn | Ala | Glu | Ala | Leu | Ala | Gly | Leu | Arg | Pro | Ala | Phe | Asp | Lys | Ala | Gly |
| 225 | | | | | 230 | | | | | 235 | | | | | 240 |
| Ser | Val | Thr | Ala | Gly | Asn | Ala | Ser | Gly | Leu | Asn | Asp | Gly | Ala | Ala | Ala |
| | | | | 245 | | | | | 250 | | | | | 255 | |
| Val | Val | Val | Met | Ser | Ala | Lys | Lys | Ala | Ala | Leu | Gly | Leu | Lys | Pro |
| | | | 260 | | | | | 265 | | | | | 270 | | |
| Leu | Ala | Arg | Ile | Ala | Ala | Phe | Gly | Thr | Ser | Gly | Leu | Asp | Pro | Ala | Thr |
| | | 275 | | | | | 280 | | | | | 285 | | | |
| Met | Gly | Met | Gly | Pro | Val | Pro | Ala | Ser | Arg | Lys | Ala | Leu | Gln | Arg | Ala |
| | 290 | | | | | 295 | | | | | 300 | | | | |
| Gly | Trp | Asn | Ala | Ala | Asp | Val | Asp | Leu | Phe | Glu | Leu | Asn | Glu | Ala | Phe |
| 305 | | | | | 310 | | | | | 315 | | | | | 320 |
| Ala | Ala | Gln | Ala | Cys | Ala | Val | Asn | Lys | Glu | Leu | Ala | Ile | Asp | Pro | Ala |
| | | | | 325 | | | | | 330 | | | | | 335 | |
| Lys | Val | Asn | Val | Asn | Gly | Gly | Ala | Ile | Ala | Ile | Gly | His | Pro | Ile | Gly |
| | | | 340 | | | | | 345 | | | | | 350 | | |
| Ala | Ser | Gly | Cys | Arg | Ile | Leu | Val | Thr | Leu | Leu | His | Glu | Met | Gln | Arg |
| | | 355 | | | | | 360 | | | | | 365 | | | |
| Arg | Asp | Ala | Lys | Lys | Gly | Leu | Ala | Ala | Leu | Cys | Ile | Gly | Gly | Gly | Met |

```
            370                 375                 380
Gly Val Ser Leu Ala Leu Glu Arg
385                 390
```

<210> SEQ ID NO 88
<211> LENGTH: 391
<212> TYPE: PRT
<213> ORGANISM: Caulobacter segnis

<400> SEQUENCE: 88

```
Met Ser Asp Val Val Ile Val Ser Ala Ala Arg Thr Pro Val Gly Ser
  1               5                  10                  15

Phe Asn Gly Ala Leu Ser Ser Leu Pro Ala Ser Glu Leu Gly Arg Val
                 20                  25                  30

Ala Ile Glu Ala Ala Ile Ser Arg Ala Gly Leu Gln Pro Ser Asp Val
             35                  40                  45

Asp Glu Val Ile Leu Gly Gln Val Leu Gln Ala Gly Ala Gly Gln Gly
         50                  55                  60

Pro Ala Arg Gln Ala Ser Val Lys Ala Gly Ile Pro Val Glu Ser Pro
 65                  70                  75                  80

Ala Trp Ser Leu Asn Gln Leu Cys Gly Ser Gly Leu Arg Ala Val Ala
                 85                  90                  95

Leu Ala Ala Gln Gln Ile Ala Ala Gly Asp Ala Ala Val Val Val Ala
            100                 105                 110

Gly Gly Gln Glu Ser Met Ser Gln Ala Pro His Ala Gln Asn Leu Arg
        115                 120                 125

Gly Gly Gln Lys Met Gly Asp Leu Ser Phe Val Asp Thr Met Ile Lys
    130                 135                 140

Asp Gly Leu Trp Asp Ala Phe His Gly Tyr His Met Gly Gln Thr Ala
145                 150                 155                 160

Glu Asn Ile Ala Ser Arg Trp Gln Ile Thr Arg Ala Asp Gln Asp Ala
                165                 170                 175

Phe Ala Val Ala Ser Gln Asn Lys Ala Glu Ala Ala Gln Lys Ala Gly
            180                 185                 190

Lys Phe Asp Ala Glu Ile Ala Pro Val Thr Ile Lys Gly Arg Lys Gly
        195                 200                 205

Asp Thr Val Val Asp Lys Asp Glu Tyr Ile Arg His Gly Val Thr Leu
    210                 215                 220

Glu Ser Ile Ser Gly Leu Lys Pro Ala Phe Thr Lys Glu Gly Ser Val
225                 230                 235                 240

Thr Ala Ala Asn Ala Ser Gly Leu Asn Asp Gly Ala Ala Ala Leu Val
                245                 250                 255

Leu Met Ser Ala Glu Glu Ala Gln Lys Arg Gly Leu Lys Pro Leu Ala
            260                 265                 270

Arg Ile Ala Ser Trp Ala Asn Ala Gly Val Glu Pro Glu Ile Met Gly
        275                 280                 285

Thr Gly Pro Ile Pro Ala Ser Lys Lys Ala Leu Glu Lys Ala Gly Trp
    290                 295                 300

Thr Val Ala Asp Leu Asp Leu Val Glu Ser Asn Glu Ala Phe Ala Ala
305                 310                 315                 320

Gln Ser Leu Cys Val Val Arg Glu Leu Gly Leu Asp Pro Ala Lys Val
                325                 330                 335

Asn Val Asn Gly Gly Ala Ile Ala Ile Gly His Pro Ile Gly Ala Ser
            340                 345                 350
```

```
Gly Ala Arg Val Leu Thr Thr Leu His Glu Met Lys Arg Ser Gly
            355                 360                 365

Ala Gln Lys Gly Leu Ala Thr Leu Cys Ile Gly Gly Met Gly Val
        370                 375                 380

Ala Met Cys Val Glu Ala Val
385                 390

<210> SEQ ID NO 89
<211> LENGTH: 392
<212> TYPE: PRT
<213> ORGANISM: Desulfosporosinus orientis

<400> SEQUENCE: 89

Met Arg Asp Val Val Ile Val Ser Ala Val Arg Thr Pro Val Gly Ser
  1               5                  10                  15

Phe Cys Gly Ala Leu Gly Gln Ile Pro Ala Ala Glu Leu Gly Ala Ile
                 20                  25                  30

Ala Val Lys Glu Ala Ile Asn Arg Ala Gly Ile Thr Pro Glu Gln Val
             35                  40                  45

Asp Glu Val Ile Leu Gly Asn Val Leu Gln Ala Gly Leu Gly Gln Asn
         50                  55                  60

Pro Ala Arg Gln Ala Ser Ile Lys Ala Gly Ile Pro Gln Glu Val Pro
65                  70                  75                  80

Ser Trp Thr Leu Asn Lys Val Cys Gly Ser Gly Leu Lys Thr Val Val
                 85                  90                  95

Cys Ala Ala Gln Ala Ile Met Thr Gly Asp Ala Asp Ile Val Val Ala
            100                 105                 110

Gly Gly Met Glu Asn Met Ser Leu Ala Pro Tyr Val Leu Thr Lys Ala
        115                 120                 125

Arg Thr Gly Tyr Arg Met Gly Asn Asp Thr Val Ile Asp Ser Met Ile
    130                 135                 140

Asn Asp Gly Leu Thr Asp Ala Phe Asn Asn Tyr His Met Gly Ile Thr
145                 150                 155                 160

Ala Glu Asn Ile Ala Glu Gln Phe Asn Ile Ser Arg Glu Glu Gln Asp
                165                 170                 175

Arg Tyr Ser Val Arg Ser Gln Asn Arg Ala Glu Ala Ala Ile Ile Ala
            180                 185                 190

Gly Lys Phe Asn Glu Glu Ile Val Pro Val Ser Ile Pro Gln Arg Lys
        195                 200                 205

Gly Asp Pro Val Val Ser Gln Asp Glu Phe Pro Arg Phe Gly Ala
    210                 215                 220

Thr Tyr Glu Ala Ile Ala Lys Leu Arg Pro Ala Phe Lys Lys Asp Gly
225                 230                 235                 240

Thr Val Thr Ala Ala Asn Ala Ser Gly Ile Asn Asp Gly Ala Ala Ala
                245                 250                 255

Ile Val Val Met Ala Lys Glu Lys Ala Glu Glu Leu Gly Leu Thr Pro
            260                 265                 270

Leu Ala Thr Ile Lys Ser Trp Ala Ser Ala Gly Val Asp Pro Lys Ile
        275                 280                 285

Met Gly Thr Gly Pro Ile Pro Ala Ser Arg Lys Ala Leu Glu Lys Ala
    290                 295                 300

Gly Leu Ser Ile Asp Asp Ile Asp Val Val Glu Ala Asn Glu Ala Phe
305                 310                 315                 320

Ala Ser Gln Thr Leu Ser Val Ala Gln Gly Leu Asn Leu Asp Pro Glu
                325                 330                 335
```

```
Lys Thr Asn Val Asn Gly Gly Ala Ile Ala Leu Gly His Pro Val Gly
            340                 345                 350

Ala Ser Gly Thr Arg Ile Leu Val Thr Leu Leu His Glu Met Lys Arg
        355                 360                 365

Ser Asn Ala His Arg Gly Leu Ala Thr Leu Cys Ile Gly Gly Gly Gln
    370                 375                 380

Gly Val Ala Leu Ile Val Glu Arg
385                 390

<210> SEQ ID NO 90
<211> LENGTH: 392
<212> TYPE: PRT
<213> ORGANISM: Pseudomonas syringae pv. pisi str.

<400> SEQUENCE: 90

Met His Asp Val Val Ile Val Ala Ala Thr Arg Thr Ala Val Gly Ser
1               5                   10                  15

Phe Gln Gly Ser Leu Ala Ser Val Ala Ala Val Asp Leu Gly Ala Ala
            20                  25                  30

Val Ile Arg Gln Leu Leu Ala Arg Thr Gly Val Asp Gly Ala Gln Val
        35                  40                  45

Asp Glu Val Ile Met Gly Gln Val Leu Thr Ala Gly Ala Gly Gln Asn
    50                  55                  60

Pro Ala Arg Gln Ala Ala Ile Lys Ala Gly Leu Pro Phe Ser Val Pro
65                  70                  75                  80

Ala Met Thr Leu Asn Lys Val Cys Gly Ser Gly Leu Lys Ala Leu His
                85                  90                  95

Leu Ala Thr Gln Ala Ile Arg Cys Gly Asp Ala Glu Ile Ile Ile Ala
            100                 105                 110

Gly Gly Gln Glu Asn Met Ser Leu Ser Asn Tyr Val Leu Pro Gly Ala
        115                 120                 125

Arg Thr Gly Leu Arg Met Gly His Ala Ser Met Val Asp Thr Met Ile
    130                 135                 140

Thr Asp Gly Leu Trp Asp Ala Phe Asn Asp Tyr His Met Gly Ile Thr
145                 150                 155                 160

Ala Glu Asn Leu Ala Gln Gln Tyr Asp Ile Ser Arg Glu Ala Gln Asp
                165                 170                 175

Glu Phe Ala Ala Leu Ser Gln Gln Lys Ala Leu Ala Ala Ile Glu Ala
            180                 185                 190

Gly Arg Phe Val Asp Glu Ile Thr Pro Ile Leu Ile Pro Gln Arg Lys
        195                 200                 205

Gly Asp Pro Leu Ser Phe Ala Thr Asp Glu Gln Pro Arg Ala Gly Thr
    210                 215                 220

Thr Ala Glu Thr Leu Ala Lys Leu Lys Pro Ala Phe Lys Lys Asp Gly
225                 230                 235                 240

Thr Val Thr Ala Gly Asn Ala Ser Ser Leu Asn Asp Gly Ala Ala Ala
                245                 250                 255

Val Met Leu Met Ser Ala Ala Arg Ala Glu Gln Leu Gly Leu Pro Val
            260                 265                 270

Leu Ala Arg Ile Ala Ala Tyr Ala Asn Ala Gly Val Asp Pro Ala Ile
        275                 280                 285

Met Gly Ile Gly Pro Val Ser Ala Thr Arg Arg Cys Leu Asn Lys Ala
    290                 295                 300

Gly Trp Ser Leu Ala Asp Leu Asp Leu Ile Glu Ala Asn Glu Ala Phe
```

```
                305                 310                 315                 320

Ala Ala Gln Ser Leu Ser Val Gly Lys Glu Leu Gly Leu Asp Pro Gln
                325                 330                 335

Lys Leu Asn Val Asn Gly Gly Ala Ile Ala Leu Gly His Pro Ile Gly
                340                 345                 350

Ala Ser Gly Cys Arg Val Leu Val Thr Leu Leu His Glu Met Ile Arg
                355                 360                 365

Arg Asp Val Lys Lys Gly Leu Ala Thr Leu Cys Ile Gly Gly Gly Gln
                370                 375                 380

Gly Val Ala Leu Ala Leu Glu Arg
385                 390

<210> SEQ ID NO 91
<211> LENGTH: 394
<212> TYPE: PRT
<213> ORGANISM: Bradyrhizobium japonicum

<400> SEQUENCE: 91

Met Pro Met Ser Asp Val Val Ile Val Ser Ala Ala Arg Thr Pro
1               5                   10                  15

Val Gly Ser Phe Asn Gly Ala Phe Ala Thr Leu Pro Ala His Asp Leu
                20                  25                  30

Gly Ala Val Ala Ile Lys Ala Ala Leu Glu Arg Gly Gly Ile Glu Pro
            35                  40                  45

Gly Arg Val Ser Glu Val Ile Met Gly Gln Ile Leu Thr Ala Ala Gln
        50                  55                  60

Gly Gln Asn Pro Ala Arg Gln Ala Ser Ile Ala Gly Ile Pro Val
65                  70                  75                  80

Glu Ser Pro Ala Trp Gly Val Asn Gln Leu Cys Gly Ser Gly Leu Arg
                85                  90                  95

Thr Val Ala Leu Gly Tyr Gln Ala Leu Leu Asn Gly Asp Ser Glu Ile
                100                 105                 110

Val Val Ala Gly Gly Gln Glu Ser Met Ser Met Ala Pro His Ala Gln
            115                 120                 125

Tyr Leu Arg Gly Gly Val Lys Met Gly Ala Leu Glu Phe Ile Asp Thr
        130                 135                 140

Met Ile Lys Asp Gly Leu Trp Asp Ala Phe Asn Gly Tyr His Met Gly
145                 150                 155                 160

Asn Thr Ala Glu Asn Val Ala Arg Gln Trp Gln Ile Thr Arg Ala Gln
                165                 170                 175

Gln Asp Glu Phe Ala Val Ala Ser Gln Gln Lys Ala Glu Ala Ala Gln
                180                 185                 190

Lys Ala Gly Lys Phe Asn Asp Glu Ile Val Pro Val Thr Ile Lys Thr
            195                 200                 205

Arg Lys Gly Asp Val Val Ser Ala Asp Glu Tyr Pro Arg His Gly
        210                 215                 220

Ala Thr Leu Asp Ala Met Ala Lys Leu Arg Pro Ala Phe Glu Lys Asp
225                 230                 235                 240

Gly Thr Val Thr Ala Gly Ser Ala Ser Gly Ile Asn Asp Gly Ala Ala
                245                 250                 255

Ala Val Val Leu Met Thr Ala Lys Gln Ala Ala Lys Glu Gly Lys Lys
                260                 265                 270

Pro Leu Ala Arg Ile Val Ser Trp Ala Gln Ala Gly Val Asp Pro Lys
            275                 280                 285
```

```
Ile Met Gly Ser Gly Pro Ile Pro Ala Ser Arg Ala Ala Leu Lys Lys
    290                 295                 300

Ala Gly Trp Asn Val Gly Asp Leu Asp Leu Ile Glu Ala Asn Glu Ala
305                 310                 315                 320

Phe Ala Ala Gln Ala Cys Ala Val Asn Lys Asp Leu Gly Trp Asp Thr
                325                 330                 335

Ser Lys Val Asn Val Asn Gly Gly Ala Ile Ala Ile Gly His Pro Val
                340                 345                 350

Gly Ala Ser Gly Ala Arg Val Leu Val Thr Leu Leu His Glu Met Gln
            355                 360                 365

Lys Arg Asp Ser Lys Lys Gly Leu Ala Thr Leu Cys Ile Gly Gly Gly
370                 375                 380

Met Gly Ile Ala Met Cys Leu Ala Arg Asp
385                 390

<210> SEQ ID NO 92
<211> LENGTH: 391
<212> TYPE: PRT
<213> ORGANISM: Phaeobacter gallaeciensis

<400> SEQUENCE: 92

Met Thr Asn Val Val Ile Ala Ser Ala Ala Arg Thr Ala Val Gly Ser
1               5                   10                  15

Phe Gly Gly Ala Phe Ala Lys Thr Pro Ala His Asp Leu Gly Ala Ala
                20                  25                  30

Val Leu Gln Ala Val Val Glu Arg Ala Gly Ile Asp Lys Ser Glu Val
            35                  40                  45

Ser Glu Thr Ile Leu Gly Gln Val Leu Thr Ala Ala Gln Gly Gln Asn
50                  55                  60

Pro Ala Arg Gln Ala His Ile Asn Ala Gly Leu Pro Gln Glu Ser Ala
65                  70                  75                  80

Ala Trp Ser Leu Asn Gln Val Cys Gly Ser Gly Leu Arg Ala Val Ala
                85                  90                  95

Leu Ala Ala Gln His Ile Gln Leu Gly Asp Ala Ala Ile Val Cys Ala
            100                 105                 110

Gly Gly Gln Glu Asn Met Thr Leu Ser Pro His Ala Ala Asn Leu Arg
        115                 120                 125

Ala Gly His Lys Met Gly Asp Met Ser Tyr Ile Asp Thr Met Ile Arg
    130                 135                 140

Asp Gly Leu Trp Asp Ala Phe Asn Gly Tyr His Met Gly Gln Thr Ala
145                 150                 155                 160

Glu Asn Val Ala Glu Lys Trp Gln Ile Ser Arg Glu Met Gln Asp Glu
                165                 170                 175

Phe Ala Val Ala Ser Gln Asn Lys Ala Glu Ala Ala Gln Lys Ala Gly
            180                 185                 190

Lys Phe Ala Asp Glu Ile Ala Ala Phe Thr Val Lys Thr Arg Lys Gly
        195                 200                 205

Asp Ile Ile Val Asp Gln Asp Glu Tyr Ile Arg His Gly Ala Thr Ile
    210                 215                 220

Glu Ala Met Gln Lys Leu Arg Pro Ala Phe Ala Lys Asp Gly Ser Val
225                 230                 235                 240

Thr Ala Ala Asn Ala Ser Gly Leu Asn Asp Gly Ala Ala Ala Thr Leu
                245                 250                 255

Leu Met Ser Ala Asp Asp Ala Glu Lys Arg Gly Ile Glu Pro Leu Ala
            260                 265                 270
```

```
Arg Ile Ala Ser Tyr Ala Thr Ala Gly Leu Asp Pro Ser Ile Met Gly
            275                 280                 285

Val Gly Pro Ile Tyr Ala Ser Arg Lys Ala Leu Glu Lys Ala Gly Trp
        290                 295                 300

Ser Val Asp Asp Leu Asp Leu Val Glu Ala Asn Glu Ala Phe Ala Ala
305                 310                 315                 320

Gln Ala Cys Ala Val Asn Lys Asp Met Gly Trp Asp Pro Ala Ile Val
                325                 330                 335

Asn Val Asn Gly Gly Ala Ile Ala Ile Gly His Pro Ile Gly Ala Ser
                340                 345                 350

Gly Cys Arg Val Leu Asn Thr Leu Leu Phe Glu Met Lys Arg Arg Asp
            355                 360                 365

Ala Lys Lys Gly Leu Ala Thr Leu Cys Ile Gly Gly Met Gly Val
        370                 375                 380

Ala Met Cys Val Glu Arg Pro
385                 390

<210> SEQ ID NO 93
<211> LENGTH: 389
<212> TYPE: PRT
<213> ORGANISM: Artificial Sequence
<220> FEATURE:
<223> OTHER INFORMATION: Unliganded Biosynthetic Thiolase From Zoogloea
      Ramigera

<400> SEQUENCE: 93

Ser Ile Val Ile Ala Ser Ala Ala Arg Thr Ala Val Gly Ser Phe Asn
 1                5                  10                  15

Gly Ala Phe Ala Asn Thr Pro Ala His Glu Leu Gly Ala Thr Val Ile
            20                  25                  30

Ser Ala Val Leu Glu Arg Ala Gly Val Ala Ala Gly Glu Val Asn Glu
        35                  40                  45

Val Ile Leu Gly Gln Val Leu Pro Ala Gly Glu Gly Gln Asn Pro Ala
    50                  55                  60

Arg Gln Ala Ala Met Lys Ala Gly Val Pro Gln Glu Ala Thr Ala Trp
65                  70                  75                  80

Gly Met Asn Gln Leu Cys Gly Ser Gly Leu Arg Ala Val Ala Leu Gly
                85                  90                  95

Met Gln Gln Ile Ala Thr Gly Asp Ala Ser Ile Ile Val Ala Gly Gly
            100                 105                 110

Met Glu Ser Met Ser Met Ala Pro His Cys Ala His Leu Arg Gly Gly
        115                 120                 125

Val Lys Met Gly Asp Phe Lys Met Ile Asp Thr Met Ile Lys Asp Gly
    130                 135                 140

Leu Thr Asp Ala Phe Tyr Gly Tyr His Met Gly Thr Thr Ala Glu Asn
145                 150                 155                 160

Val Ala Lys Gln Trp Gln Leu Ser Arg Asp Glu Gln Asp Ala Phe Ala
                165                 170                 175

Val Ala Ser Gln Asn Lys Ala Glu Ala Ala Gln Lys Asp Gly Arg Phe
            180                 185                 190

Lys Asp Glu Ile Val Pro Phe Ile Val Lys Gly Arg Lys Gly Asp Ile
        195                 200                 205

Thr Val Asp Ala Asp Glu Tyr Ile Arg His Gly Ala Thr Leu Asp Ser
    210                 215                 220

Met Ala Lys Leu Arg Pro Ala Phe Asp Lys Glu Gly Thr Val Thr Ala
```

```
                225                 230                 235                 240
        Gly Asn Ala Ser Gly Leu Asn Asp Gly Ala Ala Ala Leu Leu Met
                        245                 250                 255

Ser Glu Ala Glu Ala Ser Arg Arg Gly Ile Gln Pro Leu Gly Arg Ile
                        260                 265                 270

Val Ser Trp Ala Thr Val Gly Val Asp Pro Lys Val Met Gly Thr Gly
                        275                 280                 285

Pro Ile Pro Ala Ser Arg Lys Ala Leu Glu Arg Ala Gly Trp Lys Ile
                        290                 295                 300

Gly Asp Leu Asp Leu Val Glu Ala Asn Glu Ala Phe Ala Ala Gln Ala
        305                 310                 315                 320

Cys Ala Val Asn Lys Asp Leu Gly Trp Asp Pro Ser Ile Val Asn Val
                        325                 330                 335

Asn Gly Gly Ala Ile Ala Ile Gly His Pro Ile Gly Ala Ser Gly Ala
                        340                 345                 350

Arg Ile Leu Asn Thr Leu Leu Phe Glu Met Lys Arg Arg Gly Ala Arg
                        355                 360                 365

Lys Gly Leu Ala Thr Leu Cys Ile Gly Gly Gly Met Gly Val Ala Met
                        370                 375                 380

Cys Ile Glu Ser Leu
        385

<210> SEQ ID NO 94
<211> LENGTH: 393
<212> TYPE: PRT
<213> ORGANISM: Pseudomonas aeruginosa

<400> SEQUENCE: 94

Met Gln Asp Val Val Ile Val Ala Ala Thr Arg Thr Ala Val Gly Ser
        1               5                   10                  15

Phe Gln Gly Ser Leu Ala Gly Ile Pro Ala Pro Glu Leu Gly Ala Ala
                        20                  25                  30

Val Ile Arg Arg Leu Leu Glu Gln Thr Gly Leu Asp Ala Gly Gln Val
                        35                  40                  45

Asp Glu Val Ile Leu Gly Gln Val Leu Thr Ala Gly Ser Gly Gln Asn
            50                  55                  60

Pro Ala Arg Gln Ala Ala Ile Lys Ala Gly Leu Pro Val Gly Val Pro
        65                  70                  75                  80

Ala Met Thr Leu Asn Lys Val Cys Gly Ser Gly Leu Lys Ala Leu His
                        85                  90                  95

Leu Gly Ala Gln Ala Ile Arg Cys Gly Asp Ala Glu Val Ile Val Ala
                        100                 105                 110

Gly Gly Gln Glu Asn Met Ser Leu Ala Pro Tyr Val Met Pro Gly Ala
                        115                 120                 125

Arg Thr Gly Leu Arg Met Gly His Ala Lys Leu Val Asp Ser Met Ile
                        130                 135                 140

Glu Asp Gly Leu Trp Asp Ala Phe Asn Asp Tyr His Met Gly Ile Thr
        145                 150                 155                 160

Ala Glu Asn Leu Ala Glu Lys Tyr Gly Leu Ser Arg Glu Glu Gln Asp
                        165                 170                 175

Ala Phe Ala Ala Ala Ser Gln Gln Lys Ala Ile Ala Ala Ile Glu Gly
                        180                 185                 190

Gly Arg Phe Arg Asp Glu Ile Thr Pro Ile Gln Val Pro Gln Arg Lys
                        195                 200                 205
```

```
Gly Glu Pro Leu Ser Phe Asp Thr Asp Glu Gln Pro Arg Ala Gly Thr
    210                 215                 220

Thr Val Glu Ala Leu Ala Lys Leu Lys Pro Ala Phe Arg Lys Asp Gly
225                 230                 235                 240

Ser Val Thr Ala Gly Asn Ala Ser Ser Leu Asn Asp Gly Ala Ala Ala
                245                 250                 255

Val Leu Leu Met Ser Ala Ala Lys Ala Lys Ala Leu Gly Leu Pro Val
                260                 265                 270

Leu Ala Arg Ile Ala Ser Tyr Ala Ser Ala Gly Val Asp Pro Ala Ile
            275                 280                 285

Met Gly Ile Gly Pro Val Ser Ala Thr Arg Arg Ala Leu Asp Lys Ala
            290                 295                 300

Gly Trp Ser Leu Glu Gln Leu Asp Leu Ile Glu Ala Asn Glu Ala Phe
305                 310                 315                 320

Ala Ala Gln Ser Leu Ala Val Gly Arg Glu Leu Gly Trp Asp Ala Ala
                325                 330                 335

Arg Val Asn Val Asn Gly Gly Ala Ile Ala Leu Gly His Pro Ile Gly
            340                 345                 350

Ala Ser Gly Cys Arg Val Leu Val Thr Leu Leu His Glu Met Ile Arg
            355                 360                 365

Arg Asp Ala Lys Lys Gly Leu Ala Thr Leu Cys Ile Gly Gly Gly Gln
370                 375                 380

Gly Val Ala Leu Thr Leu Ala Arg Asp
385                 390
```

<210> SEQ ID NO 95
<211> LENGTH: 391
<212> TYPE: PRT
<213> ORGANISM: Azospirillum lipoferum

<400> SEQUENCE: 95

```
Met Thr Glu Val Val Ile Ala Gly Ala Ala Arg Thr Pro Ile Gly Ser
1               5                   10                  15

Phe Asn Gly Ala Leu Ser Ala Val Pro Ala His Val Leu Gly Glu Val
                20                  25                  30

Ala Ile Arg Glu Ala Leu Ala Arg Ala Lys Thr Asp Ala Ala Glu Val
            35                  40                  45

Asp Glu Val Ile Leu Gly Gln Ile Leu Thr Ala Gly Gln Gly Gln Asn
        50                  55                  60

Pro Ala Arg Gln Ala Ala Val Asn Ala Gly Ile Pro Val Glu Ala Thr
65                  70                  75                  80

Ala Met Gly Ile Asn Gln Leu Cys Gly Ser Gly Leu Arg Ala Val Ala
                85                  90                  95

Leu Gly Tyr Gln Ala Ile Lys Asn Gly Asp Ala Asp Val Leu Val Val
            100                 105                 110

Gly Gly Gln Glu Ser Met Ser Met Ala Pro His Val Met His Leu Arg
        115                 120                 125

Asn Gly Thr Lys Met Gly Ser Ala Glu Leu Leu Asp Thr Met Leu Arg
130                 135                 140

Asp Gly Leu Thr Asp Ala Phe His Gly Tyr His Met Gly Thr Thr Ala
145                 150                 155                 160

Glu Asn Val Ala Gln Lys Trp Gln Leu Thr Arg Glu Glu Gln Asp Ala
                165                 170                 175

Phe Ala Ala Ala Ser Gln Gln Lys Ala Glu Ala Ala Gln Lys Ala Gly
            180                 185                 190
```

```
Arg Phe Lys Asp Glu Ile Val Pro Val Thr Ile Lys Gly Arg Lys Gly
            195                 200                 205

Asp Val Val Ser Asp Glu Tyr Pro Lys His Gly Thr Thr Pro
    210                 215                 220

Glu Ser Leu Ala Lys Leu Arg Pro Ala Phe Ser Lys Asp Gly Thr Val
225                 230                 235                 240

Thr Ala Gly Asn Ala Ser Gly Ile Asn Asp Gly Ala Ala Leu Val
                245                 250                 255

Leu Met Thr Ala Glu Asn Ala Ala Lys Arg Gly Val Thr Pro Leu Ala
                260                 265                 270

Arg Ile Val Ser Trp Ala Thr Ala Gly Val Asp Pro Ala Ile Met Gly
                275                 280                 285

Thr Gly Pro Ile Pro Ala Ser Arg Lys Ala Leu Glu Lys Ala Gly Trp
    290                 295                 300

Thr Val Asp Asp Leu Asp Leu Ile Glu Ala Asn Glu Ala Phe Ala Ala
305                 310                 315                 320

Gln Ala Leu Ser Val Asn Lys Asp Leu Gly Trp Asp Thr Ser Lys Val
                325                 330                 335

Asn Val Asn Gly Gly Ala Ile Ala Leu Gly His Pro Val Gly Ala Ser
                340                 345                 350

Gly Ala Arg Val Leu Thr Thr Leu Leu Tyr Glu Met Gln Lys Arg Asp
    355                 360                 365

Ala Lys Lys Gly Leu Ala Thr Leu Cys Ile Gly Gly Met Gly Ile
370                 375                 380

Ala Leu Cys Val Gln Arg Asp
385                 390

<210> SEQ ID NO 96
<211> LENGTH: 393
<212> TYPE: PRT
<213> ORGANISM: Ralstonia solanacearum

<400> SEQUENCE: 96

Met Thr Asp Val Val Ile Val Ser Ala Val Arg Thr Ala Val Gly Lys
  1               5                  10                  15

Phe Gly Gly Ser Leu Ala Lys Ile Pro Ala Pro Glu Leu Gly Ala Ala
                20                  25                  30

Val Ile Arg Glu Ala Leu Ser Arg Ala Lys Val Ala Pro Asp Gln Val
            35                  40                  45

Ser Glu Val Ile Met Gly Gln Val Leu Thr Ala Gly Ser Gly Gln Asn
    50                  55                  60

Pro Ala Arg Gln Ala Leu Ile Lys Ala Gly Leu Pro Asp Met Val Pro
65                  70                  75                  80

Gly Met Thr Ile Asn Lys Val Cys Gly Ser Gly Leu Lys Ala Val Met
                85                  90                  95

Leu Ala Ala Asn Ala Ile Val Ala Gly Asp Ala Asp Ile Val Val Ala
                100                 105                 110

Gly Gly Gln Glu Asn Met Ser Ala Ala Pro His Val Leu Pro Gly Ser
            115                 120                 125

Arg Asp Gly Phe Arg Met Gly Asp Thr Lys Leu Ile Asp Ser Met Ile
    130                 135                 140

Val Asp Gly Leu Trp Asp Val Tyr Asn Gln Tyr His Met Gly Ile Thr
145                 150                 155                 160

Ala Glu Asn Val Ala Lys Gln Tyr Gly Ile Thr Arg Glu Ala Gln Asp
```

```
                165                 170                 175
Ala Phe Ala Val Ala Ser Gln Asn Lys Ala Glu Ala Gln Lys Ser
                180                 185                 190

Gly Arg Phe Asn Asp Glu Ile Val Pro Ile Leu Ile Pro Gln Arg Lys
                195                 200                 205

Gly Asp Pro Ile Ala Phe Ala Gln Asp Glu Phe Val Arg His Gly Ala
        210                 215                 220

Thr Leu Glu Ser Met Thr Gly Leu Lys Pro Ala Phe Asp Lys Ala Gly
225                 230                 235                 240

Thr Val Thr Ala Ala Asn Ala Ser Gly Leu Asn Asp Gly Ala Ala
                245                 250                 255

Val Val Val Met Ser Ala Ala Arg Ala Lys Glu Leu Gly Leu Thr Pro
                260                 265                 270

Leu Ala Thr Ile Arg Ala Tyr Ala Asn Ala Gly Val Asp Pro Lys Val
                275                 280                 285

Met Gly Met Gly Pro Val Pro Ala Ser Lys Arg Cys Leu Ser Arg Ala
        290                 295                 300

Gly Trp Ser Val Gly Asp Leu Asp Leu Met Glu Ile Asn Glu Ala Phe
305                 310                 315                 320

Ala Ala Gln Ala Leu Ala Val His Gln Gln Met Gly Trp Asp Thr Ala
                325                 330                 335

Lys Val Asn Val Asn Gly Gly Ala Ile Ala Ile Gly His Pro Ile Gly
                340                 345                 350

Ala Ser Gly Cys Arg Ile Leu Val Thr Leu Leu His Glu Met Gln Lys
        355                 360                 365

Arg Asp Ala Lys Lys Gly Leu Ala Ser Leu Cys Ile Gly Gly Gly Met
        370                 375                 380

Gly Val Ala Leu Ala Val Glu Arg Pro
385                 390

<210> SEQ ID NO 97
<211> LENGTH: 393
<212> TYPE: PRT
<213> ORGANISM: Burkholderia multivorans

<400> SEQUENCE: 97

Met Thr Asp Val Val Ile Val Ser Ala Ala Arg Thr Ala Val Gly Lys
1               5                   10                  15

Phe Gly Gly Ser Leu Ala Lys Val Ala Ala Pro Glu Leu Gly Ala Thr
                20                  25                  30

Val Ile Arg Ala Val Leu Glu Arg Ala Gly Val Lys Pro Glu Gln Val
            35                  40                  45

Ser Glu Val Ile Met Gly Gln Val Leu Thr Ala Gly Ser Gly Gln Asn
        50                  55                  60

Pro Ala Arg Gln Ser Leu Ile Lys Ala Gly Leu Pro Ser Ala Val Pro
65                  70                  75                  80

Gly Met Thr Ile Asn Lys Val Cys Gly Ser Gly Leu Lys Ala Val Met
                85                  90                  95

Leu Ala Ala Asn Ala Ile Val Ala Gly Asp Ala Glu Ile Val Val Ala
                100                 105                 110

Gly Gly Gln Glu Asn Met Ser Ala Ala Pro His Val Leu Pro Gly Ser
            115                 120                 125

Arg Asp Gly Phe Arg Met Gly Asp Ala Lys Leu Val Asp Thr Met Ile
        130                 135                 140
```

Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Glu Gln Asp
                165                 170                 175

Ala Phe Ala Ala Leu Ser Gln Asn Lys Ala Glu Ala Ala Gln Lys Ala
            180                 185                 190

Gly Arg Phe Asn Asp Glu Ile Val Pro Val Ser Ile Pro Gln Arg Lys
        195                 200                 205

Gly Glu Pro Leu Gln Phe Ala Thr Asp Glu Phe Val Arg His Gly Val
    210                 215                 220

Thr Ala Glu Ser Leu Ala Gly Leu Lys Pro Ala Phe Ala Lys Asp Gly
225                 230                 235                 240

Thr Val Thr Ala Ala Asn Ala Ser Gly Ile Asn Asp Gly Ala Ala Ala
                245                 250                 255

Val Leu Val Met Ser Ala Gln Lys Ala Gln Ala Leu Gly Leu Thr Pro
            260                 265                 270

Leu Ala Arg Ile Lys Ala Tyr Ala Asn Ala Gly Val Asp Pro Ser Val
        275                 280                 285

Met Gly Met Gly Pro Val Pro Ala Ser Arg Arg Cys Leu Glu Arg Ala
    290                 295                 300

Gly Trp Thr Pro Gly Asp Leu Asp Leu Met Glu Ile Asn Glu Ala Phe
305                 310                 315                 320

Ala Ala Gln Ala Leu Ala Val His Lys Gln Met Gly Trp Asp Thr Ser
                325                 330                 335

Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Val Lys
        355                 360                 365

Arg Asp Ala Lys Arg Gly Leu Ala Ser Leu Cys Ile Gly Gly Gly Met
    370                 375                 380

Gly Val Ala Leu Ala Val Glu Arg Pro
385                 390

<210> SEQ ID NO 98
<211> LENGTH: 394
<212> TYPE: PRT
<213> ORGANISM: Methylobacterium extorquens

<400> SEQUENCE: 98

Met Ala Ala Ser Glu Asp Ile Val Ile Val Gly Ala Ala Arg Thr Pro
1               5                   10                  15

Val Gly Ser Phe Ala Gly Ala Phe Gly Ser Val Pro Ala His Glu Leu
            20                  25                  30

Gly Ala Thr Ala Ile Lys Ala Ala Leu Glu Arg Ala Gly Val Ser Pro
        35                  40                  45

Asp Asp Val Asp Glu Val Ile Phe Gly Gln Val Leu Thr Ala Ala Ala
    50                  55                  60

Gly Gln Asn Pro Ala Arg Gln Ala Ala Ile Ala Ala Gly Ile Pro Glu
65                  70                  75                  80

Lys Ala Thr Ala Trp Gly Leu Asn Gln Val Cys Gly Ser Gly Leu Arg
                85                  90                  95

Thr Val Ala Val Gly Met Gln Gln Ile Ala Asn Gly Asp Ala Lys Val
            100                 105                 110

Ile Val Ala Gly Gly Gln Glu Ser Met Ser Leu Ser Pro His Ala Gln
        115                 120                 125

```
Tyr Leu Arg Gly Gly Gln Lys Met Gly Asp Leu Lys Leu Val Asp Thr
    130                 135                 140

Met Ile Lys Asp Gly Leu Trp Asp Ala Phe Asn Gly Tyr His Met Gly
145                 150                 155                 160

Gln Thr Ala Glu Asn Val Ala Gln Ala Phe Gln Leu Thr Arg Glu Gln
                165                 170                 175

Gln Asp Gln Phe Ala Val Arg Ser Gln Asn Lys Ala Glu Ala Ala Arg
            180                 185                 190

Lys Glu Gly Arg Phe Lys Glu Glu Ile Val Pro Val Thr Val Lys Gly
        195                 200                 205

Arg Lys Gly Asp Thr Val Val Asp Thr Asp Glu Tyr Ile Arg Asp Gly
    210                 215                 220

Ala Thr Val Glu Ala Met Ala Lys Leu Lys Pro Ala Phe Ala Lys Asp
225                 230                 235                 240

Gly Thr Val Thr Ala Ala Asn Ala Ser Gly Leu Asn Asp Gly Ala Ala
                245                 250                 255

Ala Leu Val Leu Met Ser Ala Ser Glu Ala Glu Arg Arg Gly Ile Thr
            260                 265                 270

Pro Leu Ala Arg Ile Val Ser Trp Ala Thr Ala Gly Val Asp Pro Lys
        275                 280                 285

Val Met Gly Thr Gly Pro Ile Pro Ala Ser Arg Lys Ala Leu Glu Lys
290                 295                 300

Ala Gly Trp Lys Pro Ala Asp Leu Asp Leu Ile Glu Ala Asn Glu Ala
305                 310                 315                 320

Phe Ala Ala Gln Ala Leu Ala Val Asn Lys Asp Met Gly Trp Asp Asp
                325                 330                 335

Glu Lys Val Asn Val Asn Gly Gly Ala Ile Ala Ile Gly His Pro Ile
            340                 345                 350

Gly Ala Ser Gly Ala Arg Val Leu Ile Thr Leu Leu His Glu Leu Lys
        355                 360                 365

Arg Arg Asp Ala Lys Lys Gly Leu Ala Thr Leu Cys Ile Gly Gly Gly
    370                 375                 380

Met Gly Val Ala Met Cys Val Glu Arg Val
385                 390

<210> SEQ ID NO 99
<211> LENGTH: 392
<212> TYPE: PRT
<213> ORGANISM: Clostridium perfringens C str.

<400> SEQUENCE: 99

Met Arg Glu Val Val Ile Ala Ser Ala Val Arg Thr Ala Leu Gly Ser
1               5                   10                  15

Phe Gly Gly Ser Leu Lys Asp Val Pro Ala Val Asp Leu Gly Ala Leu
                20                  25                  30

Val Ile Lys Glu Ala Leu Asn Lys Ala Gly Val Lys Pro Glu Cys Val
            35                  40                  45

Asp Glu Val Leu Met Gly Asn Val Ile Gln Ala Gly Leu Gly Gln Asn
        50                  55                  60

Pro Ala Arg Gln Ala Ala Val Lys Ala Gly Leu Pro Val Glu Ile Pro
65                  70                  75                  80

Ser Met Thr Ile Asn Lys Val Cys Gly Ser Gly Leu Arg Cys Val Ala
                85                  90                  95

Leu Ala Ala Gln Met Ile Lys Ala Gly Asp Ala Asp Val Ile Val Ala
```

```
              100                 105                 110
Gly Gly Met Glu Asn Met Ser Gln Gly Pro Tyr Val Leu Arg Thr Ala
            115                 120                 125

Arg Phe Gly Gln Arg Met Gly Asp Gly Lys Met Val Asp Ala Met Val
130                 135                 140

Asn Asp Ala Leu Thr Asp Ala Phe Asn Gly Tyr His Met Gly Ile Thr
145                 150                 155                 160

Ala Glu Asn Ile Ala Glu Gln Trp Gly Leu Thr Arg Glu Met Gln Asp
            165                 170                 175

Glu Phe Ala Ala Asn Ser Gln Ile Lys Ala Glu Ala Ile Lys Ala
            180                 185                 190

Gly Lys Phe Lys Asp Glu Ile Val Pro Val Ile Pro Gln Arg Lys
            195                 200                 205

Gly Asp Pro Ile Val Phe Asp Thr Asp Glu Phe Pro Arg Phe Gly Thr
210                 215                 220

Thr Ala Glu Lys Leu Ala Lys Leu Arg Pro Ala Phe Lys Lys Asp Gly
225                 230                 235                 240

Thr Val Thr Ala Gly Asn Ala Ser Gly Ile Asn Asp Gly Ala Ala Ala
            245                 250                 255

Leu Val Val Met Ser Ala Glu Lys Ala Lys Glu Leu Gly Val Thr Pro
            260                 265                 270

Ile Cys Lys Ile Val Ser Tyr Gly Ser Lys Gly Leu Asp Pro Ser Ile
            275                 280                 285

Met Gly Tyr Gly Pro Phe Tyr Ala Thr Lys Lys Ala Leu Glu Gly Thr
            290                 295                 300

Gly Leu Lys Val Glu Asp Leu Asp Leu Ile Glu Ala Asn Glu Ala Phe
305                 310                 315                 320

Ala Ala Gln Ser Leu Ala Val Ala Lys Asp Leu Glu Phe Asp Met Ser
            325                 330                 335

Lys Val Asn Val Asn Gly Gly Ala Ile Ala Leu Gly His Pro Val Gly
            340                 345                 350

Ala Ser Gly Ala Arg Ile Leu Val Thr Leu Leu His Glu Met Met Lys
            355                 360                 365

Arg Asp Ala Lys Arg Gly Leu Ala Thr Leu Cys Ile Gly Gly Gly Met
370                 375                 380

Gly Thr Ala Leu Ile Val Glu Arg
385                 390

<210> SEQ ID NO 100
<211> LENGTH: 394
<212> TYPE: PRT
<213> ORGANISM: Thiorhodococcus drewsii

<400> SEQUENCE: 100

Met Ser Glu Asn Ile Val Ile Val Asp Ala Gly Arg Thr Ala Ile Gly
1               5                   10                  15

Thr Phe Gly Gly Ser Leu Ser Ser Leu Pro Ala Thr Glu Leu Gly Thr
            20                  25                  30

Thr Val Leu Lys Ala Leu Leu Ala Arg Thr Gly Ile Ala Pro Asp Gln
            35                  40                  45

Ile Asp Glu Val Ile Leu Gly Gln Val Leu Thr Ala Gly Val Gly Gln
        50                  55                  60

Asn Pro Ala Arg Gln Thr Thr Leu Lys Ala Gly Leu Pro His Ala Val
65                  70                  75                  80
```

-continued

Pro Ala Met Thr Ile Asn Lys Val Cys Gly Ser Gly Leu Lys Ala Val
                85                  90                  95

His Leu Ala Met Gln Ala Val Ala Cys Gly Asp Ala Asp Ile Val Ile
            100                 105                 110

Ala Gly Gly Gln Glu Cys Met Ser Gln Ser Ser His Val Leu Pro Arg
        115                 120                 125

Ser Arg Asp Gly Gln Arg Met Gly Asp Trp Lys Met Val Asp Thr Met
130                 135                 140

Ile Val Asp Gly Leu Trp Asp Ala Phe Asn Gln Tyr His Met Gly Val
145                 150                 155                 160

Thr Ala Glu Asn Ile Ala Lys Gln Phe Gly Phe Thr Arg Glu Ala Gln
                165                 170                 175

Asp Thr Phe Ala Ala Glu Ser Gln Gln Lys Ala Glu Ala Ala Ile Lys
            180                 185                 190

Ala Gly Arg Phe Lys Asp Glu Ile Val Pro Val Ser Ile Pro Gln Arg
        195                 200                 205

Lys Gly Asp Pro Leu Val Val Asp Thr Asp Glu Phe Pro Arg Ala Gly
210                 215                 220

Thr Thr Ala Ala Gly Leu Gly Lys Leu Arg Pro Ala Phe Asp Lys Glu
225                 230                 235                 240

Gly Thr Val Thr Ala Gly Asn Ala Ser Gly Ile Asn Asp Gly Ala Ala
                245                 250                 255

Met Val Val Val Met Lys Glu Ser Lys Ala Lys Glu Leu Gly Leu Lys
            260                 265                 270

Pro Met Ala Arg Ile Val Ala Phe Ala Ser Ala Gly Val Asp Pro Ala
        275                 280                 285

Ile Met Gly Thr Gly Pro Ile Pro Ala Ser Thr Lys Cys Leu Glu Lys
290                 295                 300

Ala Gly Trp Thr Pro Ala Asp Leu Asp Leu Ile Glu Ala Asn Glu Ala
305                 310                 315                 320

Phe Ala Ala Gln Ala Met Ser Val Asn Lys Glu Met Gly Trp Asp Leu
                325                 330                 335

Ser Lys Val Asn Val Asn Gly Gly Ala Ile Ser Leu Gly His Pro Ile
            340                 345                 350

Gly Ala Ser Gly Ala Arg Val Leu Val Thr Leu Leu His Glu Met Gln
        355                 360                 365

His Arg Asp Ala Lys Lys Gly Leu Ala Thr Leu Cys Ile Gly Gly Gly
    370                 375                 380

Gln Gly Val Ala Leu Ala Val Glu Arg Leu
385                 390

<210> SEQ ID NO 101
<211> LENGTH: 246
<212> TYPE: PRT
<213> ORGANISM: Burkholderia pseudomallei

<400> SEQUENCE: 101

Met Ser Gln Arg Ile Ala Tyr Val Thr Gly Gly Met Gly Gly Ile Gly
1               5                   10                  15

Thr Ser Ile Cys Gln Arg Leu His Lys Asp Gly Phe Arg Val Val Ala
            20                  25                  30

Gly Cys Gly Pro Asn Ser Pro Arg Arg Val Lys Trp Leu Glu Asp Gln
        35                  40                  45

Lys Ala Leu Gly Phe Asp Phe Tyr Ala Ser Glu Gly Asn Val Gly Asp
    50                  55                  60

```
Trp Asp Ser Thr Lys Gln Ala Phe Asp Lys Val Lys Ala Glu Val Gly
 65                  70                  75                  80

Glu Ile Asp Val Leu Val Asn Asn Ala Gly Ile Thr Arg Asp Val Val
                 85                  90                  95

Phe Arg Lys Met Thr Arg Glu Asp Trp Gln Ala Val Ile Asp Thr Asn
            100                 105                 110

Leu Thr Ser Leu Phe Asn Val Thr Lys Gln Val Ile Asp Gly Met Val
        115                 120                 125

Glu Arg Gly Trp Gly Arg Ile Ile Asn Ile Ser Ser Val Asn Gly Gln
    130                 135                 140

Lys Gly Gln Phe Gly Gln Thr Asn Tyr Ser Thr Ala Lys Ala Gly Ile
145                 150                 155                 160

His Gly Phe Thr Met Ser Leu Ala Gln Glu Val Ala Thr Lys Gly Val
                165                 170                 175

Thr Val Asn Thr Val Ser Pro Gly Tyr Ile Gly Thr Asp Met Val Lys
            180                 185                 190

Ala Ile Arg Pro Asp Val Leu Glu Lys Ile Val Ala Thr Ile Pro Val
        195                 200                 205

Arg Arg Leu Gly Ser Pro Asp Glu Ile Gly Ser Ile Val Ala Trp Leu
    210                 215                 220

Ala Ser Glu Glu Ser Gly Phe Ser Thr Gly Ala Asp Phe Ser Leu Asn
225                 230                 235                 240

Gly Gly Leu His Met Gly
                245

<210> SEQ ID NO 102
<211> LENGTH: 241
<212> TYPE: PRT
<213> ORGANISM: Methylosinus trichosporium

<400> SEQUENCE: 102

Met Gly Arg Thr Ala Val Val Thr Gly Gly Thr Arg Gly Ile Gly Glu
  1               5                  10                  15

Ala Ile Ser Lys Ala Leu Lys Ala Ala Gly Tyr Asn Val Ala Ala Thr
                 20                  25                  30

Tyr Ala Gly Asn Asp Glu Ala Ala Asn Lys Phe Lys Asp Ala Thr Gly
            35                  40                  45

Ile Pro Val Tyr Lys Phe Asp Val Ser Asp Tyr Asp Ala Cys Ala Ala
         50                  55                  60

Ala Leu Ala Ala Ile Glu Thr Asp Leu Gly Pro Val Asp Val Leu Val
 65                  70                  75                  80

Asn Asn Ala Gly Ile Thr Lys Asp Arg Leu Phe His Lys Met Glu Leu
                 85                  90                  95

Ala Gln Trp Arg Ala Val Ile Asp Thr Asn Leu Asn Ser Leu Phe Asn
            100                 105                 110

Val Thr Arg Pro Val Ile Asn Gly Met Arg Asp Arg Gly Phe Gly Arg
        115                 120                 125

Ile Ile Val Ile Ser Ser Ile Asn Gly Gln Lys Gly Gln Ala Gly Gln
    130                 135                 140

Thr Asn Tyr Ser Ala Ser Lys Ala Gly Asp Ile Gly Phe Val Lys Ala
145                 150                 155                 160

Leu Ala Gln Glu Ser Ala Ala Lys Gly Ile Thr Val Asn Ala Ile Ala
                165                 170                 175

Pro Gly Tyr Ile Ala Thr Glu Met Val Lys Ala Val Pro Gln Glu Val
```

```
                    180                 185                 190
Leu Asp Lys His Ile Ile Pro His Ile Ala Val Gly Arg Leu Gly Glu
                195                 200                 205

Pro Glu Glu Ile Ala Arg Ala Val Val Phe Leu Ala Ser Asp Glu Ala
            210                 215                 220

Gly Phe Ile Thr Gly Ser Thr Leu Thr Ile Asn Gly Gly Gln Tyr Leu
225                 230                 235                 240

Thr

<210> SEQ ID NO 103
<211> LENGTH: 247
<212> TYPE: PRT
<213> ORGANISM: Burkholderia cenocepacia

<400> SEQUENCE: 103

Met Thr Lys Arg Ile Ala Val Val Thr Gly Gly Met Gly Gly Leu Gly
1               5                   10                  15

Glu Ala Val Ser Ile Arg Leu Asn Asp Ala Gly His Arg Val Val Val
            20                  25                  30

Thr Tyr Ser Pro Asn Asn Thr Gly Ala Asp Arg Trp Leu Thr Glu Met
        35                  40                  45

His Ala Ala Gly Arg Glu Phe His Ala Tyr Pro Val Asp Val Ala Asp
    50                  55                  60

His Asp Ser Cys Gln Gln Cys Ile Glu Lys Ile Val Arg Asp Val Gly
65                  70                  75                  80

Pro Val Asp Ile Leu Val Asn Asn Ala Gly Ile Thr Arg Asp Met Thr
                85                  90                  95

Leu Arg Lys Leu Asp Lys Val Asn Trp Asp Ala Val Ile Arg Thr Asn
            100                 105                 110

Leu Asp Ser Val Phe Asn Met Thr Lys Pro Val Cys Asp Gly Met Val
        115                 120                 125

Glu Arg Gly Trp Gly Arg Ile Val Asn Ile Ser Ser Val Asn Gly Ser
    130                 135                 140

Lys Gly Ser Val Gly Gln Thr Asn Tyr Ala Ala Ala Lys Ala Gly Met
145                 150                 155                 160

His Gly Phe Thr Lys Ser Leu Ala Leu Glu Ile Ala Arg Lys Gly Val
                165                 170                 175

Thr Val Asn Thr Val Ser Pro Gly Tyr Leu Ala Thr Lys Met Val Thr
            180                 185                 190

Ala Ile Pro Gln Asp Ile Leu Asp Thr Lys Ile Leu Pro Gln Ile Pro
        195                 200                 205

Ala Gly Arg Leu Gly Lys Pro Glu Glu Val Ala Ala Leu Val Ala Tyr
    210                 215                 220

Leu Cys Ser Glu Glu Ala Gly Phe Val Thr Gly Ser Asn Ile Ala Ile
225                 230                 235                 240

Asn Gly Gly Gln His Met His
                245

<210> SEQ ID NO 104
<211> LENGTH: 245
<212> TYPE: PRT
<213> ORGANISM: Vibrio cholerae

<400> SEQUENCE: 104

Met Arg Lys Ile Ala Leu Ile Thr Gly Ser Lys Gly Gly Ile Gly Ser
1               5                   10                  15
```

```
Ala Ile Ser Thr Gln Leu Val Ser Glu Gly Tyr Arg Val Ile Ala Thr
            20                  25                  30

Tyr Tyr Thr Gly Asn Tyr Gln Cys Ala Leu Asp Trp Phe Asn Glu Lys
        35                  40                  45

Gln Phe Thr Glu Asp Gln Val Arg Leu Leu Glu Leu Asp Val Thr Asn
 50                  55                  60

Thr Glu Glu Cys Ala Glu Arg Leu Ala Lys Leu Leu Glu Glu Glu Gly
65                  70                  75                  80

Thr Ile Asp Val Val Asn Asn Ala Gly Ile Thr Arg Asp Ser Val
                85                  90                  95

Phe Lys Lys Met Pro His Gln Ala Trp Lys Glu Val Ile Asp Thr Asn
                100                 105                 110

Leu Asn Ser Val Phe Asn Val Thr Gln Pro Leu Phe Ala Ala Met Cys
            115                 120                 125

Glu Lys Gly Phe Gly Arg Ile Ile Asn Ile Ser Ser Val Asn Gly Leu
130                 135                 140

Lys Gly Gln Phe Gly Gln Thr Asn Tyr Ser Ala Ala Lys Ala Gly Met
145                 150                 155                 160

Ile Gly Phe Ser Lys Ala Leu Ala Glu Gly Ala Arg Tyr Gly Val
                165                 170                 175

Thr Val Asn Val Ile Ala Pro Gly Tyr Thr Leu Thr Pro Met Val Glu
            180                 185                 190

Gln Met Arg Ala Glu Val Leu Gln Ser Ile Val Asp Gln Val Pro Met
        195                 200                 205

Lys Arg Leu Ala Lys Pro Glu Glu Ile Ala Asn Ala Val Ser Tyr Leu
            210                 215                 220

Ala Ser Asp Ala Ala Tyr Ile Thr Gly Glu Thr Leu Ser Val Asn Gly
225                 230                 235                 240

Gly Leu Tyr Met Arg
                245

<210> SEQ ID NO 105
<211> LENGTH: 240
<212> TYPE: PRT
<213> ORGANISM: Azospirillum brasilense

<400> SEQUENCE: 105

Met Ala Arg Val Ala Val Val Thr Gly Gly Thr Arg Gly Ile Gly Glu
 1               5                   10                  15

Ala Ile Ser Val Ala Leu Lys Asn Ala Gly Tyr Val Val Ala Ala Asn
            20                  25                  30

Tyr Ala Gly Asn Asp Glu Lys Ala Lys Glu Phe Ser Ala Arg Thr Gly
        35                  40                  45

Ile Ala Val Tyr Lys Phe Asp Val Ser Asp Phe Asp Ala Val Lys Asp
 50                  55                  60

Gly Ile Ala Lys Ile Ser Ala Glu Leu Gly Pro Val Asp Val Val Val
65                  70                  75                  80

Asn Asn Ala Gly Ile Thr Arg Asp Gly Val Ile His Arg Met Thr Pro
                85                  90                  95

Gln Gln Trp Asn Asp Val Ile Ala Thr Asn Leu Thr Ser Cys Phe Asn
            100                 105                 110

Leu Cys Arg Asn Val Ile Asp Gly Met Arg Glu Arg Gly Phe Gly Arg
        115                 120                 125

Ile Val Asn Ile Gly Ser Val Asn Gly Gln Ala Gly Gln Tyr Gly Gln
```

```
                130             135             140
Val Asn Tyr Ala Ala Lys Ser Gly Ile His Gly Phe Thr Lys Ala
145                 150                 155                 160

Leu Ala Gln Glu Gly Ala Ala Lys Gly Val Thr Val Asn Ala Ile Ala
                165                 170                 175

Pro Gly Tyr Ile Asp Thr Asp Met Val Arg Ala Val Pro Pro Asn Val
            180                 185                 190

Leu Glu Lys Ile Val Ala Arg Ile Pro Val Gly Arg Leu Gly Lys Ala
        195                 200                 205

Glu Glu Ile Ala Arg Gly Val Leu Phe Leu Val Gly Asp Asp Ala Gly
    210                 215                 220

Phe Ile Thr Gly Ser Thr Leu Ser Ile Asn Gly Gly Gln His Met Tyr
225                 230                 235                 240

<210> SEQ ID NO 106
<211> LENGTH: 246
<212> TYPE: PRT
<213> ORGANISM: Azospirillum brasilense

<400> SEQUENCE: 106

Met Ser Gln Lys Ile Ala Leu Val Thr Gly Ala Met Gly Gly Leu Gly
 1               5                  10                  15

Thr Ala Ile Cys Gln Ala Leu Ala Lys Asp Gly Tyr Ile Val Ala Ala
                20                  25                  30

Asn Cys Leu Pro Asn Phe Glu Pro Ala Ala Trp Leu Gly Gln Gln
            35                  40                  45

Glu Ala Leu Gly Phe Lys Phe Tyr Val Ala Glu Gly Asp Val Ser Asp
    50                  55                  60

Phe Glu Ser Cys Lys Ala Met Val Ala Lys Ile Glu Ala Asp Leu Gly
65                  70                  75                  80

Pro Val Asp Ile Leu Val Asn Asn Ala Gly Ile Thr Arg Asp Lys Phe
                85                  90                  95

Phe Ala Lys Met Glu Lys Ala Gln Trp Asp Ala Val Ile Ala Thr Asn
                100                 105                 110

Leu Ser Ser Leu Phe Asn Val Thr Gln Gln Val Ser Ala Lys Met Ala
            115                 120                 125

Glu Arg Gly Trp Gly Arg Ile Ile Asn Ile Ser Ser Val Asn Gly Val
        130                 135                 140

Lys Gly Gln Ala Gly Gln Thr Asn Tyr Ser Ala Ala Lys Ala Gly Val
145                 150                 155                 160

Ile Gly Phe Thr Lys Ala Leu Ala Ala Glu Leu Ala Thr Lys Gly Val
                165                 170                 175

Thr Val Asn Ala Ile Ala Pro Gly Tyr Ile Gly Thr Asp Met Val Met
            180                 185                 190

Ala Ile Arg Glu Asp Ile Arg Gln Ala Ile Thr Asp Ser Val Pro Met
        195                 200                 205

Lys Arg Leu Gly Arg Pro Asp Glu Ile Gly Gly Ala Val Ser Tyr Leu
    210                 215                 220

Ala Ser Glu Ile Ala Gly Tyr Val Thr Gly Ser Thr Leu Asn Ile Asn
225                 230                 235                 240

Gly Gly Leu Asn Tyr Gln
                245

<210> SEQ ID NO 107
<211> LENGTH: 246
```

<212> TYPE: PRT
<213> ORGANISM: Azoarcus sp.

<400> SEQUENCE: 107

Met Ser Arg Val Ala Leu Val Thr Gly Gly Met Gly Gly Leu Gly Glu
1               5                   10                  15

Ala Ile Cys Ile Lys Leu Ala Ala Leu Gly Tyr Arg Val Val Thr Thr
                20                  25                  30

Tyr Ser Pro Gly Asn Ser Lys Ala Ala Glu Trp Leu Gln Ala Met Asn
            35                  40                  45

Asn Met Gly Tyr Gly Phe Arg Gly Tyr Pro Cys Asp Val Ser Asp Phe
    50                  55                  60

Asp Ser Cys Lys Ala Cys Ile Ala Gln Val Thr Glu Glu Val Gly Pro
65                  70                  75                  80

Ile Asp Val Leu Val Asn Asn Ala Gly Ile Thr Arg Asp Met Thr Phe
                85                  90                  95

Lys Lys Met Thr Lys Ala Asp Trp Asp Ala Val Ile Ser Thr Asn Leu
                100                 105                 110

Asp Ser Val Phe Asn Met Thr Lys Gln Val Met Asp Gly Met Val Glu
            115                 120                 125

Arg Lys Trp Gly Arg Val Ile Asn Val Ser Ser Val Asn Gly Gln Lys
    130                 135                 140

Gly Ala Phe Gly Gln Thr Asn Tyr Ser Ala Ala Lys Ala Gly Met His
145                 150                 155                 160

Gly Phe Thr Lys Ala Leu Ala Leu Glu Val Ala Arg Ser Gly Val Thr
                165                 170                 175

Val Asn Thr Ile Ser Pro Gly Tyr Ile Gly Thr Lys Met Val Met Ala
                180                 185                 190

Ile Pro Gln Glu Ile Leu Glu Ser Lys Ile Leu Pro Gln Ile Pro Val
            195                 200                 205

Ser Arg Leu Gly Lys Pro Glu Glu Ile Ala Gly Leu Val Ala Tyr Leu
    210                 215                 220

Ser Ser Asp Glu Ala Ala Phe Val Thr Gly Ala Asn Ile Ser Ile Asn
225                 230                 235                 240

Gly Gly Gln His Met Phe
                245

<210> SEQ ID NO 108
<211> LENGTH: 246
<212> TYPE: PRT
<213> ORGANISM: Cupriavidus taiwanensis

<400> SEQUENCE: 108

Met Thr Gln Arg Ile Ala Tyr Val Thr Gly Gly Met Gly Gly Ile Gly
1               5                   10                  15

Thr Ala Ile Cys Gln Arg Leu Ala Arg Asp Gly Phe Arg Val Val Ala
                20                  25                  30

Gly Cys Gly Pro Asn Ser Pro Arg Arg Glu Lys Trp Leu Glu Gln Gln
            35                  40                  45

Lys Ala Leu Gly Phe Asp Phe Val Ala Ser Glu Gly Asn Val Ala Asp
    50                  55                  60

Trp Asp Ser Thr Lys Ala Ala Phe Asp Lys Val Lys Ala Glu Val Gly
65                  70                  75                  80

Glu Val Asp Val Leu Ile Asn Asn Ala Gly Ile Thr Arg Asp Val Val
                85                  90                  95

```
Phe Arg Lys Met Thr Arg Ala Asp Trp Asp Ala Val Ile Asp Thr Asn
            100                 105                 110

Leu Thr Ser Leu Phe Asn Val Thr Lys Gln Val Ile Asp Gly Met Ala
        115                 120                 125

Asp Arg Gly Trp Gly Arg Ile Val Asn Ile Ser Ser Val Asn Gly Gln
    130                 135                 140

Lys Gly Gln Phe Gly Gln Thr Asn Tyr Ser Thr Ala Lys Ala Gly Leu
145                 150                 155                 160

His Gly Phe Thr Met Ala Leu Ala Gln Glu Val Ala Thr Lys Gly Val
                165                 170                 175

Thr Val Asn Thr Val Ser Pro Gly Tyr Ile Ala Thr Asp Met Val Lys
            180                 185                 190

Ala Ile Arg Gln Asp Val Leu Asp Lys Ile Val Gly Thr Ile Pro Val
        195                 200                 205

Lys Arg Leu Gly Glu Pro Glu Glu Ile Ala Ser Ile Cys Ala Trp Leu
    210                 215                 220

Ala Ser Glu Glu Ser Gly Phe Ser Thr Gly Ala Asp Phe Ser Leu Asn
225                 230                 235                 240

Gly Gly Leu His Met Gly
                245

<210> SEQ ID NO 109
<211> LENGTH: 246
<212> TYPE: PRT
<213> ORGANISM: Legionella pneumophila

<400> SEQUENCE: 109

Met Asp Lys Met Ile Ala Ile Val Thr Gly Gly Thr Gly Gly Ile Gly
 1               5                  10                  15

Ser Ala Ile Ser Gln Arg Leu Ala Asp Ser Tyr Gln Val Val Ala Cys
            20                  25                  30

Tyr Tyr Lys Asp Gly Arg His Glu Glu Ala Lys Lys Trp Gln Asp Glu
        35                  40                  45

Gln Lys Gln Leu Gly Tyr Asp Ile Asp Ile Val Tyr Gly Asp Ile Ala
    50                  55                  60

Gln Tyr Ser Asp Cys Glu Lys Ile Thr Ser Leu Val Met Glu Arg Tyr
65                  70                  75                  80

Gly Arg Ile Asp Val Leu Val Asn Asn Ala Gly Ile Thr Lys Asp Cys
                85                  90                  95

Ser Leu Arg Lys Met Thr Pro Gln Gln Trp Gln Gln Val Leu Asp Ala
            100                 105                 110

Asn Leu Thr Ser Val Phe Asn Met Thr Arg Asn Val Val Pro Val Met
        115                 120                 125

Leu Glu Arg Gly Tyr Gly Arg Ile Ile Ser Ile Ser Ser Ile Asn Gly
    130                 135                 140

Arg Lys Gly Gln Phe Gly Gln Cys Asn Tyr Ala Ser Thr Lys Ala Ala
145                 150                 155                 160

Leu Phe Gly Phe Thr Lys Ser Leu Ala Leu Glu Val Ala Ser Lys Gly
                165                 170                 175

Ile Thr Val Asn Thr Val Ser Pro Gly Tyr Ile Glu Thr Pro Met Leu
            180                 185                 190

Ala Ala Leu Lys Glu Asp Val Leu Asn Ser Ile Ile Ser Ser Ile Pro
        195                 200                 205

Val Gly Arg Leu Gly Tyr Pro Lys Glu Ile Ala Asp Ala Val Ala Phe
    210                 215                 220
```

```
Leu Ala Ser Pro Asp Ser Gly Phe Ile Thr Gly Ala Asn Leu Asp Val
225                 230                 235                 240

Asn Gly Gly Gln Tyr Met
                245

<210> SEQ ID NO 110
<211> LENGTH: 248
<212> TYPE: PRT
<213> ORGANISM: Halomonas sp.

<400> SEQUENCE: 110

Met Thr Asn Gln Ala Pro Val Ala Trp Val Thr Gly Gly Thr Gly Gly
 1               5                  10                  15

Ile Gly Thr Ala Ile Cys Arg Ser Leu Ala Asp Ala Gly Tyr Leu Val
            20                  25                  30

Val Ala Gly Tyr His Asn Pro Asp Lys Ala Lys Thr Trp Leu Glu Thr
        35                  40                  45

Gln Arg Ala Asp Gly Tyr Asn Asn Ile Glu Leu Ser Gly Val Asp Leu
    50                  55                  60

Ser Asp His Asn Ala Cys Leu Glu Gly Ala Arg Glu Ile His Asp Lys
65                  70                  75                  80

Tyr Gly Pro Ile Ser Val Leu Val Asn Cys Ala Gly Ile Thr Arg Asp
                85                  90                  95

Gly Thr Met Lys Lys Met Ser Tyr Glu Gln Trp Tyr Glu Val Leu Asp
            100                 105                 110

Thr Asn Leu Asn Ser Val Phe Asn Thr Cys Arg Ser Val Ile Glu Met
        115                 120                 125

Met Leu Glu Asn Gly Tyr Gly Arg Ile Ile Asn Ile Ser Ser Ile Asn
    130                 135                 140

Gly Arg Lys Gly Gln Phe Gly Gln Val Asn Tyr Ala Ala Ala Lys Ala
145                 150                 155                 160

Gly Met His Gly Leu Thr Met Ser Leu Ala Gln Glu Thr Ala Thr Lys
                165                 170                 175

Gly Ile Thr Val Asn Thr Val Ser Pro Gly Tyr Ile Ala Thr Asp Met
            180                 185                 190

Ile Met Asn Ile Pro Glu Lys Val Arg Glu Ala Ile Arg Glu Thr Ile
        195                 200                 205

Pro Val Lys Arg Tyr Gly Thr Pro Glu Glu Ile Gly Arg Leu Val Thr
    210                 215                 220

Phe Leu Ala Asp Lys Glu Ser Gly Phe Ile Thr Gly Ala Asn Ile Asp
225                 230                 235                 240

Ile Asn Gly Gly Gln Phe Met Gly
                245

<210> SEQ ID NO 111
<211> LENGTH: 246
<212> TYPE: PRT
<213> ORGANISM: Xanthomonas campestris pv. musacearum

<400> SEQUENCE: 111

Met Thr Ser Arg Val Ala Leu Val Thr Gly Gly Thr Gly Gly Ile Gly
 1               5                  10                  15

Thr Ala Ile Cys Lys Arg Leu Ala Asp Gln Gly His Arg Val Ala Ser
            20                  25                  30

Asn Phe Arg Asn Glu Glu Lys Ala Arg Asp Trp Gln Gln Arg Met Gln
        35                  40                  45
```

```
Ala Gln Gly Tyr Ala Phe Ala Leu Phe Arg Gly Asp Val Ala Ser Ser
             50                  55                  60

Glu His Ala Arg Ala Leu Val Glu Glu Val Glu Ala Ser Leu Gly Pro
 65                  70                  75                  80

Ile Glu Val Leu Val Asn Asn Ala Gly Ile Thr Arg Asp Thr Thr Phe
                     85                  90                  95

His Arg Met Thr Ala Glu Gln Trp His Glu Val Ile Asn Thr Asn Leu
                100                 105                 110

Asn Ser Val Phe Asn Val Thr Arg Pro Val Ile Glu Gly Met Arg Lys
            115                 120                 125

Arg Gly Trp Gly Arg Val Ile Gln Ile Ser Ser Ile Asn Gly Leu Lys
130                 135                 140

Gly Gln Tyr Gly Gln Ala Asn Tyr Ala Ala Ala Lys Ala Gly Met His
145                 150                 155                 160

Gly Phe Thr Ile Ser Leu Ala Arg Glu Asn Ala Ala Phe Gly Val Thr
                165                 170                 175

Val Asn Thr Val Ser Pro Gly Tyr Val Ala Thr Asp Met Val Met Ala
                180                 185                 190

Val Pro Glu Glu Val Arg Ala Lys Ile Val Ala Asp Ile Pro Thr Gly
                195                 200                 205

Arg Leu Gly Arg Pro Glu Glu Ile Ala Tyr Ala Val Ala Phe Leu Val
210                 215                 220

Ala Glu Glu Ala Ala Trp Ile Thr Gly Ser Asn Leu Asp Ile Asn Gly
225                 230                 235                 240

Gly His His Met Gly Trp
                245

<210> SEQ ID NO 112
<211> LENGTH: 248
<212> TYPE: PRT
<213> ORGANISM: Alicycliphilus denitrificans

<400> SEQUENCE: 112

Met Asn Thr Thr Gln Arg Thr Ala Leu Val Thr Gly Gly Asn Arg Gly
  1               5                  10                  15

Leu Gly Ala Ala Ile Ala Arg Ala Leu His Asp Ala Gly His Arg Val
                 20                  25                  30

Ile Val Thr His Thr Pro Gly Asn Thr Thr Ile Gly Gln Trp Gln Gln
             35                  40                  45

Ala Gln Ala Thr Gln Gly Tyr Lys Phe Ala Ala Tyr Gly Val Asp Val
 50                  55                  60

Ser Asn Tyr Glu Ser Thr Gln Glu Leu Ala Arg Arg Ile His Ala Asp
 65                  70                  75                  80

Gly His Arg Ile Asp Ile Leu Val Asn Asn Ala Gly Ile Thr Arg Asp
                 85                  90                  95

Ala Thr Leu Arg Lys Leu Asp Lys Ala Gly Trp Asp Ala Val Leu Arg
                100                 105                 110

Thr Asn Leu Asp Ser Met Phe Asn Val Thr Lys Pro Phe Ile Asp Pro
            115                 120                 125

Met Val Glu Arg Gly Trp Gly Arg Ile Val Asn Ile Ser Ser Ile Asn
130                 135                 140

Gly Ser Lys Gly Gln Phe Gly Gln Thr Asn Tyr Ser Ala Ala Lys Ala
145                 150                 155                 160

Gly Val His Gly Phe Thr Lys Ala Leu Ala Gln Glu Val Ala Arg Lys
```

```
                165                 170                 175
Gly Val Thr Val Asn Thr Val Ser Pro Gly Tyr Leu Ala Thr Glu Met
            180                 185                 190

Val Met Ala Val Arg Glu Asp Met Arg Gln Lys Ile Ile Asp Ala Ile
        195                 200                 205

Pro Val Gly Arg Leu Gly Gln Pro Asp Glu Ile Ala Ala Leu Val Ala
    210                 215                 220

Phe Ile Ala Ser Glu Ala Ala Phe Met Thr Gly Ser Asn Val Ala
225                 230                 235                 240

Met Asn Gly Gly Gln His Met Tyr
                245

<210> SEQ ID NO 113
<211> LENGTH: 241
<212> TYPE: PRT
<213> ORGANISM: Rhodobacter sphaeroides

<400> SEQUENCE: 113

Met Ser Lys Val Ala Leu Val Thr Gly Gly Ser Arg Gly Ile Gly Ala
1               5                   10                  15

Ala Ile Ser Leu Ala Leu Lys Asn Ala Gly Tyr Thr Val Ala Ala Asn
            20                  25                  30

Tyr Ala Gly Asn Asp Glu Ala Ala Gln Lys Phe Thr Ala Glu Thr Gly
        35                  40                  45

Ile Lys Thr Tyr Lys Trp Ser Val Ala Asp Tyr Asp Ala Cys Ala Glu
    50                  55                  60

Gly Ile Ala Arg Val Glu Ala Glu Leu Gly Pro Val Ala Val Leu Val
65                  70                  75                  80

Asn Asn Ala Gly Ile Thr Arg Asp Ser Met Phe His Lys Met Thr Arg
                85                  90                  95

Glu Gln Trp Lys Glu Val Ile Asp Thr Asn Leu Ser Gly Leu Phe Asn
            100                 105                 110

Met Thr His Pro Val Trp Ser Met Arg Asp Arg Lys Phe Gly Arg
        115                 120                 125

Ile Ile Asn Ile Ser Ser Ile Asn Gly Gln Lys Gly Gln Ala Gly Gln
    130                 135                 140

Ala Asn Tyr Ser Ala Ala Lys Ala Gly Asp Leu Gly Phe Thr Lys Ala
145                 150                 155                 160

Leu Ala Gln Glu Gly Ala Arg Ala Gly Ile Thr Val Asn Ala Ile Cys
                165                 170                 175

Pro Gly Tyr Ile Gly Thr Glu Met Val Arg Ala Ile Asp Glu Lys Val
            180                 185                 190

Leu Asn Glu Arg Ile Ile Pro Gln Ile Pro Val Gly Arg Leu Gly Glu
        195                 200                 205

Pro Glu Glu Ile Ala Arg Cys Val Val Phe Leu Ala Ser Asp Asp Ala
    210                 215                 220

Gly Phe Ile Thr Gly Ser Thr Ile Thr Ala Asn Gly Gly Gln Tyr Phe
225                 230                 235                 240

Thr

<210> SEQ ID NO 114
<211> LENGTH: 241
<212> TYPE: PRT
<213> ORGANISM: Rickettsia felis

<400> SEQUENCE: 114
```

```
Met Ser Glu Ile Ala Ile Val Thr Gly Gly Thr Arg Ile Gly Lys
1               5                   10                  15

Ala Thr Ala Leu Glu Leu Lys Asn Lys Gly Leu Thr Val Val Ala Asn
            20                  25                  30

Phe Phe Ser Asn Tyr Asp Ala Ala Lys Glu Met Glu Glu Lys Tyr Gly
            35                  40                  45

Ile Lys Thr Lys Cys Trp Asn Val Ala Asp Phe Glu Glu Cys Arg Gln
50                  55                  60

Ala Val Lys Glu Ile Glu Glu Phe Lys Lys Pro Val Ser Ile Leu
65                  70                  75                  80

Val Asn Asn Ala Gly Ile Thr Lys Asp Lys Met Leu His Arg Met Ser
                85                  90                  95

His Gln Asp Trp Asn Asp Val Ile Asn Val Asn Leu Asn Ser Cys Phe
                100                 105                 110

Asn Met Ser Ser Ser Val Met Glu Gln Met Arg Asn Gln Asp Tyr Gly
            115                 120                 125

Arg Ile Val Asn Ile Ser Ser Ile Asn Ala Gln Ala Gly Gln Val Gly
            130                 135                 140

Gln Thr Asn Tyr Ser Ala Ala Lys Ala Gly Ile Ile Gly Phe Thr Lys
145                 150                 155                 160

Ala Leu Ala Arg Glu Thr Ala Ser Lys Asn Ile Thr Val Asn Cys Ile
                165                 170                 175

Ala Pro Gly Tyr Ile Ala Thr Glu Met Val Gly Ala Val Pro Glu Asp
                180                 185                 190

Val Leu Ala Lys Ile Ile Asn Ser Ile Pro Lys Lys Arg Leu Gly Gln
            195                 200                 205

Pro Glu Glu Ile Ala Arg Ala Val Ala Phe Leu Val Asp Glu Asn Ala
210                 215                 220

Gly Phe Ile Thr Gly Glu Thr Ile Ser Ile Asn Gly Gly His Asn Met
225                 230                 235                 240

Ile

<210> SEQ ID NO 115
<211> LENGTH: 240
<212> TYPE: PRT
<213> ORGANISM: Sphingomonas sp.

<400> SEQUENCE: 115

Met Ser Arg Val Ala Ile Val Thr Gly Gly Thr Arg Gly Ile Gly Glu
1               5                   10                  15

Ala Ile Ser Leu Ala Leu Lys Glu Met Gly Tyr Ala Val Ala Ala Asn
            20                  25                  30

Tyr Ala Gly Asn Asp Glu Lys Ala Lys Ala Phe Thr Asp Lys Thr Gly
            35                  40                  45

Ile Ala Ala Phe Lys Trp Asp Val Gly Asp His Gln Ala Cys Leu Asp
50                  55                  60

Gly Cys Ala Gln Val Ala Glu Val Leu Gly Pro Val Asp Ile Val Val
65                  70                  75                  80

Asn Asn Ala Gly Ile Thr Arg Asp Gly Val Leu Ala Lys Met Ser Phe
                85                  90                  95

Asp Asp Trp Asn Glu Val Met Arg Ile Asn Leu Gly Gly Cys Phe Asn
                100                 105                 110

Met Ala Lys Ala Cys Phe Gly Gly Met Arg Glu Arg Gly Trp Gly Arg
            115                 120                 125
```

```
Ile Val Asn Ile Gly Ser Ile Asn Gly Gln Ala Gly Gln Tyr Gly Gln
    130                 135                 140

Val Asn Tyr Ala Ala Ala Lys Ser Gly Ile His Gly Phe Thr Lys Ala
145                 150                 155                 160

Leu Ala Gln Glu Gly Ala Lys Tyr Gly Val Thr Val Asn Ala Ile Ala
                165                 170                 175

Pro Gly Tyr Ile Asp Thr Asp Met Val Ala Ala Val Pro Ala Pro Val
                180                 185                 190

Leu Glu Lys Ile Val Ala Lys Ile Pro Val Gly Arg Leu Gly Gln Ala
                195                 200                 205

His Glu Ile Ala Arg Gly Val Ala Phe Phe Cys Ser Glu Asp Gly Gly
    210                 215                 220

Phe Val Thr Gly Ser Thr Leu Ser Ile Asn Gly Gly Gln His Met Tyr
225                 230                 235                 240

<210> SEQ ID NO 116
<211> LENGTH: 246
<212> TYPE: PRT
<213> ORGANISM: Vibrio parahaemolyticus

<400> SEQUENCE: 116

Met Lys Lys Val Ala Leu Ile Thr Gly Ser Lys Gly Gly Ile Gly Ser
  1               5                  10                  15

Ala Ile Ser Ser Gln Leu Val Asn Asp Gly Tyr Arg Val Ile Ala Thr
                 20                  25                  30

Tyr Phe Thr Gly Asn Tyr Glu Cys Ala Leu Glu Trp Phe Asn Ser Lys
             35                  40                  45

Gly Phe Thr Lys Asp Gln Val Arg Leu Phe Glu Leu Asp Val Thr Asn
 50                  55                  60

Thr Ala Glu Cys Ala Glu Lys Leu Ala Gln Leu Leu Glu Glu Glu Gly
 65                  70                  75                  80

Thr Ile Asp Val Val Asn Asn Ala Gly Ile Thr Arg Asp Gly Val
                 85                  90                  95

Phe Lys Lys Met Thr Ala Gln Ala Trp Asn Asp Val Ile Asn Thr Asn
                100                 105                 110

Leu Asn Ser Leu Phe Asn Val Thr Gln Pro Leu Phe Ala Ala Met Cys
            115                 120                 125

Glu Lys Gly Gly Gly Arg Val Ile Asn Ile Ser Ser Val Asn Gly Leu
        130                 135                 140

Lys Gly Gln Phe Gly Gln Ala Asn Tyr Ser Ala Ala Lys Ala Gly Met
145                 150                 155                 160

Ile Gly Phe Ser Lys Ala Leu Ala Tyr Glu Gly Ala Arg Ser Gly Val
                165                 170                 175

Thr Val Asn Val Ile Ala Pro Gly Tyr Thr Gly Thr Pro Met Val Glu
                180                 185                 190

Gln Met Lys Pro Glu Val Leu Glu Ser Ile Thr Asn Gln Ile Pro Met
                195                 200                 205

Lys Arg Leu Ala Thr Pro Glu Glu Ile Ala Ala Ser Val Ser Phe Leu
    210                 215                 220

Val Ser Asp Ala Gly Ala Tyr Ile Thr Gly Glu Thr Leu Ser Val Asn
225                 230                 235                 240

Gly Gly Leu Tyr Met His
                245
```

<210> SEQ ID NO 117
<211> LENGTH: 248
<212> TYPE: PRT
<213> ORGANISM: Burkholderia multivorans

<400> SEQUENCE: 117

```
Met Ser Ala Lys Arg Val Ala Phe Val Thr Gly Gly Met Gly Gly Leu
 1               5                  10                  15

Gly Ala Ala Ile Ser Arg Arg Leu His Asp Val Gly Met Thr Val Ala
            20                  25                  30

Val Ser His Thr Glu Gly Asn Asp His Val Ala Thr Trp Leu Thr His
        35                  40                  45

Glu Arg Glu Ala Gly Arg Thr Phe His Ala Phe Glu Val Asp Val Ala
    50                  55                  60

Asp Tyr Asp Ser Cys Arg Gln Cys Ala Ser Arg Val Leu Ala Glu Phe
65                  70                  75                  80

Gly Arg Val Asp Val Leu Val Asn Asn Ala Gly Ile Thr His Asp Ala
                85                  90                  95

Thr Phe Val Lys Met Thr Lys Ser Met Trp Asp Ala Val Leu Arg Thr
            100                 105                 110

Asn Leu Asp Gly Met Phe Asn Met Thr Lys Pro Phe Val Pro Gly Met
        115                 120                 125

Ile Glu Gly Gly Phe Gly Arg Ile Val Asn Ile Gly Ser Val Asn Gly
    130                 135                 140

Ser Arg Gly Ala Tyr Gly Gln Thr Asn Tyr Ala Ala Ala Lys Ala Gly
145                 150                 155                 160

Ile His Gly Phe Thr Lys Ala Leu Ala Leu Glu Leu Ala Arg His Gly
                165                 170                 175

Val Thr Val Asn Thr Val Ala Pro Gly Tyr Leu Ala Thr Ala Met Leu
            180                 185                 190

Glu Thr Val Pro Lys Glu Val Leu Asp Thr Lys Ile Leu Pro Gln Ile
        195                 200                 205

Pro Val Gly Arg Leu Gly Asn Pro Asp Glu Ile Ala Ala Leu Val Ala
    210                 215                 220

Phe Leu Cys Ser Asp Ala Ala Ala Phe Ala Thr Gly Ala Glu Phe Asp
225                 230                 235                 240

Val Asn Gly Gly Met His Met Lys
                245
```

<210> SEQ ID NO 118
<211> LENGTH: 246
<212> TYPE: PRT
<213> ORGANISM: Burkholderia multivorans

<400> SEQUENCE: 118

```
Met Ser Gln Arg Ile Ala Tyr Val Thr Gly Gly Met Gly Gly Ile Gly
 1               5                  10                  15

Thr Ser Ile Cys Gln Arg Leu Ser Lys Asp Gly Phe Lys Val Val Ala
            20                  25                  30

Gly Cys Gly Pro Asn Ser Pro Arg Arg Val Lys Trp Leu Glu Glu Gln
        35                  40                  45

Lys Ala Leu Gly Phe Asp Phe Ile Ala Ser Glu Gly Asn Val Gly Asp
    50                  55                  60

Trp Asp Ser Thr Lys Ala Ala Phe Asp Lys Val Lys Ala Glu Val Gly
65                  70                  75                  80

Glu Ile Asp Val Leu Val Asn Asn Ala Gly Ile Thr Arg Asp Val Val
```

```
                85                  90                  95
Phe Arg Lys Met Thr His Glu Asp Trp Thr Ala Val Ile Asp Thr Asn
            100                 105                 110
Leu Thr Ser Leu Phe Asn Val Thr Lys Gln Val Ile Asp Gly Met Val
            115                 120                 125
Glu Arg Gly Trp Gly Arg Ile Ile Asn Ile Ser Ser Val Asn Gly Gln
            130                 135                 140
Lys Gly Gln Phe Gly Gln Thr Asn Tyr Ser Thr Ala Lys Ala Gly Ile
145                 150                 155                 160
His Gly Phe Thr Met Ala Leu Ala Gln Glu Val Ala Thr Lys Gly Val
                165                 170                 175
Thr Val Asn Thr Val Ser Pro Gly Tyr Ile Gly Thr Asp Met Val Lys
                180                 185                 190
Ala Ile Arg Pro Asp Val Leu Glu Lys Ile Val Ala Thr Ile Pro Val
                195                 200                 205
Arg Arg Leu Gly Thr Pro Glu Glu Ile Gly Ser Ile Val Ala Trp Leu
            210                 215                 220
Ala Ser Asn Asp Ser Gly Phe Ala Thr Gly Ala Asp Phe Ser Leu Asn
225                 230                 235                 240
Gly Gly Leu His Met Gly
                245
```

```
<210> SEQ ID NO 119
<211> LENGTH: 245
<212> TYPE: PRT
<213> ORGANISM: Acidovorax radicis

<400> SEQUENCE: 119

Met Ser Gln Lys Val Ala Tyr Val Thr Gly Gly Met Gly Gly Ile Gly
1               5                   10                  15
Thr Ala Ile Cys Gln Arg Leu His Lys Glu Gly Phe Lys Val Ile Ala
            20                  25                  30
Gly Cys Gly Pro Thr Arg Asp His Ala Lys Trp Leu Ala Glu Gln Lys
        35                  40                  45
Ala Leu Gly Tyr Thr Phe Tyr Ala Ser Val Gly Asn Val Gly Asp Trp
    50                  55                  60
Asp Ser Thr Val Glu Ala Phe Gly Lys Thr Lys Ala Glu His Gly Thr
65                  70                  75                  80
Ile Asp Val Leu Val Asn Asn Ala Gly Ile Thr Arg Asp Arg Met Phe
                85                  90                  95
Leu Lys Met Ser Arg Glu Asp Trp Asp Ala Val Ile Glu Thr Asn Leu
            100                 105                 110
Asn Ser Met Phe Asn Val Thr Lys Gln Val Val Ala Asp Met Val Glu
            115                 120                 125
Lys Gly Trp Gly Arg Ile Val Asn Ile Ser Ser Val Asn Gly Glu Lys
            130                 135                 140
Gly Gln Ala Gly Gln Thr Asn Tyr Ser Ala Ala Lys Ala Gly Met His
145                 150                 155                 160
Gly Phe Ser Met Ala Leu Ala Gln Glu Leu Ala Thr Lys Gly Val Thr
                165                 170                 175
Val Asn Thr Val Ser Pro Gly Tyr Ile Gly Thr Asp Met Val Lys Ala
                180                 185                 190
Ile Arg Pro Asp Val Leu Glu Lys Ile Val Ala Thr Val Pro Val Lys
                195                 200                 205
```

```
Arg Leu Gly Glu Pro Ser Glu Ile Ala Ser Ile Ile Ala Trp Leu Ala
    210                 215                 220

Ser Glu Glu Gly Gly Tyr Ala Thr Gly Ala Asp Phe Ser Val Asn Gly
225                 230                 235                 240

Gly Leu His Met Gly
                245

<210> SEQ ID NO 120
<211> LENGTH: 242
<212> TYPE: PRT
<213> ORGANISM: Methylobacterium extorquens

<400> SEQUENCE: 120

Met Ala Gln Glu Arg Val Ala Leu Val Thr Gly Gly Thr Arg Gly Ile
1               5                   10                  15

Gly Ala Ala Ile Ser Lys Arg Leu Lys Asp Lys Gly Tyr Lys Val Ala
                20                  25                  30

Ala Asn Tyr Gly Gly Asn Asp Glu Ala Ala Asn Ala Phe Lys Ala Glu
            35                  40                  45

Thr Gly Ile Pro Val Phe Lys Phe Asp Val Gly Asp Leu Ala Ser Cys
    50                  55                  60

Glu Ala Gly Ile Lys Ala Ile Glu Ala Glu Leu Gly Pro Ile Asp Ile
65                  70                  75                  80

Leu Val Asn Asn Ala Gly Ile Thr Arg Asp Gly Ala Phe His Lys Met
                85                  90                  95

Thr Phe Glu Lys Trp Gln Ala Val Ile Arg Thr Asn Leu Asp Ser Met
            100                 105                 110

Phe Thr Cys Thr Arg Pro Leu Ile Glu Gly Met Arg Ser Arg Asn Phe
        115                 120                 125

Gly Arg Ile Ile Ile Ile Ser Ser Ile Asn Gly Gln Lys Gly Gln Ala
    130                 135                 140

Gly Gln Thr Asn Tyr Ser Ala Ala Lys Ala Gly Val Ile Gly Phe Ala
145                 150                 155                 160

Lys Ala Leu Ala Gln Glu Ser Ala Ser Lys Gly Val Thr Val Asn Val
                165                 170                 175

Val Ala Pro Gly Tyr Ile Ala Thr Glu Met Val Met Ala Val Pro Glu
            180                 185                 190

Asp Ile Arg Asn Lys Ile Ile Ser Thr Ile Pro Thr Gly Arg Leu Gly
        195                 200                 205

Glu Ala Asp Glu Ile Ala His Ala Val Glu Tyr Leu Ala Ser Asp Glu
    210                 215                 220

Ala Gly Phe Val Asn Gly Ser Thr Leu Thr Ile Asn Gly Gly Gln His
225                 230                 235                 240

Phe Val

<210> SEQ ID NO 121
<211> LENGTH: 241
<212> TYPE: PRT
<213> ORGANISM: Bradyrhizobium sp.

<400> SEQUENCE: 121

Met Ala Arg Val Ala Leu Val Thr Gly Gly Thr Arg Gly Ile Gly Ala
1               5                   10                  15

Ala Ile Ser Lys Ala Leu Lys Ala Ala Gly His Lys Val Ala Ala Asn
                20                  25                  30

Tyr Gly Gly Asn Asp Ala Ala Ala Glu Lys Phe Lys Ser Glu Thr Glu
```

```
                35                  40                  45
Ile Pro Val Tyr Lys Trp Asp Val Ser Ser Phe Asp Ala Cys Ala Glu
 50                  55                  60

Gly Ile Lys Lys Val Glu Ala Glu Leu Gly Pro Val Asp Ile Leu Val
 65                  70                  75                  80

Asn Asn Ala Gly Ile Thr Arg Asp Thr Ala Phe His Lys Met Thr Leu
                 85                  90                  95

Glu Gln Trp Ser Ala Val Ile Asn Thr Asn Leu Gly Ser Leu Phe Asn
                100                 105                 110

Met Thr Arg Pro Val Ile Glu Gly Met Arg Ala Arg Lys Phe Gly Arg
                115                 120                 125

Ile Ile Asn Ile Ser Ser Ile Asn Gly Gln Lys Gly Gln Phe Gly Gln
        130                 135                 140

Val Asn Tyr Ser Ala Ala Lys Ala Gly Asp Ile Gly Phe Thr Lys Ala
145                 150                 155                 160

Leu Ala Leu Glu Thr Ala Lys Ala Gly Ile Thr Val Asn Val Ile Cys
                165                 170                 175

Pro Gly Tyr Ile Asn Thr Glu Met Val Gln Ala Val Pro Lys Asp Val
                180                 185                 190

Leu Glu Lys Ala Ile Leu Pro Leu Ile Pro Val Gly Arg Leu Gly Glu
            195                 200                 205

Pro Glu Glu Ile Ala Arg Ala Val Val Phe Leu Ala Ala Asp Glu Ala
210                 215                 220

Gly Ala Ile Thr Gly Ser Thr Leu Ser Ile Asn Gly Gly Gln Tyr Met
225                 230                 235                 240

Ala

<210> SEQ ID NO 122
<211> LENGTH: 240
<212> TYPE: PRT
<213> ORGANISM: Sagittula stellata

<400> SEQUENCE: 122

Met Ala Arg Val Ala Leu Val Thr Gly Gly Ser Arg Gly Ile Gly Glu
  1               5                  10                  15

Ala Ile Ser Lys Ala Leu Lys Ala Glu Gly Tyr Thr Val Ala Ala Thr
                 20                  25                  30

Tyr Ala Gly Asn Asp Glu Lys Ala Ala Ala Phe Thr Ala Asp Thr Gly
                 35                  40                  45

Ile Lys Thr Tyr Lys Trp Asn Val Ala Asp Tyr Glu Ser Ser Lys Ala
 50                  55                  60

Gly Ile Ala Gln Val Glu Ala Asp Leu Gly Pro Ile Asp Val Val Val
 65                  70                  75                  80

Ala Asn Ala Gly Ile Thr Arg Asp Ala Pro Phe His Lys Met Thr Pro
                 85                  90                  95

Ala Gln Trp Asn Glu Val Ile Asp Thr Asn Leu Thr Gly Val Phe Asn
                100                 105                 110

Thr Val His Pro Val Trp Pro Gly Met Arg Glu Arg Lys Phe Gly Arg
            115                 120                 125

Ile Ile Val Ile Ser Ser Ile Asn Gly Gln Lys Gly Gln Phe Ala Gln
        130                 135                 140

Val Asn Tyr Ala Ala Thr Lys Ala Gly Asp Leu Gly Ile Val Lys Ser
145                 150                 155                 160

Leu Ala Gln Glu Gly Ala Arg Ala Gly Ile Thr Ala Asn Ala Ile Cys
```

```
                165                 170                 175
Pro Gly Tyr Ile Ala Thr Glu Met Val Met Ala Val Pro Glu Lys Val
            180                 185                 190

Arg Glu Ser Ile Ile Gly Gln Ile Pro Ala Gly Arg Leu Gly Glu Pro
            195                 200                 205

Glu Glu Ile Ala Arg Cys Val Val Phe Leu Ala Ser Asp Asp Ala Gly
            210                 215                 220

Phe Ile Asn Gly Ser Thr Ile Ser Ala Asn Gly Ala Gln Phe Phe Val
225                 230                 235                 240

<210> SEQ ID NO 123
<211> LENGTH: 282
<212> TYPE: PRT
<213> ORGANISM: Clostridium acetobutylicum

<400> SEQUENCE: 123

Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280

<210> SEQ ID NO 124
<211> LENGTH: 783
```

<212> TYPE: DNA
<213> ORGANISM: Artificial Sequence
<220> FEATURE:
<223> OTHER INFORMATION: Codon optimized crotonase for expression in M. trichosporium.

<400> SEQUENCE: 124

| | |
|---|---:|
| atggagctga ataacgtcat cctggaaaaa gaaggcaagg tcgcggtcgt cacgatcaac | 60 |
| cgccccaagg ctctgaacgc gctcaatagc gacaccctca agagatgga ctacgtcatc | 120 |
| ggcgagatcg agaacgactc cgaggtgctg ccgtcatcc tcaccggagc gggcgagaag | 180 |
| tcgttcgtgg ctggggcgga tatcagcgag atgaaagaga tgaataccat tgaaggccgc | 240 |
| aagttcggca tcctgggcaa caaggtgttc cgtcgcctgg agctgctgga agccggtc | 300 |
| attgcggcgg tgaatggctt cgcgctcggc ggtggctgcg agatcgcgat gtcgtgcgac | 360 |
| atccgcatcg cctcgtcgaa cgcccgcttc ggacagccgg aagtcggcct cggcatcacg | 420 |
| cccggattcg gcggcactca cgcgcctcagc cgcctggtgg gcatgggcat ggctaagcag | 480 |
| ctgatcttca cggcgcagaa catcaaggct gacgaggcgc tccgcatcgg cctggtcaac | 540 |
| aaggtggtgg agccgtcgga actcatgaac acggcgaaag agattgcgaa caaaatcgtg | 600 |
| tcgaatgcgc cggtggcggt caagctgagc aagcaggcga tcaaccgtgg catgcagtgc | 660 |
| gatatcgaca ctgcgctcgc cttcgagtcc gaggcgttcg gcgagtgctt ctccaccgaa | 720 |
| gatcagaaag atgctatgac cgccttcatc gaaaagcgga gatcgaggg cttcaagaac | 780 |
| cgc | 783 |

<210> SEQ ID NO 125
<211> LENGTH: 453
<212> TYPE: DNA
<213> ORGANISM: Artificial Sequence
<220> FEATURE:
<223> OTHER INFORMATION: Codon optimized crotonyl-CoA thioesterase for expression in M.trichosporium.

<400> SEQUENCE: 125

| | |
|---|---:|
| atgcatcgca cctcgaacgg ctcccatgcc acgggtggca atctccccga cgtcgcctcg | 60 |
| cattacccg tggcgtacga gcagaccctg gacggcaccg tgggcttcgt catcgatgag | 120 |
| atgacgcccg agcgtgccac cgcctcggtg gaagttaccg acacgctccg ccagcgctgg | 180 |
| ggcctcgtcc acggcggtgc ttactgtgcg ttggcggaga tgctggccac ggaagccacg | 240 |
| gtcgccgtgg tgcatgagaa gggcatgatg gcggtcggcc agtcgaatca caccagcttc | 300 |
| ttccgccctg tgaaagaggg ccacgtgcgt gccgaggccg tgcgtattca cgcgggctcg | 360 |
| accacgtggt tctgggacgt cagcctgcgg gacgacgcgg tcgcctctg cgccgtgtcg | 420 |
| tcgatgtcca tcgcggtccg ccctcgccgt gac | 453 |

<210> SEQ ID NO 126
<211> LENGTH: 783
<212> TYPE: DNA
<213> ORGANISM: Artificial Sequence
<220> FEATURE:
<223> OTHER INFORMATION: Codon optimized 4-oxalocrotonate decarboxylase for expression in M.trichosporium.

<400> SEQUENCE: 126

| | |
|---|---:|
| atgtccacga ccagcatcac cccggatgag atcgcccagg tgctgctggc tggcgagcgc | 60 |
| aaccgcaccg aggtggcgca gttctcggcg agccaccccg acctcgacgt ccggacggcc | 120 |
| tatgcggccc agcgcgcttt cgtccaggcc aagctggatg cgggcgagca gctcgtcggc | 180 |

```
tataagctgg gcctgaccag ccgcaacaag cagcgcgcca tgggcgtcga ctgcccgctg      240
tatggccgcg tcacgtcctc gatgctcgcg acgtatggcg atcccatccc gttcgaccgc      300
ttcatccatc cgcgcgtcga atcggagatc gcgttcctgc tcaagcagga tgtgaccgct      360
ccggcgaccg tgtcgtcggt cctcgcggcc accgacgtcg tgttcggagc ggtcgacgtg      420
ctcgactcgc gctacgaggg gttcaagttc acgctcgagg atgtcgtggc cgataacgcg      480
agcgcgggag cgttctacct cggaccggtc gcccgtccgg ccaccgagct ccgcctcgac      540
ctgctgggat gcatcgttcg cgtggacggc gaggtcacca tgaccgccgc tggtgcggcc      600
gtcatgggcc atcccgccgc ggcggtcgcg tggctcgcca accagctcgc gctcgagggc      660
gaatcgctga aggccggaca gctgatcttc tcgggtggcg tcactgcgcc cgtcccggtc      720
gttcctggcg gcagcgtcac gttcgagttc gatggcctgg cgtcatcgga ggtggctggc      780
gcc                                                                    783
```

<210> SEQ ID NO 127
<211> LENGTH: 1179
<212> TYPE: DNA
<213> ORGANISM: Artificial Sequence
<220> FEATURE:
<223> OTHER INFORMATION: Codon optimized phaA for expression in M. capsulatus.

<400> SEQUENCE: 127

```
atgaccgacg tggtcatcgt gtcggcagcc cgcacagcag tgggtaaatt cggcggctcg       60
ctggccaaga tcgcagcccc ggagctgggc gcctcggtca tccgagcggt attggaacga      120
gccggagtga agcccgagca ggtgtcggaa gtcatcttgg ccaagtgct tactgccggc       180 agcggccaaa acccagcccg gcaggcgttg atcgccgcag gctcccgaa cgccgtcccg       240 ggcatgacga tcaacaaggt gtgtggcagc ggcctcaagg cggtcatgct cgcggccaat      300
gcggtcgtag caggggacgc ggaaatcgtc gtggcaggcg gccaggaaaa catgagcgct      360
gcgccgcacg tgctgcccgg ctcccgcgac ggcttccgga tgggagacgc caagttggtg      420
gattcaatga tcgttgacgg gttgtgggac gtttacaaca agtaccatat gggcatcacc      480
gcagaaaatg tggcgaaaga atatggtatc acccgcgagg cccaggacca gttcgccgcc      540
ttgagccaga acaaggccga agctgcccag aaagcgggtc gcttcgacga tgaaatcgta      600
ccgatcgaaa tcccgcaacg gaagggcgag cccctgcgct cgcgaccga tgaattcgtc       660 cggcacgggg tcacggccga gtccctcgcg agcctcaagc cggccttcgc caaagaaggc      720
accgtgaccg ccgctaacgc gagcggcatc aacgacggcg cagccgcagt cctggttatg      780
tcggcgaaga aggccgaagc cctggggctg agccccctgg cccggatcaa ggcgtacgcc      840
aatgcgggag tggatccgtc cgtaatggga atgggccctg tccccgcctc cgacggtgc       900 ctggagcgcg cagggtggtc ggtaggcgac ctcgatctca tggagatcaa tgaagcgttc      960
gcggctcagg cgctcgcggt gcacaagcag atgggctggg atacctcgaa ggttaacgtg     1020
aacggcggtg ccatcgcgat cggccacccc atcgggcct caggctgccg catcctggtc     1080
accctgctgc atgaaatgct gaagcgcgat gccaagcggg gactggcgtc gctctgcatc     1140
ggcggtggca tgggtgtcgc cttggccctc gagcggccg                            1179
```

<210> SEQ ID NO 128
<211> LENGTH: 846
<212> TYPE: DNA
<213> ORGANISM: Artificial Sequence
<220> FEATURE:
<223> OTHER INFORMATION: Codon optimized phaB for expression in M. capsulatus.

<400> SEQUENCE: 128

| | | | | | |
|---|---|---|---|---|---|
| atgaagaagg | tgtgcgtcat | cggagccggc | accatgggtt | ccgggatcgc | gcaggccttt | 60 |
| gccgccaagg | gcttcgaagt | ggtgctgcgt | gacatcaaag | acgagttcgt | cgaccgtggt | 120 |
| ttggatttca | tcaacaagaa | cctgtcgaaa | ctcgtcaaga | aggcaagat | cgaagaggca | 180 |
| acgaaggttg | agattctcac | ccgtataagc | gggacggtgg | acctgaacat | ggcggctgat | 240 |
| tgtgacctgg | tgatcgaagc | cgcggtggaa | cgcatggaca | tcaagaagca | gatcttcgca | 300 |
| gatctggaca | atatctgcaa | gccagagacg | attcttgcga | gcaataccag | cagtctgtcc | 360 |
| atcaccgagg | tcgcatccgc | gacgaaacgg | ccggacaaag | tgatcggcat | gcacttcttc | 420 |
| aaccctgcgc | ccgtcatgaa | gttggtggaa | gtgatccggg | gcatcgccac | aagccaggaa | 480 |
| accttcgacg | ctgtgaaaga | gacgtcgatc | gcgatcggga | agacccggt | cgaggtggcg | 540 |
| gaagcacccg | gcttcgtcgt | caatcggatc | ctgatcccga | tgatcaatga | agcagtcggc | 600 |
| atcttggccg | agggcattgc | cagcgtcgaa | gatatcgaca | aggccatgaa | gctgggcgcc | 660 |
| aaccatccga | tgggacccct | ggaactggga | gacttcatcg | gctggacat | ctgcctggcc | 720 |
| atcatggacg | ttctctacag | cgaaacgggc | gactcgaagt | atcgcccgca | taccctgctg | 780 |
| aagaaatacg | tccgtgcagg | ctggctggga | cgcaagtccg | gcaagggctt | ctacgactat | 840 |
| tccaag | | | | | | 846 |

<210> SEQ ID NO 129
<211> LENGTH: 783
<212> TYPE: DNA
<213> ORGANISM: Artificial Sequence
<220> FEATURE:
<223> OTHER INFORMATION: Codon optimized crotonase for expression in M. capsulatus.

<400> SEQUENCE: 129

| | | | | | |
|---|---|---|---|---|---|
| atggaactta | caatgtgat | cctggagaaa | gaaggtaaag | tcgccgtggt | gaccattaat | 60 |
| cgccccaagg | ccctgaacgc | cctgaattct | gacacgctga | agaaatgga | ctacgtgatc | 120 |
| ggcgaaatcg | agaacgactc | cgaggtgctg | gccgtgatcc | tgaccggcgc | aggcgaaaag | 180 |
| tcgttcgttg | ccggagcgga | tatctccgag | atgaaagaga | tgaacaccat | tgagggcagg | 240 |
| aagttcggca | tcctgggcaa | taaagtcttt | cgccggctcg | agctcctgga | gaagccggta | 300 |
| attgccgccg | ttaatggctt | cgcgctcggt | ggcggatgtg | aaatcgcgat | gagctgcgac | 360 |
| atccgcatag | cgagtagtaa | cgcgcggttc | ggccagcccg | aggtcggcct | gggcatcacg | 420 |
| cccggattcg | gtgcactca | gcggctgtcg | gcctggtgg | catgggat | ggccaagcag | 480 |
| ctgatcttca | ccgcgcagaa | catcaaagcc | gacgaagccc | tgcgcatagg | gttggtgaac | 540 |
| aaagtcgtgg | agccgagcga | gttgatgaac | accgccaaag | agatcgccaa | caagatcgtc | 600 |
| tcgaacgcac | cggtcgcggt | gaaattgtcg | aagcaggcca | tcaaccgcgg | catgcagtgc | 660 |
| gatatcgata | ccgccctcgc | cttcgagtcg | aagcctttg | gtgaatgctt | ctccaccgaa | 720 |
| gatcaaaaag | acgccatgac | cgccttcata | gagaagcgca | gatcgaggg | ttttaagaac | 780 |
| cgg | | | | | | 783 |

<210> SEQ ID NO 130
<211> LENGTH: 453
<212> TYPE: DNA

<213> ORGANISM: Artificial Sequence
<220> FEATURE:
<223> OTHER INFORMATION: Codon optimized crotonyl-CoA thioesterase for
     expression in M.capsulatus.

<400> SEQUENCE: 130

| | |
|---|---|
| atgcatcgga ccagcaacgg cagccacgcc acaggtggca atctgccgga cgtcgctagc | 60 |
| cactatccgg tcgcctacga gcagacccct tgatgggacgg tgggcttcgt gatcgacgag | 120 |
| atgacgccag agcgagcgac cgctagcgtc gaagtcaccg atacgttgcg gcagcggtgg | 180 |
| ggcctggtcc atggcggtgc gtattgcgcg cttgccgaaa tgctggccac cgaggctacc | 240 |
| gtcgccgtcg tccacgaaaa ggggatgatg gcggttggtc agtcgaacca tacgtcgttc | 300 |
| tttcgtcccg tgaaagaggg ccacgtgcgg gcagaagccg tccgtattca cgccggcagc | 360 |
| accacctggt tctgggatgt ttcgctgcgc gatgacgccg gcaggctgtg cgccgtcagt | 420 |
| tccatgtcaa tcgccgtccg tccacgccgg gat | 453 |

<210> SEQ ID NO 131
<211> LENGTH: 783
<212> TYPE: DNA
<213> ORGANISM: Artificial Sequence
<220> FEATURE:
<223> OTHER INFORMATION: Codon optimized 4-oxalocrotonate decarboxylase
     for expression in M.capsulatus.

<400> SEQUENCE: 131

| | |
|---|---|
| atgtcgacga cgtccattac cccggacgag attgcccagg tgctgctcgc tggggaacgg | 60 |
| aaccgcaccg aagtggccca gttctccgcg tcccatccgg acctggatgt tcgcaccgcc | 120 |
| tatgccgccc agcgtgcttt tgtccaggcc aagctggacg cgggagagca gctcgtcggc | 180 |
| tacaagctgg gccttacgag tcggaacaag cagcgtgcca tgggtgtgga ctgcccgctg | 240 |
| tacgggcgag tgacgagctc tatgctggcg acctacgggg acccgatccc gtttgaccgc | 300 |
| ttcatccatc cgcgggtcga aagcgagatt gcgttcctgt tgaaacagga cgtgaccgct | 360 |
| ccggccaccg tgtcgtccgt tctggccgcc acggacgtcg tctttggcgc ggtcgacgta | 420 |
| ctggactccc ggtacgaagg cttcaagttc accctcgaag atgtggtggc cgacaacgcc | 480 |
| agcgctggcg cgttctatct cggacccgtg gcacgtcccg ctaccgagtt gcgcctggac | 540 |
| ttgttggggt gcatcgtacg tgtggacggc gaagtcacga tgaccgcggc tggcgcagcc | 600 |
| gtgatgggcc acccggcagc ggcagtggcc tggctcgcga accagctggc gctggaaggg | 660 |
| gaatccctga agccggtca actgatcttc tcgggtgggg tcacggcacc cgtcccttgtg | 720 |
| gtgcctggcg gatcggtgac cttcgagttc gatggccttg gcgtgatcga ggtggccgga | 780 |
| gca | 783 |

<210> SEQ ID NO 132
<211> LENGTH: 783
<212> TYPE: DNA
<213> ORGANISM: Artificial Sequence
<220> FEATURE:
<223> OTHER INFORMATION: Codon optimized crotonase for expression in M.
     extorquens.

<400> SEQUENCE: 132

| | |
|---|---|
| atggagctga caacgtcat cctcgaaaaa gagggcaagg tggcggtcgt caccatcaac | 60 |
| cgccccaagg ccctcaacgc gctcaacagc gacacgctca agaaatgga ttacgtcatc | 120 |
| ggcgagatcg agaacgattc cgaggtgctc gccgtgatcc tcaccggtgc gggcgaaaag | 180 |

```
tcgttcgtgg cgggtgcgga tatctccgaa atgaaagaaa tgaacacgat cgagggccgg      240
aagttcggca tcctcggcaa caaggttttc cgccgtctcg agttgttgga gaagccggtc      300
attgccgccg tgaatggctt cgccctcggt ggtggctgcg agatcgccat gagctgcgac      360
atccggatcg cgtcgagcaa cgcccgtttc ggccagccgg aagtcggctt gggcatcacc      420
ccgggcttcg gcggcacgca gcgcctctcg cggctcgtcg gcatgggcat ggccaagcag      480
ctcatcttca ccgcccagaa tatcaaggcg gacgaggcgc tgcgcattgg cctcgttaac      540
aaggtcgtgg agccctcgga gctcatgaac accgcgaaag agatcgcgaa caagatcgtg      600
tccaacgcac cggtggccgt caagctctcg aagcaggcca tcaaccgcgg catgcagtgc      660
gatatcgaca ccgcgctcgc gttcgagagc gaggcgttcg gggagtgctt ctcgaccgaa      720
gatcagaagg acgccatgac cgccttcatc gagaagcgca agatcgaagg cttcaagaac      780
cgc                                                                   783

<210> SEQ ID NO 133
<211> LENGTH: 453
<212> TYPE: DNA
<213> ORGANISM: Artificial Sequence
<220> FEATURE:
<223> OTHER INFORMATION: Codon optimized crotonyl-CoA thioesterase for
      expression in M.extorquens.

<400> SEQUENCE: 133
atgcaccgca cctcgaacgg ctcgcacgcc accggtggca acctgccgga cgtcgcctcg       60 cattcccgg tcgcgtacga acagaccctg gacgggacgg tgggcttcgt catcgatgag      120
atgacgcccg agcgcgcgac ggcctcggtc gaggtgaccg acacgctccg ccagcgctgg      180
ggcctcgtcc acggcggtgc gtactgcgcc ctcgccgaga tgctcgccac cgaggcgacg      240
gtggccgtgg tccatgagaa gggcatgatg gcggtggggc agagcaacca cacgagcttc      300
tttcgcccgg tgaaagaggg ccacgtccgc gcagaggccg tgcgcatcca cgcgggctcc      360
accacctggt tttgggatgt gtcgctgcgc gatgacgcag gccgcctttg cgccgtgtcc      420
agcatgtcga tcgcggtgcg gccccgccgc gac                                  453

<210> SEQ ID NO 134
<211> LENGTH: 783
<212> TYPE: DNA
<213> ORGANISM: Artificial Sequence
<220> FEATURE:
<223> OTHER INFORMATION: Codon optimized 4-oxalocrotonate decarboxylase
      for expression in M.extorquens.

<400> SEQUENCE: 134
atgagcacca cgtcgatcac cccggacgag atcgcgcagg tgctgctggc aggcgagcgc       60
aaccggaccg aggtcgccca gttcagcgcc tcgcacccgg acctcgacgt gcgcacggcg      120
tatgctgcgc agcgggcgtt cgtgcaggcc aagctcgatg ccggcgagca gttggtcggc      180
tacaagctcg gcctgacctc gcggaataag cagcgggcca tgggcgtcga ctgcccgttg      240
tatggtcgcg tcaccagcag catgctggcg acctacggcg accccatccc cttcgaccgc      300
ttcatccatc cgcgcgtcga atcggaaatc gccttcctgc tgaagcagga tgtcaccgcc      360
ccggccaccg tctcgtcggt cctcgccgcg accgacgtcg ttttcggcgc tgtcgacgtg      420
ctggatagcc gctacgaggg cttcaagttc acgctggaag atgtggtcgc ggacaacgcc      480
agcgccggag ccttctacct cggtcccgtc gcccgtccgg ccacggagct ccggctcgac      540
ttgctcggct gcatcgtccg ggtcgacggc gaggttacca tgaccgcagc gggagccgcc      600
```

| gtgatgggcc accccgcagc cgcggtggcc tggctcgcca accagctcgc cctcgagggc | 660 |
| gagtcgctga aagccggcca gctgatcttc agcggcggtg tgacggcgcc ggtccccgtc | 720 |
| gtgcccggtg ctcggtcac cttcgagttc gacggactgg cgtcatcga ggtggccggc | 780 |
| gcc | 783 |

<210> SEQ ID NO 135
<211> LENGTH: 1179
<212> TYPE: DNA
<213> ORGANISM: Artificial Sequence
<220> FEATURE:
<223> OTHER INFORMATION: Codon optimized phaA for expression in C. autoethanogenum.

<400> SEQUENCE: 135

| atgacagatg tagtgatagt ttcagcagct agaacagctg ttggtaaatt cggtggttcg | 60 |
| ttagcgaaaa tagctgctcc tgaattagga gcttcagtaa ttagagctgt attagaaaga | 120 |
| gcaggtgtaa aacctgagca agtgtctgaa gtcatattag gcaagtcctt gactgcaggg | 180 |
| tcaggtcaga atcctgcaag acaagcctta atagctgcgg gacttcctaa tgcagtacct | 240 |
| gggatgacaa tcaataaagt ttgtggatca ggtctaaaag cagttatgtt ggctgcaaat | 300 |
| gcggttgtag ctggagacgc tgaaatagtt gtggcgggtg acaagaaaaa catgagtgca | 360 |
| gcaccacatg ttctacctgg cagtagagat ggatttcgaa tggagatgc aaagctagta | 420 |
| gatagcatga tagtagatgg attatgggat gtttacaata agtatcatat gggaataact | 480 |
| gcagaaaatg tagcaaaaga atatggaatt acacgtgaag ctcaagacca atttgcagca | 540 |
| ctttcacaga ataaggctga agcagcacaa aaagctggaa gatttgatga tgaaatagtt | 600 |
| cctattgaaa ttccacaaag aaagggagaa ccacttagat tgccactga tgaatttgta | 660 |
| aggcatggag taacagctga atctcttgca gtttgaaaac cagcgtttgc caagaggga | 720 |
| actgtgactc tgctaatgc ttcaggcata atgatggag ctgcagcagt ccttgttatg | 780 |
| tctgcgaaga aagcagaagc tcttggcctt gaacctttgg cacgtattaa ggcttatgcc | 840 |
| aatgctggag ttgatccttc tgttatggga atgggacctg taccggcaag tagaagatgc | 900 |
| ctagaaagag caggatggag tgtaggtgat ttagatctta tggagattaa tgaggctttt | 960 |
| gctgcacaag cgttggctgt tcataagcaa atgggttggg atacatcaaa agttaatgta | 1020 |
| aatggcggtg caatagcaat tggacatcca ataggagcat ctggttgcag atacttgtt | 1080 |
| actcttcttc atgaaatgtt gaaaagagat gctaaaagag ttagcatc attatgtata | 1140 |
| ggtggtggca tgggagtagc tttagcatta gaaagaccg | 1179 |

<210> SEQ ID NO 136
<211> LENGTH: 846
<212> TYPE: DNA
<213> ORGANISM: Artificial Sequence
<220> FEATURE:
<223> OTHER INFORMATION: Codon optimized phaB for expression in C. autoethanogenum.

<400> SEQUENCE: 136

| atgaaaaagg tttgtgttat aggtgcaggt actatgggtt caggtattgc tcaggcattt | 60 |
| gcagccaaag ggtttgaagt tgttttaagg gacataaaag atgaattcgt ggatagggga | 120 |
| ttagatttta taaataagaa cttaagtaag cttgtaaaga agggcaaaat tgaagaggct | 180 |
| actaaagtag aaatcttgac gagaataagt ggtaccgtag atcttaacat ggctgcagat | 240 |

```
tgtgatttag ttattgaagc tgcggtcgaa agaatggaca ttaagaaaca gattttttgca      300 gacttagata acatatgtaa gccagaaact atcttagcca gtaatacaag ctcattatca      360
attactgaag tagcaagtgc gacaaaaagg cctgataaag taattggaat gcatttcttt      420
aatccagcac ctgttatgaa attagtgaaa gttataaggg gaatagcaac ttcacaagaa      480
acttttgatg cagtgaaaga aacctcaatt gcaataggta agacccccgt tgaagttgct      540
gaagcaccag gttttgttgt taatagaata ctaataccaa tgataaatga agcagttgga      600
atccttgcag aaggtatagc aagtgtagaa gatattgaca aagcaatgaa attaggtgca      660
aaccatccaa tgggtccttt ggaattagga gatttcattg gattagatat atgtttagca      720
ataatggatg tactatattc tgagactgga gattctaagt acaggcctca tactttactt      780
aagaaatatg taagggcggg atggttagga agaaagtctg gaaagggctt ttatgattat      840
agtaag                                                                 846

<210> SEQ ID NO 137
<211> LENGTH: 783
<212> TYPE: DNA
<213> ORGANISM: Artificial Sequence
<220> FEATURE:
<223> OTHER INFORMATION: Codon optimized crotonase for expression in C.
      autoethanogenum.

<400> SEQUENCE: 137
atggaactta caatgtaat acttgaaaaa gaaggcaaag tagctgttgt aacaataaac       60
aggccaaaag ctctaaatgc acttaattcc gacactctta agaaatggat tacgttata         120 ggtgagatag aaatgattc tgaagtacta gctgtaatac ttacaggtgc tggtgagaaa       180
tcatttgtgg caggagcaga tatttctgaa atgaaagaaa tgaatactat tgaggggaga       240
aaattcggga tacttggaaa caaggttttt agaaggttag aattacttga gaaaccagta     300
atagctgccg taaatggatt tgcattaggt ggcggatgtg aaatagcaat gtcatgcgat     360
atccgaatcg catcttctaa tgcaagattt gggcaacctg aagttggatt aggaatcact     420
cccggatttg gcggtacaca agacttagc agattagtag gtatgggaat ggctaagcaa       480
ctaattttta cggctcagaa cataaaagca gatgaagctc ttaggattgg acttgtgaat     540
aaagtagtag aaccgtcgga gcttatgaat acagcaaaag aaattgcaaa caaaatagta     600
agtaatgcac cagtggcagt taaactttcg aaacaagcaa tcatagggg catgcaatgc       660 gatatagata cggctttggc atttgaaagt gaagcatttg gggatgtttt ttcaacggaa     720
gatcaaaaag atgctatgac agcctttatt gagaaaagaa agatagaggg atttaagaat     780
aga                                                                  783

<210> SEQ ID NO 138
<211> LENGTH: 453
<212> TYPE: DNA
<213> ORGANISM: Artificial Sequence
<220> FEATURE:
<223> OTHER INFORMATION: Codon optimized crotonyl-CoA thioesterase for
      expression in C. autoethanogenum.

<400> SEQUENCE: 138
atgcacagaa catctaatgg atcacatgca acaggtggca atctaccaga tgttgcaagt       60
cattatccgg tagcttatga acagacatta gatggaaccg ttggttttgt gatagatgaa     120
atgactccag aaaagctac agcttccgtc gaggtaactg atacattacg tcagaggtgg     180
ggtttggttc atggtggagc atattgtgct cttgcggaaa tgttggctac tgaagcaaca   240
```

```
gttgcagttg tacatgaaaa aggtatgatg gcagttggtc aatctaatca caccagcttt      300
ttcaggccag ttaaagaagg tcatgttaga gccgaggcgg ttaggataca tgcaggaagt      360
acaacctggt tttgggatgt ttctttaaga gatgatgctg gtagattatg tgctgttagc      420
agtatgtcca ttgcagtaag accaagaaga gat                                   453
```

<210> SEQ ID NO 139
<211> LENGTH: 783
<212> TYPE: DNA
<213> ORGANISM: Artificial Sequence
<220> FEATURE:
<223> OTHER INFORMATION: Codon optimized 4-oxalocrotonate decarboxylase
      for expression in C. autoethanogenum.

<400> SEQUENCE: 139

```
atgagcacta ctagtataac accagatgaa attgctcaag tactattagc tggagaaaga       60
aatagaacag aagtagcaca gttttcagct tcacacccgg atttagatgt aagaacggct      120
tatgctgctc aaagagcatt tgttcaagca aaacttgatg caggagagca gttagtaggc      180
tataagcttg gacttacatc taggaataaa caaagagcta tgggtgtaga ttgcccactt      240
tatggaagag ttacgtcctc tatgttggcc acatatggaa tccaataccc attcgacaga      300
ttcatacatc ctagagttga gtctgaaatt gcattcttat tgaaacaaga tgttactgct      360
cctgctacag tatcatccgt acttgctgca actgatgtag tttttggtgc agtggatgtt      420
ttggattcaa gatatgaagg atttaagttt actctagaag atgtagttgc agataatgcc      480
agtgcaggag cttttttacct tggacctgtt gctagacctg ctacagagtt aagacttgat      540
ttactaggat gtatagttag agttgacgga gaagttacaa tgacagcggc tggtgccgct      600
gttatgggac accctgctgc tgctgtagca tggttagcta atcaacttgc acttgagggt      660
gaaagcttga aggcaggtca gcttatcttt agcggtgggg tcactgctcc tgttccagta      720
gttcctggtg gaagcgtgac ctttgaattt gatggcctag gtgtaataga agtagcagga      780
gcc                                                                    783
```

<210> SEQ ID NO 140
<211> LENGTH: 1179
<212> TYPE: DNA
<213> ORGANISM: Artificial Sequence
<220> FEATURE:
<223> OTHER INFORMATION: Codon optimized phaA for expression in E. coli.

<400> SEQUENCE: 140

```
atgaccgacg tggtgatcgt gagcgctgcg cgcacggcgg ttggcaagtt tggtggtagc       60
ctggcgaaga tcgcggcacc ggagttgggc gccagcgtta ttcgtgccgt cctggaacgc      120
gcaggtgtga accggagca ggtgagcgaa gtgatcctgg gtcaagtgct gaccgcaggc      180
agcggtcaaa accggcacg tcaagccttg attgccgcag gtctgccaaa cgctgttccg      240
ggcatgacca ttaacaaagt gtgtggttct ggtctgaaag cggtgatgct ggctgcgaac      300
gcggttgtcg ccggtgatgc ggaaattgtg gtcgcgggtg gccaggagaa tatgtccgca      360
gctccgcacg tgctgccggg cagccgtgac ggtttccgta tgggcgatgc taaattggta      420
gatagcatga ttgttgacgg cttgtgggac gtgtataaca aatatcacat gggtatcacc      480
gcggaaaacg ttgcgaaaga gtacggtatc acccgtgagg cgcaggacca gtttgccgca      540
ctgagccaga caaggccga agcggcgcaa aaagcaggcc gttttgatga tgagatcgtt      600
ccgattgaga ttccgcagcg taaaggtgaa ccgctgcgct tcgctaccga cgagtttgtc      660
```

```
cgtcacggcg ttaccgccga atccctggcc tctttgaaac cggcgtttgc taaagagggt    720
accgtcaccg cggcaaacgc aagcggtatt aacgatggcg cagcagctgt cctggttatg    780
tccgcgaaga aggcagaagc gttgggcctg gagccgctgg ctcgcattaa agcatatgcc    840
aatgccggcg ttgatccgag cgttatgggc atgggtccgg tcccggcaag ccgtcgttgc    900
ctggagcgtg caggctggtc cgttggcgac ctggatctga tggagatcaa tgaagccttc    960
gcagcgcagg cgctggcagt gcacaagcag atgggttggg acaccagcaa ggttaatgtc   1020
aatggtggcg caatcgccat tggccatcct atcggtgcga cggttgtcg tattttggtt    1080 accctgctgc atgaaatgct gaaacgcgac gccaagcgtg gcctggctag cctgtgcatc   1140
ggtggtggta tgggtgtggc gctggcgctg gaacgtcca                          1179

<210> SEQ ID NO 141
<211> LENGTH: 846
<212> TYPE: DNA
<213> ORGANISM: Artificial Sequence
<220> FEATURE:
<223> OTHER INFORMATION: Codon optimized phaB for expression in E. coli.

<400> SEQUENCE: 141
atgaagaaag tatgcgtcat cggtgcgggc accatgggca gcggtattgc gcaggcgttt     60
gcagccaagg gcttcgaggt ggtcctgcgc gatatcaaag atgagttcgt tgatcgcgt    120 ttggacttca tcaacaaaaa cctgagcaag ctggttaaga agggtaagat cgaagaggcg    180
acgaaggttg aaattctgac ccgcatcagc ggtactgttg acctgaatat ggcggcagac    240
tgcgatttgg ttattgaagc tgcggtcgag cgtatggaca ttaagaagca gattttcgcc    300
gatctggaca catttgtaa gccggagacg attctggcga gcaacaccag cagcttgagc    360
attaccgagg tggcctctgc cacgaagcgt ccggataagg tcatcggtat gcacttcttt    420
aacccggctc cggtgatgaa actggtcgag gtgatccgcg gtattgctac cagccaagaa    480
acgtttgacg ctgtgaaaga gacgtcgatc gctatcggca aggatccggt tgaggtggca    540
gaagctccgg ttttgtggt gaatcgcatc ctgatcccga tgatcaacga ggccgtaggt    600
atcctggccg agggtattgc ctctgtggaa gatatcgaca aggcgatgaa actgggtgct    660
aatcacccga tgggtccgtt ggagctgggt gacttcatcg gtctggacat ttgtctggcg    720
atcatggacg ttctgtactc tgagacgggc gacagcaaat atcgcccgca caccctgctg    780
aaaaagtacg ttcgtgctgg ttggctgggt cgtaagtctg gcaaaggctt ctacgattac    840
agcaag                                                                846

<210> SEQ ID NO 142
<211> LENGTH: 783
<212> TYPE: DNA
<213> ORGANISM: Artificial Sequence
<220> FEATURE:
<223> OTHER INFORMATION: Codon optimized crotonase for expression in
      E.coli.

<400> SEQUENCE: 142
atggagctga ataatgtgat tctggagaaa gagggcaaag tcgctgttgt tacgattaac     60
cgcccgaagg cattgaacgc cctgaacagc gataccctga agagatgga ttacgtgatt    120 ggcgagatcg aaaacgacag cgaagttctg gccgtcattc tgactggtgc cggtgaaaag    180
agctttgtcg cgggtgcaga tattagcgag atgaaagaga tgaatacgat cgaaggtcgt    240
aaattcggta tcctgggcaa taaagtctt cgtcgtttgg aactgctgga gaaacctgtc    300
```

```
atcgctgccg tgaatggctt cgcgctgggc ggtggctgcg agattgcaat gagctgcgat    360
atccgtatcg cgagcagcaa tgcgcgtttc ggtcaaccgg aagtgggtct gggtatcacg    420
ccgggttttg gtggcaccca acgcctgagc cgtttggttg gcatgggtat ggcaaaacaa    480
ctgatcttta ccgcgcagaa catcaaagca gatgaagctc tgcgcattgg cttggtcaat    540
aaggtggttg agccgagcga actgatgaac acggcgaaag agatcgcgaa caagatcgtg    600
agcaatgcac cggtggccgt caaactgagc aaacaggcca tcaatcgtgg tatgcaatgt    660
gatatcgaca ccgcgctggc attcgaaagc gaggcatttg tgagtgctt cagcacggaa     720 gatcaaaagg atgcaatgac ggcgttcatt gaaaaacgta agattgaagg cttcaagaac    780
cgc                                                                  783

<210> SEQ ID NO 143
<211> LENGTH: 453
<212> TYPE: DNA
<213> ORGANISM: Artificial Sequence
<220> FEATURE:
<223> OTHER INFORMATION: Codon optimized crotonyl-CoA thioesterase for
      expression in E. coli.

<400> SEQUENCE: 143
atgcatcgta cgagcaacgg cagccacgcc accggtggca atctgcctga tgtcgcgagc     60
cattatccgg ttgcatacga acagaccctg gacggcaccg tcggtttcgt gattgacgaa    120
atgactccgg agcgtgccac cgcgagcgtt gaggtcaccg ataccctgcg ccagcgttgg    180
ggtctggttc atggtggtgc atattgtgcg ttggcagaga tgttggcgac tgaagcgacc    240
gtcgcagtag tccatgaaaa gggcatgatg gcggtgggcc aaagcaatca caccagcttt    300
ttccgtccgg ttaaagaggg ccatgttcgc gcagaggcgg tgcgtattca cgcgggtagc    360
acgacctggt tctgggacgt tagcctgcgc gatgacgcag gtcgtctgtg tgcagttagc    420
agcatgtcta ttgctgtccg tccgcgtcgc gac                                 453

<210> SEQ ID NO 144
<211> LENGTH: 783
<212> TYPE: DNA
<213> ORGANISM: Artificial Sequence
<220> FEATURE:
<223> OTHER INFORMATION: Codon optimized 4-oxalocrotonate decarboxylase
      for expression in E. coli.

<400> SEQUENCE: 144
atgagcacca cgagcattac cccggacgaa atcgcgcagg ttctgctggc aggcgagcgt     60
aatcgcaccg aggtggcgca atttctctgcg tcgcacccgg atttggatgt ccgtaccgcg    120
tacgcggcac aacgtgcgtt cgttcaggct aaactggacg caggtgaaca actggtcggt    180
tacaaattgg gtctgacgtc tcgtaataag cagcgcgcaa tgggtgtcga ctgcccgctg    240
tacggccgtg ttaccagcag catgctggcc acctatggtg atccgattcc gtttgaccgc    300
tttattcacc cacgtgtgga gtccgaaatt gcgttcctgc tgaagcaaga tgtgaccgca    360
ccggcgacgg tcagcagcgt tctggcagcg actgacgtcg tgtttggcgc ggttgacgtc    420
ctggatagcc gttacgaggg cttcaagttc accctggaag atgttgttgc agacaatgca    480
tctgcgggtg ctttctatct gggtccagtt gcacgtccag cgacggagct gcgtctggat    540
ctgctgggtt gcattgtgcg cgtcgacggc gaagtgacca tgaccgcagc gggtgccgcg    600
gttatgggcc acccggcagc ggccgttgcg tggctggcca atcagctggc cctggaaggt    660
```

```
gaaagcctga aggcgggtca gctgatcttc agcggtggtg tcactgcgcc ggtcccggtt    720
gtgccgggtg gcagcgtgac cttcgagttt gacggcctgg gtgtcatcga agtggcaggt    780
gca                                                                  783
```